United States Patent
Mao et al.

(10) Patent No.: US 10,898,505 B2
(45) Date of Patent: Jan. 26, 2021

(54) REAGENTS FOR TREATMENT OF HEPATITIS B VIRUS (HBV) INFECTION AND USE THEREOF

(71) Applicant: Benitec Biopharma Limited, North Sydney (AU)

(72) Inventors: Tin Mao, Millbrae, CA (US); Shih-Chu Kao, Mountain View, CA (US); David Suhy, San Ramon, CA (US); Michael Graham, San Mateo, CA (US)

(73) Assignee: Benitec Biopharma Limited, North Sydney (AU)

( * ) Notice: Subject to any disclaimer, the term of this patent is extended or adjusted under 35 U.S.C. 154(b) by 106 days.

(21) Appl. No.: 15/572,143

(22) PCT Filed: May 6, 2016

(86) PCT No.: PCT/AU2016/050340
§ 371 (c)(1),
(2) Date: Nov. 6, 2017

(87) PCT Pub. No.: WO2016/176745
PCT Pub. Date: Nov. 10, 2016

(65) Prior Publication Data
US 2019/0022124 A1 Jan. 24, 2019

Related U.S. Application Data

(60) Provisional application No. 62/319,971, filed on Apr. 8, 2016.

(30) Foreign Application Priority Data

May 6, 2015 (AU) .............................. 2015901617

(51) Int. Cl.
*C12N 15/11* (2006.01)
*C07H 21/02* (2006.01)
(Continued)

(52) U.S. Cl.
CPC ........ *A61K 31/7105* (2013.01); *A61K 31/713* (2013.01); *A61K 48/005* (2013.01);
(Continued)

(58) Field of Classification Search
CPC ............ C12N 2310/14; C12N 2310/51; C12N 2310/531; C12N 15/1131; C12N 15/63;
(Continued)

(56) References Cited

U.S. PATENT DOCUMENTS

| | | | |
|---|---|---|---|
| 8,809,293 | B2 | 8/2014 | Chin et al. |
| 2003/0206887 | A1 | 11/2003 | Morrissey et al. |
| 2014/0273213 | A1 | 9/2014 | Pachuk et al. |

FOREIGN PATENT DOCUMENTS

| | | |
|---|---|---|
| CN | 1566131 A | 1/2005 |
| CN | 101322847 A | 12/2008 |

(Continued)

OTHER PUBLICATIONS

PCT International Search Report & Written Opinion, International Application No. PCT/AU2016/050340, dated Aug. 24, 2016, 37 Pages.
(Continued)

*Primary Examiner* — Terra C Gibbs
(74) *Attorney, Agent, or Firm* — Goodwin Procter LLP

(57) ABSTRACT

This disclosure relates to RNA interference (RNAi) reagents for treatment of hepatitis B virus (HBV) infection, compositions comprising same, and use thereof to treat individuals infected with HBV.

20 Claims, 46 Drawing Sheets
Specification includes a Sequence Listing.

(51) Int. Cl.
    *C07H 21/04* (2006.01)
    *A61K 31/7105* (2006.01)
    *C12N 15/113* (2010.01)
    *A61K 31/713* (2006.01)
    *A61P 31/20* (2006.01)
    *A61K 48/00* (2006.01)
    *C12N 15/63* (2006.01)

(52) U.S. Cl.
    CPC .......... *A61P 31/20* (2018.01); *C12N 15/1131* (2013.01); *C12N 15/63* (2013.01); *C12N 2310/14* (2013.01); *C12N 2310/51* (2013.01); *C12N 2310/531* (2013.01); *C12N 2320/11* (2013.01)

(58) Field of Classification Search
    CPC .......... C12N 2320/11; C12N 2310/141; C12N 2330/51; A61K 31/713; A61K 48/005; A61P 31/20
    See application file for complete search history.

(56) References Cited

FOREIGN PATENT DOCUMENTS

| CN | 103014045 A | 4/2013 | |
|---|---|---|---|
| WO | WO-2006069064 A2 * | 6/2006 | ......... C12N 15/1131 |
| WO | WO 2012/024170 A2 | 2/2012 | |
| WO | WO 2012/055362 A1 | 5/2012 | |
| WO | WO 2012/109798 A1 | 8/2012 | |
| WO | 2013/159109 A1 | 10/2013 | |

OTHER PUBLICATIONS

McCaffrey, A.P., et al., "Inhibition of hepatitis B virus in mice by RNA interference," Nature Biotechnology, 2003, vol. 21, No. 6, pp. 639-644.

Panjaworayan, N., et al., "Effects of HBV genetic variability on RNAi strategies," Hepatitis Research and Treatment, 2011, vol. 2011, Article ID 367908, 9 Pages.

Wang, X.J., et al., "A simple and robust vector-based shRNA expression system used for RNA interference," PLoS One, 2013, vol. 8: e56110, 8 Pages.

Wu, H.L., et al., "RNA interference-mediated control of hepatitis B virus and emergence of resistant mutant," Gastroenterology, 2005, vol. 128, pp. 708-716.

Zhang, Y.L., et al., "RNA Interference inhibits hepatitis B virus of different genotypes in vitro and in vivo," BMC Microbiology, 2010, vol. 10:214.

McCaffrey, A. et al., "Inhibition of hepatitis B virus in mice by RNA interference," Nature Biotechnology, 2003, vol. 21, pp. 639-644.

Panjaworayan, N. et al., "Effects of HBV genetic variability on RNAi strategies," Hepatitis Research and Treatment, 2011, vol. 2011, Article ID 367908, 8 pages.

Wang, X. et al., "A simple and robust vector-based shRNA expression system used for RNA interference," PLoS One, 2013, vol. 8: e56110, eight pages.

Wu, H. et al., "RNA interference-mediated control of hepatitis B virus and emergence of resistant mutant," Gastroenterology, 2005, vol. 128, pp. 708-716.

Zhang, Y. et al., "RNA Interference inhibits hepatitis B virus of different genotypes in vitro and in vivo," BMC Microbiology, 2010, vol. 10, 214, ten pages.

* cited by examiner

REAGENTS FOR TREATMENT OF HEPATITIS B VIRUS (HBV) INFECTION AND USE THEREOF

RELATED APPLICATION DATA

This application is the National Stage of International Application No. PCT/AU2016/050340, filed May 6, 2016, which claims priority from Australian Provisional Application No. 2015901617 filed on 6 May 2015 and U.S. Provisional Application No. 62/319,971 filed on 8 Apr. 2016, the full contents of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Aug. 22, 2018, is named 38892US_CRF_sequencelisting.txt and is 40,013 bytes in size.

TECHNICAL FIELD

The present disclosure relates to RNA interference (RNAi) reagents for treatment of hepatitis B virus (HBV) infection, compositions comprising same, and use thereof to treat individuals infected with HBV.

BACKGROUND

HBV is a serious and common infectious disease of the liver, affecting millions of people throughout the world. HBV is a hepatotrophic DNA virus belonging to the Hepadnaviridae. The full-length of the viral genome is about 3.2 kb, and it has four open reading frames (ORFs) including surface antigen (the "S gene"), core antigen (the "C gene"), DNA polymerase (the "P gene") and a gene of undetermined function referred to as the "X gene". More than 2 billion people worldwide have been infected with HBV at some time in their lives, and of these about 350-400 million remain chronically infected and are carriers of the virus. HBV infection can cause acute and chronic type B hepatitis, and may eventually lead to the development of chronic hepatic insufficiency, cirrhosis, and hepatocellular carcinoma. In addition, HBV carriers can transmit the disease for many years. Persons with chronic HBV infection i.e., carriers, have at least 12 times higher risk of developing hepatocellular carcinoma than non-carriers, and HBV causes 60-80% of the world's primary liver cancers. As a consequence, HBV ranks second only to tobacco as a known human carcinogen.

Although vaccines against HBV are available, the rate of HBV infection in the population remains high. Furthermore, current therapies for chronic HBV infection have only limited inhibitory effects on viral gene expression and replication in the majority of chronically infected patients. Another limitation of existing therapies for chronic HBV infection is the development of viral resistance to drugs.

For these reasons, there remains a need for new therapeutic agents to treat HBV infection.

SUMMARY

The present disclosure is based, in part, on the recognition that existing vaccines and therapeutic agents for treatment and/or prevention of HBV infection are limited in their efficacy, such as where long term treatment is necessary e.g., due to the development of viral resistance to therapy and/or variation in responsiveness to therapy between genotypes of HBV. The present disclosure provides RNAi reagents targeting one or more conserved regions of RNA transcripts produced by the HBV genome i.e., regions conserved among a plurality of different genotypes of HBV. The inventors have shown that these RNAi reagents are effective for inhibiting expression of HBV genes e.g., HBV pol gene, in cells infected with HBV. For example, it has been shown that exemplary RNAi reagents of the disclosure inhibit or reduce expression of HBV gene transcripts in HepG2.2.15 cells harbouring active HBV. It has also been shown that exemplary RNAi reagents of the disclosure inhibit or reduce expression of HBV gene transcripts, reduce intracellular and extracellular HBV DNA, and reduce HBV covalently-closed circular DNA (cccDNA) in human hepatocytes inoculated with HBV and in a PXB chimeric mouse infected with HBV. These findings by the inventors provide new compounds that inhibit or reduce expression of a nucleic acid and/or protein expressed by HBV and uses of such compounds e.g., to treat a HBV infection in a subject.

Accordingly, the present disclosure provides a RNA comprising an effector sequence of at least 17 nucleotides in length and an effector complement sequence, wherein the effector sequence is substantially complementary to a RNA transcript encoded by a region of the HBV genome, wherein the region comprises a sequence set forth in any one of SEQ ID NOs: 1-10. For example, the effector sequence will be less than 30 nucleotides in length. For example, a suitable effector sequence may be in the range of 17-29 nucleotides in length.

The effector sequence may comprise 4 base pair mismatches relative to the sequence set forth in any one of SEQ ID NOs: 1-10 to which the effector sequence is substantially complementary. In another example, the effector sequence comprises 3 base pair mismatches relative to the sequence set forth in any one of SEQ ID NOs: 1-10 to which the effector sequence is substantially complementary. In another example, the effector sequence comprises 2 base pair mismatches relative to the sequence set forth in any one of SEQ ID NOs: 1-10 to which the effector sequence is substantially complementary. In another example, the effector sequence comprises 1 base pair mismatch relative to the sequence set forth in any one of SEQ ID NOs: 1-10 to which the effector sequence is substantially complementary. In yet another example, the effector sequence is 100% complementary to a region of equivalent length within a sequence set forth in any one of SEQ ID NOs: 1-10.

In one example, the RNA may be selected from the group consisting of:

a RNA comprising: (i) an effector sequence which is complementary to the sequence set forth in SEQ ID NO:12, optionally with the exception of 1, 2, 3 or 4 base mismatches, provided that the effector sequence is capable of forming a duplex with a sequence set forth in SEQ ID NO:12; and (ii) an effector complement sequence comprising a sequence which is substantially complementary to the effector sequence;

a RNA comprising: (i) an effector sequence which is complementary to the sequence set forth in SEQ ID NO:14, optionally with the exception of 1, 2, 3 or 4 base mismatches, provided that the effector sequence is capable of forming a duplex with a sequence set forth in SEQ ID NO:14; and (ii) an effector complement sequence comprising a sequence which is substantially complementary to the effector sequence;

a RNA comprising: (i) an effector sequence which is complementary to the sequence set forth in SEQ ID NO:16, optionally with the exception of 1, 2, 3 or 4 base mismatches, provided that the effector sequence is capable of forming a duplex with a sequence set forth in SEQ ID NO:16; and (ii) an effector complement sequence comprising a sequence which is substantially complementary to the effector sequence;

a RNA comprising: (i) an effector sequence which is complementary to the sequence set forth in SEQ ID NO:18, optionally with the exception of 1, 2, 3 or 4 base mismatches, provided that the effector sequence is capable of forming a duplex with a sequence set forth in SEQ ID NO:18; and (ii) an effector complement sequence comprising a sequence which is substantially complementary to the effector sequence;

a RNA comprising: (i) an effector sequence which is complementary to the sequence set forth in SEQ ID NO:20, optionally with the exception of 1, 2, 3 or 4 base mismatches, provided that the effector sequence is capable of forming a duplex with a sequence set forth in SEQ ID NO:20; and (ii) an effector complement sequence comprising a sequence which is substantially complementary to the effector sequence;

a RNA comprising: (i) an effector sequence which is complementary to the sequence set forth in SEQ ID NO:22, optionally with the exception of 1, 2, 3 or 4 base mismatches, provided that the effector sequence is capable of forming a duplex with a sequence set forth in SEQ ID NO:22; and (ii) an effector complement sequence comprising a sequence which is substantially complementary to the effector sequence;

a RNA comprising: (i) an effector sequence which is complementary to the sequence set forth in SEQ ID NO:24, optionally with the exception of 1, 2, 3 or 4 base mismatches, provided that the effector sequence is capable of forming a duplex with a sequence set forth in SEQ ID NO:24; and (ii) an effector complement sequence comprising a sequence which is substantially complementary to the effector sequence;

a RNA comprising: (i) an effector sequence which is complementary to the sequence set forth in SEQ ID NO:26, optionally with the exception of 1, 2, 3 or 4 base mismatches, provided that the effector sequence is capable of forming a duplex with a sequence set forth in SEQ ID NO:26; and (ii) an effector complement sequence comprising a sequence which is substantially complementary to the effector sequence;

a RNA comprising: (i) an effector sequence which is complementary to the sequence set forth in SEQ ID NO:28, optionally with the exception of 1, 2, 3 or 4 base mismatches, provided that the effector sequence is capable of forming a duplex with a sequence set forth in SEQ ID NO:28; and (ii) an effector complement sequence comprising a sequence which is substantially complementary to the effector sequence;

a RNA comprising: (i) an effector sequence which is complementary to the sequence set forth in SEQ ID NO:30, optionally with the exception of 1, 2, 3 or 4 base mismatches, provided that the effector sequence is capable of forming a duplex with a sequence set forth in SEQ ID NO:30; and (ii) an effector complement sequence comprising a sequence which is substantially complementary to the effector sequence;

a RNA comprising: (i) an effector sequence which is complementary to the sequence set forth in SEQ ID NO:32, optionally with the exception of 1, 2, 3 or 4 base mismatches, provided that the effector sequence is capable of forming a duplex with a sequence set forth in SEQ ID NO:32; and (ii) an effector complement sequence comprising a sequence which is substantially complementary to the effector sequence;

a RNA comprising: (i) an effector sequence which is complementary to the sequence set forth in SEQ ID NO:34, optionally with the exception of 1, 2, 3 or 4 base mismatches, provided that the effector sequence is capable of forming a duplex with a sequence set forth in SEQ ID NO:34; and (ii) an effector complement sequence comprising a sequence which is substantially complementary to the effector sequence;

a RNA comprising: (i) an effector sequence which is complementary to the sequence set forth in SEQ ID NO:36, optionally with the exception of 1, 2, 3 or 4 base mismatches, provided that the effector sequence is capable of forming a duplex with a sequence set forth in SEQ ID NO:36; and (ii) an effector complement sequence comprising a sequence which is substantially complementary to the effector sequence;

a RNA comprising: (i) an effector sequence which is complementary to the sequence set forth in SEQ ID NO:38, optionally with the exception of 1, 2, 3 or 4 base mismatches, provided that the effector sequence is capable of forming a duplex with a sequence set forth in SEQ ID NO:38; and (ii) an effector complement sequence comprising a sequence which is substantially complementary to the effector sequence;

a RNA comprising: (i) an effector sequence which is complementary to the sequence set forth in SEQ ID NO:40, optionally with the exception of 1, 2, 3 or 4 base mismatches, provided that the effector sequence is capable of forming a duplex with a sequence set forth in SEQ ID NO:40; and (ii) an effector complement sequence comprising a sequence which is substantially complementary to the effector sequence;

a RNA comprising: (i) an effector sequence which is complementary to the sequence set forth in SEQ ID NO:42, optionally with the exception of 1, 2, 3 or 4 base mismatches, provided that the effector sequence is capable of forming a duplex with a sequence set forth in SEQ ID NO:42; and (ii) an effector complement sequence comprising a sequence which is substantially complementary to the effector sequence;

a RNA comprising: (i) an effector sequence which is complementary to the sequence set forth in SEQ ID NO:44, optionally with the exception of 1, 2, 3 or 4 base mismatches, provided that the effector sequence is capable of forming a duplex with a sequence set forth in SEQ ID NO:44; and (ii) an effector complement sequence comprising a sequence which is substantially complementary to the effector sequence;

a RNA comprising: (i) an effector sequence which is complementary to the sequence set forth in SEQ ID NO:46, optionally with the exception of 1, 2, 3 or 4 base mismatches, provided that the effector sequence is capable of forming a duplex with a sequence set forth in SEQ ID NO:46; and (ii) an effector complement sequence comprising a sequence which is substantially complementary to the effector sequence;

a RNA comprising: (i) an effector sequence which is complementary to the sequence set forth in SEQ ID NO:48, optionally with the exception of 1, 2, 3 or 4 base mismatches, provided that the effector sequence is capable of forming a duplex with a sequence set forth in SEQ ID NO:48; and (ii) an effector complement sequence comprising a sequence which is substantially complementary to the effector sequence;

a RNA comprising: (i) an effector sequence which is complementary to the sequence set forth in SEQ ID NO:50, optionally with the exception of 1, 2, 3 or 4 base mismatches, provided that the effector sequence is capable of forming a duplex with a sequence set forth in SEQ ID NO:50; and (ii) an effector complement sequence comprising a sequence which is substantially complementary to the effector sequence; and a RNA comprising: (i) an effector sequence which is complementary to the sequence set forth in SEQ ID NO:52, optionally with the exception of 1, 2, 3 or 4 base mismatches, provided that the effector sequence is capable of forming a duplex with a sequence set forth in SEQ ID NO:52; and (ii) an effector complement sequence comprising a sequence which is substantially complementary to the effector sequence.

In another example, the RNA may be selected from the group consisting of:

a RNA comprising an effector sequence set forth in SEQ ID NO:11 and an effector complement sequence which is substantially complementary to the sequence set forth in SEQ ID NO:11 and capable of forming a duplex therewith;

a RNA comprising an effector sequence set forth in SEQ ID NO:13 and an effector complement sequence which is substantially complementary to the sequence set forth in SEQ ID NO:13 and capable of forming a duplex therewith;

a RNA comprising an effector sequence set forth in SEQ ID NO:15 and an effector complement sequence which is substantially complementary to the sequence set forth in SEQ ID NO:15 and capable of forming a duplex therewith;

a RNA comprising an effector sequence set forth in SEQ ID NO:17 and an effector complement sequence which is substantially complementary to the sequence set forth in SEQ ID NO:17 and capable of forming a duplex therewith;

a RNA comprising an effector sequence set forth in SEQ ID NO:19 and an effector complement sequence which is substantially complementary to the sequence set forth in SEQ ID NO:19 and capable of forming a duplex therewith;

a RNA comprising an effector sequence set forth in SEQ ID NO:21 and an effector complement sequence which is substantially complementary to the sequence set forth in SEQ ID NO:21 and capable of forming a duplex therewith;

a RNA comprising an effector sequence set forth in SEQ ID NO:23 and an effector complement sequence which is substantially complementary to the sequence set forth in SEQ ID NO:23 and capable of forming a duplex therewith;

a RNA comprising an effector sequence set forth in SEQ ID NO:25 and an effector complement sequence which is substantially complementary to the sequence set forth in SEQ ID NO:25 and capable of forming a duplex therewith;

a RNA comprising an effector sequence set forth in SEQ ID NO:27 and an effector complement sequence which is substantially complementary to the sequence set forth in SEQ ID NO:27 and capable of forming a duplex therewith;

a RNA comprising an effector sequence set forth in SEQ ID NO:29 and an effector complement sequence which is substantially complementary to the sequence set forth in SEQ ID NO:29 and capable of forming a duplex therewith;

a RNA comprising an effector sequence set forth in SEQ ID NO:31 and an effector complement sequence which is substantially complementary to the sequence set forth in SEQ ID NO:31 and capable of forming a duplex therewith;

a RNA comprising an effector sequence set forth in SEQ ID NO:33 and an effector complement sequence which is substantially complementary to the sequence set forth in SEQ ID NO:33 and capable of forming a duplex therewith;

a RNA comprising an effector sequence set forth in SEQ ID NO:35 and an effector complement sequence which is substantially complementary to the sequence set forth in SEQ ID NO:35 and capable of forming a duplex therewith;

a RNA comprising an effector sequence set forth in SEQ ID NO:37 and an effector complement sequence which is substantially complementary to the sequence set forth in SEQ ID NO:37 and capable of forming a duplex therewith;

a RNA comprising an effector sequence set forth in SEQ ID NO:39 and an effector complement sequence which is substantially complementary to the sequence set forth in SEQ ID NO:39 and capable of forming a duplex therewith;

a RNA comprising an effector sequence set forth in SEQ ID NO:41 and an effector complement sequence which is substantially complementary to the sequence set forth in SEQ ID NO:41 and capable of forming a duplex therewith;

a RNA comprising an effector sequence set forth in SEQ ID NO:43 and an effector complement sequence which is substantially complementary to the sequence set forth in SEQ ID NO:43 and capable of forming a duplex therewith;

a RNA comprising an effector sequence set forth in SEQ ID NO:45 and an effector complement sequence which is substantially complementary to the sequence set forth in SEQ ID NO:45 and capable of forming a duplex therewith;

a RNA comprising an effector sequence set forth in SEQ ID NO:47 and an effector complement sequence which is substantially complementary to the sequence set forth in SEQ ID NO:47 and capable of forming a duplex therewith;

a RNA comprising an effector sequence set forth in SEQ ID NO:49 and an effector complement sequence which is substantially complementary to the sequence set forth in SEQ ID NO:49 and capable of forming a duplex therewith; and a RNA comprising an effector sequence set forth in SEQ ID NO:51 and an effector complement sequence which is substantially complementary to the sequence set forth in SEQ ID NO:51 and capable of forming a duplex therewith.

For example, an effector complement sequence of a RNA of the disclosure may comprise 1, 2, 3 or 4 mismatches relative to the corresponding effector sequence provided that the cognate effector and effector complement sequences are capable of forming a duplex.

In another example, the RNA may be selected from the group consisting of:

a RNA comprising an effector sequence set forth in SEQ ID NO:11 and an effector complement sequence set forth in SEQ ID NO:12;

a RNA comprising an effector sequence set forth in SEQ ID NO:13 and an effector complement sequence set forth in SEQ ID NO:14;

a RNA comprising an effector sequence set forth in SEQ ID NO:15 and an effector complement sequence set forth in SEQ ID NO:16;

a RNA comprising an effector sequence set forth in SEQ ID NO:17 and an effector complement sequence set forth in SEQ ID NO:18;

a RNA comprising an effector sequence set forth in SEQ ID NO:19 and an effector complement sequence set forth in SEQ ID NO: 20;

a RNA comprising an effector sequence set forth in SEQ ID NO:21 and an effector complement sequence set forth in SEQ ID NO:22;

a RNA comprising an effector sequence set forth in SEQ ID NO:23 and an effector complement sequence set forth in SEQ ID NO:24;
a RNA comprising an effector sequence set forth in SEQ ID NO:25 and an effector complement sequence set forth in SEQ ID NO:26;
a RNA comprising an effector sequence set forth in SEQ ID NO:27 and an effector complement sequence set forth in SEQ ID NO:28;
a RNA comprising an effector sequence set forth in SEQ ID NO:29 and an effector complement sequence set forth in SEQ ID NO:30;
a RNA comprising an effector sequence set forth in SEQ ID NO:31 and an effector complement sequence set forth in SEQ ID NO:32;
a RNA comprising an effector sequence set forth in SEQ ID NO:33 and an effector complement sequence set forth in SEQ ID NO:34;
a RNA comprising an effector sequence set forth in SEQ ID NO:35 and an effector complement sequence set forth in SEQ ID NO:36;
a RNA comprising an effector sequence set forth in SEQ ID NO:37 and an effector complement sequence set forth in SEQ ID NO:38;
a RNA comprising an effector sequence set forth in SEQ ID NO:39 and an effector complement sequence set forth in SEQ ID NO:40;
a RNA comprising an effector sequence set forth in SEQ ID NO:41 and an effector complement sequence set forth in SEQ ID NO:42;
a RNA comprising an effector sequence set forth in SEQ ID NO:43 and an effector complement sequence set forth in SEQ ID NO:44;
a RNA comprising an effector sequence set forth in SEQ ID NO:45 and an effector complement sequence set forth in SEQ ID NO:46;
a RNA comprising an effector sequence set forth in SEQ ID NO:47 and an effector complement sequence set forth in SEQ ID NO:48;
a RNA comprising an effector sequence set forth in SEQ ID NO:49 and an effector complement sequence set forth in SEQ ID NO:50; and
a RNA comprising an effector sequence set forth in SEQ ID NO:51 and an effector complement sequence set forth in SEQ ID NO:52.

In one example, the RNA is a RNAi reagent.

The RNA of the disclosure may be provided in the form of a short hairpin RNA (shRNA). When provided as a shRNA, the RNA of the disclosure may comprise a loop sequence positioned between the effector sequence and the effector complement sequence. Suitable loop sequences may be selected from those known in the art. For example, an shRNA in accordance with the present disclosure may comprise a sequence set forth in any one of SEQ ID NOs: 65-98.

Alternatively, the RNA of the disclosure may be provided in the form of a short interfering RNA (siRNA) duplex or a double-stranded RNA (dsRNA).

It will be understood by a person of skill in the art that a RNA in accordance with the present disclosure may be combined or used in conjunction with other therapeutic agents for treating HBV. Accordingly, the present disclosure provides a RNA as described herein in combination with one or more other agents for treating HBV. In one example, a plurality of RNAs are provided comprising:
(a) at least one RNA as described herein; and
(b) at least one RNA selected from:
   (i) a RNA in accordance with the RNA described herein; or
   (ii) a RNA comprising an effector sequence of at least 17 nucleotides in length and a effector complement sequence, wherein the effector sequence is substantially complementary to a RNA sequence set forth in any one of SEQ ID NOs: 54, 56, 58, 60, 62 and 64;
wherein the RNA at (a) and the RNA at (b) comprise different effector sequences.

In one example, a plurality of RNAs of the disclosure comprises:
(a) at least one RNA selected from the group consisting of:
   a RNA comprising an effector sequence set forth in SEQ ID NO:11 and an effector complement sequence set forth in SEQ ID NO:12;
   a RNA comprising an effector sequence set forth in SEQ ID NO:13 and an effector complement sequence set forth in SEQ ID NO:14;
   a RNA comprising an effector sequence set forth in SEQ ID NO:15 and an effector complement sequence set forth in SEQ ID NO:16;
   a RNA comprising an effector sequence set forth in SEQ ID NO:17 and an effector complement sequence set forth in SEQ ID NO:18;
   a RNA comprising an effector sequence set forth in SEQ ID NO:19 and an effector complement sequence set forth in SEQ ID NO: 20;
   a RNA comprising an effector sequence set forth in SEQ ID NO:21 and an effector complement sequence set forth in SEQ ID NO:22;
   a RNA comprising an effector sequence set forth in SEQ ID NO:23 and an effector complement sequence set forth in SEQ ID NO:24;
   a RNA comprising an effector sequence set forth in SEQ ID NO:25 and an effector complement sequence set forth in SEQ ID NO:26;
   a RNA comprising an effector sequence set forth in SEQ ID NO:27 and an effector complement sequence set forth in SEQ ID NO:28;
   a RNA comprising an effector sequence set forth in SEQ ID NO:29 and an effector complement sequence set forth in SEQ ID NO:30;
   a RNA comprising an effector sequence set forth in SEQ ID NO:31 and an effector complement sequence set forth in SEQ ID NO:32;
   a RNA comprising an effector sequence set forth in SEQ ID NO:33 and an effector complement sequence set forth in SEQ ID NO:34;
   a RNA comprising an effector sequence set forth in SEQ ID NO:35 and an effector complement sequence set forth in SEQ ID NO:36;
   a RNA comprising an effector sequence set forth in SEQ ID NO:37 and an effector complement sequence set forth in SEQ ID NO:38;
   a RNA comprising an effector sequence set forth in SEQ ID NO:39 and an effector complement sequence set forth in SEQ ID NO:40;
   a RNA comprising an effector sequence set forth in SEQ ID NO:41 and an effector complement sequence set forth in SEQ ID NO:42;
   a RNA comprising an effector sequence set forth in SEQ ID NO:43 and an effector complement sequence set forth in SEQ ID NO:44;
   a RNA comprising an effector sequence set forth in SEQ ID NO:45 and an effector complement sequence set forth in SEQ ID NO:46;

a RNA comprising an effector sequence set forth in SEQ ID NO:47 and an effector complement sequence set forth in SEQ ID NO:48;
a RNA comprising an effector sequence set forth in SEQ ID NO:49 and an effector complement sequence set forth in SEQ ID NO:50; and
a RNA comprising an effector sequence set forth in SEQ ID NO:51 and an effector complement sequence set forth in SEQ ID NO:52; and
(b) at least one RNA selected from:
(i) a RNA selected from the group described at (a); or
(ii) a RNA comprising an effector sequence of at least 17 nucleotides in length and a effector complement sequence, wherein the effector sequence is substantially complementary to a RNA sequence set forth in any one of SEQ ID NOs: 54, 56, 58, 60, 62 and 64; wherein the RNA at (a) and the RNA at (b) comprise different effector sequences.

For example, the effector sequence which is substantially complementary to a RNA sequence set forth in any one of SEQ ID NOs: 54, 56, 58, 60, 62 and 64 will be less than 30 nucleotides in length. For example, a suitable effector sequence may be in the range of 17-29 nucleotides in length.

A plurality of RNAs in accordance with the present disclosure may comprise up to 10 RNAs, such as two RNAs or three RNAs or four RNAs or five RNAs or six RNAs or seven RNAs or eight RNAs or nine RNAs or ten RNAs. In one example, the plurality of RNAs comprises two of the RNAs described herein. In another example, the plurality of RNAs comprises three of the RNAs described herein. In one example, the plurality of RNAs comprises four of the RNAs described herein. In one example, the plurality of RNAs comprises five of the RNAs described herein. In one example, the plurality of RNAs comprises six of the RNAs described herein. In one example, the plurality of RNAs comprises seven of the RNAs described herein. In one example, the plurality of RNAs comprises eight of the RNAs described herein. In one example, the plurality of RNAs comprises nine of the RNAs described herein. In one example, the plurality of RNAs comprises ten of the RNAs described herein.

In one example, the plurality of RNAs described herein are provided in a single composition.

In another example, the plurality of RNAs described herein are provided as multiple compositions. For example, each of the RNAs of the plurality may be provided separately. Alternatively, at least one RNA of the plurality may be provided separately and two or more of the plurality provided together in a composition.

As described herein, a RNA comprising an effector sequence which is substantially complementary to a RNA sequence set forth in any one of SEQ ID NOs: 54, 56, 58, 60, 62 and 64, may be selected from the group consisting of:
a RNA comprising an effector sequence set forth in SEQ ID NO:53 and an effector complement sequence set forth in SEQ ID NO:54;
a RNA comprising an effector sequence set forth in SEQ ID NO:55 and an effector complement sequence set forth in SEQ ID NO:56;
a RNA comprising an effector sequence set forth in SEQ ID NO:57 and an effector complement sequence set forth in SEQ ID NO:58;
a RNA comprising an effector sequence set forth in SEQ ID NO:59 and an effector complement sequence set forth in SEQ ID NO:60;
a RNA comprising an effector sequence set forth in SEQ ID NO:61 and an effector complement sequence set forth in SEQ ID NO:62; and
a RNA comprising an effector sequence set forth in SEQ ID NO:63 and an effector complement sequence set forth in SEQ ID NO:64.

At least one or each of the RNAs in the plurality of RNAs described herein may be present in the form of a shRNA. For example, the present disclosure may provide a plurality of shRNAs. Thus, one or more of the RNAs in the plurality of RNAs may comprise a loop sequence positioned between the corresponding effector sequence and effector complement sequence. Suitable loop sequences may be selected from those known in the art. Alternatively, suitable stem loops may be developed de novo.

In one example, a plurality of RNAs in accordance with the present disclosure may comprise:
(a) at least one RNA which is a shRNA comprising a sequence set forth in any one of SEQ ID NOs: 65-98; and
(b) at least one RNA which is selected from:
(i) a RNA which is a shRNA comprising a sequence set forth in any one of SEQ ID NOs: 65-98; or
(ii) a shRNA comprising a sequence set forth in any one of SEQ ID NOs: 99-104; and wherein the shRNA at (a) and the shRNA at (b) are different.

The present disclosure also provides a nucleic acid comprising a sequence which encodes one or more RNAs as described herein. In one example, the nucleic acid comprises a DNA sequence. In one example, the nucleic acid is DNA.

The present disclosure also provides a plurality nucleic acids comprising:
(a) a first nucleic acid comprising a sequence which encodes a RNA as described herein; and
(b) a second nucleic acid comprising a sequence which encodes a RNA selected from:
(i) a RNA as described herein; or
(ii) a RNA comprising an effector sequence of at least 17 nucleotides in length and a effector complement sequence, wherein the effector sequence is substantially complementary to a RNA sequence set forth in any one of SEQ ID NOs: 54, 56, 58, 60, 62 and 64; and
wherein the RNAs encoded by the first and second nucleic acids comprise different effector sequences. For example, the RNA encoded by the second nucleic acid comprises an effector sequence which is less than 30 nucleotides in length. For example, a suitable effector sequence may be in the range of 17-29 nucleotides in length.

In one example, the first and second nucleic acids form separate parts of the same polynucleotide (i.e., series of covalently linked nucleotide residues). In another example, the first and second nucleic acids form parts of different polynucleotides.

As described herein, a RNA comprising an effector sequence which is substantially complementary to a RNA sequence set forth in any one of SEQ ID NOs: 54, 56, 58, 60, 62 and 64 may be selected from the group consisting of:
a RNA comprising an effector sequence set forth in SEQ ID NO:53 and an effector complement sequence set forth in SEQ ID NO:54;
a RNA comprising an effector sequence set forth in SEQ ID NO:55 and an effector complement sequence set forth in SEQ ID NO:56;
a RNA comprising an effector sequence set forth in SEQ ID NO:57 and an effector complement sequence set forth in SEQ ID NO:58;

a RNA comprising an effector sequence set forth in SEQ ID NO:59 and an effector complement sequence set forth in SEQ ID NO:60;

a RNA comprising an effector sequence set forth in SEQ ID NO:61 and an effector complement sequence set forth in SEQ ID NO:62; and a RNA comprising an effector sequence set forth in SEQ ID NO:63 and an effector complement sequence set forth in SEQ ID NO:64.

In one example, one or more of the nucleic acids encodes a shRNA. For example, each of the nucleic acids encodes a shRNA. In one example, the or each nucleic acid also encodes a loop sequence positioned between the effector sequence and the effector complement sequence. Suitable loop sequences will be apparent to the skilled person and/or described herein.

In one example, the plurality of nucleic acids comprise:
(a) a first nucleic acid comprising a sequence which encodes a shRNA comprising a sequence set forth in any one of SEQ ID NOs: 65-98; and
(b) a second nucleic acid comprising a sequence which encodes a shRNA selected from:
  (i) a shRNA comprising a sequence set forth in any one of SEQ ID NOs: 65-98; or
  (ii) a shRNA comprising a sequence set forth in any one of SEQ ID NOs: 99-104; and
wherein the shRNAs encoded by the first and second nucleic acids are different.

The or each nucleic acid in accordance with the present disclosure may comprise, or be in operable linkage with, one or more transcriptional terminator sequences. For example, the or each nucleic acid may comprise a transcriptional terminator sequence at the 3' terminus of the sequence encoding the RNA. Such sequences will be known to a person of skill in the art, but may include 'TTTTT' or 'TTTTTT'.

Alternatively, or in addition, the or each nucleic acid in accordance with the present disclosure may comprise, or be in operable linkage with, transcription initiator sequence. For example, the or each nucleic acid may comprise a transcription initiator sequence at the 5' terminus of the sequence encoding the RNA. Such sequences will be known to a person of skill in the art, but may include 'G'.

Alternatively, or in addition, the or each nucleic acid in accordance with the present disclosure may comprise one or more restriction sites e.g., to facilitate cloning of the nucleic acid(s) into cloning or expression vectors. For example, the nucleic acids described herein may include a restriction site upstream and/or downstream of the sequence encoding a RNA of the disclosure. Suitable restriction enzyme recognition sequences will be known to a person of skill in the art. However, in one example, the nucleic acid(s) of the disclosure may include a BamH1 restriction site (GGATCC) at the 5' terminus i.e., upstream of the sequence encoding the RNA, and a EcoR1 restriction site (GAATTC) at the 3' terminus i.e., downstream of the sequence encoding the RNA.

A nucleic acid in accordance with the present disclosure may also be provided in the form of, or be comprised in, a DNA-directed RNA interference (ddRNAi) construct which is capable of expressing one or more RNAs of the present disclosure which is/are encoded by the nucleic acid. In this regard, one or more ddRNAi constructs comprising a nucleic acid of the disclosure is also provided.

In another example, a plurality of ddRNAi constructs, each encoding an shRNA described herein is provided, wherein:

(a) at least one of the plurality of ddRNAi constructs comprises a first nucleic acid of the plurality of nucleic acids as described herein; and
(b) at least one of the plurality of ddRNAi constructs comprises a second nucleic acid of the plurality of nucleic acids described herein; and
wherein the first and second nucleic acids are different to one another.

In yet another example, a ddRNAi construct of the disclosure encodes at least two shRNAs, wherein the ddRNAi construct comprises:
(a) a nucleic acid encoding a first shRNA comprising a sequence set forth in any one of SEQ ID NOs: 65-98; and
(b) a nucleic acid comprising a DNA sequence encoding a second shRNA, wherein the second shRNA comprises an effector sequence of at least 17 nucleotides in length and a effector complement sequence, wherein the effector sequence is substantially complementary to a region of a RNA transcript encoded by the genome of the Hepatitis B virus; and
wherein the first and second shRNAs are different.

For example, the second shRNA comprises an effector sequence which is less than 30 nucleotides in length. For example, a suitable effector sequence may be in the range of 17-29 nucleotides in length.

In one example, the ddRNAi construct encoding at least two shRNAs comprises the plurality of nucleic acids described herein.

In yet another example, a ddRNAi construct encoding at least two shRNAs comprises a nucleic acid comprising a DNA sequence encoding a third shRNA, wherein the third shRNA comprises an effector sequence of at least 17 nucleotides in length and a effector complement sequence, wherein the effector sequence is substantially complementary to a region of a RNA transcript encoded by the genome of the Hepatitis B virus, and
wherein the third shRNA is different to the first and second shRNAs.

For example, the third shRNA comprises an effector sequence which is less than 30 nucleotides in length. For example, a suitable effector sequence may be in the range of 17-29 nucleotides in length.

In an exemplified form of the disclosure, the nucleic acid encoding the third shRNA is a nucleic acid selected from any one of the nucleic acids in the plurality of nucleic acids described herein.

One example of a ddRNAi construct of the disclosure comprises:
(a) a nucleic acid encoding a shRNA comprising or consisting of the sequence set forth in SEQ ID NO:92:
(b) a nucleic acid selected from any one of the nucleic acids in the plurality of nucleic acids described herein; and
(c) a nucleic acid encoding a shRNA comprising or consisting of the sequence set forth in SEQ ID NO:78;
wherein the nucleic acid at (b) encodes a shRNA which is different to the shRNA encoded by the nucleic acid at (a) and (c).

In another example, the ddRNAi construct of the disclosure comprises:
(a) a first nucleic acid encoding a shRNA comprising or consisting of the sequence set forth in SEQ ID NO:92:
(b) a second nucleic acid encoding a shRNA comprising or consisting of the sequence set forth in SEQ ID NO:101; and
(c) a third nucleic acid encoding a shRNA comprising or consisting of the sequence set forth in SEQ ID NO:78.

In yet another example, the ddRNAi construct of the disclosure comprises:

(a) a first nucleic acid encoding a shRNA comprising or consisting of the sequence set forth in SEQ ID NO:92:
(b) a second nucleic acid encoding a shRNA comprising or consisting of the sequence set forth in SEQ ID NO:79; and
(c) a third nucleic acid encoding a shRNA comprising or consisting of the sequence set forth in SEQ ID NO:78.

An exemplary ddRNAi construct of the disclosure comprises, in a 5' to 3' direction:
(a) a first nucleic acid encoding a shRNA comprising or consisting of the sequence set forth in SEQ ID NO:78:
(b) a second nucleic acid encoding a shRNA comprising or consisting of the sequence set forth in SEQ ID NO:101; and
(c) a third nucleic acid encoding a shRNA comprising or consisting of the sequence set forth in SEQ ID NO:92.

A further exemplary the ddRNAi construct of the disclosure comprises, in a 5' to 3' direction:
(a) a first nucleic acid encoding a shRNA comprising or consisting of the sequence set forth in SEQ ID NO:78:
(b) a second nucleic acid encoding a shRNA comprising or consisting of the sequence set forth in SEQ ID NO:79; and
(c) a third nucleic acid encoding a shRNA comprising or consisting of the sequence set forth in SEQ ID NO:92.

In one example, a ddRNAi construct as described herein comprises a single promoter which is operably-linked to the or each nucleic acid encoding an shRNA of the disclosure.

In another example, each nucleic acid encoding an shRNA of the disclosure is operably-linked to a separate promoter. For example, the promoter(s) is(are) positioned upstream of the respective nucleic acid(s) encoding the shRNA(s). In a ddRNAi construct comprising multiple promoters, the promoters may be the same or different. Exemplary promoters are RNA pol III promoters, such as for example, the U6 and H1 promoters.

In one example of a ddRNAi construct comprising nucleic acids encoding three shRNAs each of which are linked to a separate promoter, the promoter linked to two of the nucleic acids is the same and the promoter linked to the third nucleic acid is different. For example, in the context of a ddRNAi construct described above comprising three nucleic acids encoding shRNAs, the first and third nucleic acids are linked to separate promoters that are the same and the second nucleic acid is linked to a different promoter.

In one example of a ddRNAi construct comprising nucleic acids encoding three shRNAs each of which are linked to a separate promoter, all of the promoters are the same.

An exemplary ddRNAi construct of the disclosure comprises, in a 5' to 3' direction:
(a) a first nucleic acid encoding a shRNA comprising or consisting of the sequence set forth in SEQ ID NO:78 operably-linked to a U6 promoter:
(b) a second nucleic acid encoding a shRNA comprising or consisting of the sequence set forth in SEQ ID NO:101 operably-linked to a U6 promoter; and
(c) a third nucleic acid encoding a shRNA comprising or consisting of the sequence set forth in SEQ ID NO:92 operably-linked to a U6 promoter.

A further exemplary the ddRNAi construct of the disclosure comprises, in a 5' to 3' direction:
(a) a first nucleic acid encoding a shRNA comprising or consisting of the sequence set forth in SEQ ID NO:78 operably-linked to a U6 promoter:
(b) a second nucleic acid encoding a shRNA comprising or consisting of the sequence set forth in SEQ ID NO:79 operably-linked to a U6 promoter; and
(c) a third nucleic acid encoding a shRNA comprising or consisting of the sequence set forth in SEQ ID NO:92 operably-linked to a U6 promoter.

The present disclosure also provides an expression vector, comprising a ddRNAi constructs of the disclosure.

The present disclosure also provides plurality of expression vectors each of which comprises a ddRNAi construct of the disclosure. For example, one or more of the plurality of expression vectors comprises a plurality of ddRNAi constructs as disclosed herein. In another example, each of the plurality of expression vectors comprises a plurality of ddRNAi constructs as disclosed herein. In a further example, each of the plurality of expression vectors comprises a single ddRNAi construct as described herein. In any of the foregoing ways in this paragraph, the plurality of expression vectors may collectively express a plurality of shRNAs in accordance with the present disclosure.

In one example, the or each expression vector is a plasmid or a minicircle.

In one example, the plasmid or minicircle or expression vector or ddRNAi construct is complexed with a cationic DNA binding polymer.

In another example, the or each expression vector is a viral vector. For example, the viral vector is selected from the group consisting of an adeno-associated viral (AAV) vector, a retroviral vector, an adenoviral vector (AdV) and a lentiviral (LV) vector.

The present disclosure also provides a composition comprising a ddRNAi construct and/or expression vector as described herein. In one example, the composition may also comprise one or more pharmaceutically acceptable carriers and/or diluents.

The present disclosure also provides a method of treating HBV infection in a subject, the method comprising administering a therapeutically effective amount of a RNA, plurality of RNAs, nucleic acid, plurality of nucleic acids, ddRNAi construct, plurality of ddRNAi constructs, expression vector, plurality of expression vectors and/or composition described herein to the subject.

The present disclosure also provides a method of reducing HBV viral load in a subject infected with HBV, the method comprising administering a therapeutically effective amount of a RNA, plurality of RNAs, nucleic acid, plurality of nucleic acids, ddRNAi construct, plurality of ddRNAi constructs, expression vector, plurality of expression vectors and/or composition described herein to the subject.

The present disclosure also provides a method of reducing severity of one or more symptoms associated with HBV infection in a subject suffering therefrom, the method comprising administering to the subject a therapeutically effective amount of a RNA, plurality of RNAs, nucleic acid, plurality of nucleic acids, ddRNAi construct, plurality of ddRNAi constructs, expression vector, plurality of expression vectors and/or composition described herein to the subject.

The present disclosure also provides a method of reducing the infectivity of HBV in a subject infected therewith, the method comprising administering to the subject a therapeutically effective amount of a RNA, plurality of RNAs, nucleic acid, plurality of nucleic acids, ddRNAi construct, plurality of ddRNAi constructs, expression vector, plurality of expression vectors and/or composition described herein to the subject.

The present disclosure also provides a method for reducing the risk of a subject suffering from a HBV infection developing chronic hepatic insufficiency, cirrhosis, and/or hepatocellular carcinoma, the method comprising administering to the subject a therapeutically effective amount of a RNA, plurality of RNAs, nucleic acid, plurality of nucleic acids, ddRNAi construct, plurality of ddRNAi constructs, expression vector, plurality of expression vectors and/or composition described herein to the subject.

In accordance with any method described herein, in one example, the subject is suffering from acute HBV infection. Alternatively, in one example, the subject is suffering from chronic HBV infection.

In one example, the methods described herein comprise inhibiting expression of one or more transcripts encoded by the HBV genome in the subject.

In one example, the subject to which the RNA, plurality of RNAs, nucleic acid, plurality of nucleic acids, ddRNAi construct, plurality of ddRNAi constructs, expression vector, plurality of expression vectors and/or composition of the disclosure is/are administered has already received treatment with another therapeutic agent for treating HBV infection. For example, the subject and/or the HBV is refractory or resistant to treatment with the other agent known for treating HBV infection.

In another example, the RNA, plurality of RNAs, nucleic acid, plurality of nucleic acids, ddRNAi construct, plurality of ddRNAi constructs, expression vector, plurality of expression vectors and/or composition of the disclosure is administered in combination with another therapeutic agent known for treating HBV infection i.e., as an adjunctive therapy.

In one example, a composition of the present disclosure is provided in a kit. For example, a composition of the present disclosure is packaged together with one or more other therapeutic agents known for treating HBV infections. Such other therapeutic agents will be known to a person of skill in the art. In another example, the composition is packaged with instruction for use in a method of the disclosure.

The present disclosure also provides use of a RNA, plurality of RNAs, nucleic acid, plurality of nucleic acids, ddRNAi construct, plurality of ddRNAi constructs, expression vector, plurality of expression vectors and/or composition described herein in the preparation of a medicament, e.g., for treating HBV infection in a subject and/or in a method disclosed herein. In one example, the subject is suffering from acute HBV infection. In an alternative example, the subject is suffering from chronic HBV infection.

The present disclosure also provides a RNA, plurality of RNAs, nucleic acid, plurality of nucleic acids, ddRNAi construct, plurality of ddRNAi constructs, expression vector, plurality of expression vectors and/or composition described herein for use in therapy. For example, the RNA, plurality of RNAs, nucleic acid, plurality of nucleic acids, ddRNAi construct, plurality of ddRNAi constructs, expression vector, plurality of expression vectors and/or composition may be for use in treating HBV infection in a subject and/or in a method disclosed herein. The subject may be suffering from acute HBV infection. In an alternative example, the subject may be suffering from chronic HBV infection.

Treatment of HBV in accordance with any example described herein, may comprise one or more of reducing HBV viral load in the subject, reducing severity of symptoms associated with HBV infection and/or reducing the infectivity of HBV in a subject. In one example, the medicament will reduce HBV gene transcription products in the subject to which the medicament is administered.

KEY TO THE SEQUENCE LISTING

Figure 1:
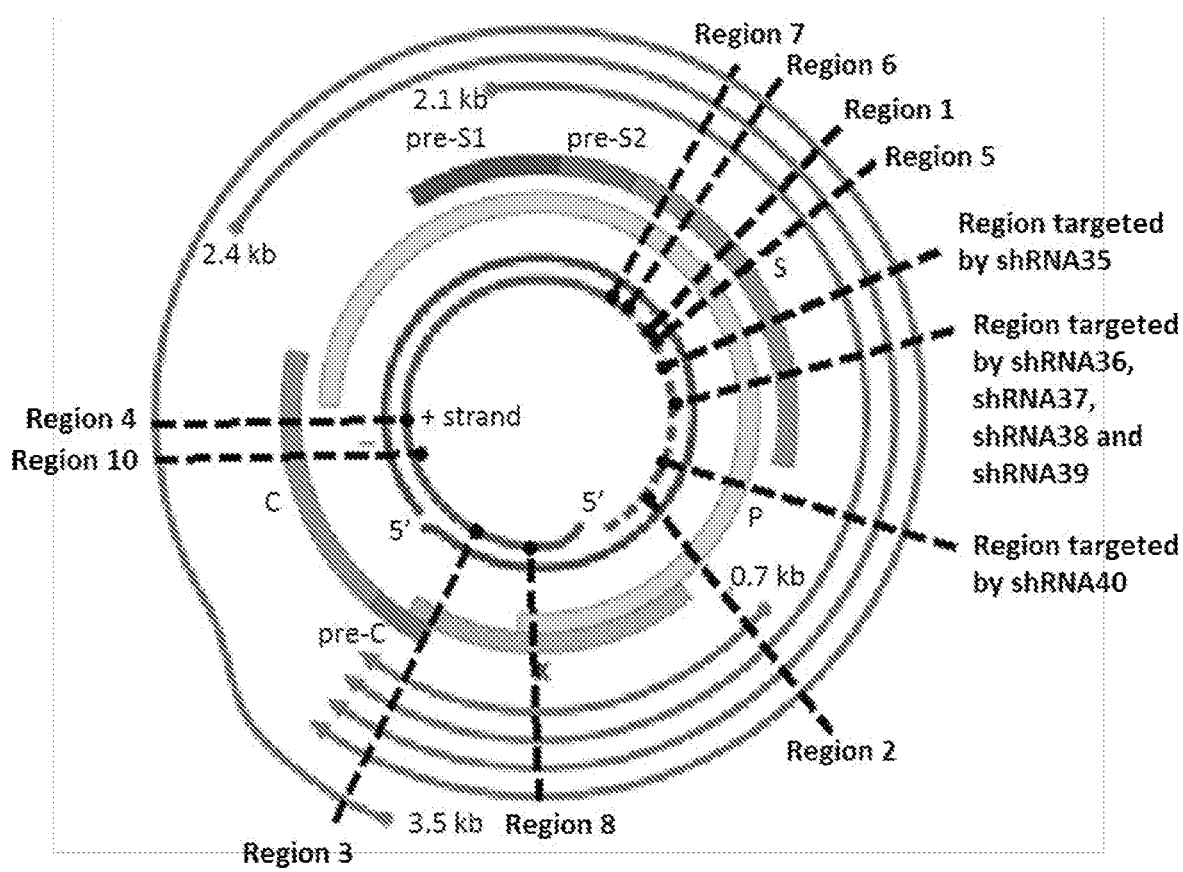
FIG. 1 shows a map of the HBV genome and the position of siRNA target regions. The inner circle represents the HBV genome, boxes around these represent the indicated protein coding sequences and the outer curved arrows represent HBV mRNAs. The positions of highly conserved regions listed in Table 1 (Region 1 to Region 10) and regions targeted by additional shRNAs in Table 4 (shRNAs 3, 8 and 11) are indicated by broken lines.

SEQ ID NO: 1: DNA sequence for target region within HBV genome designated Region 1.
SEQ ID NO: 2: DNA sequence for target region within HBV genome designated Region 2.
SEQ ID NO: 3: DNA sequence for target region within HBV genome designated Region 3.
SEQ ID NO: 4: DNA sequence for target region within HBV genome designated Region 4.
SEQ ID NO: 5: DNA sequence for target region within HBV genome designated Region 5.
SEQ ID NO: 6: DNA sequence for target region within HBV genome designated Region 6.
SEQ ID NO: 7: DNA sequence for target region within HBV genome designated Region 7.
SEQ ID NO: 8: DNA sequence for target region within HBV genome designated Region 8.
SEQ ID NO: 9: DNA sequence for target region within HBV genome designated Region 9.
SEQ ID NO: 10: DNA sequence for target region within HBV genome designated Region 10.
SEQ ID NO: 11: RNA effector sequence for shRNAs designated shRNA1 and shRNA4.
SEQ ID NO: 12: RNA effector complement sequence for shRNAs designated shRNA1 and shRNA4.
SEQ ID NO: 13: RNA effector sequence for shRNA designated shRNA2.
SEQ ID NO: 14: RNA effector complement sequence for shRNA designated shRNA2.
SEQ ID NO: 15: RNA effector sequence for shRNA designated shRNA3.
SEQ ID NO: 16: RNA effector complement sequence for shRNA designated shRNA3.
SEQ ID NO: 17: RNA effector sequence for shRNAs designated shRNA5 and shRNA6.
SEQ ID NO: 18: RNA effector complement sequence for shRNAs designated shRNA5 and shRNA6.

SEQ ID NO: 19: RNA effector sequence for shRNAs designated shRNA7 and shRNA8.
SEQ ID NO: 20: RNA effector complement sequence for shRNAs designated shRNA7 and shRNA8.
SEQ ID NO: 21: RNA effector sequence for shRNAs designated shRNA9 and shRNA10.
SEQ ID NO: 22: RNA effector complement sequence for shRNAs designated shRNA9 and shRNA10.
SEQ ID NO: 23: RNA effector sequence for shRNAs designated shRNA11 and shRNA12.
SEQ ID NO: 24: RNA effector complement sequence for shRNAs designated shRNA11 and shRNA12.
SEQ ID NO: 25: RNA effector sequence for shRNA designated shRNA13.
SEQ ID NO: 26: RNA effector complement sequence for shRNA designated shRNA13
SEQ ID NO: 27: RNA effector sequence for shRNA designated shRNA14.
SEQ ID NO: 28: RNA effector complement sequence for shRNA designated shRNA14
SEQ ID NO: 29: RNA effector sequence for shRNAs designated shRNA15 and shRNA18.
SEQ ID NO: 30: RNA effector complement sequence for shRNAs designated shRNA15 and shRNA18.
SEQ ID NO: 31: RNA effector sequence for shRNA designated shRNA16.
SEQ ID NO: 32: RNA effector complement sequence for shRNA designated shRNA16.
SEQ ID NO: 33: RNA effector sequence for shRNA designated shRNA17.
SEQ ID NO: 34: RNA effector complement sequence for shRNA designated shRNA17.
SEQ ID NO: 35: RNA effector sequence for shRNAs designated shRNA19 and shRNA20.
SEQ ID NO: 36: RNA effector complement sequence for shRNAs designated shRNA19 and shRNA20.
SEQ ID NO: 37: RNA effector sequence for shRNA designated shRNA21.
SEQ ID NO: 38: RNA effector complement sequence for shRNA designated shRNA21.
SEQ ID NO: 39: RNA effector sequence for shRNA designated shRNA22.
SEQ ID NO: 40: RNA effector complement sequence for shRNA designated shRNA22.
SEQ ID NO: 41: RNA effector sequence for shRNAs designated shRNA23 and shRNA24.
SEQ ID NO: 42: RNA effector complement sequence for shRNAs designated shRNA23 and shRNA24.
SEQ ID NO: 43: RNA effector sequence for shRNAs designated shRNA25 and shRNA26.
SEQ ID NO: 44: RNA effector complement sequence for shRNAs designated shRNA25 and shRNA26.
SEQ ID NO: 45: RNA effector sequence for shRNAs designated shRNA27 and shRNA30.
SEQ ID NO: 46: RNA effector complement sequence for shRNAs designated shRNA27 and shRNA30.
SEQ ID NO: 47: RNA effector sequence for shRNAs designated shRNA28 and shRNA31.
SEQ ID NO: 48: RNA effector complement sequence for shRNAs designated shRNA28 and shRNA31.
SEQ ID NO: 49: RNA effector sequence for shRNAs designated shRNA29 and shRNA32.
SEQ ID NO: 50: RNA effector complement sequence for shRNAs designated shRNA29 and shRNA32.
SEQ ID NO: 51: RNA effector sequence for shRNAs designated shRNA33 and shRNA34.
SEQ ID NO: 52: RNA effector complement sequence for shRNAs designated shRNA33 and shRNA34.
SEQ ID NO: 53: RNA effector sequence for shRNA designated shRNA35.
SEQ ID NO: 54: RNA effector complement sequence for shRNA designated shRNA35.
SEQ ID NO: 55: RNA effector sequence for shRNA designated shRNA 36.
SEQ ID NO: 56: RNA effector complement sequence for shRNA designated shRNA35.
SEQ ID NO: 57: RNA effector sequence for shRNA designated shRNA37.
SEQ ID NO: 58: RNA effector complement sequence for shRNA designated shRNA37.
SEQ ID NO: 59: RNA effector sequence for shRNA designated shRNA38.
SEQ ID NO: 60: RNA effector complement sequence for shRNA designated shRNA38.
SEQ ID NO: 61: RNA effector sequence for shRNA designated shRNA39.
SEQ ID NO: 62: RNA effector complement sequence for shRNA designated shRNA39.
SEQ ID NO: 63: RNA effector sequence for shRNA designated shRNA40.
SEQ ID NO: 64: RNA effector complement sequence for shRNA designated shRNA40.
SEQ ID NO: 65: RNA sequence for shRNA designated shRNA1.
SEQ ID NO: 66: RNA sequence for shRNA designated shRNA2
SEQ ID NO: 67: RNA sequence for shRNA designated shRNA3
SEQ ID NO: 68: RNA sequence for shRNA designated shRNA4
SEQ ID NO: 69: RNA sequence for shRNA designated shRNA5
SEQ ID NO: 70: RNA sequence for shRNA designated shRNA6
SEQ ID NO: 71: RNA sequence for shRNA designated shRNA7
SEQ ID NO: 72: RNA sequence for shRNA designated shRNA8
SEQ ID NO: 73: RNA sequence for shRNA designated shRNA9
SEQ ID NO: 74: RNA sequence for shRNA designated shRNA10
SEQ ID NO: 75: RNA sequence for shRNA designated shRNA11
SEQ ID NO: 76: RNA sequence for shRNA designated shRNA12
SEQ ID NO: 77: RNA sequence for shRNA designated shRNA13
SEQ ID NO: 78: RNA sequence for shRNA designated shRNA14
SEQ ID NO: 79: RNA sequence for shRNA designated shRNA15
SEQ ID NO: 80: RNA sequence for shRNA designated shRNA16
SEQ ID NO: 81: RNA sequence for shRNA designated shRNA17
SEQ ID NO: 82: RNA sequence for shRNA designated shRNA18
SEQ ID NO: 83: RNA sequence for shRNA designated shRNA19
SEQ ID NO: 84: RNA sequence for shRNA designated shRNA20

SEQ ID NO: 85: RNA sequence for shRNA designated shRNA21
SEQ ID NO: 86: RNA sequence for shRNA designated shRNA22
SEQ ID NO: 87: RNA sequence for shRNA designated shRNA23
SEQ ID NO: 88: RNA sequence for shRNA designated shRNA24
SEQ ID NO: 89: RNA sequence for shRNA designated shRNA25
SEQ ID NO: 90: RNA sequence for shRNA designated shRNA26
SEQ ID NO: 91: RNA sequence for shRNA designated shRNA27
SEQ ID NO: 92: RNA sequence for shRNA designated shRNA28
SEQ ID NO: 93: RNA sequence for shRNA designated shRNA29
SEQ ID NO: 94: RNA sequence for shRNA designated shRNA30
SEQ ID NO: 95: RNA sequence for shRNA designated shRNA31
SEQ ID NO: 96: RNA sequence for shRNA designated shRNA32
SEQ ID NO: 97: RNA sequence for shRNA designated shRNA33
SEQ ID NO: 98: RNA sequence for shRNA designated shRNA34
SEQ ID NO: 99: RNA sequence for shRNA designated shRNA35
SEQ ID NO: 100: RNA sequence for shRNA designated shRNA36
SEQ ID NO: 101: RNA sequence for shRNA designated shRNA37
SEQ ID NO: 102: RNA sequence for shRNA designated shRNA38
SEQ ID NO: 103: RNA sequence for shRNA designated shRNA39
SEQ ID NO: 104: RNA sequence for shRNA designated shRNA40
SEQ ID NO: 105: DNA sequence for pBL183_HBV_Triple_V2
SEQ ID NO: 106: DNA sequence for pBL183_HBV_Triple_V1

DETAILED DESCRIPTION

General

Throughout this specification, unless specifically stated otherwise or the context requires otherwise, reference to a single step, feature, composition of matter, group of steps or group of features or compositions of matter shall be taken to encompass one and a plurality (i.e. one or more) of those steps, features, compositions of matter, groups of steps or groups of features or compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant DNA, recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

The term "and/or", e.g., "X and/or Y" shall be understood to mean either "X and Y" or "X or Y" and shall be taken to provide explicit support for both meanings or for either meaning.

Selected Definitions

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA. In one example, all of the residues in the RNA are ribonucleotides.

As used herein, the term "RNAi reagent" refers to a RNA that is capable of eliciting "RNA interference" or "RNAi".

The term "RNA interference" or "RNAi" refers generally to RNA-dependent silencing of gene expression initiated by double stranded RNA (dsRNA) molecules in a cell's cytoplasm. The dsRNA molecule reduces or inhibits transcription products of a target nucleic acid sequence, thereby silencing the gene.

As used herein, the term "double stranded RNA" or "dsRNA" refers to a RNA molecule having a duplex structure and comprising an effector sequence and an effector complement sequence which are of similar length to one another. The effector sequence and the effector complement sequence can be in a single RNA strand or in separate RNA strands. The "effector sequence" (often referred to as a "guide strand") is substantially complementary to a target sequence, which in the present case, is a region of a RNA transcription product of the HBV genome. The "effector sequence" can also be referred to as the "antisense sequence". The "effector complement sequence" will be of sufficient complementarity to the effector sequence such that it can anneal to the effector sequence to form a duplex. In this regard, the effector complement sequence will be substantially homologous to a region of target sequence. As will be apparent to the skilled person, the term "effector complement sequence" can also be referred to as the "complement of the effector sequence" or the sense sequence.

As used herein, the term "duplex" refers to regions in two complementary or substantially complementary nucleic acids (e.g., RNAs), or in two complementary or substantially complementary regions of a single-stranded nucleic acid (e.g., RNA), that form base pairs with one another, either by Watson-Crick base pairing or any other manner that allows for a stabilized duplex between the nucleotide sequences that are complementary or substantially complementary. It will be understood by the skilled person that within a duplex region, 100% complementarity is not required; substantial complementarity is allowable. Substantial complementarity includes may include 79% or greater complementarity. For example, a single mismatch in a duplex region consisting of 19 base pairs (i.e., 18 base pairs and one mismatch) results in 94.7% complementarity, rendering the duplex region substantially complementary. In another example, two mismatches in a duplex region consisting of 19 base pairs (i.e., 17 base pairs and two mismatches) results in 89.5% complementarity, rendering the duplex region substantially complementary. In yet another example, three mismatches in a duplex region consisting of 19 base pairs (i.e., 16 base pairs and three mismatches) results in 84.2% complementarity, rendering the duplex region substantially complementary, and so on.

The dsRNA may be provided as a hairpin or stem loop structure, with a duplex region comprised of an effector sequence and effector complement sequence linked by at least 2 nucleotide sequence which is termed a stem loop. When a dsRNA is provided as a hairpin or stem loop structure it can be referred to as a "hairpin RNA" or "short hairpin RNAi agent" or "shRNA".

As used herein, the term "complementary" with regard to a sequence refers to a complement of the sequence by Watson-Crick base pairing, whereby guanine (G) pairs with cytosine (C), and adenine (A) pairs with either uracil (U) or thymine (T). A sequence may be complementary to the entire length of another sequence, or it may be complementary to a specified portion or length of another sequence. One of skill in the art will recognize that U may be present in RNA, and that T may be present in DNA. Therefore, an A within either of a RNA or DNA sequence may pair with a U in a RNA sequence or T in a DNA sequence.

As used herein, the term "substantially complementary" is used to indicate a sufficient degree of complementarity or precise pairing such that stable and specific binding occurs between nucleic acid sequences e.g., between the effector sequence and the effector complement sequence or between the effector sequence and the target sequence. It is understood that the sequence of a nucleic acid need not be 100% complementary to that of its target or complement. The term encompasses a sequence complementary to another sequence with the exception of an overhang. In some cases, the sequence is complementary to the other sequence with the exception of 1-2 mismatches. In some cases, the sequences are complementary except for 1 mismatch. In some cases, the sequences are complementary except for 2 mismatches. In other cases, the sequences are complementary except for 3 mismatches. In yet other cases, the sequences are complementary except for 4 mismatches.

The term "encoded", as used in the context of a RNA of the disclosure, shall be understood to mean a RNA is capable of being transcribed from a DNA template. Accordingly, a nucleic acid that encodes a RNA of the disclosure will comprise a DNA sequence which serves as a template for transcription of the respective RNA.

The term "DNA-directed RNAi construct" or "ddRNAi construct" refers to a nucleic acid comprising a DNA sequence which, when transcribed produces a RNA molecule which elicits RNAi. The ddRNAi construct may comprise a nucleic acid which is transcribed as a single RNA that is capable of self-annealing into a hairpin structure with a duplex region linked by a stem loop of at least 2 nucleotides i.e., shRNA, or as a single RNA with multiple shRNA or as multiple RNA transcripts each capable of folding as a single shRNA respectively. The ddRNAi construct may be within an expression vector i.e., "ddRNAi expression construct", e.g., operably linked to a promoter. In one example, the ddRNAi construct comprises only DNA.

As used herein, the term "operably-linked" or "operable linkage" (or similar) means that a coding nucleic acid sequence is linked to, or in association with, a regulatory sequence, e.g., a promoter, in a manner which facilitates expression of the coding sequence. Regulatory sequences include promoters, enhancers, and other expression control elements that are art-recognized and are selected to direct expression of the coding sequence.

A "vector" will be understood to mean a vehicle for introducing a nucleic acid into a cell. Vectors include, but are not limited to, plasmids, phagemids, viruses, bacteria, and vehicles derived from viral or bacterial sources. A "plasmid" is a circular, double-stranded DNA molecule. A useful type of vector for use in accordance with the present disclosure is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome. As used herein, the term "expression vector" will be understood to mean a vector capable of expressing a RNA molecule of the disclosure.

As used herein, the terms "treating", "treat" or "treatment" and variations thereof, refer to clinical intervention designed to alter the natural course of the individual or cell being treated during the course of clinical pathology. Desirable effects of treatment include decreasing the rate of disease progression, ameliorating or palliating the disease state, and remission or improved prognosis. It follows that treatment of HBV infection includes reducing HBV viral load in a subject infected with HBV, reducing severity of symptoms associated with HBV infection, and reducing the infectivity of HBV in a subject. An individual is successfully "treated", for example, if one or more of the above treatment outcomes is achieved.

A "therapeutically effective amount" is at least the minimum concentration or amount required to effect a measurable improvement of a particular disease (e.g., a HBV infection). A therapeutically effective amount herein may vary according to factors such as the disease state, age, sex, and weight of the patient, and the ability of the RNA, ddRNAi or expression construct to elicit a desired response in the individual. A therapeutically effective amount is also one in which any toxic or detrimental effects of the RNA, ddRNAi or expression construct are outweighed by the therapeutically beneficial effects.

As used herein, the "subject" or "patient" can be a human or non-human animal infected with HBV. The "non-human animal" may be a primate, livestock (e.g. sheep, horses, cattle, pigs, donkeys), companion animal (e.g. pets such as dogs and cats), laboratory test animal (e.g. mice, rabbits, rats, guinea pigs), performance animal (e.g. racehorses, camels, greyhounds) or captive wild animal. In one example, the subject or patient is a mammal. In one example, the subject or patient is a primate. In one example, the subject or patient is a human.

The terms "reduced expression", "reduction in expression" or similar, refer to the absence or an observable decrease in the level of protein and/or mRNA product from the target gene e.g., the HBV pol gene or other HBV gene. The decrease does not have to be absolute, but may be a partial decrease sufficient for there to a detectable or observable change as a result of the RNAi effected by the RNA of the disclosure. The decrease can be measured by determining a decrease in the level of mRNA and/or protein product from a target nucleic acid relative to a cell lacking the RNA, ddRNAi construct or expression construct, and may be as little as 1%, 5% or 10%, or may be absolute i.e., 100% inhibition. The effects of the decrease may be determined by examination of the outward properties i.e., quantitative and/or qualitative phenotype of the cell or organism, and may also include an assessment of the viral load following administration of a ddRNAi construct of the disclosure.

Agents for RNAi

In one example, the present disclosure provides a RNA, i.e., capable of eliciting RNAi, wherein the RNA comprises an effector sequence of at least 17 nucleotides in length and a effector complement sequence, wherein the effector sequence is substantially complementary to a RNA transcript encoded by a region of the HBV genome set forth in Table 1. For example, the RNA of the disclosure will comprise an effector sequence which is less than 30 nucleotides in length. For example, suitable effector sequences may be in the range of 17-29 nucleotides in length.

In one example, the effector sequence is substantially complementary to a RNA transcript encoded by Region 1 set forth in Table 1. For example, the effector sequence may be substantially complementary to a RNA transcript encoded by Region 1 set forth in Table 1 and contain 4 mismatch bases relative thereto. For example, the effector sequence may be substantially complementary to a RNA transcript encoded by Region 1 set forth in Table 1 and contain 3 mismatch bases relative thereto. For example, the effector sequence may be substantially complementary to a RNA transcript encoded by Region 1 set forth in Table 1 and contain 2 mismatch bases relative thereto. For example, the effector sequence may be substantially complementary to a RNA transcript encoded by Region 1 set forth in Table 1 and contain 1 mismatch base relative thereto. For example, the effector sequence may be 100% complementary to a RNA transcript encoded by Region 1 set forth in Table 1.

In one example, the effector sequence is substantially complementary to a RNA transcript encoded by Region 2 set forth in Table 1. For example, the effector sequence may be substantially complementary to a RNA transcript encoded by Region 2 set forth in Table 1 and contain 4 mismatch bases relative thereto. For example, the effector sequence may be substantially complementary to a RNA transcript encoded by Region 2 set forth in Table 1 and contain 3 mismatch bases relative thereto. For example, the effector sequence may be substantially complementary to a RNA transcript encoded by Region 2 set forth in Table 1 and contain 2 mismatch bases relative thereto. For example, the effector sequence may be substantially complementary to a RNA transcript encoded by Region 2 set forth in Table 1 and contain 1 mismatch base relative thereto. For example, the effector sequence may be 100% complementary to a RNA transcript encoded by Region 2 set forth in Table 1.

In one example, the effector sequence is substantially complementary to a RNA transcript encoded by Region 3 set forth in Table 1. For example, the effector sequence may be substantially complementary to a RNA transcript encoded by Region 3 set forth in Table 1 and contain 4 mismatch bases relative thereto. For example, the effector sequence may be substantially complementary to a RNA transcript encoded by Region 3 set forth in Table 1 and contain 3 mismatch bases relative thereto. For example, the effector sequence may be substantially complementary to a RNA transcript encoded by Region 3 set forth in Table 1 and contain 2 mismatch bases relative thereto. For example, the effector sequence may be substantially complementary to a RNA transcript encoded by Region 3 set forth in Table 1 and contain 1 mismatch base relative thereto. For example, the effector sequence may be 100% complementary to a RNA transcript encoded by Region 3 set forth in Table 1.

In one example, the effector sequence is substantially complementary to a RNA transcript encoded by Region 4 set forth in Table 1. For example, the effector sequence may be substantially complementary to a RNA transcript encoded by Region 4 set forth in Table 1 and contain 4 mismatch bases relative thereto. For example, the effector sequence may be substantially complementary to a RNA transcript encoded by Region 4 set forth in Table 1 and contain 3 mismatch bases relative thereto. For example, the effector sequence may be substantially complementary to a RNA transcript encoded by Region 4 set forth in Table 1 and contain 2 mismatch bases relative thereto. For example, the effector sequence may be substantially complementary to a RNA transcript encoded by Region 4 set forth in Table 1 and contain 1 mismatch base relative thereto. For example, the effector sequence may be 100% complementary to a RNA transcript encoded by Region 4 set forth in Table 1.

In one example, the effector sequence is substantially complementary to a RNA transcript encoded by Region 5 set forth in Table 1. For example, the effector sequence may be substantially complementary to a RNA transcript encoded by Region 5 set forth in Table 1 and contain 4 mismatch bases relative thereto. For example, the effector sequence may be substantially complementary to a RNA transcript encoded by Region 5 set forth in Table 1 and contain 3 mismatch bases relative thereto. For example, the effector sequence may be substantially complementary to a RNA transcript encoded by Region 5 set forth in Table 1 and contain 2 mismatch bases relative thereto. For example, the effector sequence may be substantially complementary to a RNA transcript encoded by Region 5 set forth in Table 1 and contain 1 mismatch base relative thereto. For example, the effector sequence may be 100% complementary to a RNA transcript encoded by Region 5 set forth in Table 1.

In one example, the effector sequence is substantially complementary to a RNA transcript encoded by Region 6 set forth in Table 1. For example, the effector sequence may be substantially complementary to a RNA transcript encoded by Region 6 set forth in Table 1 and contain 4 mismatch bases relative thereto. For example, the effector sequence may be substantially complementary to a RNA transcript encoded by Region 6 set forth in Table 1 and contain 3 mismatch bases relative thereto. For example, the effector sequence may be substantially complementary to a RNA transcript encoded by Region 6 set forth in Table 1 and contain 2 mismatch bases relative thereto. For example, the effector sequence may be substantially complementary to a RNA transcript encoded by Region 6 set forth in Table 1 and contain 1 mismatch base relative thereto. For example, the effector sequence may be 100% complementary to a RNA transcript encoded by Region 6 set forth in Table 1.

In one example, the effector sequence is substantially complementary to a RNA transcript encoded by Region 7 set forth in Table 1. For example, the effector sequence may be substantially complementary to a RNA transcript encoded by Region 7 set forth in Table 1 and contain 4 mismatch bases relative thereto. For example, the effector sequence may be substantially complementary to a RNA transcript encoded by Region 7 set forth in Table 1 and contain 3 mismatch bases relative thereto. For example, the effector sequence may be substantially complementary to a RNA transcript encoded by Region 7 set forth in Table 1 and contain 2 mismatch bases relative thereto. For example, the effector sequence may be substantially complementary to a RNA transcript encoded by Region 7 set forth in Table 1 and contain 1 mismatch base relative thereto. For example, the effector sequence may be 100% complementary to a RNA transcript encoded by Region 7 set forth in Table 1.

In one example, the effector sequence is substantially complementary to a RNA transcript encoded by Region 8 set forth in Table 1. For example, the effector sequence may be substantially complementary to a RNA transcript encoded by Region 8 set forth in Table 1 and contain 4 mismatch bases relative thereto. For example, the effector sequence may be substantially complementary to a RNA transcript encoded by Region 8 set forth in Table 1 and contain 3 mismatch bases relative thereto. For example, the effector sequence may be substantially complementary to a RNA transcript encoded by Region 8 set forth in Table 1 and contain 2 mismatch bases relative thereto. For example, the effector sequence may be substantially complementary to a RNA transcript encoded by Region 8 set forth in Table 1 and contain 1 mismatch base relative thereto. For example, the effector sequence may be 100% complementary to a RNA transcript encoded by Region 8 set forth in Table 1.

In one example, the effector sequence is substantially complementary to a RNA transcript encoded by Region 9 set forth in Table 1. For example, the effector sequence may be substantially complementary to a RNA transcript encoded by Region 9 set forth in Table 1 and contain 4 mismatch bases relative thereto. For example, the effector sequence may be substantially complementary to a RNA transcript encoded by Region 9 set forth in Table 1 and contain 3 mismatch bases relative thereto. For example, the effector sequence may be substantially complementary to a RNA transcript encoded by Region 9 set forth in Table 1 and contain 2 mismatch bases relative thereto. For example, the effector sequence may be substantially complementary to a RNA transcript encoded by Region 9 set forth in Table 1 and contain 1 mismatch base relative thereto. For example, the effector sequence may be 100% complementary to a RNA transcript encoded by Region 9 set forth in Table 1.

In one example, the effector sequence is substantially complementary to a RNA transcript encoded by Region 10 set forth in Table 1. For example, the effector sequence may be substantially complementary to a RNA transcript encoded by Region 10 set forth in Table 1 and contain 4 mismatch bases relative thereto. For example, the effector sequence may be substantially complementary to a RNA transcript encoded by Region 10 set forth in Table 1 and contain 3 mismatch bases relative thereto. For example, the effector sequence may be substantially complementary to a RNA transcript encoded by Region 10 set forth in Table 1 and contain 2 mismatch bases relative thereto. For example, the effector sequence may be substantially complementary to a RNA transcript encoded by Region 10 set forth in Table 1 and contain 1 mismatch base relative thereto. For example, the effector sequence may be 100% complementary to a RNA transcript encoded by Region 10 set forth in Table 1.

In one example, the RNA of the disclosure comprises is a RNA comprising an effector sequence which is substantially complementary to a RNA transcript encoded by Region 1, Region 5, Region 9, Region 4 or Region 6 set forth in Table 1 as described herein.

In one example, the RNA of the disclosure is a short interfering RNA (siRNA) duplex or a double-stranded RNA (dsRNA).

In one example, the disclosure provides a plurality of RNAs, i.e., capable of eliciting RNAi, wherein each RNA comprises an effector sequence of at least 17 nucleotides in length and a effector complement sequence, wherein the effector sequence of each RNA is substantially complementary to a RNA transcript encoded by a region of the HBV genome set forth in Table 1. For example, each RNA of the plurality comprises an effector sequence which is less than 30 nucleotides in length. For example, suitable effector sequences may be in the range of 17-29 nucleotides in length.

A plurality of RNAs in accordance with the present disclosure may comprise up to 10 RNAs as described herein. In one example, the plurality of RNAs comprises two RNAs described herein. In another example, the plurality of RNAs comprises three RNAs described herein. In one example, the plurality of RNAs comprises four RNAs described herein. In one example, the plurality of RNAs comprises five RNAs described herein. In one example, the plurality of RNAs comprises six RNAs described herein. In one example, the plurality of RNAs comprises seven RNAs described herein. In one example, the plurality of RNAs comprises eight RNAs described herein. In one example, the plurality of RNAs comprises nine RNAs described herein. In one example, the plurality of RNAs comprises ten RNAs described herein.

Thus, the plurality of RNAs in accordance with the present disclosure may comprise one or more of the RNAs described herein comprising an effector sequence substantially complementary to a RNA transcript encoded by a region of the HBV genome set forth in Table 1.

In one example, the plurality of RNAs described herein are provided together as a single composition.

In another example, the plurality of RNAs described herein are provided as multiple compositions. For example, each of the RNAs of the plurality may be provided separately. Alternatively, at least one RNA of the plurality may be provided separately and two or more of the plurality provided together in a composition.

In one example, the effector sequence of a RNA in the plurality is substantially complementary to a RNA transcript encoded by Region 1 in Table 1.

In one example, the effector sequence of a RNA in the plurality is substantially complementary to a RNA transcript encoded by Region 5 in Table 1.

In one example, the effector sequence of a RNA in the plurality is substantially complementary to a RNA transcript encoded by Region 9 in Table 1.

In one example, the effector sequence of a RNA in the plurality is substantially complementary to a RNA transcript encoded by Region 4 in Table 1.

In one example, the effector sequence of a RNA in the plurality is substantially complementary to a RNA transcript encoded by Region 6 in Table 1.

In one example, the effector sequence of a RNA in the plurality is substantially complementary to a RNA transcript encoded by Region 9 in Table 1 and the effector sequence of another RNA in the plurality is substantially complementary to a RNA transcript encoded by Region 4 in Table 1.

In one example, the effector sequence of a RNA in the plurality is substantially complementary to a RNA transcript encoded by Region 9 in Table 1 and the effector sequence of another RNA in the plurality is substantially complementary to a RNA transcript encoded by Region 4 in Table 1 and the effector sequence of another RNA in the plurality is a RNA transcript encoded by Region 5 in Table 1.

In one example, the disclosure provides a plurality of RNA i.e., capable of eliciting RNAi, wherein:

(i) at least one RNA comprises an effector sequence of at least 17 nucleotides in length and a effector complement sequence, wherein the effector sequence of each RNA is substantially complementary to a RNA transcript encoded by a region of the HBV genome set forth in Table 1; and (ii) at least one RNA comprises an effector sequence and an effector complement sequence, wherein the effector sequence of each RNA comprises or consists of a sequence set forth in the column labelled "Effector" in Table 4. In one example, the effector complement sequence of the RNA comprises or consists of a sequence set forth in the column labelled "Effector complement" in Table 4.

For example, each RNA comprises an effector sequence which is less than 30 nucleotides in length. For example, suitable effector sequences may be in the range of 17-29 nucleotides in length.

In one example, the RNA at (i) comprises an effector sequence that is substantially complementary to a RNA transcript encoded by Region 1 in Table 1 and the RNA at (ii) comprises an effector sequence consisting of a sequence set forth in SEQ ID NO: 57. In one example, the RNA at (ii) comprises an effector complement sequence which consists of a sequence set forth in SEQ ID NO: 58.

In one example, the RNA at (i) comprises an effector sequence that is substantially complementary to a RNA transcript encoded by Region 5 in Table 1 and the RNA at (ii) comprises an effector sequence consisting of a sequence set forth in SEQ ID NO: 57. In one example, the RNA at (ii) comprises an effector complement sequence which consists of a sequence set forth in SEQ ID NO: 58.

In one example, the RNA at (i) comprises an effector sequence that is substantially complementary to a RNA transcript encoded by Region 9 in Table 1 and the RNA at (ii) comprises an effector sequence consisting of a sequence set forth in SEQ ID NO: 57. In one example, the RNA at (ii) comprises an effector complement sequence which consists of a sequence set forth in SEQ ID NO: 58.

In one example, the RNA at (i) comprises an effector sequence that is substantially complementary to a RNA transcript encoded by Region 4 in Table 1 and the RNA at (ii) comprises an effector sequence consisting of a sequence set forth in SEQ ID NO: 57. In one example, the RNA at (ii) comprises an effector complement sequence which consists of a sequence set forth in SEQ ID NO: 58.

In one example, the RNA at (i) comprises an effector sequence that is substantially complementary to a RNA transcript encoded by Region 6 in Table 1 and the RNA at (ii) comprises an effector sequence consisting of a sequence set forth in SEQ ID NO: 57. In one example, the RNA at (ii) comprises an effector complement sequence which consists of a sequence set forth in SEQ ID NO: 58.

In one example, a RNA at (i) comprises an effector sequence that is substantially complementary to a RNA transcript encoded by Region 9 in Table 1 and another RNA at (i) comprises an effector sequence that is substantially complementary to a RNA transcript encoded by Region 4 in Table 1 and the RNA at (ii) comprises an effector sequence consisting of a sequence set forth in SEQ ID NO: 57. In one example, the RNA at (ii) comprises an effector complement sequence which consists of a sequence set forth in SEQ ID NO: 58.

In one example, a RNA at (i) comprises an effector sequence that is substantially complementary to a RNA transcript encoded by Region 9 in Table 1 and another RNA at (i) comprises an effector sequence that is substantially complementary to a RNA transcript encoded by Region 4 in Table 1 and the effector sequence of another RNA in the plurality is a RNA transcript encoded by Region 5 in Table 1 and the RNA at (ii) comprises an effector sequence consisting of a sequence set forth in SEQ ID NO: 57. In one example, the RNA at (ii) comprises an effector complement sequence which consists of a sequence set forth in SEQ ID NO: 58.

An exemplary RNA in accordance with the present disclosure comprises an effector sequence and an effector complement sequence, wherein the effector sequence is substantially complementary to an effector complement sequence described in the column labelled "Effector complement" in Table 2.

In one example, the present disclosure provides a RNA i.e., capable of eliciting RNAi, comprising an effector sequence which is substantially complementary to a sequence described in the column labelled "Effector complement" in Table 2, with the exception of 4 base mismatches.

In one example, the present disclosure provides a RNA i.e., capable of eliciting RNAi, comprising an effector sequence which is substantially complementary to a sequence described in the column labelled "Effector complement" in Table 2, with the exception of 3 base mismatches.

In one example, the present disclosure provides a RNA i.e., capable of eliciting RNAi, comprising an effector sequence which is substantially complementary to a sequence described in the column labelled "Effector complement" in Table 2, with the exception of 2 base mismatches.

In one example, the present disclosure provides a RNA i.e., capable of eliciting RNAi, comprising an effector sequence which is substantially complementary to a sequence described in the column labelled "Effector complement" in Table 2, with the exception of a single base mismatch.

Where a RNA of the disclosure comprises an effector sequence which is substantially complementary to a sequence described in the column labelled "Effector complement" in Table 2 with the exception of 1, 2, 3 or 4 mismatches, the effector sequence will still be able to form a duplex with the corresponding effector complement sequence in Table 2.

In one example, the present disclosure provides a RNA i.e., capable of eliciting RNAi, comprising an effector sequence and an effector complement sequence, wherein the effector sequence is 100% complementary to a sequence described in the column labelled "Effector complement" in Table 2. In one example, the effector complement sequence of the RNA is substantially complementary to the effector sequence thereof. For example, the effector complement sequence of the RNA may comprise 1, 2, 3 or 4 mismatches relative to the cognate effector sequence, but still be capable of forming a duplex therewith.

Exemplary RNAs in accordance with the present disclosure comprise corresponding effector and effector complement sequences as described in Table 2. In one example, the corresponding effector and effector complement sequences of the RNAs may be provided as separate nucleic acids which are duplexed (dsRNA) e.g., by Watson-Crick base pairing.

In one example, the disclosure provides a RNA, i.e., capable of eliciting RNAi, wherein the RNA comprises an effector sequence and an effector complement sequence, wherein the effector sequence consists of a sequence set forth in the column labelled "Effector" in Table 2. In one example, the effector complement sequence consists of a sequence set forth in the column labelled "Effector complement" in Table 2.

An exemplary RNA of the disclosure comprises an effector sequence consisting of the sequence set forth in SEQ ID NO: 47 and an effector complement sequence consisting of the sequence set forth in SEQ ID NO: 48.

An exemplary RNA of the disclosure comprises an effector sequence consisting of the sequence set forth in SEQ ID NO: 27 and an effector complement sequence consisting of the sequence set forth in SEQ ID NO: 28.

An exemplary RNA of the disclosure comprises an effector sequence consisting of the sequence set forth in SEQ ID NO: 29 and an effector complement sequence consisting of the sequence set forth in SEQ ID NO: 30.

An exemplary RNA of the disclosure comprises an effector sequence consisting of the sequence set forth in SEQ ID NO: 11 and an effector complement sequence consisting of the sequence set forth in SEQ ID NO: 12.

An exemplary RNA of the disclosure comprises an effector sequence consisting of the sequence set forth in SEQ ID NO: 45 and an effector complement sequence consisting of the sequence set forth in SEQ ID NO: 46.

An exemplary RNA of the disclosure comprises an effector sequence consisting of the sequence set forth in SEQ ID NO: 35 and an effector complement sequence consisting of the sequence set forth in SEQ ID NO: 36.

An exemplary RNA of the disclosure comprises an effector sequence consisting of the sequence set forth in SEQ ID NO: 21 and an effector complement sequence consisting of the sequence set forth in SEQ ID NO: 22.

In one example, the disclosure provides a plurality of RNAs, i.e., capable of eliciting RNAi, wherein each RNA comprises an effector sequence and an effector complement sequence, wherein the effector sequence of each RNA is substantially complementary to an effector complement sequence set forth in the column labelled "Effector complement" in Table 2. Exemplary RNAs comprising an effector sequence which is substantially complementary to an effector complement sequence set forth in the column labelled "Effector complement" in Table 2 are described herein.

In one example, the effector sequence of each RNA consists of a sequence set forth in the column labelled "Effector" in Table 2. In one example, the effector complement sequence of each RNA consists of a sequence set forth in the column labelled "Effector complement" in Table 2.

In one example, the disclosure provides a plurality of RNAs, i.e., capable of eliciting RNAi, wherein:
(i) at least one RNA comprises an effector sequence and a effector complement sequence, wherein the effector sequence of the RNA consists of a sequence set forth in the column labelled "Effector" in Table 2 (in one example, the effector complement sequence of each RNA consists of a sequence set forth in the column labelled "Effector complement" in Table 2); and
(ii) at least one RNA comprises an effector sequence and an effector complement sequence, wherein the effector sequence of the RNA consists of a sequence set forth in the column labelled "Effector" in Table 4 (in one example, the effector complement sequence of the RNA comprises or consists of a sequence set forth in the column labelled "Effector complement" in Table 4).

An exemplary plurality of RNAs of the disclosure comprises:
(i) a RNA comprising an effector sequence consisting of the sequence set forth in SEQ ID NO: 47 and an effector complement sequence consisting of the sequence set forth in SEQ ID NO: 48; and
(ii) a RNA comprising an effector sequence consisting of the sequence set forth in SEQ ID NO: 27 and an effector complement sequence consisting of the sequence set forth in SEQ ID NO: 28.

An exemplary plurality of RNAs of the disclosure comprises:
(i) a RNA comprising an effector sequence consisting of the sequence set forth in SEQ ID NO: 47 and an effector complement sequence consisting of the sequence set forth in SEQ ID NO: 48;
(ii) a RNA comprising an effector sequence consisting of the sequence set forth in SEQ ID NO: 27 and an effector complement sequence consisting of the sequence set forth in SEQ ID NO: 28; and
(iii) a RNA comprising an effector sequence consisting of the sequence set forth in SEQ ID NO: 29 and an effector complement sequence consisting of the sequence set forth in SEQ ID NO: 30.

An exemplary plurality of RNAs of the disclosure comprises:
(i) a RNA comprising an effector sequence consisting of the sequence set forth in SEQ ID NO: 47 and an effector complement sequence consisting of the sequence set forth in SEQ ID NO: 48;
(ii) a RNA comprising an effector sequence consisting of the sequence set forth in SEQ ID NO: 27 and an effector complement sequence consisting of the sequence set forth in SEQ ID NO: 28; and
(iii) a RNA comprising an effector sequence consisting of the sequence set forth in SEQ ID NO: 57 and an effector complement sequence consisting of the sequence set forth in SEQ ID NO: 58.

RNA of the disclosure may comprise either synthetic RNAs or DNA-directed RNAs (ddRNAs). Synthetic RNAs may be manufactured by methods known in the art such as by typical oligonucleotide synthesis, and may incorporate chemical modifications to increase half-life and/or efficacy of the siRNA agent, and/or to allow for a more robust delivery formulation. Many chemical modifications of oligonucleotides are known and well described in the art.

In one example, substantially all of the nucleotides of a RNA of the disclosure are modified. In other example, all of the nucleotides of a RNA of the disclosure are modified. RNAs of the disclosure in which "substantially all of the nucleotides are modified" are largely but not wholly modified and can include not more than 5, 4, 3, 2, or 1 unmodified nucleotides.

In one example, the RNA of the disclosure comprises one or more overhang regions and/or capping groups at the 3'-end, 5'-end, or both ends of one or both strands of the duplex. The overhang regions can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one example, the nucleotides in the overhang region of the RNA each independently are a modified or unmodified nucleotide including, but no limited to 2'-sugar modified, such as, 2-F, 2'-O-methyl, thymidine (T), deoxy-thymine (dT), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, dTdT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNA can be phosphorylated. In some examples, the overhang region(s) contains two nucleotides having a phosphorothioate between the two nucleotides, where the two nucleotides can be the same or different.

In one example, the RNA contains only a single overhang, which can strengthen the interference activity of the RNA, without affecting its overall stability. For example, the single-stranded overhang is be located at the 3'-terminal end of the effector sequence or, alternatively, at the 3'-terminal end of the effector complement sequence. In one example, the RNA also comprises a blunt end, located at the 5'-end of the effector complement sequence (or the 3'-end of the effector sequence) or vice versa.

Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of RNAs useful in the disclosure include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some example, a modified RNA will have a phosphorus atom in its internucleoside backbone. Representative U.S. patents that teach the preparation of phosphorus-containing linkages include, but are not limited to, U.S. Pat. Nos. 7,015,315; 7,041,816; 7,273,933; 7,321,029; and U.S. Pat. RE39464.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach exemplary forms of these oligonucleosides include, but are not limited to, U.S. Pat. Nos. 5,663,312; 5,633,360; 5,677,437; and 5,677,439.

In one example, the RNA of the disclosure comprises only unmodified or natural bases, e.g., a described below.

In other examples, the RNAs of the disclosure comprise or are a RNA mimetic, e.g., the backbone, of the nucleotide units are replaced with novel groups. The base units are maintained for hybridization with an appropriate nucleic acid target compound. One such oligomeric compound, a RNA mimetic that has been shown to have excellent hybridization properties, is referred to as a peptide nucleic acid (PNA). In PNA compounds, the sugar backbone of a RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262.

Modified RNAs can also contain one or more substituted sugar moieties. The RNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_1)_nNH_2$, $O(CH_2)_nCH_3$, $O(CH_2)_nONH_2$, and $O(CH_2)_nON[(CH_2)_nCH_3)]_2$, where n and m are from 1 to about 10.

A RNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine.*

The RNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447).

Potentially stabilizing modifications to the ends of RNA can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

In another example, the exemplary RNAs of the disclosure (e.g., as set forth in Table 2 and/or Table 4) may be provided as short hairpin RNAs (shRNAs) comprising a stem loop sequence positioned between the effector sequence and the effector complement sequence such that the respective RNA forms a single contiguous sequence. A stem loop sequence is of sufficient length to permit the effector sequence and the effector complement sequence to anneal to one another. Suitable stem loop sequences may for instance be selected from those known in the art. For example, an shRNA in accordance with the present disclosure may comprise a sequence set forth in Table 3, optionally modified as described herein.

In one example, a RNA of the disclosure is chemically synthesized. Oligonucleotides (e.g., certain modified oligonucleotides or portions of oligonucleotides lacking ribonucleotides) are synthesized using protocols known in the art, for example as described in Caruthers et al., 1992, *Methods in Enzymology* 211, 3-19, WO 99/54459, Wincott et al., 1995, *Nucleic Acids Res.* 23, 2677-2684, Wincott et al., 1997, *Methods Mol. Bio.*, 74, 59, Brennan et al., 1998, *Biotechnol Bioeng.*, 61, 33-45, and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end.

RNA without modifications are synthesized using procedures as described in Usman et al., 1987, *J. Am. Chem. Soc.*, 109, 7845; Scaringe et al., 1990, *Nucleic Acids Res.*, 18, 5433. These syntheses makes use of common nucleic acid protecting and coupling groups, such as dimethoxytrityl at the 5'-end, and phosphoramidites at the 3'-end that can be used for certain RNA of the disclosure.

In certain examples, the RNAs of the disclosure are synthesized, deprotected, and analyzed according to methods described in U.S. Pat. Nos. 6,995,259, 6,686,463, 6,673,918, 6,649,751, and/or 6,989,442.

In an alternative example, a RNA of the disclosure is synthesized as discrete components and joined together post-synthetically, for example, by ligation (Moore et al., 1992, Science 256, 9923 or WO 93/23569), or by hybridization following synthesis and/or deprotection.

In one example, an exemplary shRNA comprises or consists of the sequence set forth in SEQ ID NO: 92. In one example, an exemplary shRNA comprises or consists of the sequence set forth in SEQ ID NO: 95.

In one example, an exemplary shRNA comprises or consists of the sequence set forth in SEQ ID NO: 78.

In one example, an exemplary shRNA comprises or consists of the sequence set forth in SEQ ID NO: 79. In one example, an exemplary shRNA comprises or consists of the sequence set forth in SEQ ID NO: 82.

In one example, an exemplary shRNA comprises or consists of the sequence set forth in SEQ ID NO: 65. In one example, an exemplary shRNA comprises or consists of the sequence set forth in SEQ ID NO: 68.

In one example, an exemplary shRNA comprises or consists of the sequence set forth in SEQ ID NO: 91. In one example, an exemplary shRNA comprises or consists of the sequence set forth in SEQ ID NO: 94.

In one example, an exemplary shRNA comprises or consists of the sequence set forth in SEQ ID NO: 83. In one example, an exemplary shRNA comprises or consists of the sequence set forth in SEQ ID NO: 84.

The present disclosure also provides a plurality of RNAs, wherein the plurality comprises a shRNA comprising or consisting of the sequence set forth in SEQ ID NO: 92 and at least one other RNA of the disclosure.

The present disclosure also provides a plurality of RNAs, wherein the plurality comprises a shRNA comprising or consisting of the sequence set forth in SEQ ID NO: 95 and at least one other RNA of the disclosure. The present disclosure also provides a plurality of RNAs, wherein the plurality comprises a shRNA comprising or consisting of the sequence set forth in SEQ ID NO: 78 and at least one other RNA of the disclosure.

The present disclosure also provides a plurality of RNAs, wherein the plurality comprises a shRNA comprising or consisting of the sequence set forth in SEQ ID NO: 79 and at least one other RNA of the disclosure.

The present disclosure also provides a plurality of RNAs, wherein the plurality comprises a shRNA comprising or consisting of the sequence set forth in SEQ ID NO: 82 and at least one other RNA of the disclosure.

The present disclosure also provides a plurality of RNAs, wherein the plurality comprises a shRNA comprising or consisting of the sequence set forth in SEQ ID NO: 65 and at least one other RNA of the disclosure.

The present disclosure also provides a plurality of RNAs, wherein the plurality comprises a shRNA comprising or consisting of the sequence set forth in SEQ ID NO: 68 and at least one other RNA of the disclosure.

The present disclosure also provides a plurality of RNAs, wherein the plurality comprises a shRNA comprising or consisting of the sequence set forth in SEQ ID NO: 91 and at least one other RNA of the disclosure.

The present disclosure also provides a plurality of RNAs, wherein the plurality comprises a shRNA comprising or consisting of the sequence set forth in SEQ ID NO: 94 and at least one other RNA of the disclosure.

The present disclosure also provides a plurality of RNAs, wherein the plurality comprises a shRNA comprising or consisting of the sequence set forth in SEQ ID NO: 83 and at least one other RNA of the disclosure.

The present disclosure also provides a plurality of RNAs, wherein the plurality comprises a shRNA comprising or consisting of the sequence set forth in SEQ ID NO: 84 and at least one other RNA of the disclosure.

The present disclosure also provides a plurality of RNAs, wherein the plurality comprises:

(i) a shRNA comprising or consisting of the sequence set forth in SEQ ID NO: 92;
(ii) a shRNA comprising or consisting of the sequence set forth in SEQ ID NO: 78; and
(iii) at least one other RNA of the disclosure.

In one example, the other RNA of the disclosure is a shRNA comprising a sequence set forth in SEQ ID NO: 79, 82, 65, 68, 91, 94, 83 or 84.

The present disclosure also provides a plurality of RNAs, wherein the plurality comprises or consists of:
(i) a shRNA comprising or consisting of the sequence set forth in SEQ ID NO: 92;
(ii) a shRNA comprising or consisting of the sequence set forth in SEQ ID NO: 78; and
(iii) a shRNA comprising or consisting of the sequence set forth in SEQ ID NO: 79.

The present disclosure also provides a plurality of RNAs, wherein the plurality comprises or consists of:
(i) a shRNA comprising or consisting of the sequence set forth in SEQ ID NO: 92;
(ii) a shRNA comprising or consisting of the sequence set forth in SEQ ID NO: 78; and
(iii) a shRNA comprising or consisting of the sequence set forth in SEQ ID NO: 101.

ddRNAi

A RNA of the disclosure can be transcribed from a nucleic acid. Accordingly, in one example, the disclosure provides a nucleic acid encoding a RNA of the disclosure.

In one example, the nucleic acid is DNA.

In another example, the disclosure provides a nucleic acid encoding a plurality of RNAs of the disclosure.

In another example, the disclosure provides a plurality of nucleic acids encoding a plurality of RNAs of the disclosure. For example, each nucleic acid of the plurality may encode a single RNA described herein. In another example, one or more nucleic acids encodes a plurality of RNAs e.g., a nucleic acid of the plurality encodes two or more RNAs of the disclosure and another nucleic acid of the plurality encodes one or more RNAs of the disclosure.

In one example, the plurality of nucleic acids described herein are provided together e.g., in a single composition.

In another example, the plurality of nucleic acids described herein are provided as multiple components e.g., multiple compositions. For example, each of the nucleic acids of the plurality may be provided separately. Alternatively, in an example where at least three nucleic acids of the disclosure are provided, at least one of the nucleic acids may be provided separately and two or more of the plurality provided together.

In some examples, a nucleic acid of the disclosure comprises one or more additional elements e.g., to facilitate transcription of the RNA. For example, the nucleic acid may comprise a promoter operably linked to a sequence encoding a RNA of the disclosure. Other elements e.g., transcriptional terminators, are known in the art and/or described herein.

In one example, the nucleic acid is a DNA-directed RNAi (ddRNAi) construct.

In one example, the ddRNAi construct comprises a sequence encoding a RNA of the disclosure operably linked to a promoter.

In one example, the ddRNAi construct comprises a sequence encoding a RNA comprising an effector sequence and an effector complement sequence of the disclosure. Exemplary effector sequences and effector complement sequences are set forth in Table 2.

For example, the sequences may be operably linked to a promoter. In one example, both sequences may be operably linked to the same promoter. In one example, both sequences may be operably linked to different promoters.

In one example, the disclosure provides a ddRNAi construct comprising a sequence encoding an effector sequence and a sequence encoding an effector complement sequence, wherein the effector sequence is substantially complementary to an effector complement sequence described in the column labelled "Effector complement" in Table 2. For example, an effector sequence which is substantially complementary to an effector complement sequence described in the column labelled "Effector complement" in Table 2 may comprise 0, 1, 2, 3 or 4 mismatches when duplexed with the corresponding effector complement sequence in Table 2.

In one example, the disclosure provides an ddRNAi construct comprising a sequence encoding an effector sequence which is substantially complementary to a sequence described in the column labelled "Effector complement" in Table 2, with the exception of 4 base mismatches.

In one example, the disclosure provides an ddRNAi construct comprising a sequence encoding an effector sequence which is substantially complementary to a sequence described in the column labelled "Effector complement" in Table 2, with the exception of 3 base mismatches.

In one example, the disclosure provides an ddRNAi construct comprising a sequence encoding an effector sequence which is substantially complementary to a sequence described in the column labelled "Effector complement" in Table 2, with the exception of 2 base mismatches.

In one example, the disclosure provides an ddRNAi construct comprising a sequence encoding an effector sequence which is substantially complementary to a sequence described in the column labelled "Effector complement" in Table 2, with the exception of a single base mismatch.

In one example, the present disclosure provides a ddRNAi construct comprising a sequence encoding an effector sequence and an effector complement sequence, wherein the effector sequence is 100% complementary to a sequence described in the column labelled "Effector complement" in Table 2. In one example, ddRNAi construct comprises a sequence encoding an effector complement sequence which is substantially complementary to the effector sequence encoded by the ddRNAi construct.

Exemplary ddRNAi constructs of the disclosure comprise sequences encoding corresponding effector and effector complement sequences as described in Table 2.

In one example, the disclosure provides a ddRNAi construct comprising a sequence which encodes an effector sequence and a sequence encoding an effector complement sequence, wherein the effector sequence consists of a sequence set forth in the column labelled "Effector" in Table 2. In one example, the effector complement sequence consists of a sequence set forth in the column labelled "Effector complement" in Table 2.

An exemplary ddRNAi construct of the disclosure comprises a sequence encoding an effector sequence consisting of the sequence set forth in SEQ ID NO: 47 and a sequence encoding an effector complement sequence consisting of the sequence set forth in SEQ ID NO: 48.

Another exemplary ddRNAi construct of the disclosure comprises a sequence encoding an effector sequence consisting of the sequence set forth in SEQ ID NO: 27 and a sequence encoding an effector complement sequence consisting of the sequence set forth in SEQ ID NO: 28.

A further exemplary ddRNAi construct of the disclosure comprises a sequence encoding an effector sequence consisting of the sequence set forth in SEQ ID NO: 29 and a sequence encoding an effector complement sequence consisting of the sequence set forth in SEQ ID NO: 30.

A further exemplary ddRNAi construct of the disclosure comprises a sequence encoding an effector sequence consisting of the sequence set forth in SEQ ID NO: 11 and a sequence encoding an effector complement sequence consisting of the sequence set forth in SEQ ID NO: 12.

A further exemplary ddRNAi construct of the disclosure comprises a sequence encoding an effector sequence consisting of the sequence set forth in SEQ ID NO: 45 and a sequence encoding an effector complement sequence consisting of the sequence set forth in SEQ ID NO: 46.

A further exemplary ddRNAi construct of the disclosure comprises a sequence encoding an effector sequence consisting of the sequence set forth in SEQ ID NO: 35 and a sequence encoding an effector complement sequence consisting of the sequence set forth in SEQ ID NO: 36.

A further exemplary ddRNAi construct of the disclosure comprises a sequence encoding an effector sequence consisting of the sequence set forth in SEQ ID NO: 21 and a sequence encoding an effector complement sequence consisting of the sequence set forth in SEQ ID NO: 22.

In another example, the disclosure provides a ddRNAi construct encoding a plurality of RNAs of the disclosure or comprising a sequence encoding a RNA of the disclosure and at least one other RNA capable of eliciting RNAi.

In one example, the disclosure provides a ddRNAi construct encoding a plurality of RNAs of the disclosure, wherein each RNA comprises an effector sequence and an effector complement sequence, wherein the effector sequence of at least one (or each) RNA is substantially complementary to a sequence described in the column labelled "Effector complement" in Table 2. Exemplary RNAs of the disclosure comprising an effector sequence which is "substantially complementary" to a sequence described in the column labelled "Effector complement" in Table 2 have been described and shall be taken to apply mutatis mutandis to this example of the disclosure. However, in one example, the disclosure provides a ddRNAi construct encoding a plurality of RNAs of the disclosure, wherein each RNA comprises an effector sequence and an effector complement sequence, wherein the effector sequence of at least one (or each) RNA consists of a sequence set forth in the column labelled "Effector" in Table 2. In one example, the effector complement sequence of at least one (or each) RNA consists of a sequence set forth in the column labelled "Effector complement" in Table 2.

In one example, the disclosure provides a ddRNAi construct encoding a plurality of RNAs of the disclosure, wherein:

(i) at least one RNA comprises an effector sequence and a effector complement sequence, wherein the effector sequence of the RNA consists of a sequence set forth in the column labelled "Effector" in Table 2 (in one example, the effector complement sequence of each RNA consists of a sequence set forth in the column labelled "Effector complement" in Table 2); and (ii) at least one RNA comprises an effector sequence and an effector complement sequence, wherein the effector sequence of the RNA consists of a sequence set forth in the column labelled "Effector" in Table 4 (in one example, the effector complement sequence of the RNA comprises or consists of a sequence set forth in the column labelled "Effector complement" in Table 4).

Exemplary combinations of RNAs are described herein and shall be taken to apply mutatis mutandis to this example of the disclosure.

An exemplary ddRNAi construct of the disclosure comprises:

(i) a sequence encoding a RNA comprising an effector sequence consisting of the sequence set forth in SEQ ID NO: 47 and an effector complement sequence consisting of the sequence set forth in SEQ ID NO: 48; and (ii) a sequence encoding a RNA comprising an effector sequence consisting of the sequence set forth in SEQ ID NO: 27 and an effector complement sequence consisting of the sequence set forth in SEQ ID NO: 28.

An exemplary ddRNAi construct of the disclosure comprises:

(i) a sequence encoding a RNA comprising an effector sequence consisting of the sequence set forth in SEQ ID NO: 47 and an effector complement sequence consisting of the sequence set forth in SEQ ID NO: 48;

(ii) a sequence encoding a RNA comprising an effector sequence consisting of the sequence set forth in SEQ ID NO: 27 and an effector complement sequence consisting of the sequence set forth in SEQ ID NO: 28; and (iii) a sequence encoding a RNA comprising an effector sequence consisting of the sequence set forth in SEQ ID NO: 29 and an effector complement sequence consisting of the sequence set forth in SEQ ID NO: 30.

For example, the ddRNAi construct of the disclosure may comprise, in a 5'-3' direction:

(i) a DNA sequence encoding a RNA comprising an effector sequence consisting of the sequence set forth in SEQ ID NO: 27 and an effector complement sequence consisting of the sequence set forth in SEQ ID NO: 28;

(ii) a DNA sequence encoding a RNA comprising an effector sequence consisting of the sequence set forth in SEQ ID NO: 29 and an effector complement sequence consisting of the sequence set forth in SEQ ID NO: 30; and (iii) a DNA sequence encoding a RNA comprising an effector sequence consisting of the sequence set forth in SEQ ID NO: 47 and an effector complement sequence consisting of the sequence set forth in SEQ ID NO: 48.

Each of the DNA sequences encoding the RNAs at (i) to (iii) in the ddRNAi construct may also be in operable linkage with a separate promoter in the ddRNAi construct e.g., a U6 or H1 promoter.

Another exemplary ddRNAi of the disclosure comprises:

(i) a sequence encoding a RNA comprising an effector sequence consisting of the sequence set forth in SEQ ID NO: 47 and an effector complement sequence consisting of the sequence set forth in SEQ ID NO: 48;

(ii) a sequence encoding a RNA comprising an effector sequence consisting of the sequence set forth in SEQ ID NO: 27 and an effector complement sequence consisting of the sequence set forth in SEQ ID NO: 28; and (iii) a sequence encoding a RNA comprising an effector sequence consisting of the sequence set forth in SEQ ID NO: 57 and an effector complement sequence consisting of the sequence set forth in SEQ ID NO: 58.

For example, the ddRNAi construct of the disclosure may comprise, in a 5'-3' direction:

(i) a DNA sequence encoding a RNA comprising an effector sequence consisting of the sequence set forth in SEQ ID NO: 27 and an effector complement sequence consisting of the sequence set forth in SEQ ID NO: 28;

(ii) a DNA sequence encoding a RNA comprising an effector sequence consisting of the sequence set forth in SEQ ID NO: 57 and an effector complement sequence consisting of the sequence set forth in SEQ ID NO: 58; and (iii) a DNA sequence encoding a RNA comprising an effector sequence consisting of the sequence set forth in SEQ ID NO: 47 and an effector complement sequence consisting of the sequence set forth in SEQ ID NO: 48.

Each of the DNA sequences encoding the RNAs at (i) to (iii) in the ddRNAi construct may also be in operable linkage with a separate promoter in the ddRNAi construct e.g., a U6 or H1 promoter.

In one example, the ddRNAi construct comprises a sequence encoding a shRNA of the disclosure operably linked to a promoter. For example, the ddRNAi construct of the disclosure comprises a sequence encoding a shRNA comprising or consisting of a sequence set forth in Table 3 operably linked to a promoter e.g., a U6 or H1 promoter.

For example, the ddRNAi construct may comprise a sequence encoding a shRNA comprising or consisting of the sequence set forth in SEQ ID NO: 92.

In one example, the ddRNAi construct may comprise a sequence encoding a shRNA comprising or consisting of the sequence set forth in SEQ ID NO: 95.

In one example, the ddRNAi construct may comprise a sequence encoding a shRNA comprising or consisting of the sequence set forth in SEQ ID NO: 78.

In one example, the ddRNAi construct may comprise a sequence encoding a shRNA comprising or consisting of the sequence set forth in SEQ ID NO: 79.

In one example, the ddRNAi construct may comprise a sequence encoding a shRNA comprising or consisting of the sequence set forth in SEQ ID NO: 82.

In one example, the ddRNAi construct may comprise a sequence encoding a shRNA comprising or consisting of the sequence set forth in SEQ ID NO: 65.

In one example, the ddRNAi construct may comprise a sequence encoding a shRNA comprising or consisting of the sequence set forth in SEQ ID NO: 68.

In one example, the ddRNAi construct may comprise a sequence encoding a shRNA comprising or consisting of the sequence set forth in SEQ ID NO: 91.

In one example, the ddRNAi construct may comprise a sequence encoding a shRNA comprising or consisting of the sequence set forth in SEQ ID NO: 94.

In one example, the ddRNAi construct may comprise a sequence encoding a shRNA comprising or consisting of the sequence set forth in SEQ ID NO: 83.

In one example, the ddRNAi construct may comprise a sequence encoding a shRNA comprising or consisting of the sequence set forth in SEQ ID NO: 84.

The present disclosure also provides a ddRNAi construct comprising a sequence encoding a plurality of RNAs, the plurality comprising a shRNA comprising or consisting of a sequence set forth in Table 3 and at least one other RNA of the disclosure. For example, the other RNA may be a shRNA, e.g., comprising or consisting of a sequence set forth in Table 3 or in Table 5.

In one example, the disclosure also provides a ddRNAi construct comprising a sequence encoding a plurality of RNAs, the plurality comprising a shRNA comprising or consisting of the sequence set forth in SEQ ID NO: 92 and at least one other RNA of the disclosure. The present disclosure also provides a ddRNAi construct comprising a sequence encoding a plurality of RNAs, the plurality comprising a shRNA comprising or consisting of the sequence set forth in SEQ ID NO: 95 and at least one other RNA of the disclosure.

The present disclosure also provides a ddRNAi construct comprising a sequence encoding a plurality of RNAs, the plurality comprising a shRNA comprising or consisting of the sequence set forth in SEQ ID NO: 78 and at least one other RNA of the disclosure.

The present disclosure also provides a ddRNAi construct comprising a sequence encoding a plurality of RNAs, the plurality comprising a shRNA comprising or consisting of the sequence set forth in SEQ ID NO: 79 and at least one other RNA of the disclosure.

The present disclosure also provides a ddRNAi construct comprising a sequence encoding a plurality of RNAs, the plurality comprising a shRNA comprising or consisting of the sequence set forth in SEQ ID NO: 82 and at least one other RNA of the disclosure.

The present disclosure also provides a ddRNAi construct comprising a sequence encoding a plurality of RNAs, the plurality comprising a shRNA comprising or consisting of the sequence set forth in SEQ ID NO: 65 and at least one other RNA of the disclosure.

In one example, the disclosure also provides a ddRNAi construct comprising a sequence encoding a plurality of RNAs, the plurality comprising a shRNA comprising or consisting of the sequence set forth in SEQ ID NO: 68 and at least one other RNA of the disclosure.

The present disclosure also provides a ddRNAi construct comprising a sequence encoding a plurality of RNAs, the plurality comprising a shRNA comprising or consisting of the sequence set forth in SEQ ID NO: 91 and at least one other RNA of the disclosure.

In one example, the disclosure also provides a ddRNAi construct comprising a sequence encoding a plurality of RNAs, the plurality comprising a shRNA comprising or consisting of the sequence set forth in SEQ ID NO: 94 and at least one other RNA of the disclosure.

The present disclosure also provides a ddRNAi construct comprising a sequence encoding a plurality of RNAs, the plurality comprising a shRNA comprising or consisting of the sequence set forth in SEQ ID NO: 83 and at least one other RNA of the disclosure.

In one example, the disclosure provides a ddRNAi construct comprising a sequence encoding a plurality of RNAs, the plurality comprising a shRNA comprising or consisting of the sequence set forth in SEQ ID NO: 84 and at least one other RNA of the disclosure.

The present disclosure also provides a ddRNAi comprising a sequence encoding a plurality of RNAs wherein the plurality comprises:

(i) a shRNA comprising or consisting of the sequence set forth in SEQ ID NO: 92;

(ii) a shRNA comprising or consisting of the sequence set forth in SEQ ID NO: 78; and (iii) at least one other RNA of the disclosure.

In one example, the other RNA encoded by the ddRNAi construct of the disclosure is a shRNA comprising a sequence set forth in SEQ ID NO: 79, 82, 65, 68, 91, 94, 83 or 84.

The present disclosure also provides a ddRNAi construct comprising a sequence encoding a plurality of RNAs, the plurality comprising:

(i) a shRNA comprising or consisting of the sequence set forth in SEQ ID NO: 92;

(ii) a shRNA comprising or consisting of the sequence set forth in SEQ ID NO: 78; and (iii) a shRNA comprising or consisting of the sequence set forth in SEQ ID NO: 79.

The present disclosure also provides a ddRNAi construct comprising a sequence encoding a plurality of RNAs, the plurality comprising:

(i) a shRNA comprising or consisting of the sequence set forth in SEQ ID NO: 92;

(ii) a shRNA comprising or consisting of the sequence set forth in SEQ ID NO: 78; and (iii) a shRNA comprising or consisting of the sequence set forth in SEQ ID NO: 101.

As discussed above, a ddRNAi construct generally comprises a sequence encoding a RNA of the disclosure (e.g., a shRNA of the disclosure) operably linked to a promoter. Often the ddRNAi construct is within a vector, e.g., a plasmid or a miniplasmid or a viral vector.

In one example, the sequences encoding a plurality of RNAs (e.g., shRNAs) in a ddRNAi construct are operably linked to the same promoter. For example, the construct may comprise multiple copies of the same promoter with each copy operably linked to a sequence encoding a different RNA of the disclosure.

In another example, each promoter operably linked to a RNA of the disclosure is different. For example, in a ddRNAi construct encoding three RNAs (e.g., three shRNAs), the three sequences encoding the RNAs are each operably linked to a different promoter.

In a further example, in a ddRNAi construct encoding three or more RNAs (e.g., shRNAs), two (or more) of the sequences encoding the RNAs are linked to the same promoter and one (or more) of the sequences encoding the RNAs is linked to a different promoter.

In one example, the promoter is a constitutive promoter. The term "constitutive" when made in reference to a promoter means that the promoter is capable of directing transcription of an operably linked nucleic acid sequence in the absence of a specific stimulus (e.g., heat shock, chemicals, light, etc.). Typically, constitutive promoters are capable of directing expression of a coding sequence in substantially any cell and any tissue. The promoters used to transcribe the RNA of the disclosure include a promoter for ubiquitin, CMV, β-actin, histone H4, EF-1α or pgk genes controlled by RNA polymerase II, or promoter elements controlled by RNA polymerase I.

In one example, a Pol II promoter such as CMV, SV40, U1, β-actin or a hybrid Pol II promoter is employed.

In another example, a promoter controlled by RNA polymerase III is used, such as a U6 promoter (U6-1, U6-8, U6-9), H1 promoter, 7SL promoter, a human Y promoter (hY1, hY3, hY4 (see Maraia, et al., *Nucleic Acids Res* 22(15):3045-52(1994)) and hY5 (see Maraia, et al., *Nucleic Acids Res* 24(18):3552-59(1994)), a human MRP-7-2 promoter, an Adenovirus VA1 promoter, a human tRNA promoter, or a 5s ribosomal RNA promoter.

Suitable promoters for use in a ddRNAi construct of the disclosure are described in U.S. Pat. Nos. 8,008,468 and 8,129,510.

In one example, the promoter is a RNA pol III promoter. For example, the promoter is a U6 promoter. In another example, the promoter is a H1 promoter.

In the case of a ddRNAi construct encoding a plurality of RNAs of the disclosure (e.g., shRNAs of the disclosure) a sequence encoding at least one of the RNAs is operably linked to a U6 promoter and a sequence encoding at least one other of the RNAs is operably linked to a H1 promoter.

In the case of a ddRNAi construct encoding three RNAs of the disclosure (e.g., shRNAs of the disclosure), the sequences encoding the RNAs are each operably linked to a U6 promoter and a sequence encoding the other of the RNAs is operably linked to a H1 promoter. For example, when considered in a 5' to 3' direction, the first and third sequences are operably linked to the U6 promoter and the second sequence is operably linked to a H1 promoter.

In another example, sequences encoding two of the RNAs are each operably linked to a H1 promoter and a sequence encoding the other of the RNAs is operably linked to a U6 promoter. For example, when considered in a 5' to 3' direction, the first and third sequences are operably linked to the H1 promoter and the second sequence is operably linked to a U6 promoter.

In one example, the promoter in a construct is a U6 promoter. For example, the promoter is a U6-1 promoter. For example, the promoter is a U6-8 promoter. For example, the promoter is a U6-9 promoter.

In some examples, promoters of variable strength are employed. For example, use of two or more strong promoters (such as a Pol III-type promoter) may tax the cell, by, e.g., depleting the pool of available nucleotides or other cellular components needed for transcription. In addition or alternatively, use of several strong promoters may cause a toxic level of expression of RNAi agents in the cell. Thus, in some examples one or more of the promoters in the multiple-promoter ddRNAi construct is weaker than other promoters in the construct, or all promoters in the construct may express RNAs at less than a maximum rate. Promoters may also be modified using various molecular techniques, or otherwise, e.g., through modification of various regulatory elements, to attain weaker levels or stronger levels of transcription. One means of achieving reduced transcription is to modify sequence elements within promoters known to control promoter activity. For example the Proximal Sequence Element (PSE) is known to effect the activity of human U6 promoters (see Domitrovich, et al., *Nucleic Acids Res* 31: 2344-2352 (2003). Replacing the PSE elements present in strong promoters, such as the human U6-1, U6-8 or U6-9 promoters, with the element from a weak promoter, such as the human U6-7 promoter, reduces the activity of the hybrid U6-1, U6-8 or U6-9 promoters. This approach has been used in the examples described in this application, but other means to achieve this outcome are known in the art.

Promoters useful in some examples of the present disclosure can be tissue-specific or cell-specific. The term "tissue specific" as it applies to a promoter refers to a promoter that is capable of directing selective transcription of a nucleic acid of interest to a specific type of tissue (e.g., liver tissue) in the relative absence of expression of the same nucleotide sequence of interest in a different type of tissue (e.g., muscle). The term "cell-specific" as applied to a promoter refers to a promoter which is capable of directing selective transcription of a nucleic acid of interest in a specific type of cell in the relative absence of expression of the same nucleotide sequence of interest in a different type of cell within the same tissue.

In one example, a ddRNAi construct of the disclosure may additionally comprise one or more enhancers to increase expression of the RNA(s). Enhancers appropriate for use in examples of the present disclosure include the Apo E HCR enhancer, a CMV enhancer (Xia et al, *Nucleic Acids Res* 31-17(2003)), and other enhancers known to those skilled in the art. Suitable enhancers for use in a ddRNAi construct of the disclosure are described in U.S. Pat. No. 8,008,468.

In a further example, a ddRNAi construct of the disclosure may comprise a transcriptional terminator linked to a nucleic acid encoding a RNA of the disclosure. In the case of a ddRNAi construct encoding multiple RNAs, the terminators linked to each nucleic acid can be the same or different. In one example, the terminator is a contiguous stretch of 4 or more or 5 or more or 6 or more T residues.

In some examples, where different promoters are used, the terminators can be different and are matched to the promoter from the gene from which the terminator is derived. Such terminators include the SV40 poly A, the AdV VA1 gene, the 5S ribosomal RNA gene, and the terminators for human t-RNAs. In addition, promoters and terminators may be mixed and matched, as is commonly done with RNA pol II promoters and terminators.

In one example, the promoter and terminator in each promoter/RNA encoding sequence/terminator component in a ddRNAi construct encoding multiple RNAs are all different to decrease the likelihood of DNA recombination events between components.

In an example, a ddRNAi construct of the disclosure comprises a sequence encoding a RNA of the disclosure operably linked to a U6 promoter and linked to a terminator comprising at least four thymidine residues e.g., 4 or 5 or 6 thymidine residues. In one example, the sequence encoding the RNA is also linked to a transcription initiator comprising a single guanine.

In an example, a ddRNAi construct of the disclosure comprises a sequence encoding a shRNA consisting of a sequence set forth in Table 3 operably linked to a promoter, e.g., a U6 promoter. In one example, the sequence encoding the shRNA is linked to a terminator e.g., comprising at least four thymidine residues, such as 4 or 5 or 6 thymidine residues. In one example, the sequence encoding the shRNA is linked to a transcription initiator e.g., comprising a single guanine residue.

One exemplary ddRNAi construct comprises a sequence encoding a shRNA comprising or consisting of the sequence set forth in SEQ ID NO: 92 operably linked to a U6 promoter, a transcription initiator sequence comprising a single guanine residue and a terminator sequence comprising five contiguous thymidine residues.

Another exemplary ddRNAi construct comprises a sequence encoding a shRNA comprising or consisting of the sequence set forth in SEQ ID NO: 78 operably linked to a U6 promoter and a terminator comprising six contiguous thymidine residues. Another exemplary ddRNAi construct comprises a sequence encoding a shRNA comprising or consisting of the sequence set forth in SEQ ID NO: 79 operably linked to a U6 promoter, a transcription initiator sequence comprising a single guanine residue and a terminator comprising six contiguous thymidine residues. In another example, the disclosure provides a ddRNAi construct comprising a sequence encoding a plurality of RNAs, wherein the ddRNAi construct comprises (i) a sequence encoding a shRNA comprising or consisting of a sequence set forth in Table 3 operably linked to a promoter e.g., a U6 promoter, and (ii) a sequence encoding at least one other RNA of the disclosure operably linked to a promoter. In one example, the sequence at (i) is linked to a terminator e.g., comprising at least five thymidine residues. In one example, the sequence at (i) is linked to a transcription initiator e.g., comprising a single guanine residue. In one example, the sequence at (i) is linked to a terminator e.g., comprising at least five thymidine residues, and linked to a transcription initiator e.g., comprising a single guanine residue. In one example, the sequence at (ii) is linked to a terminator e.g., comprising at least five thymidine residues. In one example, the sequence at (ii) is linked to a transcription initiator e.g., comprising a single guanine residue. In one example, the sequence at (ii) is linked to a terminator e.g., comprising at least five thymidine residues, and linked to a transcription initiator e.g., comprising a single guanine residue. In one example, the sequences at (i) and (ii) are each linked to a terminator e.g., comprising at least five thymidine residues. In one example, the sequences at (i) and (ii) are each linked to a transcription initiator e.g., comprising a single guanine residue. In one example, the sequences at (i) and (ii) are each linked to a terminator e.g., comprising at least five thymidine residues, and linked to a transcription initiator e.g., comprising a single guanine residue.

In one example, the disclosure provides a ddRNAi construct comprising a sequence encoding a plurality of RNAs, wherein the ddRNAi construct comprises: (i) a sequence encoding a shRNA comprising or consisting of the sequence set forth in SEQ ID NO: 92 operably linked to a U6 promoter, a transcription initiator sequence comprising a single guanine residue and a terminator comprising five contiguous thymidine residues; and (ii) a sequence encoding at least one other RNA of the disclosure operably linked to a promoter and a terminator comprising at least five thymidine residues and optionally a transcription initiator sequence. In one example, the present disclosure provides a ddRNAi construct comprising a sequence encoding a plurality of RNAs, wherein the ddRNAi construct comprises: (i) a sequence encoding a shRNA comprising or consisting of the sequence set forth in SEQ ID NO: 78 operably linked to a U6 promoter, a transcription initiator sequence comprising a single guanine residue and a terminator comprising six contiguous thymidine residues; and (ii) a sequence encoding at least one other RNA of the disclosure operably linked to a promoter and a terminator comprising at least five thymidine residues and optionally a transcription initiator sequence.

In one example, the present disclosure provides a ddRNAi construct comprising a sequence encoding a plurality of RNAs, wherein the ddRNAi construct comprises: (i) a sequence encoding a shRNA comprising or consisting of the sequence set forth in SEQ ID NO: 79 operably linked to a U6 promoter, a transcription initiator sequence comprising a single guanine residue and a terminator comprising six contiguous thymidine residues; and (ii) a sequence encoding at least one other RNA of the disclosure operably linked to a promoter and a terminator comprising at least five thymidine residues and optionally a transcription initiator sequence.

The present disclosure also provides a ddRNAi construct comprising a sequence encoding a plurality of RNAs, wherein the ddRNAi construct comprises:

(i) a sequence encoding a shRNA comprising or consisting of the sequence set forth in SEQ ID NO: 92 operably linked to a U6 promoter, a transcription initiator sequence comprising a single guanine residue and a terminator comprising five contiguous thymidine residues;

(ii) a sequence encoding a shRNA comprising or consisting of the sequence set forth in SEQ ID NO: 78 operably linked to a U6 promoter and a terminator comprising six contiguous thymidine residues; and (iii) a sequence encoding at least one other RNA of the disclosure operably linked to a promoter and a terminator comprising at least five thymidine residues and optionally a transcription initiator sequence.

In one example, the other RNA at (iii) is a shRNA set forth in Table 3 or 5.

The present disclosure also provides a ddRNAi comprising a sequence encoding a plurality of RNAs, wherein the ddRNAi construct comprises:

(i) a sequence encoding a shRNA comprising or consisting of the sequence set forth in SEQ ID NO: 78 operably linked to a U6 promoter and a terminator comprising six contiguous thymidine residues;

(ii) a sequence encoding a shRNA comprising or consisting of the sequence set forth in SEQ ID NO: 79 operably linked to a U6 promoter, a transcription initiator sequence comprising a single guanine residue and a terminator comprising six contiguous thymidine residues; and (iii) a sequence encoding a shRNA comprising or consisting of the sequence set forth in SEQ ID NO: 92 operably linked to a U6 promoter, a transcription initiator sequence comprising a single guanine residue and a terminator comprising five contiguous thymidine residues.

For example, the present disclosure provides a ddRNAi comprising a sequence encoding a plurality of RNAs, wherein the ddRNAi construct comprises, in a 5' to 3' direction:

(i) a sequence encoding a shRNA comprising or consisting of the sequence set forth in SEQ ID NO: 78 operably linked to a U6 promoter and a terminator comprising six contiguous thymidine residues;

(ii) a sequence encoding a shRNA comprising or consisting of the sequence set forth in SEQ ID NO: 79 operably linked to a U6 promoter, a transcription initiator sequence comprising a single guanine residue and a terminator comprising six contiguous thymidine residues; and (iii) a sequence encoding a shRNA comprising or consisting of the sequence set forth in SEQ ID NO: 92 operably linked to a U6 promoter, a transcription initiator sequence comprising a single guanine residue and a terminator comprising five contiguous thymidine residues.

An exemplary ddRNAi construct of the disclosure encoding a plurality of RNAs comprises a sequence set forth in SEQ ID NO: 105.

The present disclosure also provides a ddRNAi comprising a sequence encoding a plurality of RNAs, wherein the ddRNAi construct comprises:

(i) a sequence encoding a shRNA comprising or consisting of the sequence set forth in SEQ ID NO: 78 operably linked to a U6 promoter and a terminator comprising six contiguous thymidine residues;

(ii) a sequence encoding a shRNA comprising or consisting of the sequence set forth in SEQ ID NO: 101 operably linked to a U6 promoter, a transcription initiator sequence comprising a single guanine residue and a terminator comprising five contiguous thymidine residues; and (iii) a sequence encoding a shRNA comprising or consisting of the sequence set forth in SEQ ID NO: 92 operably linked to a U6 promoter, a transcription initiator sequence comprising a single guanine residue and a terminator comprising five thymidine residues.

For example, the present disclosure provides a ddRNAi comprising a sequence encoding a plurality of RNAs, wherein the ddRNAi construct comprises, in a 5' to 3' direction:

(i) a sequence encoding a shRNA comprising or consisting of the sequence set forth in SEQ ID NO: 78 operably linked to a U6 promoter and a terminator comprising six contiguous thymidine residues;

(ii) a sequence encoding a shRNA comprising or consisting of the sequence set forth in SEQ ID NO: 101 operably linked to a U6 promoter, a transcription initiator sequence comprising a single guanine residue and a terminator comprising five contiguous thymidine residues; and (iii) a sequence encoding a shRNA comprising or consisting of the sequence set forth in SEQ ID NO: 92 operably linked to a U6 promoter, a transcription initiator sequence comprising a single guanine residue and a terminator comprising five thymidine residues.

An exemplary ddRNAi construct of the disclosure encoding a plurality of RNAs comprises a sequence set forth in SEQ ID NO: 106.

In another example, the disclosure provides a ddRNAi construct comprising a sequence encoding a plurality of RNAs, wherein the ddRNAi construct comprises (i) a sequence encoding a shRNA comprising or consisting of a sequence set forth in Table 3 operably linked to a promoter e.g., a U6 promoter, and (ii) a sequence encoding at least one other RNA of the disclosure operably linked to a promoter. In one example, the sequence at (i) is linked to a terminator e.g., comprising at least five thymidine residues. In one example, the sequence at (i) is linked to a transcription initiator e.g., comprising a single guanine residue. In one example, the sequence at (i) is linked to a terminator e.g., comprising at least five thymidine residues, and linked to a transcription initiator e.g., comprising a single guanine residue. In one example, the sequence at (ii) is linked to a terminator e.g., comprising at least five thymidine residues. In one example, the sequence at (ii) is linked to a transcription initiator e.g., comprising a single guanine residue. In one example, the sequence at (ii) is linked to a terminator e.g., comprising at least five thymidine residues, and linked to a transcription initiator e.g., comprising a single guanine residue. In one example, the sequences at (i) and (ii) are each linked to a terminator e.g., comprising at least five thymidine residues. In one example, the sequences at (i) and (ii) are each linked to a transcription initiator e.g., comprising a single guanine residue. In one example, the sequences at (i) and (ii) are each linked to a terminator e.g., comprising at least five thymidine residues, and linked to a transcription initiator e.g., comprising a single guanine residue.

In one example, the disclosure provides a ddRNAi construct comprising a sequence encoding a plurality of RNAs, wherein the ddRNAi construct comprises: (i) a sequence encoding a shRNA comprising or consisting of the sequence set forth in SEQ ID NO: 92 operably linked to a U6 promoter, a transcription initiator sequence comprising a single guanine residue and a terminator comprising five contiguous thymidine residues; and (ii) a sequence encoding at least one other RNA of the disclosure operably linked to a promoter and a terminator comprising at least five thymidine residues and optionally a transcription initiator sequence. In one example, the present disclosure provides a ddRNAi construct comprising a sequence encoding a plurality of RNAs, wherein the ddRNAi construct comprises: (i) a sequence encoding a shRNA comprising or consisting of the sequence set forth in SEQ ID NO: 78 operably linked to a U6 promoter, a transcription initiator sequence comprising a single guanine residue and a terminator comprising six contiguous thymidine residues; and (ii) a sequence encoding at least one other RNA of the disclosure operably linked to a promoter and a terminator comprising at least five thymidine residues and optionally a transcription initiator sequence.

In one example, the present disclosure provides a ddRNAi construct comprising a sequence encoding a plurality of RNAs, wherein the ddRNAi construct comprises: (i) a sequence encoding a shRNA comprising or consisting of the sequence set forth in SEQ ID NO: 79 operably linked to a U6 promoter, a transcription initiator sequence comprising a single guanine residue and a terminator comprising six contiguous thymidine residues; and (ii) a sequence encoding at least one other RNA of the disclosure operably linked to a promoter and a terminator comprising at least five thymidine residues and optionally a transcription initiator sequence. In another example, the present disclosure provides a plurality of ddRNAi constructs each encoding a RNA i.e., capable of eliciting RNAi, wherein at least one of the ddRNAi constructs in the plurality is a ddRNAi construct comprising a sequence encoding a RNA of the disclosure. For example, at least one ddRNAi construct of the plurality comprises a sequence encoding a shRNA described in Table 3 operably linked to a promoter e.g., a U6 promoter. In one example, the present disclosure provides a plurality of ddRNAi constructs comprising two or more ddRNAi constructs, each comprising a sequence encoding a RNA of the disclosure. For example, each ddRNAi construct of the plurality may comprise a sequence encoding a shRNA described in Table 3 operably linked to a promoter e.g., a U6 promoter.

In one example, the plurality of ddRNAi constructs comprises:

(i) a ddRNAi construct comprising a sequence encoding a shRNA comprising or consisting of the sequence set forth in SEQ ID NO: 92 operably linked to a U6 promoter, a transcription initiator sequence comprising a single guanine residue and a terminator sequence comprising five contiguous thymidine residues; and (ii) a ddRNAi construct comprising a sequence encoding at least one other RNA of the disclosure operably linked to a promoter and a terminator comprising at least five thymidine residues and optionally a transcription initiator sequence; or (iii) a ddRNAi construct comprising a sequence encoding a shRNA comprising or consisting of the sequence set forth in SEQ ID NO: 101 operably linked to a U6 promoter, a transcription initiator sequence comprising a single guanine residue and a terminator comprising five contiguous thymidine residues.

In one example, the plurality of ddRNAi constructs comprises:

(i) a ddRNAi construct comprising a sequence encoding a shRNA comprising or consisting of the sequence set forth in SEQ ID NO: 78 operably linked to a U6 promoter and a terminator comprising six contiguous thymidine residues; and (ii) a ddRNAi construct comprising a sequence encoding at least one other RNA of the disclosure operably linked to a promoter and a terminator comprising at least five thymidine residues and optionally a transcription initiator sequence; or (iii) a ddRNAi construct comprising a sequence encoding a shRNA comprising or consisting of the sequence set forth in SEQ ID NO: 101 operably linked to a U6 promoter, a transcription initiator sequence comprising a single guanine residue and a terminator comprising five contiguous thymidine residues.

In another example, the plurality of ddRNAi constructs comprises:

(i) a ddRNAi construct comprising a sequence encoding a shRNA comprising or consisting of the sequence set forth in SEQ ID NO: 79 operably linked to a U6 promoter, a transcription initiator sequence comprising a single guanine residue and a terminator comprising six contiguous thymidine residues; and (ii) a ddRNAi construct comprising a sequence encoding at least one other RNA of the disclosure operably linked to a promoter and a terminator comprising at least five thymidine residues and optionally a transcription initiator sequence; or (iii) a ddRNAi construct comprising a sequence encoding a shRNA comprising or consisting of the sequence set forth in SEQ ID NO: 101 operably linked to a U6 promoter, a transcription initiator sequence comprising a single guanine residue and a terminator comprising five contiguous thymidine residues.

The present disclosure also provides a plurality of ddRNAi constructs, wherein the plurality comprises:

(i) a ddRNAi construct comprising a sequence encoding a shRNA comprising or consisting of the sequence set forth in SEQ ID NO: 92 operably linked to a U6 promoter, a transcription initiator sequence comprising a single guanine residue and a terminator comprising five contiguous thymidine residues;

(ii) a ddRNAi construct comprising a sequence encoding a shRNA comprising or consisting of the sequence set forth in SEQ ID NO: 78 operably linked to a U6 promoter and a terminator comprising six contiguous thymidine residues; and (iii) a ddRNAi construct comprising a sequence encoding at least one other RNA of the disclosure operably linked to a promoter and a terminator comprising at least five thymidine residues and optionally a transcription initiator sequence.

The present disclosure also provides a plurality of ddRNAi constructs, wherein the plurality comprises:

(i) a ddRNAi construct comprising a sequence encoding a shRNA comprising or consisting of the sequence set forth in SEQ ID NO: 92 operably linked to a U6 promoter, a transcription initiator sequence comprising a single guanine residue and a terminator comprising five contiguous thymidine residues;

(ii) a ddRNAi construct comprising a sequence encoding a shRNA comprising or consisting of the sequence set forth in SEQ ID NO: 78 operably linked to a U6 promoter and a terminator comprising six contiguous thymidine residues; and (iii) a ddRNAi construct comprising a sequence encoding a shRNA comprising or consisting of the sequence set forth in SEQ ID NO: 79 operably linked to a U6 promoter, a transcription initiator sequence comprising a single guanine residue and a terminator comprising six contiguous thymidine residues.

The present disclosure also provides a plurality of ddRNAi constructs, wherein the plurality comprises:

(i) a ddRNAi construct comprising a sequence encoding a shRNA comprising or consisting of the sequence set forth in SEQ ID NO: 92 operably linked to a U6 promoter, a transcription initiator sequence comprising a single guanine residue and a terminator comprising five thymidine residues;

(ii) a ddRNAi construct comprising a sequence encoding a shRNA comprising or consisting of the sequence set forth in SEQ ID NO: 78 operably linked to a U6 promoter and a terminator comprising six contiguous thymidine residues; and (iii) a ddRNAi construct comprising a sequence encoding a shRNA comprising or consisting of the sequence set forth in SEQ ID NO: 101 operably linked to a U6 promoter, a transcription initiator sequence comprising a single guanine residue and a terminator comprising five contiguous thymidine residues.

In addition, the or each ddRNAi construct can comprise one or more multiple cloning sites and/or unique restriction sites that are located strategically, such that the promoter, RNA encoding sequence and/or terminator elements are easily removed or replaced. The or each ddRNAi construct can be assembled from smaller oligonucleotide components using strategically located restriction sites and/or complementary sticky ends. The base vector for one approach according to the present disclosure comprises plasmids with a multilinker in which all sites are unique (though this is not an absolute requirement). Sequentially, each promoter is inserted between its designated unique sites resulting in a base cassette with one or more promoters, all of which can have variable orientation. Sequentially, again, annealed primer pairs are inserted into the unique sites downstream of each of the individual promoters, resulting in a single-, double- or multiple-expression cassette construct. The insert can be moved into, e.g. an AdV backbone using two unique restriction enzyme sites (the same or different ones) that flank the single-, double- or multiple-expression cassette insert.

Generation of the or each construct can be accomplished using any suitable genetic engineering techniques known in the art, including without limitation, the standard techniques of PCR, oligonucleotide synthesis, restriction endonuclease digestion, ligation, transformation, plasmid purification, and DNA sequencing. If the or each construct is a viral construct, the construct comprises, for example, sequences necessary to package the ddRNAi construct into viral particles and/or sequences that allow integration of the ddRNAi construct into the target cell genome. In some examples, the or each viral construct additionally contains genes that allow for replication and propagation of virus, however such genes will be supplied in trans. Additionally, the or each viral construct cam contain genes or genetic sequences from the genome of any known organism incorporated in native form or modified. For example, a viral construct may comprise sequences useful for replication of the construct in bacteria.

The or each construct also may contain additional genetic elements. The types of elements that may be included in the construct are not limited in any way and may be chosen by one with skill in the art. For example, additional genetic elements may include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines.

Other genetic elements that may find use in embodiments of the present disclosure include those coding for proteins which confer a selective growth advantage on cells such as adenosine deaminase, aminoglycodic phosphotransferase, dihydrofolate reductase, hygromycin-B-phosphotransferase, drug resistance, or those genes coding for proteins that provide a biosynthetic capability missing from an auxotroph. If a reporter gene is included along with the or each construct, an internal ribosomal entry site (IRES) sequence can be included. In one example, the additional genetic elements are operably linked with and controlled by an independent promoter/enhancer. In addition a suitable origin of replication for propagation of the construct in bacteria may be employed. The sequence of the origin of replication generally is separated from the ddRNAi construct and other genetic sequences. Such origins of replication are known in the art and include the pUC, ColE1, 2-micron or SV40 origins of replication.

Expression Constructs

In one example, a ddRNAi construct of the disclosure is included within an expression construct.

In one example, the expression construct is an expression vector.

In one example, the expression vector is a plasmid, e.g., as is known in the art. In one example, a suitable plasmid expression vector is a pSsh vector e.g., with a U6 promoter and proximal sequence element 7 (PSE7).

In one example, the expression vector is mini-circle DNA. Mini-circle DNA is described in U.S. Patent Publication No. 2004/0214329. Mini-circle DNA are useful for persistently high levels of nucleic acid transcription. The circular vectors are characterized by being devoid of expression-silencing bacterial sequences. For example, mini-circle vectors differ from bacterial plasmid vectors in that they lack an origin of replication, and lack drug selection markers commonly found in bacterial plasmids, e.g. β-lactamase, tet, and the like. Consequently, minicircle DNA becomes smaller in size, allowing more efficient delivery.

In one example, the expression vector is a viral vector.

A viral vector based on any appropriate virus may be used to deliver a ddRNAi of the disclosure. In addition, hybrid viral systems may be of use. The choice of viral delivery system will depend on various parameters, such as the tissue targeted for delivery, transduction efficiency of the system, pathogenicity, immunological and toxicity concerns, and the like.

Commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses). In one example, a viral vector of the disclosure integrates into a host cell's chromatin. In another example, a viral vector of the disclosure persists in a host cell's nucleus as an extrachomosomal episome.

In one example, a viral vector is an adenoviral (AdV) vector. Adenoviruses are medium-sized double-stranded, non-enveloped DNA viruses with linear genomes that is between 26-48 Kbp. Adenoviruses gain entry to a target cell by receptor-mediated binding and internalization, penetrating the nucleus in both non-dividing and dividing cells. Adenoviruses are heavily reliant on the host cell for survival and replication and are able to replicate in the nucleus of vertebrate cells using the host's replication machinery.

In one example, a viral vector is from the Parvoviridae family. The Parvoviridae is a family of small single-stranded, non-enveloped DNA viruses with genomes approximately 5000 nucleotides long. Included among the family members is adeno-associated virus (AAV). In one example, a viral vector of the disclosure is an AAV. AAV is a dependent parvovirus that generally requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells. Because progeny virus is not produced from AAV infection in the absence of helper virus, the extent of transduction is restricted only to the initial cells that are infected with the virus. It is this feature which makes AAV a desirable vector for the present disclosure. Furthermore, unlike retrovirus, adenovirus, and herpes simplex virus, AAV appears to lack human pathogenicity and toxicity (Kay, et al., *Nature*. 424: 251 (2003)). Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as shRNA.

Another viral delivery system useful with the ddRNAi constructs of the disclosure is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some examples, a viral vector is a lentivirus. Lentivirus vectors are often pseudotyped with vesicular steatites virus glycoprotein (VSV-G), and have been derived from the human immunodeficiency virus (HIV); visan-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain<5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization. One of the main advantages to the use of lentiviral vectors is that gene transfer is persistent in most tissues or cell types, even following cell division of the transduced cell.

A lentiviral-based construct used to express a RNA of the disclosure comprises sequences from the 5' and 3' long terminal repeats (LTRs) of a lentivirus. In one example, the viral construct comprises an inactivated or self-inactivating 3' LTR from a lentivirus. The 3' LTR may be made self-inactivating by any method known in the art. For example, the U3 element of the 3' LTR contains a deletion of its enhancer sequence, e.g., the TATA box, Sp1 and NF-kappa B sites. As a result of the self-inactivating 3' LTR, the provirus that is integrated into the host genome will comprise an inactivated 5' LTR. The LTR sequences may be LTR sequences from any lentivirus from any species. The lentiviral-based construct also may incorporate sequences for MMLV or MSCV, RSV or mammalian genes. In addition, the U3 sequence from the lentiviral 5' LTR may be replaced with a promoter sequence in the viral construct. This may increase the titer of virus recovered from the packaging cell line. An enhancer sequence may also be included.

Other viral or non-viral systems known to those skilled in the art may be used to deliver the ddRNAi or nucleic acid of the present disclosure to cells of interest, including but not limited to gene-deleted adenovirus-transposon vectors (see Yant, et al., Nature Biotech. 20:999-1004 (2002)); systems derived from Sindbis virus or Semliki forest virus (see Perri, et al, J. Virol. 74(20):9802-07 (2002)); systems derived from Newcastle disease virus or Sendai virus.

Testing a RNA or ddRNAi Construct of the Disclosure
Cell Culture Models

HBV does not infect cells in culture. However, transfection of HBV DNA (either as a head-to-tail dimer or as an "overlength" genome of >100%) into HuH7 or Hep G2 hepatocytes results in viral gene expression and production of HBV virions released into the media. An example of such a cell line is HepG2.2.15, which is a sub-cell line of the HepG2 human hepatocellular carcinoma cell line which stably harbors the complete HBV genome (serotype ayw, genotype D). HepG2.2.15 expresses all HBV viral RNA and proteins, produce viral genomes, and secretes virus-like particles. As exemplified herein, activity of a RNA of the disclosure is determined by administering the RNA to the cell and subsequently measuring the level of expression of a RNA or protein encoded by the HBV genome. Intracellular HBV gene expression can be assayed either by a Taqman™ assay or other real time PCR assay for HBV RNA or by ELISA for HBV protein. Extracellular virus can be assayed either by PCR for DNA or ELISA for protein. Antibodies are commercially available for HBV surface antigen and core protein. Various means for normalizing differences in transfection efficiency and sample recovery are known in the art. Recent advances in cell culture systems using primary human hepatocytes show promise for determining the activity of HBV therapeutics.

A RNA of the disclosure that reduces expression of a RNA or protein encoded by the HBV genome by at least 50% compared to in the absence of the RNA of the disclosure is considered to be useful in a method of the disclosure.

Animal Models

There are several small animal models available to study HBV replication. One is the transplantation of HBV-infected liver tissue into irradiated mice. Viremia (as evidenced by measuring HBV DNA by PCR) is first detected 8 days after transplantation and peaks between 18-25 days (Ilan et al., 1999, Hepatology, 29, 553-562).

Transgenic mice that express HBV have also been used as a model to evaluate potential anti-virals. HBV DNA is detectable in both liver and serum of the transgenic mice (Morrey et al., Antiviral Res., 42, 97-108, 1999).

An additional model is to establish subcutaneous tumors in nude mice with Hep G2 cells transfected with HBV. Tumors develop in about 2 weeks after inoculation and express HBV surface and core antigens. HBV DNA and surface antigen are also detected in the circulation of tumor-bearing mice (Yao et al., J. Viral Hepat., 3, 19-22, 1996).

An additional model is to use is the PXB mouse, a chimeric group of mice in which immunodeficient mice that have liver disease (uPA/SCID) have been transplanted with human hepatocytes. Because the uPA/SCID mice exhibit significant liver toxicity, transplanting healthy human cells can result in the production of a mouse with a healthy and functional liver that has been 70 to 90 percent repopulated by human hepatocytes. Because PXB mice exhibit normal histological structures in the liver and exhibit many of the hallmark of human liver cells, the mice can sustain active HBV infection in the chimeric hepatic tissues.

An additional model is the use of the Quantum B model which is a 3 dimensional cell culture platform in which the human hepatocytes supplied into the model, assemble in such a way that mimics the architecture and physiology of the human liver. Because the model is solely comprised of liver hepatocytes, it is thought to be the first long term stable fully human full viral lifecycle model of Hepatitis B and recapitulates some critical features of the HBV infectious life cycle.

Any of the foregoing animal models can be used to determine the efficacy of a RNA of the disclosure in treating or reducing a HBV infection.

Carriers

In some examples, a RNA or ddRNAi or expression construct of the disclosure is in a composition with a carrier.

In some examples, the carrier is a lipid-based carrier, cationic lipid, or liposome nucleic acid complex, a liposome, a micelle, a virosome, a lipid nanoparticle or a mixture thereof.

In some examples, the carrier is a polymer-based carrier such as a cationic polymer-nucleic acid complex.

In a further example, the carrier is a cyclodextrin-based carrier such as a cyclodextrin polymer-nucleic acid complex.

In a further example, the carrier is a protein-based carrier such as a cationic peptide-nucleic acid complex.

In another example, the carrier is a lipid nanoparticle. Exemplary nanoparticles are described, for example, in U.S. Pat. No. 7,514,099.

In some examples, a RNA or ddRNAi or expression construct of the disclosure is formulated with a lipid nanoparticle composition comprising a cationic lipid/Cholesterol/PEG-C-DMA/DSPC (e.g., in a 40/48/2/10 ratio), a cationic lipid/Cholesterol/PEG-DMG/DSPC (e.g., in a 40/48/2/10 ratio), or a cationic lipid/Cholesterol/PEG-DMG (e.g., in a 60/38/2 ratio). In some examples, the cationic lipid is Octyl CL in DMA, DL in DMA, L-278, DLinKC2DMA, or MC3.

In another example, a RNA or ddRNAi or expression construct of the disclosure is formulated with any of the cationic lipid formulations described in WO 2010/021865; WO 2010/080724; WO 2010/042877; WO 2010/105209 or WO 2011/022460.

In another example, a RNA or ddRNAi or expression construct of the disclosure is conjugated to or complexed with another compound, e.g., to facilitate delivery of the RNA or ddRNAi or expression construct. Non-limiting, examples of such conjugates are described in US 2008/0152661 and US 2004/0162260 (e.g., CDM-LBA, CDM-Pip-LBA, CDM-PEG, CDM-NAG, etc.).

In another example, polyethylene glycol (PEG) is covalently attached to a RNA or ddRNAi or expression construct of the disclosure. The attached PEG can be any molecular weight, e.g., from about 100 to about 50,000 daltons (Da).

In yet other example, a RNA or ddRNAi or expression construct of the disclosure is formulated with a carrier comprising surface-modified liposomes containing poly (ethylene glycol) lipids (PEG-modified, or long-circulating liposomes or stealth liposomes), such as is disclosed in for example, WO 96/10391; WO 96/10390; or WO 96/10392.

In some examples, a RNA or ddRNAi or expression construct of the disclosure can also be formulated or complexed with polyethyleneimine or a derivative thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one example, a RNA or ddRNAi or expression construct of the disclosure is formulated as described in U.S. Patent Application Publication No. 2003/0077829.

In other examples, a RNA or ddRNAi or expression construct of the disclosure is complexed with membrane disruptive agents such as those described in U.S. Patent Application Publication No. 2001/0007666.

Other carriers include cyclodextrins (see for example, Gonzalez et al., 1999, *Bioconjugate Chem.*, 10, 1068-1074; or WO 03/46185), poly(lactic-co-glycolic)acid (PLGA) and PLCA microspheres (see for example US 2002130430).

Compositions and Methods of Treatment

A RNA or ddRNAi or expression construct of the disclosure is used in compositions for preventing or treating HBV infection. The therapeutic compositions of the disclosure may be used alone or in combination with one or more materials, including other antiviral agents. Currently, lamivudine, adefovir dipivoxil, and interferon alpha have been approved for treatment of HBV. Since a RNA or ddRNAi or expression construct of the disclosure act against HBV through a different mechanism to other approved drugs, combination therapy of the agents of the disclosure and other antivirals is expected to significantly increase the efficacy of therapy while substantially reducing the development of drug resistance, e.g., the development of lamivudine resistance, a problem of major concern with long term lamivudine therapy.

Compositions will desirably include materials that increase the biological stability of the RNA or ddRNAi or expression construct of the disclosure and/or materials that increase the ability of the compositions to penetrate hepatocytes selectively. The therapeutic compositions of the disclosure may be administered in pharmaceutically acceptable carriers (e.g., physiological saline), which are selected on the basis of the mode and route of administration, and standard pharmaceutical practice. One having ordinary skill in the art can readily formulate a pharmaceutical composition that comprises a RNA or ddRNAi or expression construct of the disclosure. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some examples, a vasoconstriction agent is added to the formulation. The compositions according to the present disclosure are provided sterile and pyrogen free. Suitable pharmaceutical carriers, as well as pharmaceutical necessities for use in pharmaceutical formulations, are described in Remington: The Science and Practice of Pharmacy (formerly Remington's Pharmaceutical Sciences), Mack Publishing Co., a standard reference text in this field, and in the USP/NF.

Routes of administration include, but are not limited to, intramuscular, intraperitoneal, intradermal, subcutaneous, intravenous, intrathecal, intraarterially, intraoccularly and oral as well as transdermal or by inhalation or suppository. Exemplary routes of administration include intravenous, intramuscular, oral, intraperitoneal, intradermal, intraarterial and subcutaneous injection. Targeted transfection of hepatocytes in vivo for delivery of a RNA or ddRNAi or expression construct of the disclosure may be accomplished through IV injection with a composition comprising a DNA or RNA expression vector as described herein complexed with a mixture (e.g., a 35%/65% ratio) of a lactosyl spermine (mono or trilactosylated) and cholesteryl spermine (containing spermine to DNA at a charge ratio of 0.8). Such compositions are useful for pharmaceutical applications and may readily be formulated in a suitable sterile, non-pyrogenic vehicle, e.g., buffered saline for injection, for parenteral administration, e.g., IV (including IV infusion), IM, SC, and for intraperitoneal administration. In certain compositions, a ddRNAi construct of the disclosure complexed with an endosomolytic spermine such cholesteryl spermine alone, without a targeting spermine; some routes of administration, such as intraperitoneal injection or infusion, may achieve effective hepatic delivery and transfection of a ddRNAi construct, and expression of RNA.

Intraperitoneal administration (e.g., ultrasound guided intraperitoneal injection) of a sterile pharmaceutical composition comprising a RNA or ddRNAi or expression construct of the disclosure in a specially formulated delivery vehicle may be an advantageous route of delivery to promote uptake by liver cells, including hepatocytes.

The volume, concentration, and formulation of the pharmaceutical composition as well as the dosage regimen may be tailored specifically to maximize cellular delivery while minimizing toxicity such as an inflammatory response. E.g, relatively large volumes (5, 10, 20, 50 ml or more) with corresponding low concentrations of active ingredients, as well as the inclusion of an anti-inflammatory compound such as a corticosteroid, may be utilized if desired.

In HBV infected individuals it is anticipated that a RNA or ddRNAi or expression construct of the disclosure is useful as a pre-treatment in conjunction with therapeutic vaccination protocols designed to boost immunity against the virus. It is also anticipated that the RNA or ddRNAi or expression construct of the disclosure is useful for prophylaxis in a regimen of periodic administrations to individuals who because of occupational or other potential for exposure are considered at high risk of exposure to HBV.

Kits

The present disclosure also provides a RNA or ddRNAi or expression construct of the disclosure in a kit. The kit may comprise a container. The kit typically contains a RNA or ddRNAi or expression construct of the disclosure with instructions for its administration. In some examples, the kit contains more than one RNA or ddRNAi or expression construct of the disclosure and/or another RNA or ddRNAi or expression construct of the disclosure.

TABLE 1

Target regions within HBV genome

| Region ID | Region sequence (5'-3') | SEQ ID NO: |
|---|---|---|
| Region 1 | CATCCTGCTGCTATGCCTCA | SEQ ID NO: 1 |
| Region 2 | TTTGCTGACGCAACCCCCACTGG | SEQ ID NO: 2 |
| Region 3 | AAGCCTCCAAGCTGTGCCTT | SEQ ID NO: 3 |
| Region 4 | GCAGGTCCCCTAGAAGAAGAACTCCCTCGCCTCA | SEQ ID NO: 4 |
| Region 5 | CAAGGTATGTTGCCCGTTTGTCC | SEQ ID NO: 5 |
| Region 6 | CTCGTGGTGGACTTCTCTCA | SEQ ID NO: 6 |
| Region 7 | CTCGTGTTACAGGCGGGGTTTTT | SEQ ID NO: 7 |
| Region 8 | CCGTGTGCACTTCGCTTCACCTCTGCACGT | SEQ ID NO: 8 |
| Region 9 | TACGTCCCGTCGGCGCTGAATC | SEQ ID NO: 9 |
| Region 10 | AAATGCCCCTATCTTATCA | SEQ ID NO: 10 |

TABLE 2

RNAs duplexes

| shRNA ID | Effector (5'-3') | SEQ ID NO: | Effector complement (5'-3') | SEQ ID NO: |
|---|---|---|---|---|
| shRNA1 | UGAGGCAUAGCAGCAGGAUG | SEQ ID NO: 11 | CAUCCUGCUGCUAUGCCUCA | SEQ ID NO: 12 |
| shRNA2 | GAUGAGGCAUAGCAGCAGGA | SEQ ID NO: 13 | UCCUGCUGCUAUGCCUCAUC | SEQ ID NO: 14 |
| shRNA3 | GAGGCAUAGCAGCAGGAUGC | SEQ ID NO: 15 | GCAUCCUGCUGCUAUGCCUC | SEQ ID NO: 16 |
| shRNA4 | UGAGGCAUAGCAGCAGGAUG | SEQ ID NO: 11 | CAUCCUGCUGCUAUGCCUCA | SEQ ID NO: 12 |
| shRNA5 | CCAGUGGGGUUGCGUCAGC | SEQ ID NO: 17 | GCUGACGCAACCCCCACUGG | SEQ ID NO: 18 |
| shRNA6 | CCAGUGGGGUUGCGUCAGC | SEQ ID NO: 17 | GCUGACGCAACCCCCACUGG | SEQ ID NO: 18 |
| shRNA7 | AAGGCACAGCUUGGAGGCUU | SEQ ID NO: 19 | AAGCCUCCAAGCUGUGCCUU | SEQ ID NO: 20 |
| shRNA8 | AAGGCACAGCUUGGAGGCUU | SEQ ID NO: 19 | AAGCCUCCAAGCUGUGCCUU | SEQ ID NO: 20 |
| shRNA9 | GAGUUCUUCUUCUAGGGGACC | SEQ ID NO: 21 | GGUCCCCUAGAAGAAGAACUC | SEQ ID NO: 22 |
| shRNA10 | GAGUUCUUCUUCUAGGGGACC | SEQ ID NO: 21 | GGUCCCCUAGAAGAAGAACUC | SEQ ID NO: 22 |
| shRNA11 | GAGGGAGUUCUUCUUCUAGGG | SEQ ID NO: 23 | CCCUAGAAGAAGAACUCCCUC | SEQ ID NO: 24 |
| shRNA12 | GAGGGAGUUCUUCUUCUAGGG | SEQ ID NO: 23 | CCCUAGAAGAAGAACUCCCUC | SEQ ID NO: 24 |
| shRNA13 | GCGAGUUCUUCUUCUAGGGGA | SEQ ID NO: 25 | UCCCCUAGAAGAAGAACUCGC | SEQ ID NO: 26 |
| shRNA14 | UUCUUCUUCUAGGGGACCUGC | SEQ ID NO: 27 | GCAGGUCCCCUAGAAGAAGAA | SEQ ID NO: 28 |
| shRNA15 | ACAAACGGGCAACAUACCUUG | SEQ ID NO: 29 | CAAGGUAUGUUGCCCGUUUGU | SEQ ID NO: 30 |
| shRNA16 | GGACAAACGGGCAACAUACCU | SEQ ID NO: 31 | AGGUAUGUUGCCCGUUUGUCC | SEQ ID NO: 32 |
| shRNA17 | GACAAACGGGCAACAUACCUU | SEQ ID NO: 33 | AAGGUAUGUUGCCCGUUUGUC | SEQ ID NO: 34 |
| shRNA18 | ACAAACGGGCAACAUACCUUG | SEQ ID NO: 29 | CAAGGUAUGUUGCCCGUUUGU | SEQ ID NO: 30 |
| shRNA19 | UGAGAGAAGUCCACCACGAG | SEQ ID NO: 35 | CUCGUGGUGGACUUCUCUCA | SEQ ID NO: 36 |
| shRNA20 | UGAGAGAAGUCCACCACGAG | SEQ ID NO: 35 | CUCGUGGUGGACUUCUCUCA | SEQ ID NO: 36 |

TABLE 2-continued

RNAs duplexes

| shRNA ID | Effector (5'-3') | SEQ ID NO: | Effector complement (5'-3') | SEQ ID NO: |
|---|---|---|---|---|
| shRNA21 | AUUGAGAGAAGUCCACCACG | SEQ ID NO: 37 | CGUGGUGGACUUCUCUCAAU | SEQ ID NO: 38 |
| shRNA22 | AGAGAAGUCCACCACGAGUC | SEQ ID NO: 39 | GACUCGUGGUGGACUUCUCU | SEQ ID NO: 40 |
| shRNA23 | AAACCCCGCCUGUAACACGAG | SEQ ID NO: 41 | CUCGUGUUACAGGCGGGGUUU | SEQ ID NO: 42 |
| shRNA24 | AAACCCCGCCUGUAACACGAG | SEQ ID NO: 41 | CUCGUGUUACAGGCGGGGUUU | SEQ ID NO: 42 |
| shRNA25 | UGCAGAGGUGAAGCGAAGUGC | SEQ ID NO: 43 | GCACUUCGCUUCACCUCUGCA | SEQ ID NO: 44 |
| shRNA26 | UGCAGAGGUGAAGCGAAGUGC | SEQ ID NO: 43 | GCACUUCGCUUCACCUCUGCA | SEQ ID NO: 44 |
| shRNA27 | GAUUCAGCGCCGACGGGACGU | SEQ ID NO: 45 | ACGUCCCGUCGGCGCUGAAUC | SEQ ID NO: 46 |
| shRNA28 | GGAUUCAGCGCCGACGGGACG | SEQ ID NO: 47 | CGUCCCGUCGGCGCUGAAUCC | SEQ ID NO: 48 |
| shRNA29 | AUUCAGCGCCGACGGGACGUA | SEQ ID NO: 49 | UACGUCCCGUCGGCGCUGAAU | SEQ ID NO: 50 |
| shRNA30 | GAUUCAGCGCCGACGGGACGU | SEQ ID NO: 45 | ACGUCCCGUCGGCGCUGAAUC | SEQ ID NO: 46 |
| shRNA31 | GGAUUCAGCGCCGACGGGACG | SEQ ID NO: 47 | CGUCCCGUCGGCGCUGAAUCC | SEQ ID NO: 48 |
| shRNA32 | AUUCAGCGCCGACGGGACGUA | SEQ ID NO: 49 | UACGUCCCGUCGGCGCUGAAU | SEQ ID NO: 50 |
| shRNA33 | UGAUAAGAUAGGGGCAUUU | SEQ ID NO: 51 | AAAUGCCCCUAUCUUAUCA | SEQ ID NO: 52 |
| shRNA34 | UGAUAAGAUAGGGGCAUUU | SEQ ID NO: 51 | AAAUGCCCCUAUCUUAUCA | SEQ ID NO: 52 |

TABLE 3 shRNAs

| shRNA ID | shRNA sequence (5'-3') | SEQ ID NO: |
|---|---|---|
| shRNA1 | CAUCCUGCUGCUAUGCCUCACAAGAGAUGAGGCAUAGCAGCAGGAUG | SEQ ID NO: 65 |
| shRNA2 | UCCUGCUGCUAUGCCUCAUCCAAGAGAGAUGAGGCAUAGCAGCAGGA | SEQ ID NO: 66 |
| shRNA3 | GCAUCCUGCUGCUAUGCCUCCAAGAGAGAGGCAUAGCAGCAGGAUGC | SEQ ID NO: 67 |
| shRNA4 | UGAGGCAUAGCAGCAGGAUGCAAGAGACAUCCUGCUGCUAUGCCUCA | SEQ ID NO: 68 |
| shRNA5 | GCUGACGCAACCCCCACUGGCAAGAGACCAGUGGGGGUUGCGUCAGC | SEQ ID NO: 69 |
| shRNA6 | CCAGUGGGGGUUGCGUCAGCCAAGAGAGCUGACGCAACCCCCACUGG | SEQ ID NO: 70 |
| shRNA7 | AAGCCUCCAAGCUGUGCCUUUGUGCUUAAGGCACAGCUUGGAGGCUU | SEQ ID NO: 71 |
| shRNA8 | AAGGCACAGCUUGGAGGCUUUGUGCUUAAGCCUCCAAGCUGUGCCUU | SEQ ID NO: 72 |
| shRNA9 | GGUCCCUAGAAGAAGAACUCCAAGAGAGAGUUCUUCUUCUAGGGGACC | SEQ ID NO: 73 |
| shRNA10 | GAGUUCUUCUUCUAGGGGACCCAAGAGAGGUCCCCUAGAAGAAGAACUC | SEQ ID NO: 74 |
| shRNA11 | CCCUAGAAGAAGAACUCCUCCAAGAGAGAGGGAGUUCUUCUUCUAGGG | SEQ ID NO: 75 |
| shRNA12 | GAGGGAGUUCUUCUUCUAGGGCAAGAGACCCUAGAAGAAGAACUCCCUC | SEQ ID NO: 76 |
| shRNA13 | UCCCUAGAAGAAGAACUCGCCAAGAGAGCGAGUUCUUCUUCUAGGGA | SEQ ID NO: 77 |
| shRNA14 | GCAGGUCCCCUAGAAGAAGAACAAGAGAUUCUUCUUCUAGGGGACCUGC | SEQ ID NO: 78 |
| shRNA15 | CAAGGUAUGUUGCCCGUUUGUCAAGAGAACAAACGGGCAACAUACCUUG | SEQ ID NO: 79 |
| shRNA16 | AGGUAUGUUGCCCGUUUGUCCCAAGAGAGGACAAACGGGCAACAUACCU | SEQ ID NO: 80 |
| shRNA17 | AAGGUAUGUUGCCCGUUUGUCCAAGAGAGACAAACGGGCAACAUACCUU | SEQ ID NO: 81 |
| shRNA18 | ACAAACGGGCAACAUACCUUGCAAGAGACAAGGUAUGUUGCCCGUUUGU | SEQ ID NO: 82 |
| shRNA19 | CUCGUGGUGGACUUCUCUCACAAGAGAUGAGAGAAGUCCACCACGAG | SEQ ID NO: 83 |
| shRNA20 | UGAGAGAAGUCCACCACGAGCAAGAGACUCGUGGUGGACUUCUCUCA | SEQ ID NO: 84 |

TABLE 3-continued shRNAs

| shRNA ID | shRNA sequence (5'-3') | SEQ ID NO: |
|---|---|---|
| shRNA21 | AUUGAGAGAAGUCCACCACGCAAGAGACGUGGUGGACUUCUCUCAAU | SEQ ID NO: 85 |
| shRNA22 | AGAGAAGUCCACCACGAGUCCAAGAGAGACUCGUGGUGGACUUCUCU | SEQ ID NO: 86 |
| shRNA23 | CUCGUGUUACAGGCGGGGUUUUGUGCUUAAACCCCGCCUGUAACACGAG | SEQ ID NO: 87 |
| shRNA24 | AAACCCCGCCUGUAACACGAGUGUGCUUCUCGUGUUACAGGCGGGGUUU | SEQ ID NO: 88 |
| shRNA25 | GCACUUCGCUUCACCUCUGCACAAGAGAUGCAGAGGUGAAGCGAAGUGC | SEQ ID NO: 89 |
| shRNA26 | UGCAGAGGUGAAGCGAAGUGCCAAGAGAGCACUUCGCUUCACCUCUGCA | SEQ ID NO: 90 |
| shRNA27 | ACGUCCCGUCGGCGCUGAAUCUGUGCUUGAUUCAGCGCCGACGGGACGU | SEQ ID NO: 91 |
| shRNA28 | CGUCCCGUCGGCGCUGAAUCCUGUGCUUGGAUUCAGCGCCGACGGGACG | SEQ ID NO: 92 |
| shRNA29 | UACGUCCCGUCGGCGCUGAAUUGUGCUUAUUCAGCGCCGACGGGACGUA | SEQ ID NO: 93 |
| shRNA30 | GAUUCAGCGCCGACGGGACGUUGUGCUUACGUCCCGUCGGCGCUGAAUC | SEQ ID NO: 94 |
| shRNA31 | GGAUUCAGCGCCGACGGGACGUGUGCUUCGUCCCGUCGGCGCUGAAUCC | SEQ ID NO: 95 |
| shRNA32 | AUUCAGCGCCGACGGGACGUAUGUGCUUUACGUCCCGUCGGCGCUGAAU | SEQ ID NO: 96 |
| shRNA33 | AAAUGCCCCUAUCUUAUCAUGUGCUUUGAUAAGAUAGGGGCAUUU | SEQ ID NO: 97 |
| shRNA34 | UGAUAAGAUAGGGGCAUUUUGUGCUUAAAUGCCCCUAUCUUAUCA | SEQ ID NO: 98 |

TABLE 4

Additional RNAs duplexes

| shRNA ID | Effector (5'-3') | SEQ ID NO: | Effector complement (5'-3') | SEQ ID NO: |
|---|---|---|---|---|
| shRNA35 | UGAGGCCCACUCCCAUAGGUAU | SEQ ID NO: 53 | AUACCUAUGGGAGUGGGCCUCA | SEQ ID NO: 54 |
| shRNA36 | GGAAAGCCCUACGAACCACUGA | SEQ ID NO: 55 | UCAGUGGUUCGUAGGGCUUUCC | SEQ ID NO: 56 |
| shRNA37 | GGGAAAGCCCUACGAACCACUG | SEQ ID NO: 57 | CAGUGGUUCGUAGGGCUUUCCC | SEQ ID NO: 58 |
| shRNA38 | GGGGAAAGCCCUACGAACCACU | SEQ ID NO: 59 | AGUGGUUCGUAGGGCUUUCCCC | SEQ ID NO: 60 |
| shRNA39 | GGGAAAGCCCUACGAACCACUG | SEQ ID NO: 61 | CAUUGUUUCGUCGGGCUUUCCC | SEQ ID NO: 62 |
| shRNA40 | CCGGGCAACGGGGUAAAGGUUC | SEQ ID NO: 63 | GAACCUUUACCCCGUUGCCCGG | SEQ ID NO: 64 |

TABLE 5

Additional shRNAs

| shRNA ID | shRNA sequence (5'-3') | SEQ ID NO: |
|---|---|---|
| shRNA35 | AUACCUAUGGGAGUGGGCCUCACAAGAGAUGAGGCCCACUCCCAUAGGUAU | SEQ ID NO: 99 |
| shRNA36 | UCAGUGGUUCGUAGGGCUUUCCCAAGAGAGGAAAGCCCUACGAACCACUGA | SEQ ID NO: 100 |
| shRNA37 | CAGUGGUUCGUAGGGCUUUCCCCAAGAGAGGGAAAGCCCUACGAACCACUG | SEQ ID NO: 101 |
| shRNA38 | AGUGGUUCGUAGGGCUUUCCCCCAAGAGAGGGGAAAGCCCUACGAACCACU | SEQ ID NO: 102 |
| shRNA39 | GGGAAAGCCCUACGAACCACUGCAAGAGACAUUGUUUCGUCGGGCUUUCCC | SEQ ID NO: 103 |
| shRNA40 | GAACCUUUACCCCGUUGCCCGGCAAGAGACCGGGCAACGGGGUAAAGGUUC | SEQ ID NO: 104 |

EXAMPLES

Example 1—Target Regions for Design of ddRNAi Constructs

Sequences representing potential targets for design of ddRNAi constructs were identified from the full length HBV genome. Briefly, a database of HBV sequence was compiled from sequences retrieved from non-proprietary, public domain sources. The initial collection was compiled from Release 202.0 of Genbank (Jun. 15, 2014) using the search terms {hepatitis b virus complete genome} and {hepatitis b virus complete genome+genotype}; only human HBV sequences were included. Initial sequence alignments were performed using Sequence Assembly, Clustal, MUSCLE and SEQUENCHER, Release 5.0.1/5.2. Initial alignments were manually curated to remove formatting derived sequence differences (e.g., variation in sequence start sites), artificial viral sequences (e.g., HBV-based constructs), obvious outliers (e.g., poor alignments or alignments with Ns, indicative of poor quality sequences) and incorrectly annotated sequences, including duplicate entries. The remaining sequences, of which there were 4345 sequences representing all HBV genotypes (A-H), were re-aligned using CLUSTALW (both fast and slow) and Megalign, Lasergene, Release 12. Alignments were scanned for regions of highest conservation (at least 18/20 nucleotides) across all genotypes. The 10 most highly conserved regions were chosen as targets for design of shRNAs. The sequences of the target regions identified are presented in Table 1.

Example 2—siRNA Duplexes siRNA duplexes comprising effector sequences substantially complementary to the target regions described in Table 1 were designed and are presented in Table 2 The siRNA duplexes were synthesized with two nucleotide 3' dTdT overhangs.

Example 3—Activity of siRNAs in Dual-Luciferase Reporter Assay

To test the efficacy of the siRNAs of the disclosure to knockdown expression of HBV transcripts, dual-luciferase reporter assays were performed in HEK293 cells.

Plasmid reporter constructs based on the pGL3 Luciferase Reporter Vector were constructed for HBV siRNAs targeting each of regions Region 4, Region 5 or Region 9. The Luciferase reporter constructs were generated by inserting a HBV shRNA target sequence for Region 4, Region 5 or Region 9 with 20 bp flanking sequences at each end onto the pGL3-control vector (Promega, Madison, Wis.). The inserts were subcloned using FseI and XbaI restriction enzyme sites within the 3' UTR of the luciferase reporter gene.

The dual-luciferase reporter assays were performed in HEK293 cells. The HEK293 cell line was purchased from ATCC (Manassas, Va.). The HEK293 cells were cultured in DMEM medium containing 10% fetal bovine serum, 2 mM glutamine, penicillin (100 U/mL), and streptomycin (100 µg/mL) at 37° C. humid incubator with 5% CO2. Briefly, the HEK293 cell were seeded at a density of $2 \times 10^4$ cells per well into 96-well culture plate one day prior to transfection.

The HBV siRNAs having antisense and sense sequences of shRNAs designated shRNA9, shRNA15 and shRNA27 respectively and their corresponding Luciferase reporter constructs were co-transfected into HEK293 cells using Lipofectamine 2000 reagents (Life Technologies, Carlsbad, Calif.) according to manufacturer's instructions. For each well of transfection, 1 or 2 pmol of one of the HBV siRNA, 10 ng of the corresponding Luciferase reporter construct and 1 ng of Renilla reporter construct (served as loading controls) were co-transfected using 0.3 uL of Lipotectamine 2000. 48 hour post-transfection, cell lysates were collected and analyzed using Dual Luciferase Reporter Assay System (Promega, Madison, Wis.). The firefly/Renilla activity ratios were determined for each well, and the inhibition efficiency of siRNAs were calculated by normalizing to an irrelevant siRNA, namely the siGlo control. Percent inhibition of HBV reporter constructs in HEK293 cells for the sense and antisense strands of each of HBV siRNAs shRNA9, shRNA15 and shRNA27 relative to the siGlo control is presented in Table 8 and illustrated in FIG. 2.

TABLE 8

Inhibitory activity of siRNAs having antisense and sense sequence of shRNA9, shRNA15 and shRNA27 in dual-luciferase reporter assay

| siRNA | siRNA strand | % Inhibition of HBV reporter | |
|---|---|---|---|
| | | 1 pmol siRNA | 2 pmol siRNA |
| shRNA9 | Antisense | 89.71 | 86.87 |
| | Sense | 6.57 | 7.98 |
| shRNA15 | Antisense | 91.47 | 92.27 |
| | Sense | 6.03 | 7.40 |
| shRNA27 | Antisense | 84.61 | 84.75 |
| | Sense | −8.73 | −1.29 |

Figure 2:
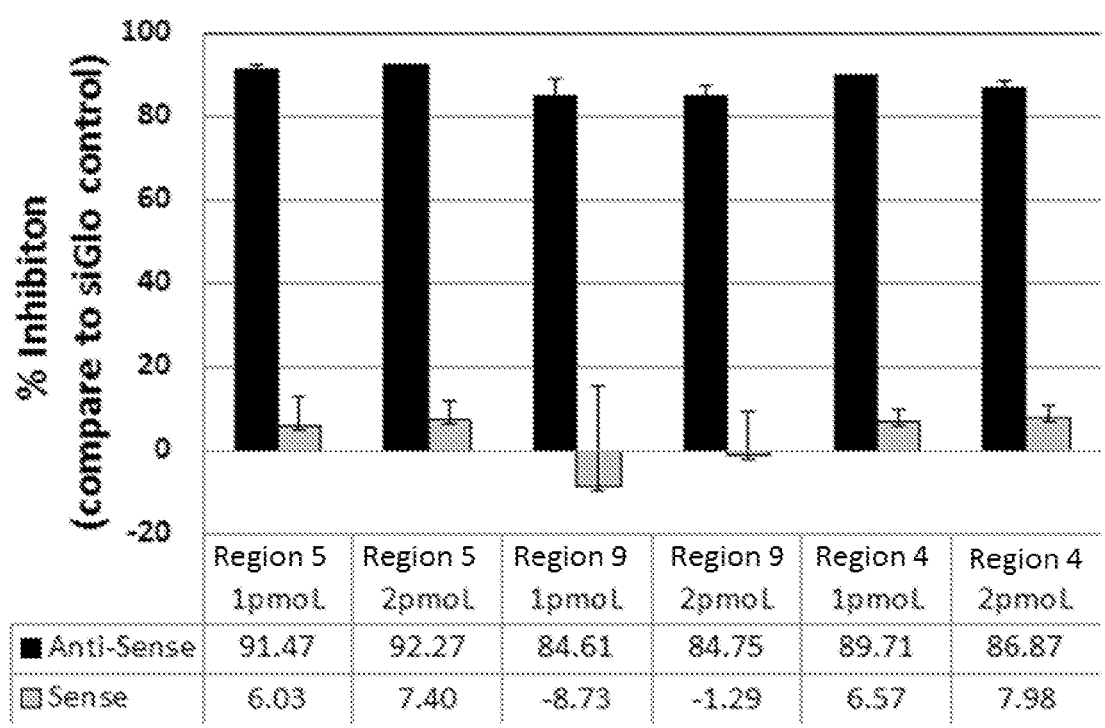
FIG. 2 illustrates the HBV inhibitory activity of siRNAs having antisense and sense sequence of shRNA9, shRNA15 and shRNA27 respectively in a Luciferase reporter assay system.

As is apparent from Table 8 and FIG. 2, even when present in an amount as low as 1 pmol, the exemplary siRNAs having antisense and sense sequences of shRNAs designated shRNA9, shRNA15 and shRNA27 respectively downregulated the level of luciferase expressed from the pGL3 Luciferase reporter vector in HEK293 cells.

Example 4—Activity of siRNAs Against HBV Antigens Expressed in HepG2.2.15 Cells

To test the efficacy of siRNAs of the disclosure to knockdown expression of HBV genes, HepG2.2.15 were transfected with representative siRNA of the disclosure and inhibition of HBV gene expression was assayed.

HepG2.2.15 is a sub-cell line of the HepG2 human hepatocellular carcinoma cell line which stably harbors the complete HBV genome (serotype ayw, genotype D). HepG2.2.15 expresses all HBV viral RNA and proteins, produces viral genomes, and secretes virus-like particles. The HepG2.2.15 cells were provided by Dr. Brent Korba of Georgetown University. The HepG2.2.15 cells were maintained in the RPMI1640 medium supplemented with 4% fetal bovine serum, 4 mM glutamine, penicillin (100 U/mL), and streptomycin (100 µg/mL) and propagated in a 37° C. humid incubator in an atmosphere of 5% $CO_2$.

Cells were transfected with HBV siRNAs having antisense and sense sequences of the shRNAs designated shRNA9, shRNA15 and shRNA27 respectively in suspension using Lipofectamine RNAiMax reagents (Life Technologies, Carlsbad, Calif.). Transfections were performed according to manufacturer's instructions. For each transfection, HepG2.2.15 cells were seeded at a density of $9 \times 10^4$ cells per well onto 24-well culture plates and transfected with 5 pmol of one of the HBV siRNAs using 1.5 uL Lipotectamine RNAiMax. 72 hr post-transfection, cells were harvested for RNA.

Total RNA was isolated using miRNeasy Mini Kit (Qiagen, Valencia, Calif.). Total RNA was quantified using the NanoDrop 1000 Spectrophotometer (Thermo Scientific) and diluted to a working concentration of 10 ng/µl. One hundred nanogram of total RNA was used to synthesize cDNA using High Capacity cDNA Reverse Transcription Kit (Life Technologies, Carlsbad, Calif.) according to manufacturer's instructions.

Quantitative PCR amplifications of regions within HBV antigens HBsAg, HBcAg, HbxAg, and GAPDH were performed using Power SYBR Green PCR Master Mix (Life Technologies) and the following primer sets listed in Table 9. Standard real-time PCR conditions were used: initial denaturation at 95° C. for 10 min followed by 40 cycles of 95° C. for 15 sec and 60° C. for 1 min.

TABLE 9

Primer sets for RT-qPCR

| HBV Antigen | Primer | Sequence (5' - 3') | SEQ ID NO |
|---|---|---|---|
| HBsAg | HBsAg_fwd | ATGTTGCCCGTTTGTCCTCT | 107 |
|  | HBsAg_rev | CCGTCCGAAGGTTTGGTACA | 108 |
| HBxAg | HBxAg_fwd | CGTCCTTTGTTTACGTCCCG | 109 |
|  | HBxAg_rev | AGTCCGCGTAAAGAGAGGTG | 110 |
| HBcAg | HBcAg_fwd | CCACCAAATGCCCCTATCCT | 111 |
|  | HBcAg_rev | ATTGAGACCTTCGTCTGCGA | 112 |
| GAPDH | GAPDH_fwd | ACACCATGGGGAAGGTGAAG | 113 |
|  | GAPDH_rev | GTGACCAGGCGCCCAATA | 114 |

Figure 3:
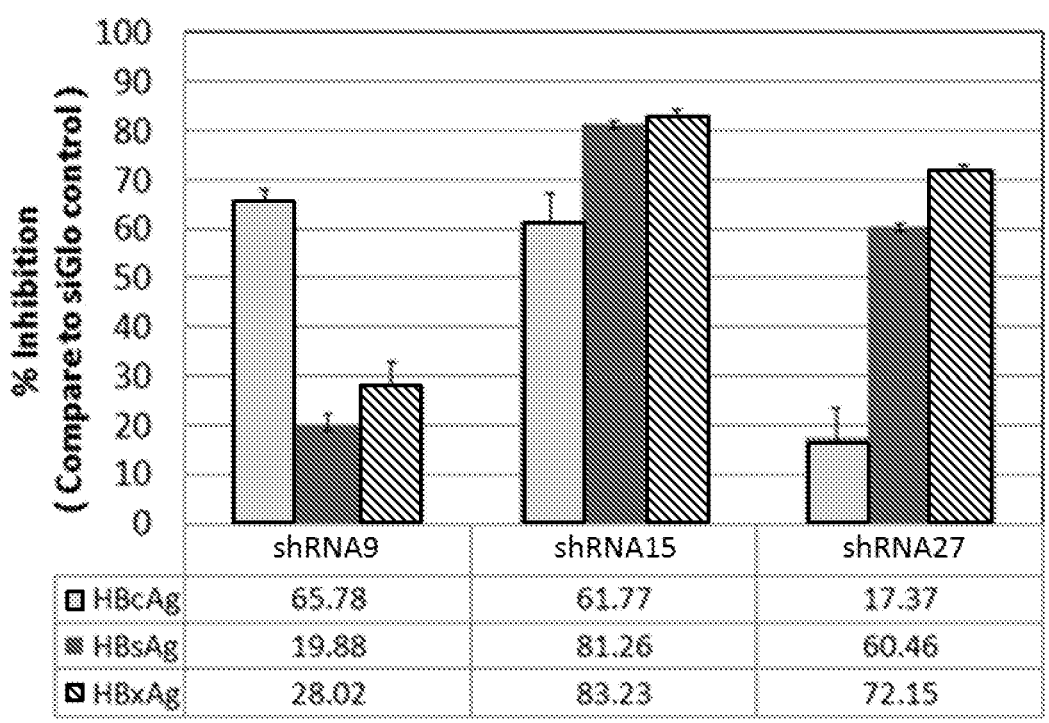
FIG. 3 illustrates the activity of siRNAs having antisense and sense sequence of shRNA9, shRNA27 and shRNA27 respectively to inhibit HBV transcripts from regions corresponding to HBV antigens HBsAg, HBcAg and HbxAg in HepG2.2.15 cells.
Figure 4:
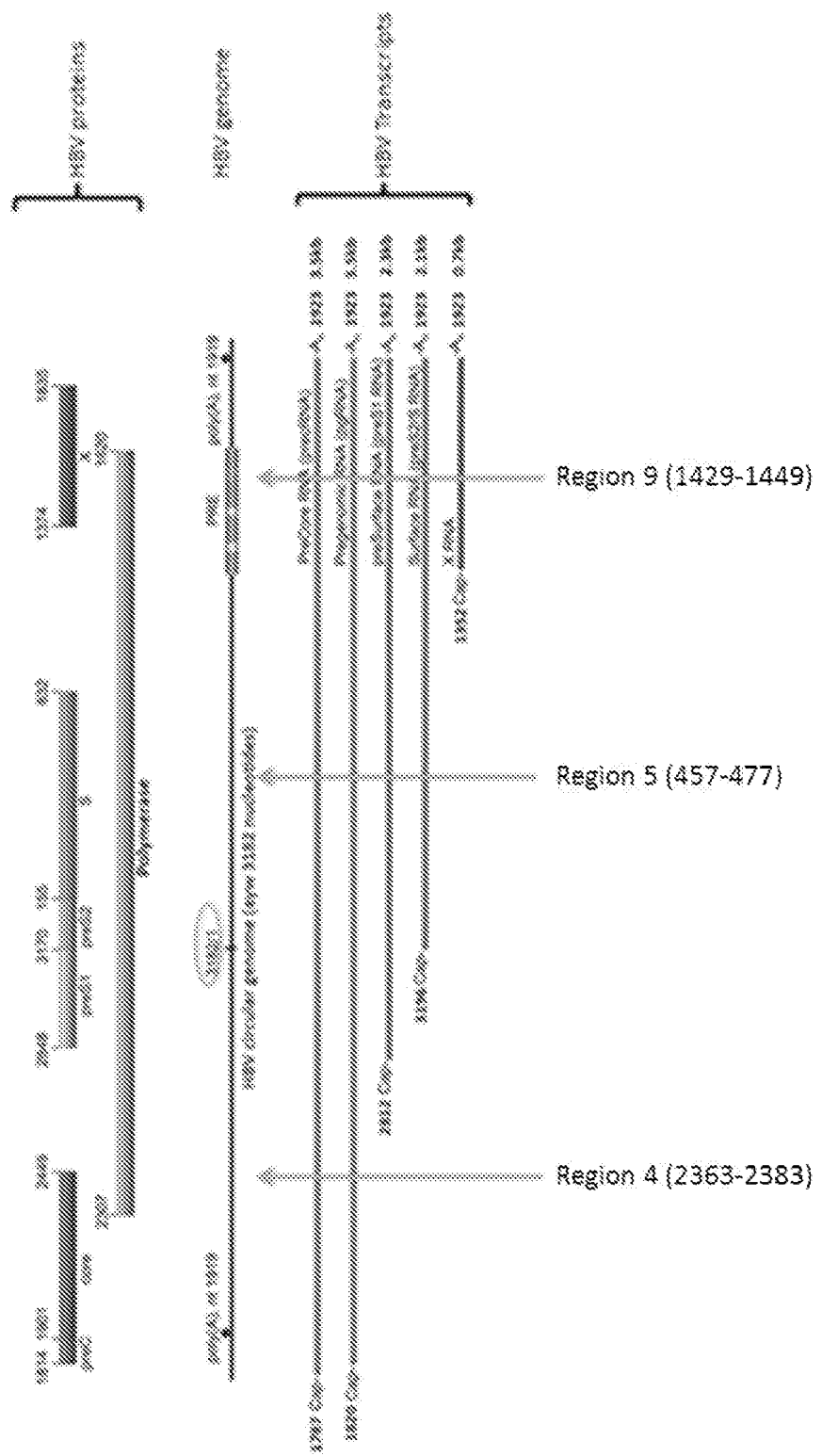
FIG. 4 shows location of the HBV siRNAs relative to the polymerase gene and the respective HBV antigens HBsAg, HBcAg and HbxAg.
Figure 5A:
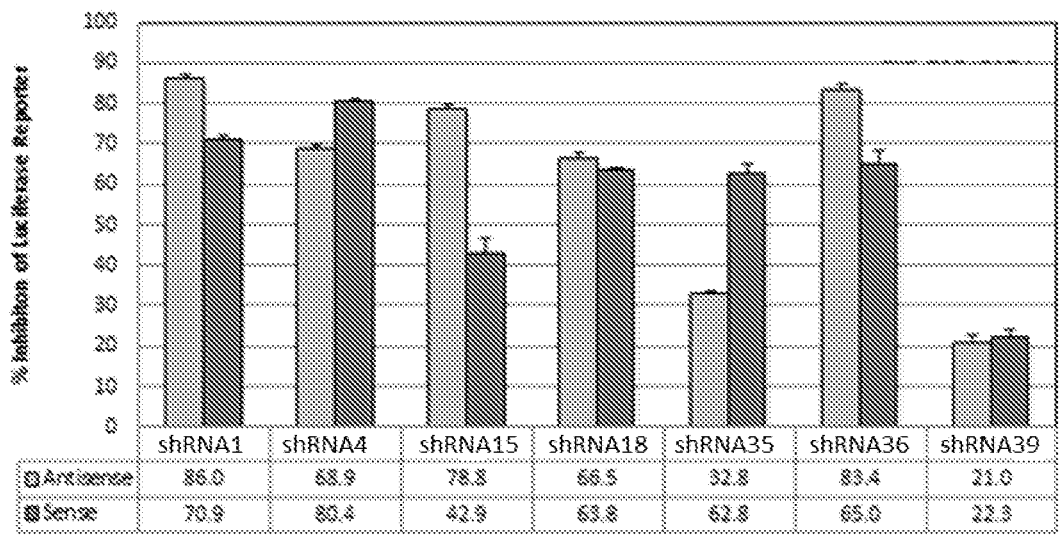
FIGS. 5 (a)-(b) illustrate the ability of shRNAs designated shRNA1, shRNA4, shRNA15, shRNA18, shRNA35, shRNA36 and shRNA39 to inhibit luciferase protein expression in a Luciferase reporter assay system; (c)-(d) illustrate the ability of the shRNAs designated shRNA5, shRNA6, shRNA7, shRNA8, shRNA35, shRNA26, shRNA27, shRNA30 and shRNA40 to inhibit luciferase protein expression in Luciferase reporter assay; and (e)-(f) illustrate the ability of the shRNAs designated shRNA9, shRNA10, shRNA11, shRNA12, shRNA33, shRNA34, shRNA19, shRNA20, shRNA23 and shRNA24 to inhibit expression of luciferase protein expression in Luciferase reporter assay.
Figure 5B:
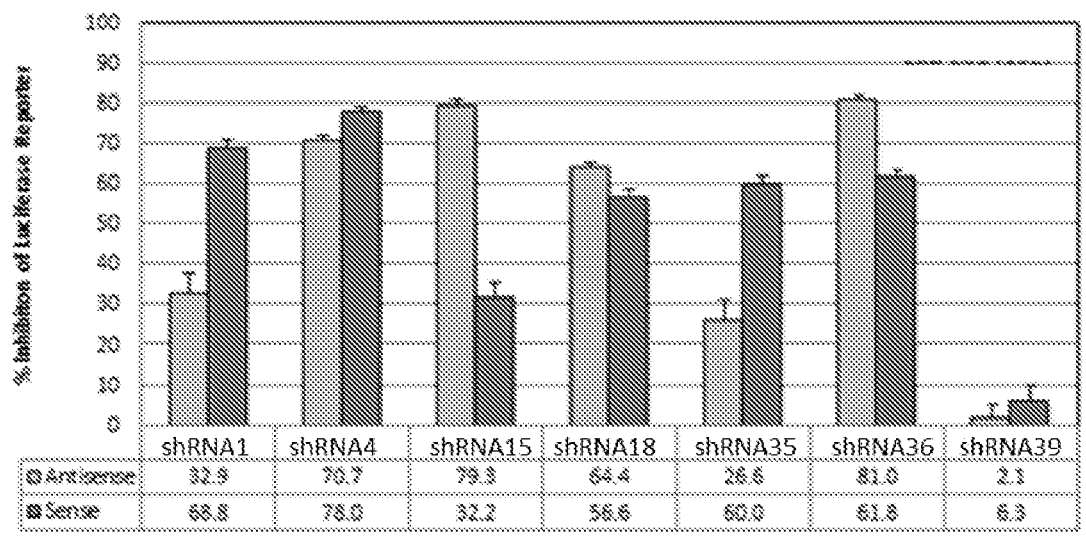
Figure 5C:
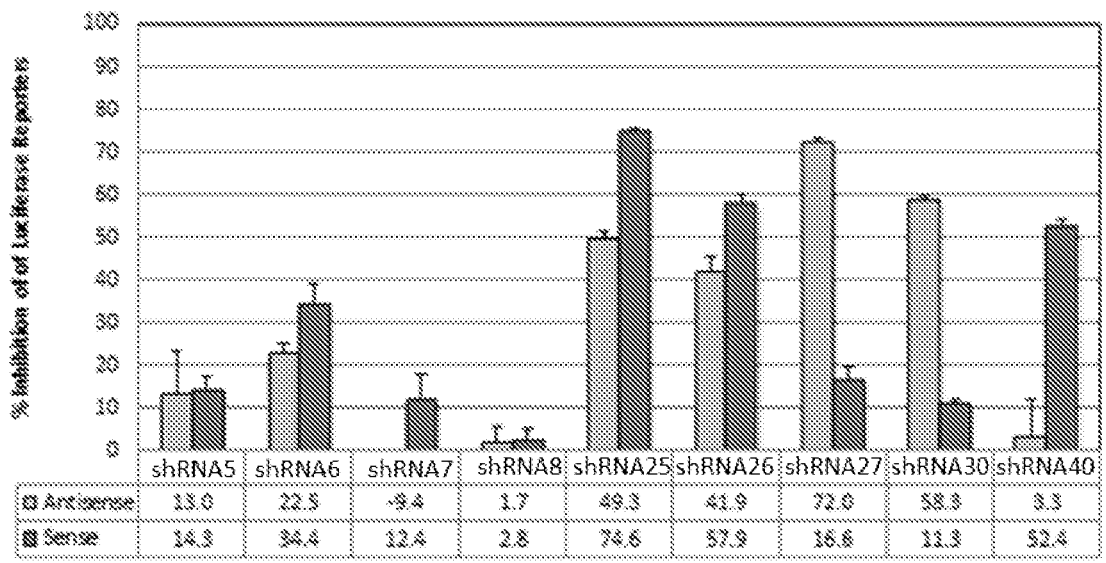
Figure 5D:
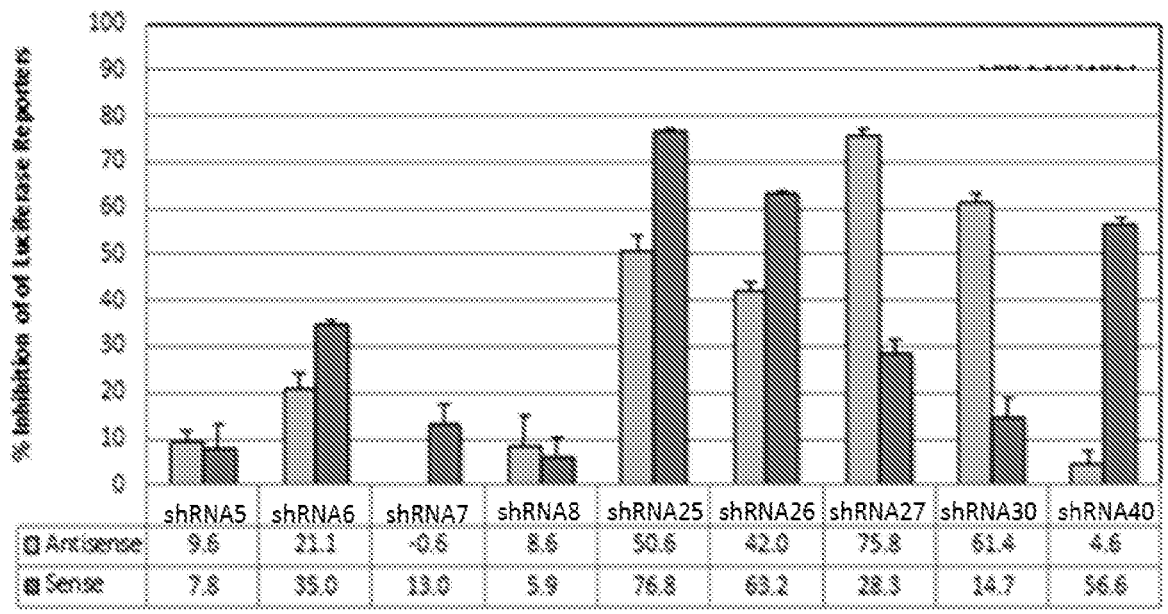
Figure 5E:
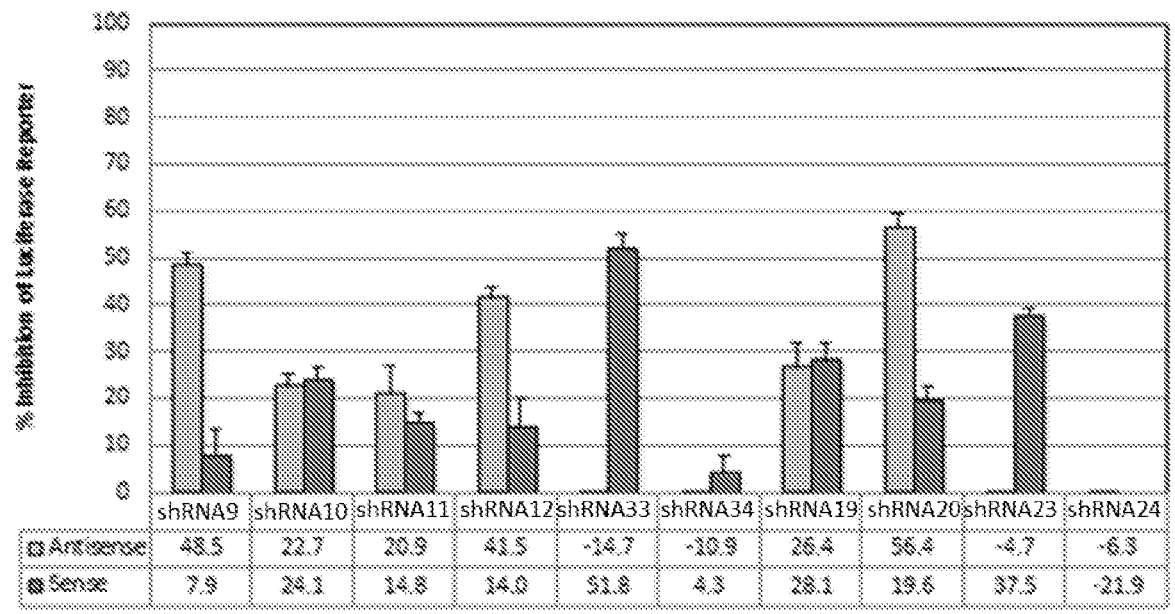
Figure 5F:
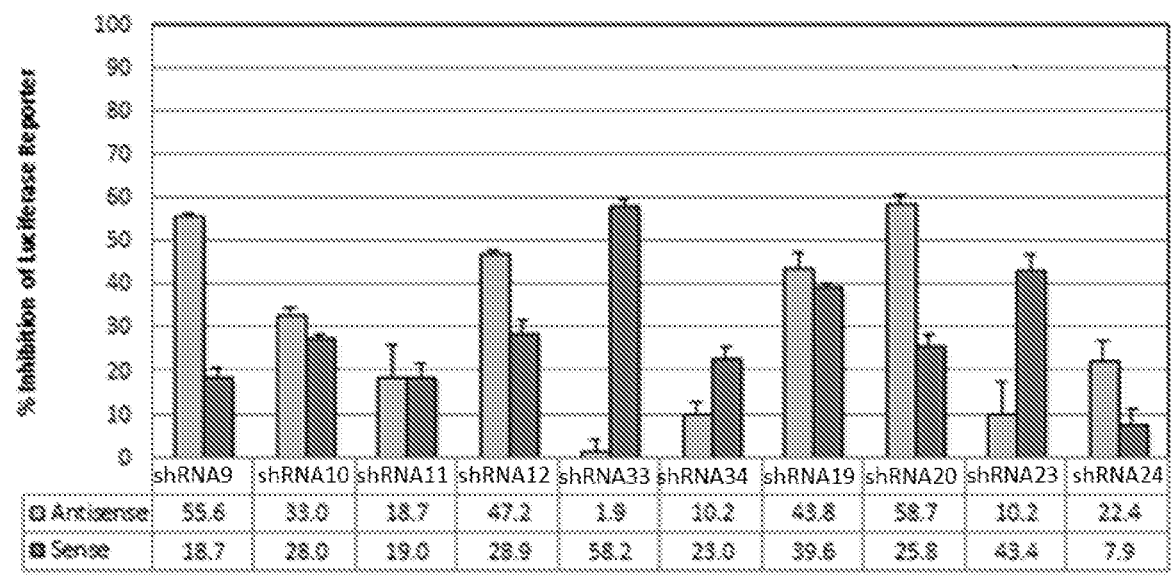
Figure 6A:
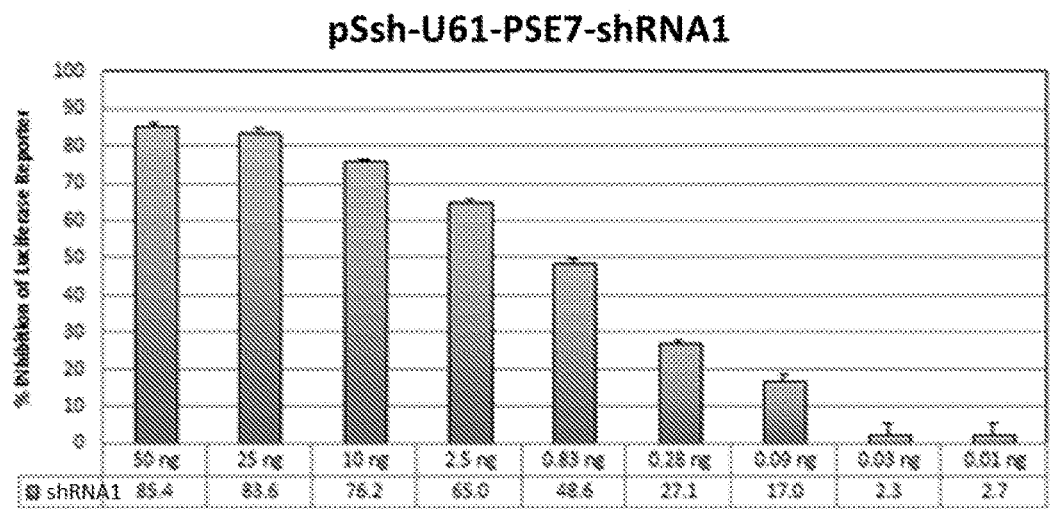
FIGS. 6 (a)-(j) illustrate the ability of shRNAs designated shRNA1, shRNA15, shRNA40, shRNA27, shRNA30, shRNA9 and shRNA20 to inhibit luciferase protein expression in a Luciferase reporter assay system in dose-dependent manner.
Figure 6B:
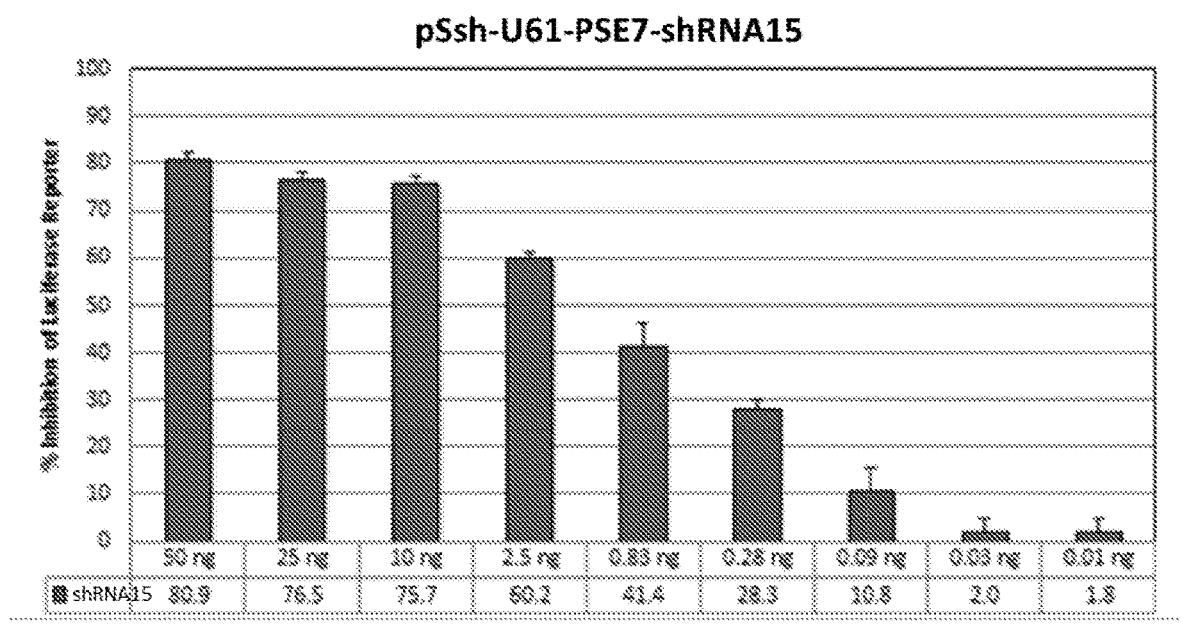
Figure 6C:
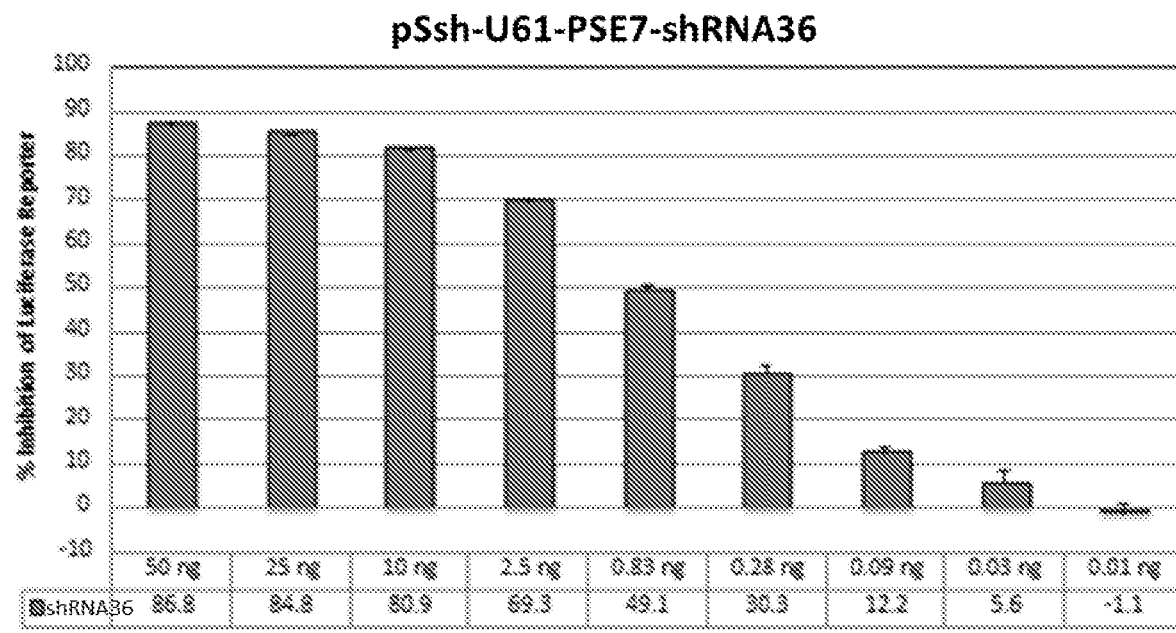
Figure 6D:
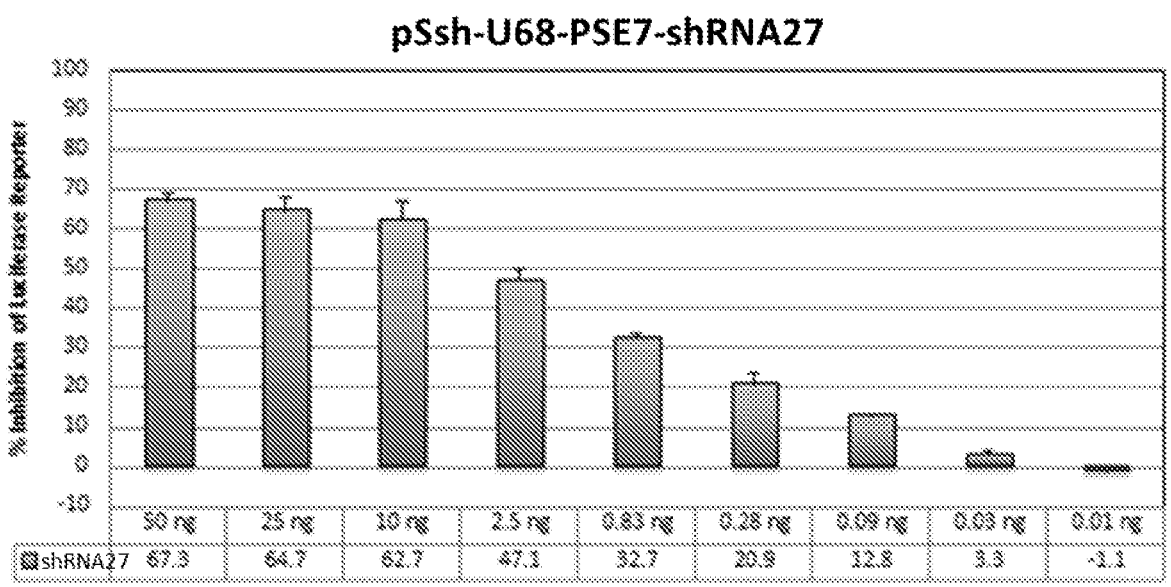
Figure 6E:
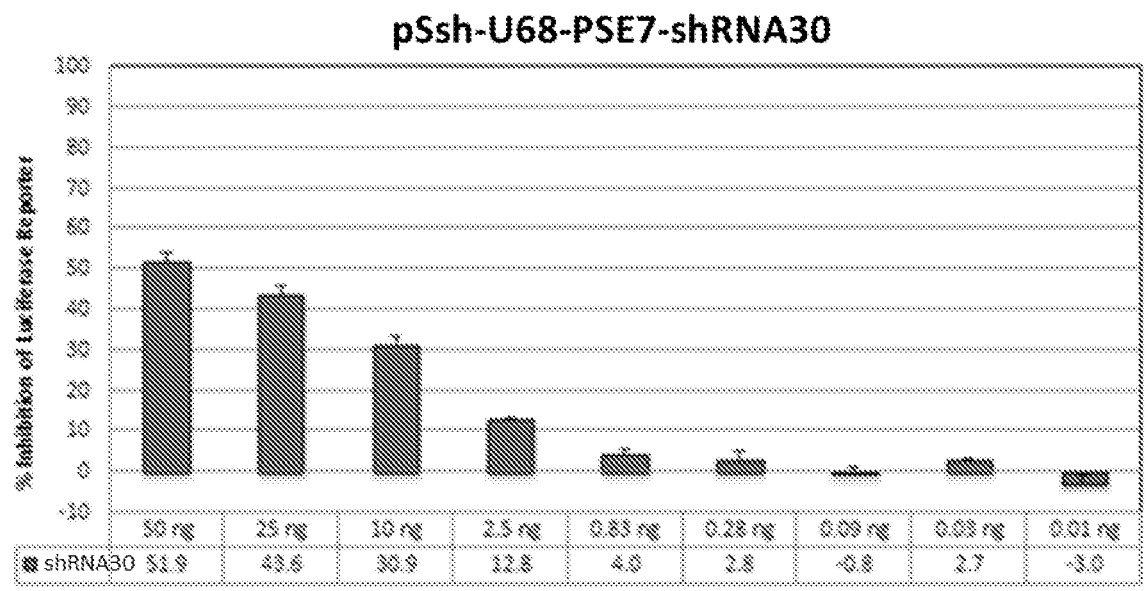
Figure 6F:
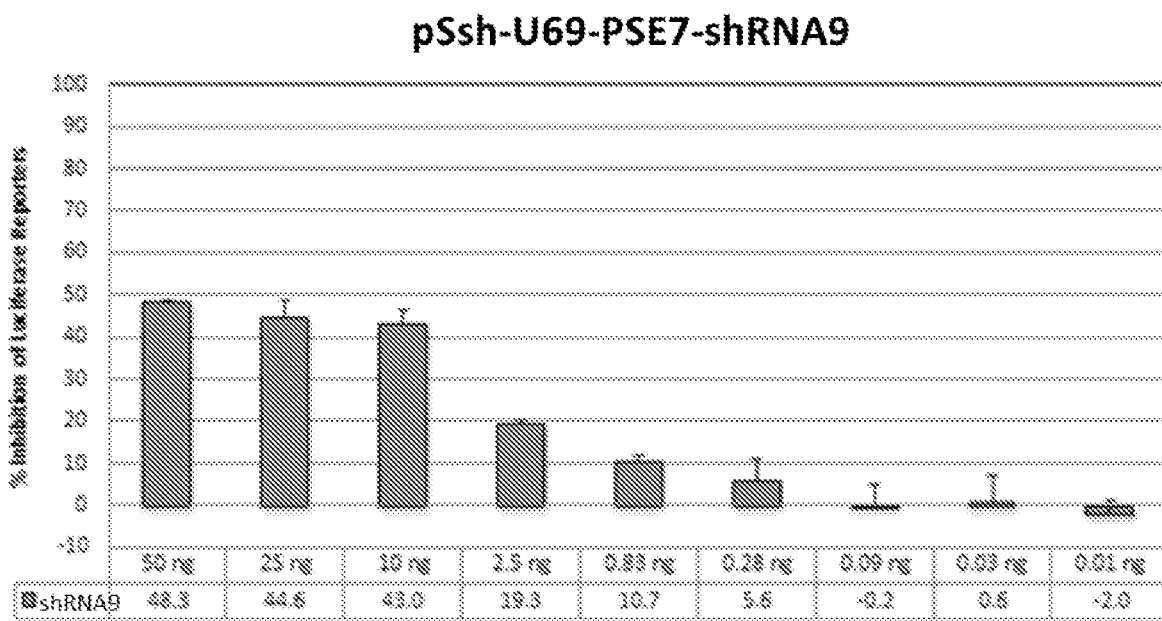
Figure 6G:
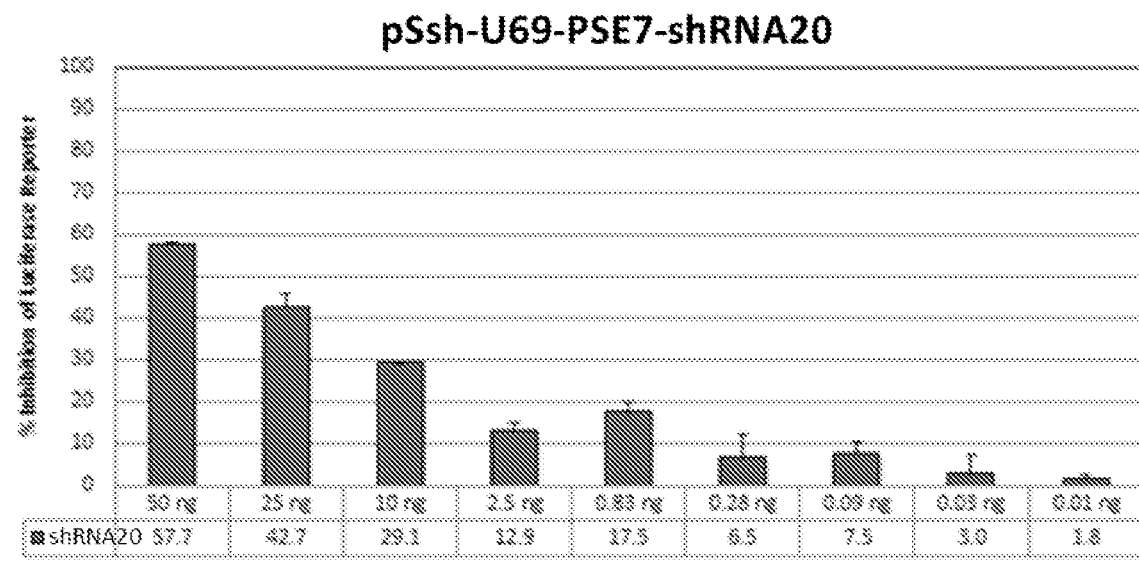
Figure 6H:
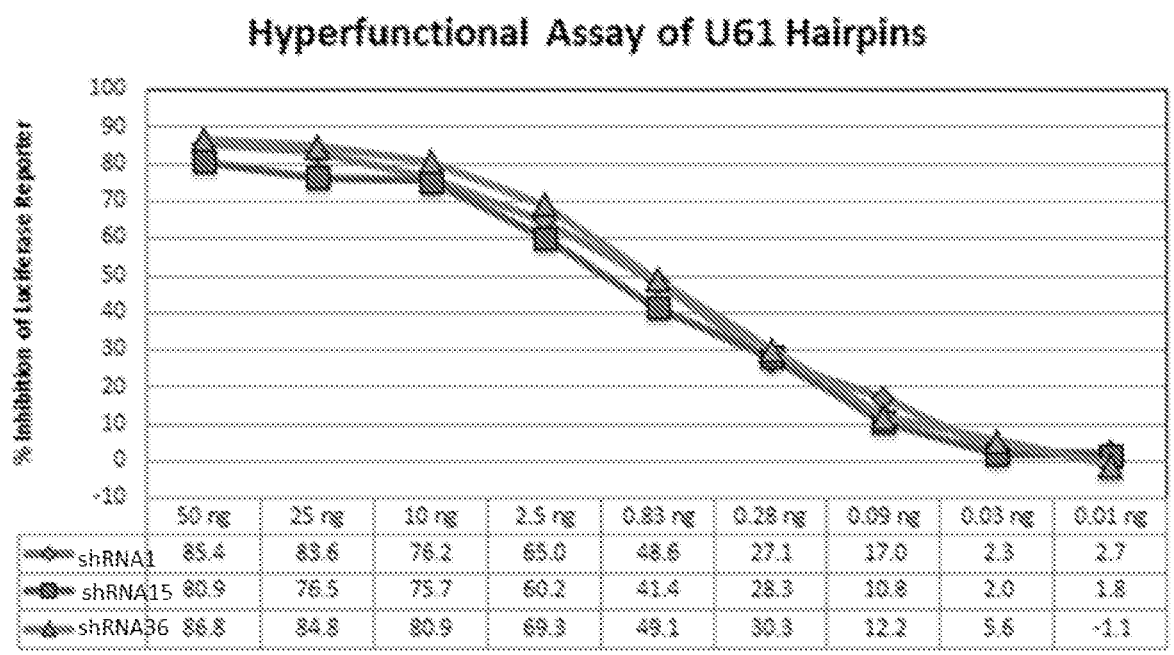
Figure 6I:
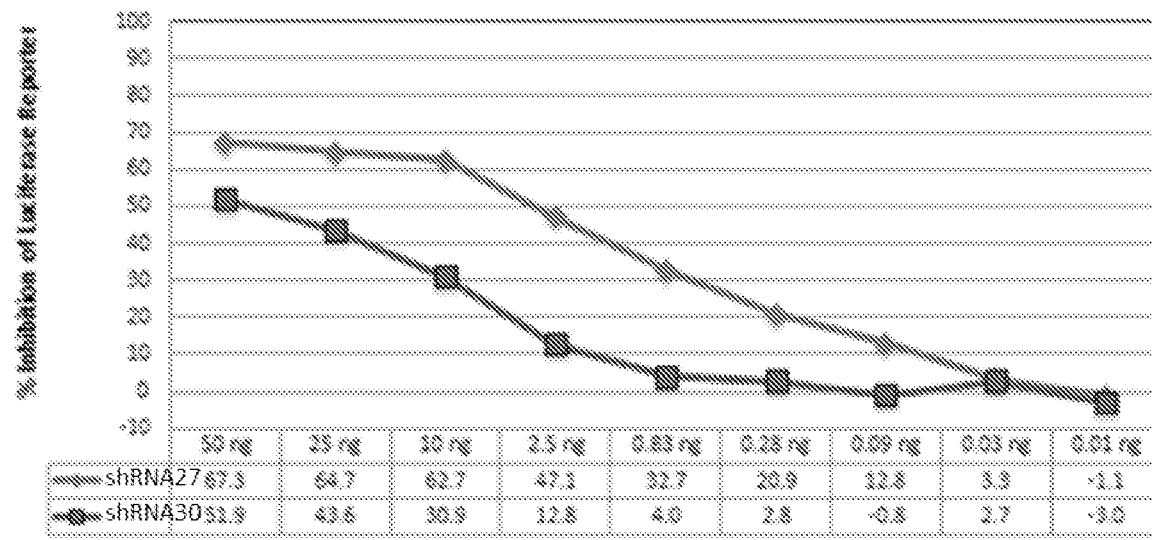
Figure 6J:
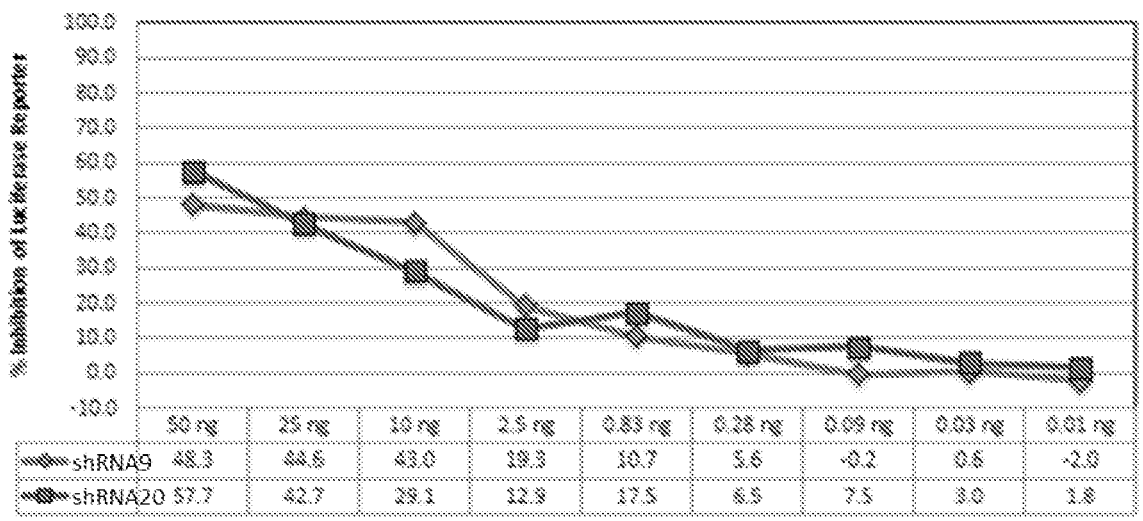
Figure 7A:
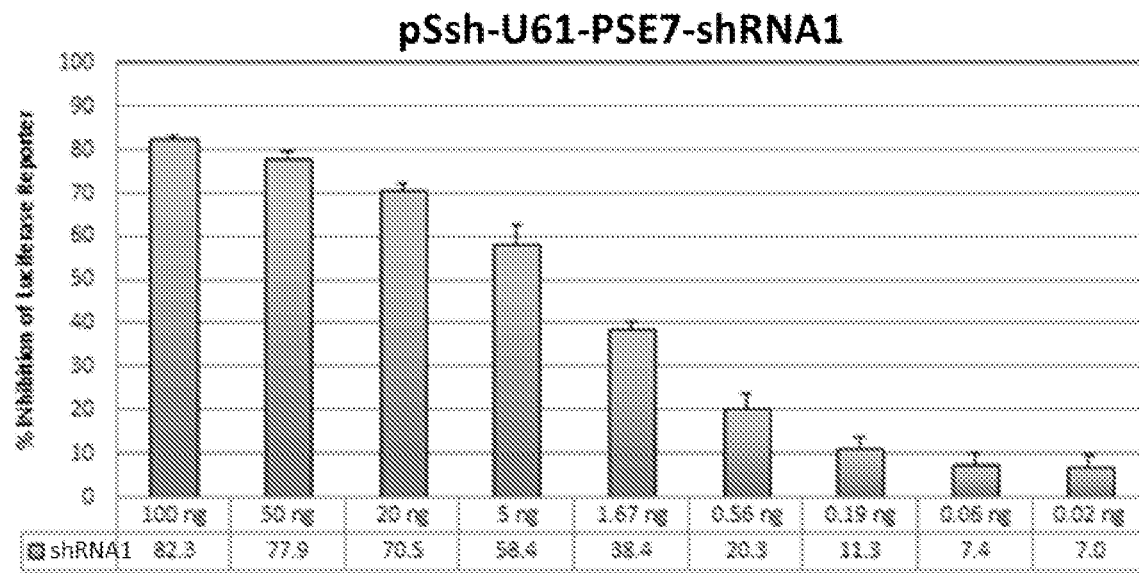
FIGS. 7 (a)-(j) illustrate the ability of shRNAs designated shRNA1, shRNA15, shRNA40, shRNA27, shRNA30, shRNA9 and shRNA20 to inhibit luciferase protein expression in a Luciferase reporter assay system in a dose-dependent manner.
Figure 7B:
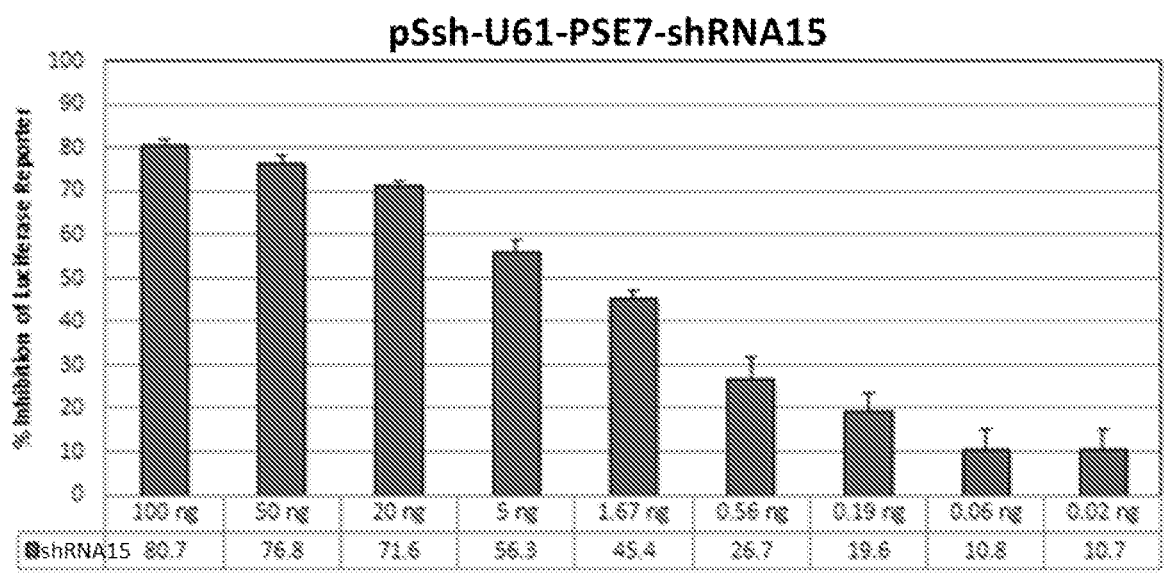
Figure 7C:
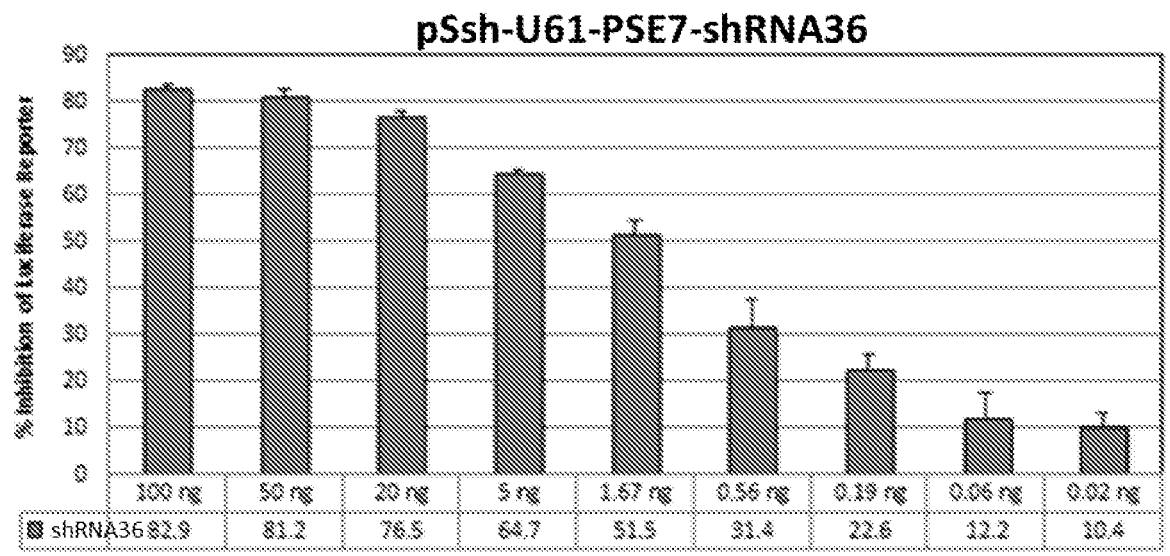
Figure 7D:
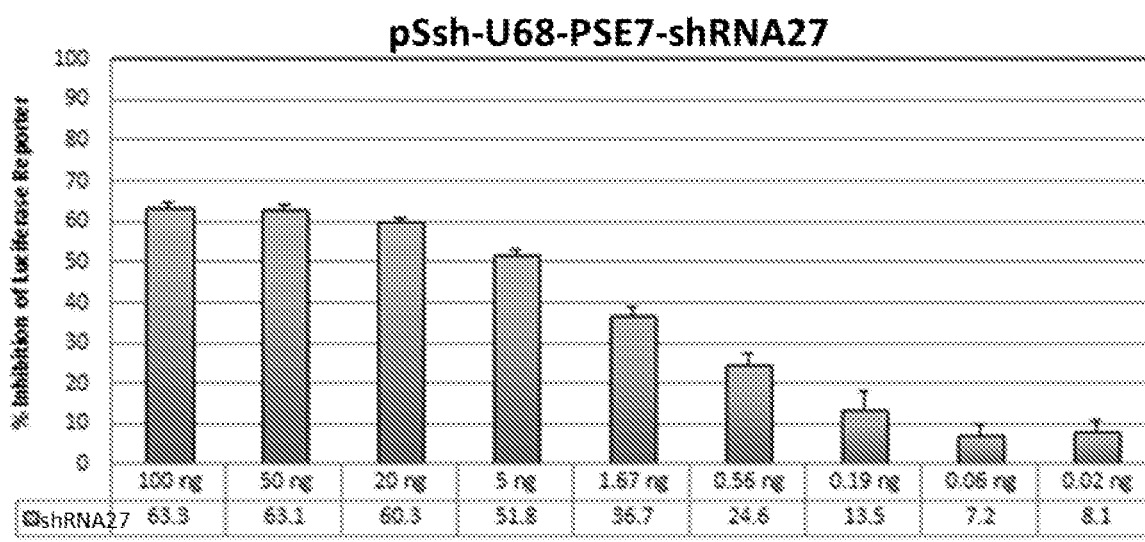
Figure 7E:
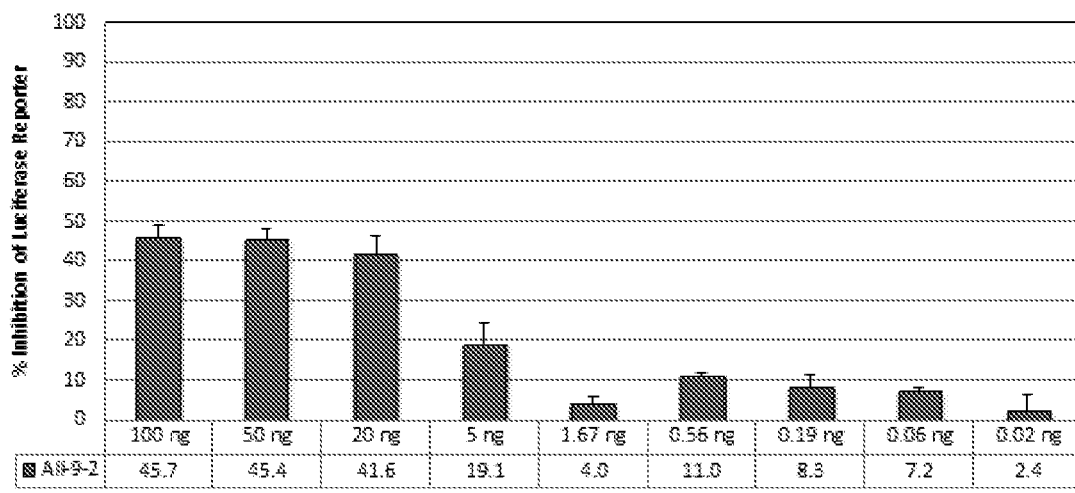
Figure 7F:
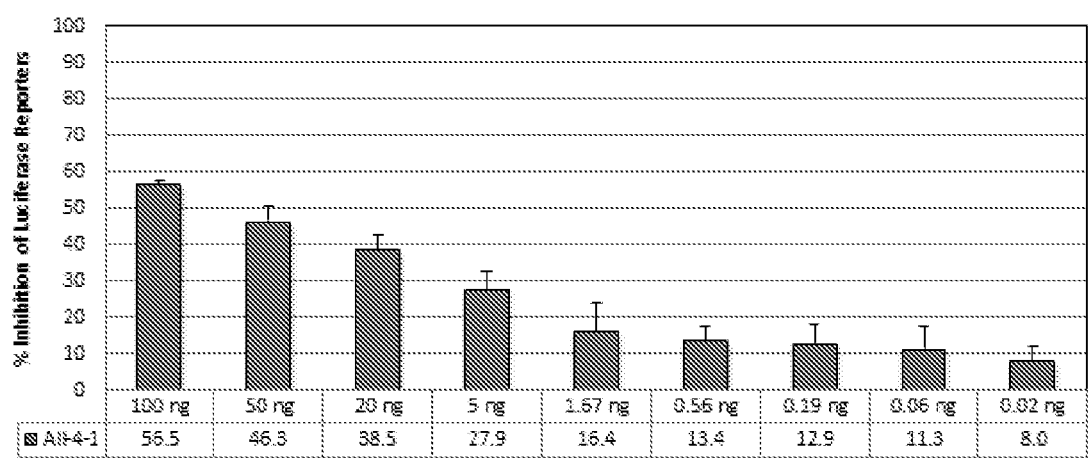
Figure 7G:
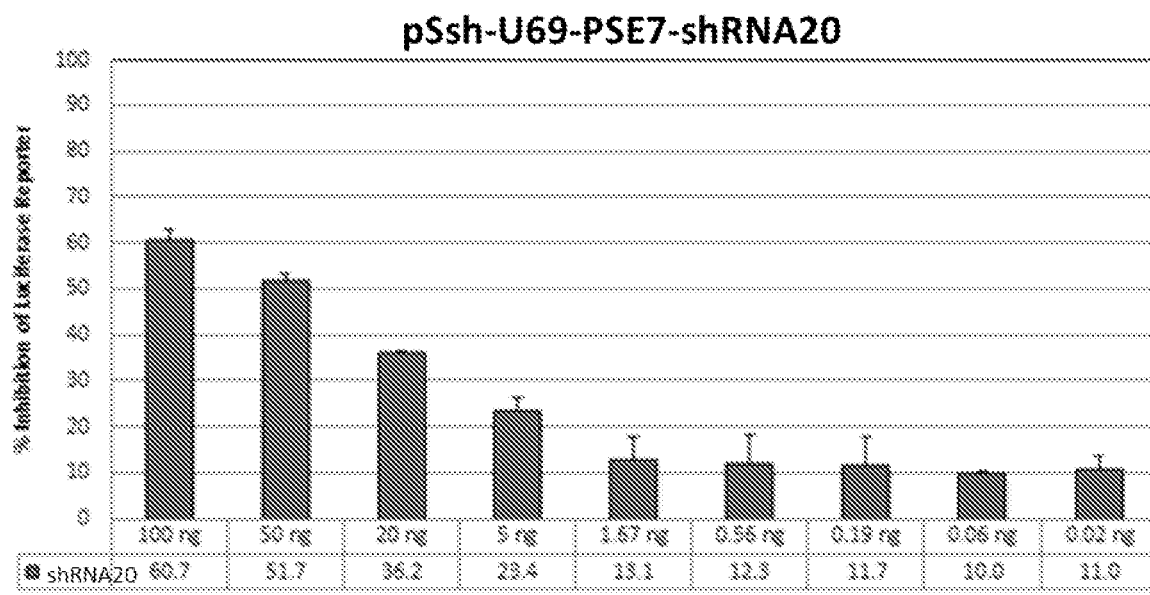
Figure 7H:
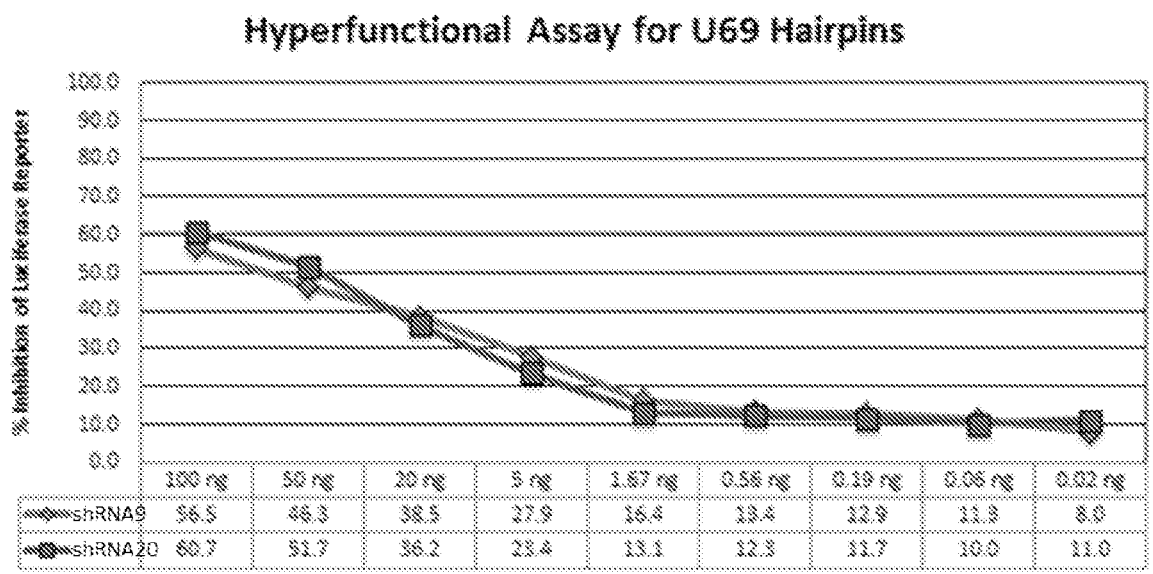
Figure 7I:
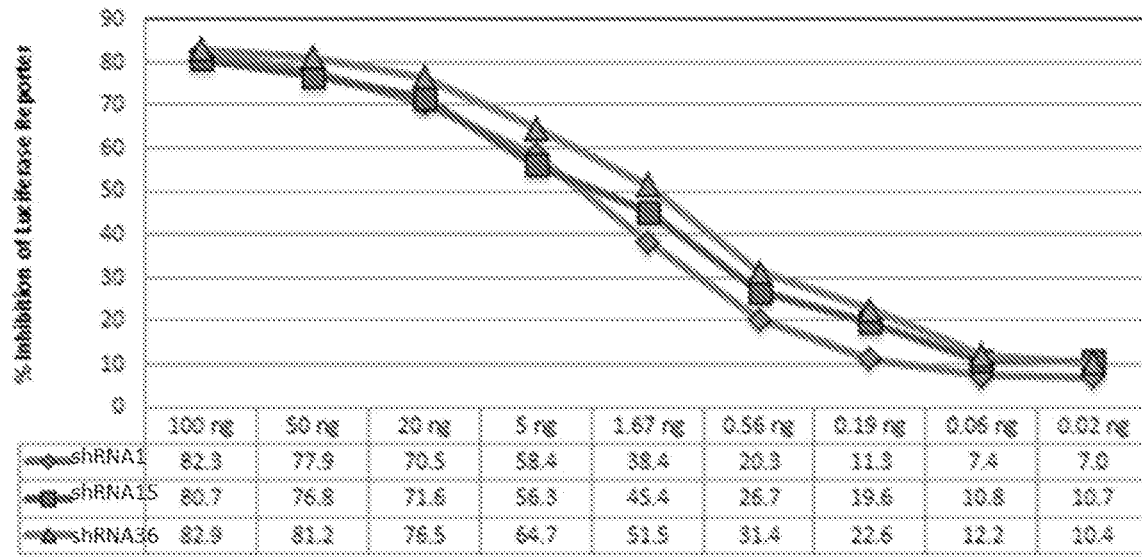
Figure 7J:
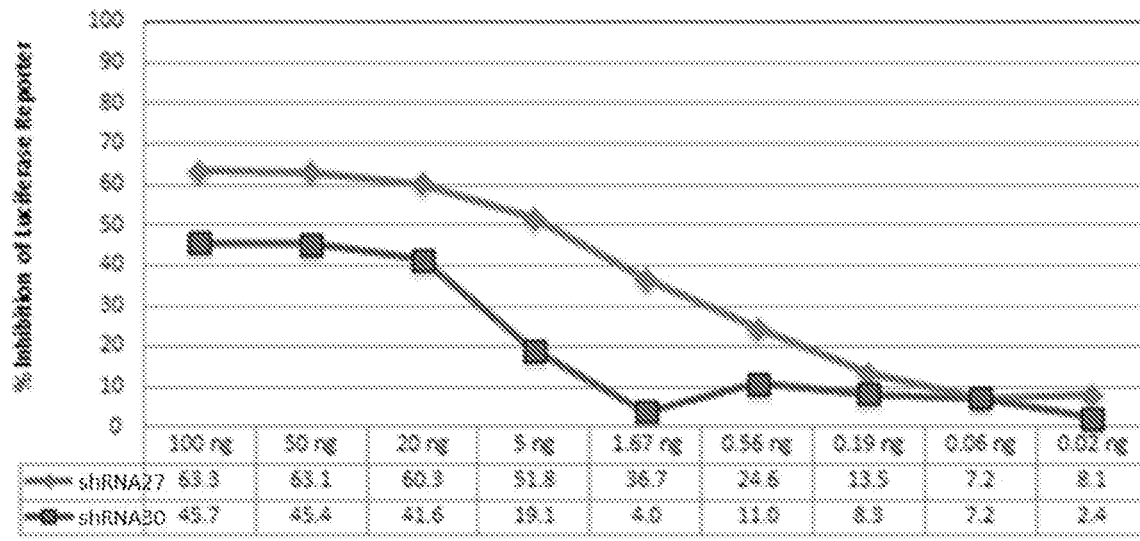
Figure 8A:
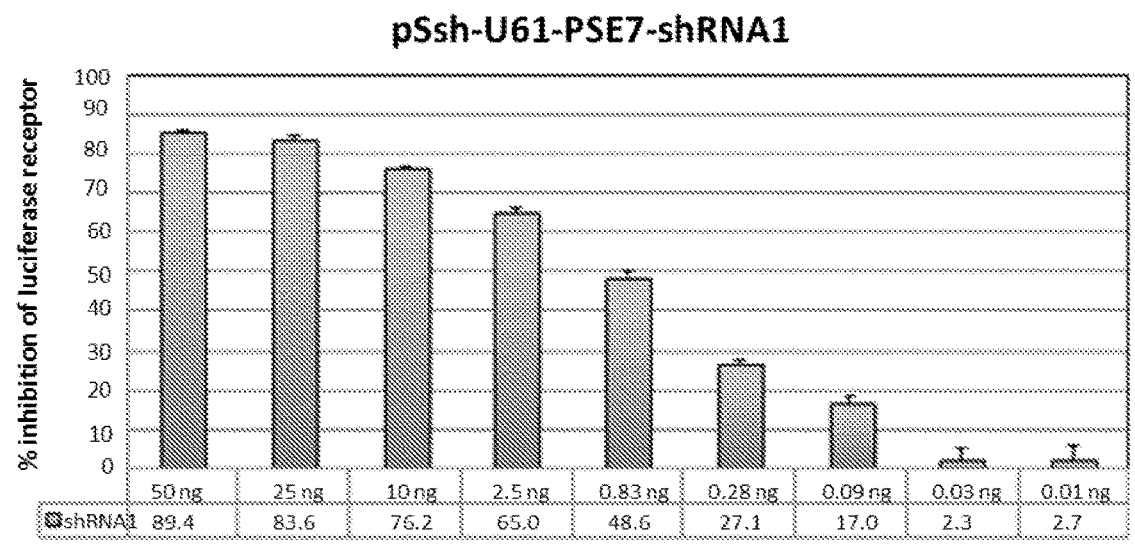
FIGS. 8 (a)-(j) illustrate the ability of shRNAs designated shRNA1, shRNA15, shRNA40, shRNA27, shRNA30, shRNA9 and shRNA20 to inhibit luciferase protein expression in a Luciferase reporter assay system in a dose-dependent manner in HEK293 cells co-transfected with a non-specific filler plasmid to ensure that constant levels of DNA are being transfected into cells.
Figure 8B:
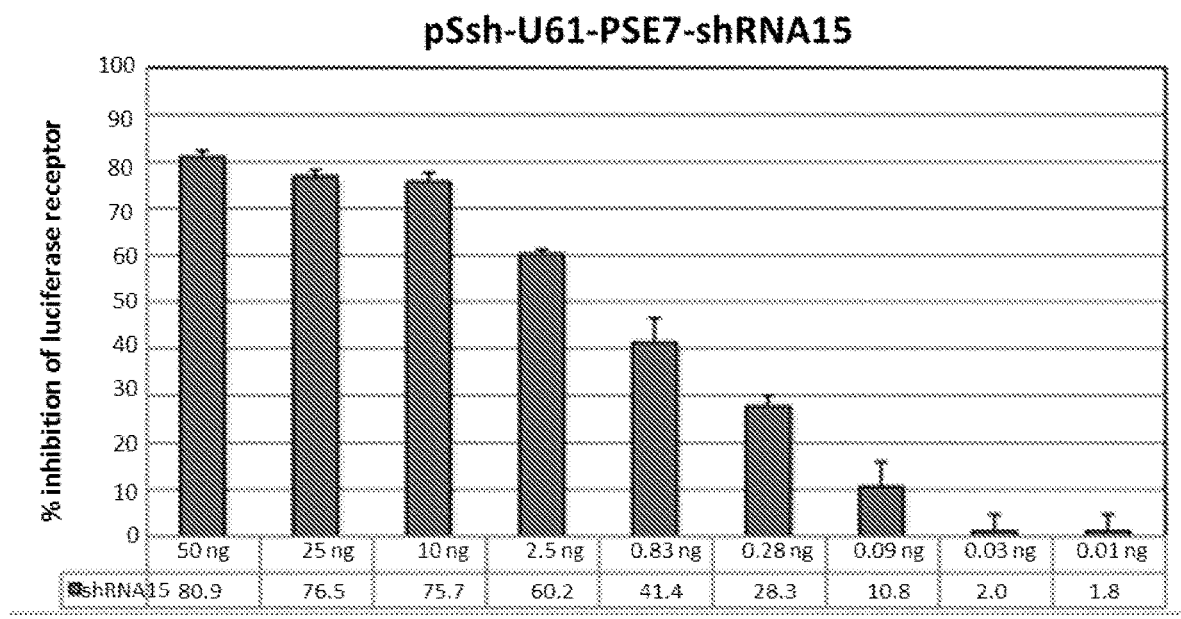
Figure 8C:
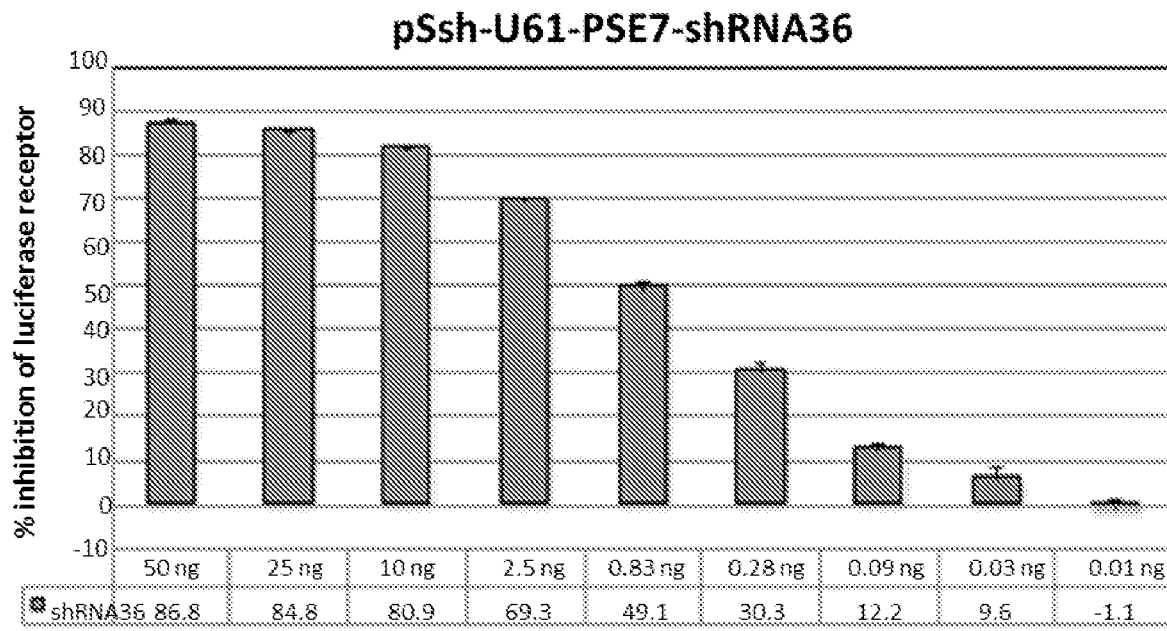
Figure 8D:
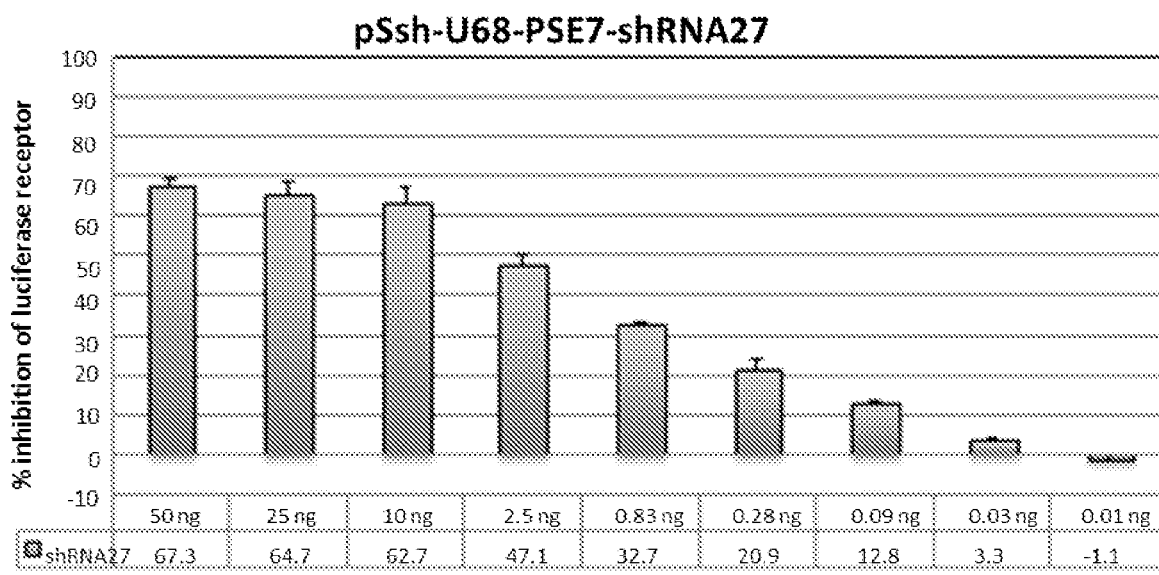
Figure 8E:
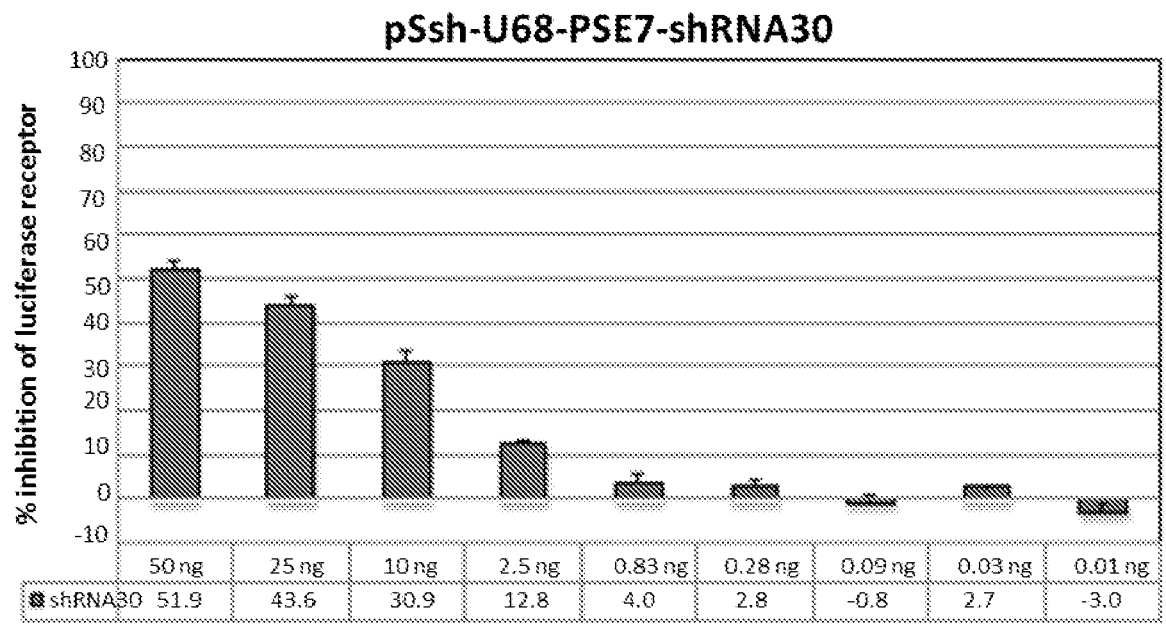
Figure 8F:
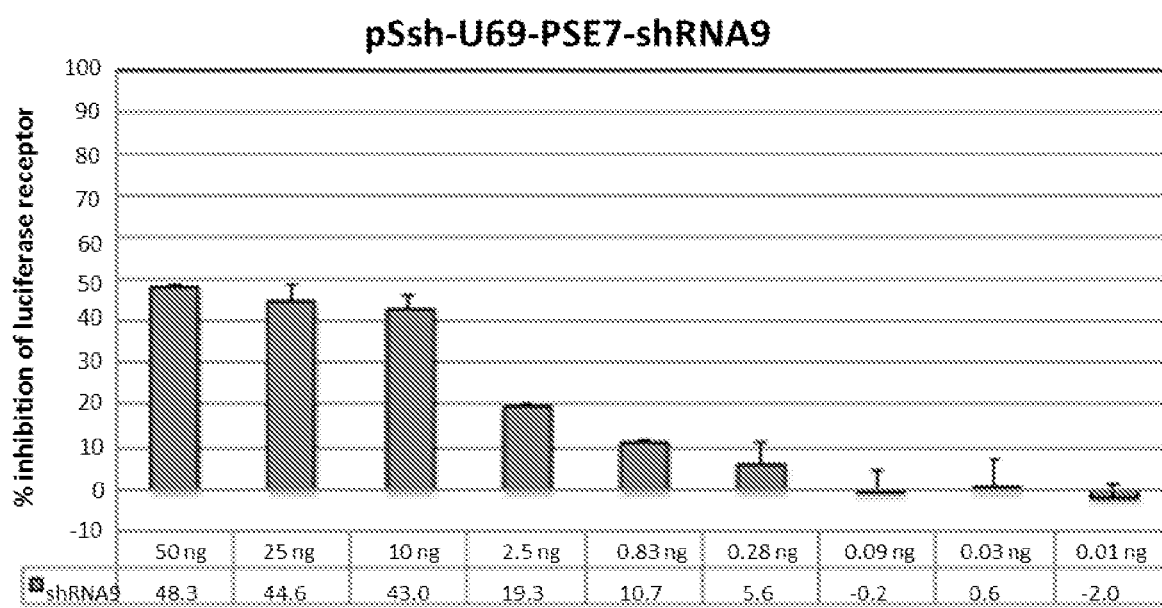
Figure 8G:
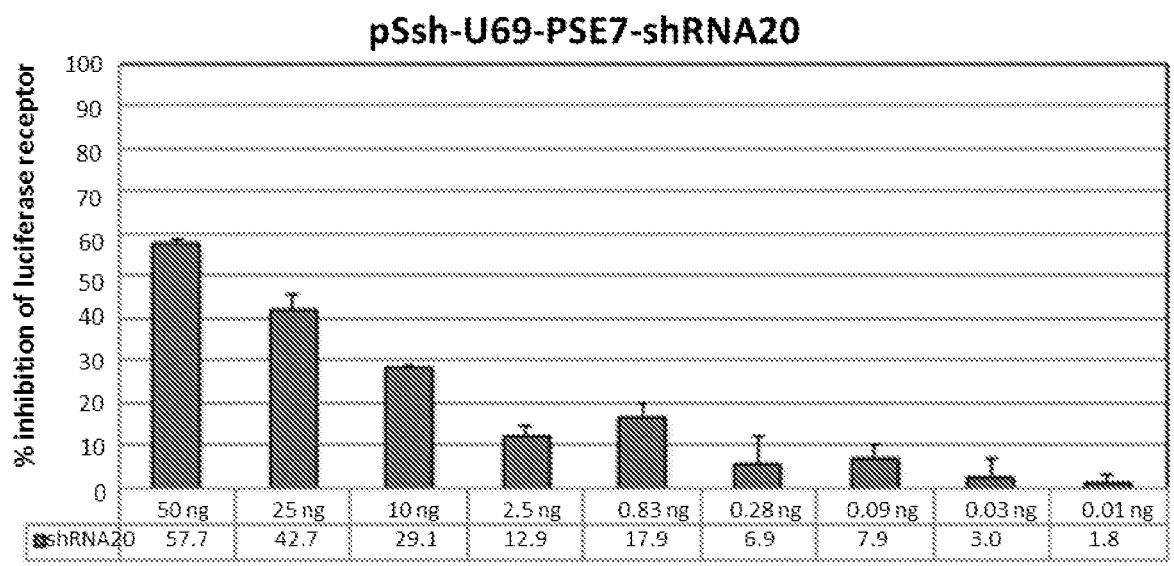
Figure 8H:
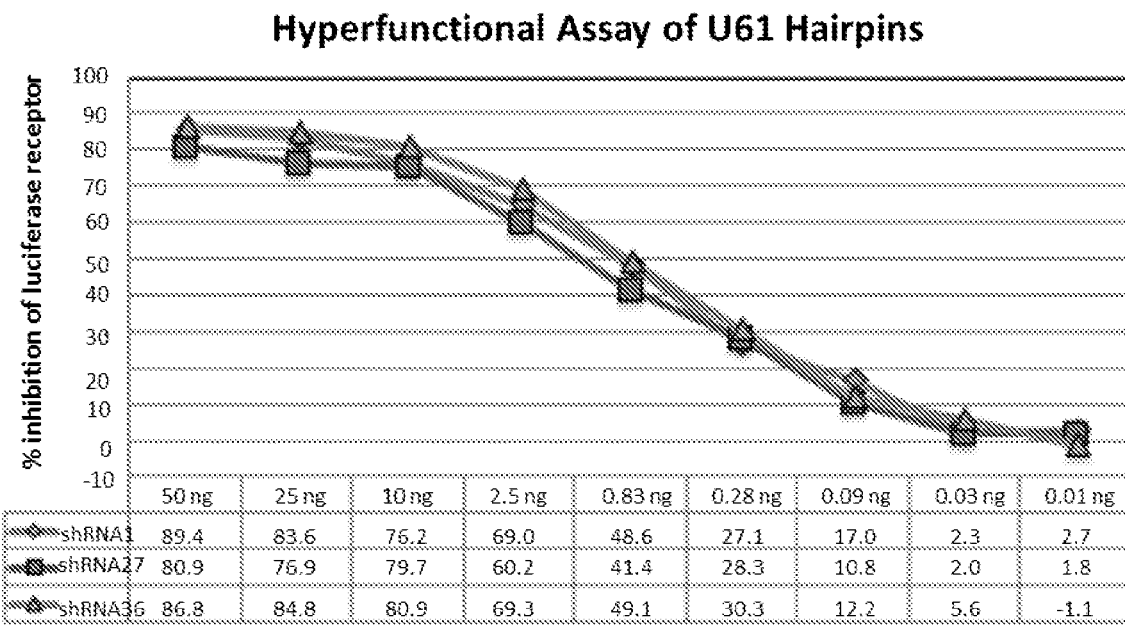
Figure 8I:
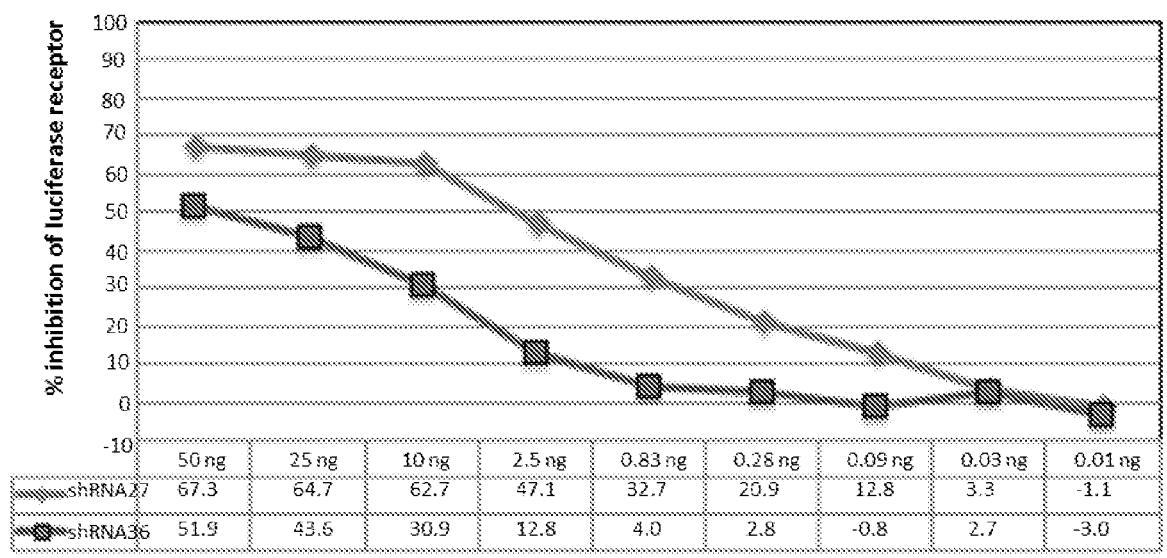
Figure 8J:
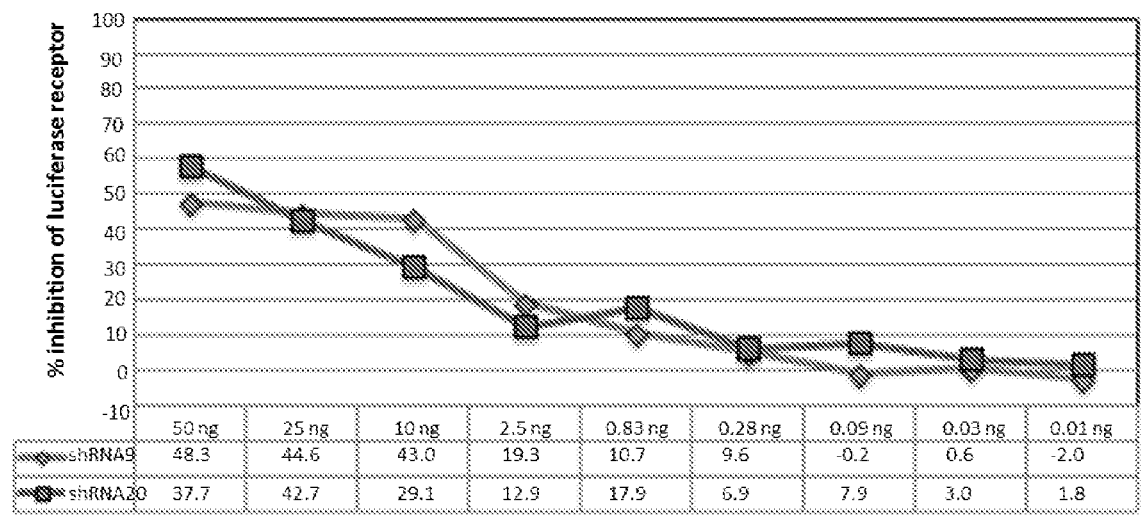

The level of inhibition of HBV transcripts at regions corresponding to HBV antigens HBsAg, HBcAg and HbxAg were determined relative to levels of GAPDH mRNA. Percentage inhibition of HBsAg, HBcAg, HbxA mRNA expression were calculated relative to a negative control, in this instance a siGlo siRNA (Dharmacon). The level of inhibition of HBV transcripts at regions corresponding to HBV antigens HBsAg, HBcAg and HbxAg, is presented in Table 10 and illustrated FIG. 3. FIG. 4 shows location of the HBV siRNAs relative to the HBV polymerase gene and the respective HBV antigens HBsAg, HBcAg and HbxAg.

TABLE 10

Inhibition of expression of HBV antigens in HepG2.2.15 cells by siRNA

| siRNA corresponding to | HBV Antigen | Inhibition (%) |
|---|---|---|
| shRNA9 | HBsAg | 19.88 |
|  | HBxAg | 28.02 |
|  | HBcAg | 65.78 |
| shRNA15 | HBsAg | 81.26 |
|  | HBxAg | 83.23 |
|  | HBcAg | 61.77 |
| shRNA27 | HBsAg | 60.46 |
|  | HBxAg | 72.15 |
|  | HBcAg | 17.37 |

Example 5—Activity of ddRNAi Expression Constructs in Dual-Luciferase Reporter Assay To test the efficacy of ddRNAi expression constructs expressing shRNAs of the disclosure to knockdown HBV transcripts, dual-luciferase reporter assays were performed in HEK293 cells.

Initial screens were performed to determine strand preference for the following 26 shRNAs of the disclosure: shRNA1, shRNA4, shRNA15, shRNA18, shRNA35, shRNA36, shRNA39, shRNA5, shRNA6, shRNA7, shRNA8, shRNA25, shRNA26, shRNA30, shRNA40, shRNA9, shRNA10, shRNA11, shRNA12, shRNA33, shRNA34, shRNA19, shRNA20, shRNA23 and shRNA24.

Plasmid reporter constructs based on the pGL3 Luciferase Reporter Vector were constructed for the sense strand and antisense strand of each of the 26 shRNA sequences. The Luciferase reporter constructs were generated by inserting the sense strand sequence or the antisense strand sequence of the respective shRNA (as appropriate) with 20 bp flanking sequences at each end into the pGL3-control vector (Promega, Madison, Wis.). The inserts were subcloned using FseI and XbaI restriction enzyme sites following the luciferase reporter gene.

The HEK293 cell line was purchased from ATCC (Manassas, Va.). The HEK293 cells were cultured in DMEM medium containing 10% fetal bovine serum, 2 mM glutamine, penicillin (100 U/mL), and streptomycin (100 μg/mL) at 37° C. humid incubator with 5% CO2. Briefly, the HEK293 cells were seeded at a density of $2\times10^4$ cells per well into 96-well culture plate one day prior to transfection.

For each shRNA, a ddRNAi expression construct was constructed by inserting the respective shRNA sequence into a pSsh vector with a U6 promoter and proximal sequence element 7 (PSE7). The U6 promoters were based on either human U6-1, U6-8 or U6-9 sequences For each well of transfection, the corresponding ddRNAi expression construct and one of the two Luciferase reporter constructs were co-transfected into HEK293 cells at a ratio of 10:1 (ddRNAi expression construct: Luciferase reporter construct) using 0.3 uL of Lipofectamine 2000 reagent (Life Technologies, Carlsbad, Calif.) according to manufacturer's instructions. The cells were also transfected with 1 ng of a Renilla reporter construct (serving as a transfection control). 48 hour post-transfection, cell lysates were collected and analyzed using Dual Luciferase Reporter Assay System (Promega, Madison, Wis.). The firefly/Renilla activity ratios were determined for each well. Percentage inhibition of reporter expression were calculated relative to a negative control, in this instance a construct that used the U6-9 promoter to express a random non-targeting sequence with no homology to human or mouse sequences, termed U6-9cont. U6-9cont was designed to express the sequence CGTCGGTAC-CACAAGCAAGAGTCGGCAGTAAGAA-GATGGCGTATATATTATGAAAGGT ACCGAGAT-TGGCCATTCGGAGTGTTTAGTCGACCAAACTGAT (SEQ ID NO: 115). The experiment was performed in replicate.

The ability of each shRNA to inhibit expression of luciferase protein from the respective Luciferase reporter constructs is illustrated in FIGS. 5a-5f.

Seven of the 26 shRNA assayed were selected for further testing based on their ability to inhibit expression of luciferase protein from the respective Luciferase reporter constructs i.e., shRNA1, shRNA15, shRNA36, shRNA27, shRNA30, shRNA9 and shRNA20. These 7 shRNA were subjected to a nine point dose response curve to assess hyperfunctional properties of the hairpins. Two dose curve experiments were undertaken:
Experiment 1: HEK293 cells were transfected with a shRNA:target ratio ranging from 1:1 to 1:5000; and
Experiment 2: HEK293 cells were transfected with a shRNA:target ratio ranging from 10:1 to 1:500.

In each of Experiments 1 and 2, the seven shRNAs were tested against Luciferase reporter constructs designed to detect inhibition of luciferase activity by the antisense strand i.e., comprising sense strand sequence. The reporter constructs were designed as described above. The ddRNAi expression constructs for the respective shRNAs were also as described above.

Experiment 1

HEK293 cells were seeded at a density of $2.5\times10^4$ cells per well into 96-well culture plates one day prior to transfection. For each of the seven ddRNAi expression constructs, a well containing HEK293 cells was co-transfected with 50 ng, 25 ng, 10 ng, 2.5 ng, 0.83 ng, 0.28 ng, 0.09 ng, 0.03 ng, or 0.01 ng of the respective ddRNAi expression construct and 50 ng of the corresponding Luciferase reporter construct using 0.3 uL of Lipofectamine 2000 reagent (Life Technologies, Carlsbad, Calif.) according to manufacturer's instructions. The cells were also transfected with 1 ng of a Renilla reporter construct (serving as a loading control). 48 hour post-transfection, cell lysates were collected and analyzed using Dual Luciferase Reporter Assay System (Promega, Madison, Wis.). The firefly/Renilla activity ratios were determined for each well, and the inhibition efficiency of ddRNAi expression constructs were calculated.

The ability of each of the ddRNAi expression constructs to inhibit expression of luciferase from the respective Luciferase reporter constructs in a dose-dependent manner is illustrated in FIGS. 6a-6j.

Experiment 2

HEK293 cells were seeded at a density of $2.5 \times 10^4$ cells per well into 96-well culture plates one day prior to transfection. For each of the seven ddRNAi expression constructs, a well containing HEK293 cells was co-transfected with 100 ng, 50 ng, 20 ng, 5 ng, 1.67 ng, 0.56 ng, 0.19 ng, 0.06 ng, or 0.02 ng of the respective ddRNAi expression construct and 10 ng of the corresponding Luciferase reporter construct using 0.3 uL of Lipofectamine 2000 reagent (Life Technologies, Carlsbad, Calif.) according to manufacturer's instructions. The cells were also transfected with 1 ng of a Renilla reporter construct (serving as a loading control). 48 hour post-transfection, cell lysates were collected and analyzed using Dual Luciferase Reporter Assay System (Promega, Madison, Wis.). The firefly/Renilla activity ratios were determined for each well, and the inhibition efficiency of ddRNAi expression constructs were calculated.

The ability of each of the ddRNAi expression constructs to inhibit expression of luciferase from the respective Luciferase reporter constructs in a dose-dependent manner is illustrated in FIGS. 7a-7j.

Example 6—Hyperfunctional Properties of ddRNAs Co-Transfected with Filler Plasmid The hyperfunctional properties of the seven lead ddRNAi constructs described in Example 5 were then assessed when co-transfected with a U69-PSE7fix-Random100 (pBL-153) filler plasmid in HEK293 cells.

Plasmid reporter constructs based on the pGL3 Luciferase Reporter Vector were prepared for the sense and antisense strands of each of the seven shRNA sequences of the ddRNAi constructs, as previously described.

HEK293 cells cultured in accordance with the methods previously described and were seeded at a density of $2.5 \times 10^4$ cells per well into 96-well culture plates one day prior to transfection. For each of the seven ddRNAi expression constructs, a well containing HEK293 cells was co-transfected with (i) 50 ng, 25 ng, 10 ng, 2.5 ng, 0.83 ng, 0.28 ng, 0.09 ng, 0.03 ng, or 0.01 ng of the respective ddRNAi expression construct, (ii) various amounts of filler plasmid to adjust the final DNA content to 50 ng, and (iii) 50 ng of the corresponding Luciferase reporter construct, using 0.3 uL of Lipofectamine 2000 reagent (Life Technologies, Carlsbad, Calif.) according to manufacturer's instructions. The cells were also transfected with 1 ng of a Renilla reporter construct (serving as a loading control). 48 hour post-transfection, cell lysates were collected and analyzed using Dual Luciferase Reporter Assay System (Promega, Madison, Wis.). The firefly/Renilla activity ratios were determined for each well, and the inhibition efficiency of ddRNAi expression constructs were calculated.

The ability of each of the ddRNAi expression constructs to inhibit expression of luciferase from the respective Luciferase reporter constructs in a dose-dependent manner when co-transfected with a filler plasmid is illustrated in FIGS. 8a-8j.

Example 7—HBV Inhibitory Activity of Variant shRNAs

Two variant shRNAs were designed and prepared for each of shRNAs designated shRNA 9 (SEQ ID NO: 73) and shRNA20 (SEQ ID NO: 84). The variants prepared were as follows:
shRNA13 (SEQ ID NO:77);
shRNA14 (SEQ ID NO: 78);
shRNA21 (SEQ ID NO: 85); and
shRNA22 (SEQ ID NO: 86).

ddRNAi constructs were prepared by inserting each of the original and variant shRNA sequences into two pPsh vectors, one comprising a U69-PSE7-U68 hybrid promoter and the other comprising a U69-PSE7 promoter. Dual-luciferase reporter assays were then performed in HEK293 cells to test efficacy of the various shRNAs to knockdown expression of HBV genes.

Luciferase reporter constructs were prepared for the sense and antisense strands of the shRNAs in each of the ddRNAi expression constructs in accordance with the methodology previously described.

HEK293 cells were cultured in DMEM medium containing 10% fetal bovine serum, 2 mM glutamine, penicillin (100 U/mL), and streptomycin (100 μg/mL) at 37° C. humid incubator with 5% CO2. The HEK293 cells were seeded at a density of $2 \times 10^4$ cells per well into 96-well culture plate one day prior to transfection.

Figure 9A:
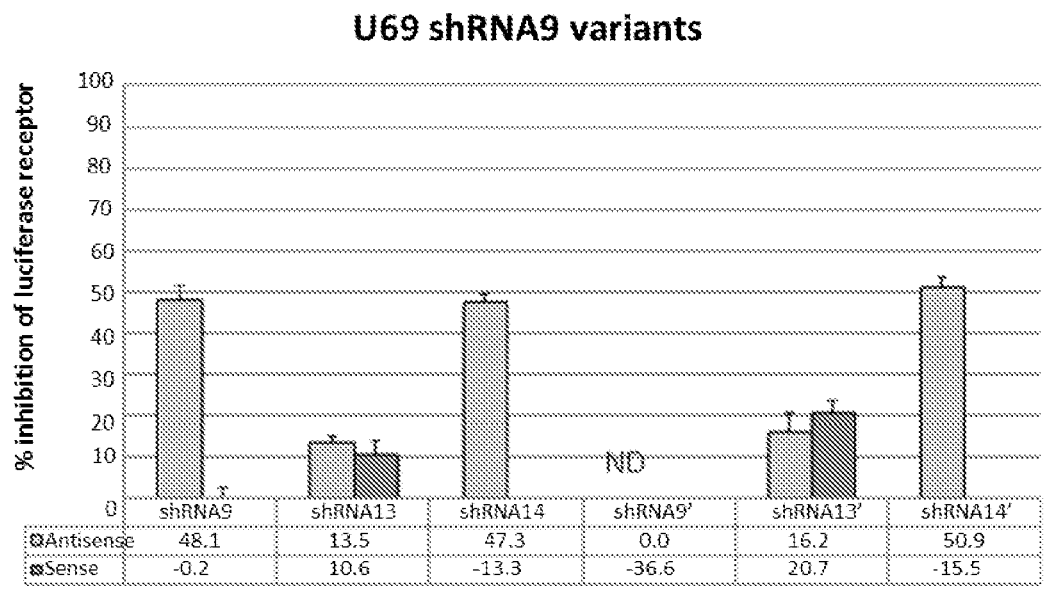
FIGS. 9 (a)-(b) illustrate the ability of ddRNAi constructs expressing shRNAs designated shRNA9, shRNA13, shRNA14, shRNA20, shRNA21 and shRNA22 to inhibit expression of luciferase protein in Luciferase reporter assay system.
Figure 9B:
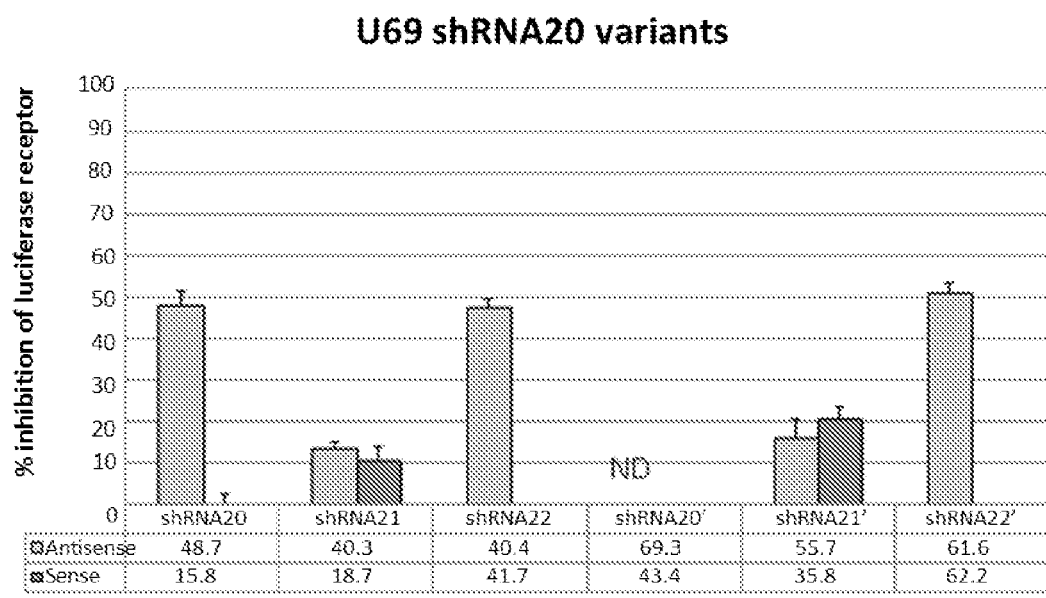

For each well of transfection, 10 ng of the corresponding ddRNAi expression construct and 100 ng of one of the two Luciferase reporter constructs were co-transfected into HEK293 cells using 0.3 uL of Lipofectamine 2000 reagent (Life Technologies, Carlsbad, Calif.) according to manufacturer's instructions. The cells were also transfected with 5 ng of a Renilla reporter construct (serving as a loading control). 48 hour post-transfection, cell lysates were collected and analyzed using Dual Luciferase Reporter Assay System (Promega, Madison, Wis.). The firefly/Renilla activity ratios were determined for each well, and the inhibition efficiency of respective shRNA were calculated. The ability of each shRNA to inhibit expression of luciferase protein from the respective Luciferase reporter constructs is illustrated in FIGS. 9a-9b.

Example 8—Preparation of AdV-shRNA Vectors

HBV shRNA sequences for shRNAs designated shRNA14, shRNA15, shRNA37 and shRNA28 were synthesized and cloned downstream of modified U6-1, U6-8, or U6-9 promoters. The entire expression cassette was subcloned into adenovirus (AdV) construct for virus production from Vector Biolabs (Malvern, Pa.).

Example 9—shRNA Knockdown of HBV Transcripts in HepG2.2.15 Cells

HBV shRNA AdV vectors were prepared for shRNAs designated shRNA14, shRNA15, shRNA37 and shRNA28 in accordance with Example 8.

HepG2.2.15 cells were prepared in accordance with methods described in Example 4 for subsequent transduction with the HBV shRNA AdV vectors. The HepG2.2.15 cells were then infected with the HBV shRNA AdV vectors in cell suspension and cultured on 24-well plates. Briefly, each well contained a suspension of $1.0 \times 10^5$ HepG2.2.15 cells and one of the HBV shRNA AdV vectors at the following MOIs: 6, 15, 30, 60, 90, or 120. To simulate treatment with a triple HBV shRNA expression cassette, cell cultures were also simultaneously infected with three HBV shRNA adenovirus at the following MOI of each: 2, 5, 10, 20, 30, 40, 60, or 90. The triple HBV shRNA expression cassettes simulated were (i) shRNA14/shRNA15/shRNA28 and (ii) shRNA14/shRNA37/shRNA28. After transduction, the cells were cultured at 37° C. at 5% $CO_2$ for 72 h before being harvested for RNA and DNA extraction using Qiagen miRNeasy mini kit and QiAmp DNA mini kit, respectively (Valencia, Calif.).

Total RNA was isolated using miRNeasy Mini Kit (Qiagen, Valencia, Calif.). Total RNA was quantified using the NanoDrop 1000 Spectrophotometer (Thermo Scientific) and diluted to a working concentration of 10 ng/µl.

Production of shRNA by the AdV vectors was measured using Qiagen's miScript PCR system (Valencia, Calif.). For each RT-qPCR analysis, 50 ng of total RNA were converted into cDNA using Qiagen's miScript II RT kit. Quantitative PCR of shRNA was then carried out using Qiagen miScript SYBR green PCR kit with custom primers set forth in Table 11 and the following real-time PCR conditions: initial denaturation at 95° C. for 15 min followed by 40 cycles of 94° C. for 15 sec, 55° C. for 30 sec and 70° C. for 30 sec.

TABLE 11

Custom primers for quantifying shRNA expression

| Primer | Sequence (5' - 3') | SEQ ID NO |
|---|---|---|
| shRNA15_fwd | ACAAACGGGCAACATACCTTG | 116 |
| shRNA37_fwd | GGGAAAGCCCTACGAACCACTG | 117 |
| shRNA28_fwd | GGATTCAGCGCCGACGGGACG | 118 |
| shRNA14_fwd | TTCTTCTTCTAGGGGACCTGC | 119 |

To assist in determining the expression levels of the various shRNAs, qPCR standard assays were developed for the guide RNA sequences (Table 12) which were predicted to be processed from the shRNAs.

TABLE 12

Guide RNA sequences

| Primer | Sequence (5' - 3') | SEQ ID NO |
|---|---|---|
| shRNA15_std | ACAAACGGGCAACAUACCUUG | 120 |
| shRNA37_std | GGGAAAGCCCUACGAACCACUG | 121 |
| shRNA28_std | GGAUUCAGCGCCGACGGGACG | 122 |
| shRNA14_std | UUCUUCUUCUAGGGGACCUGC | 123 |

Figure 10:
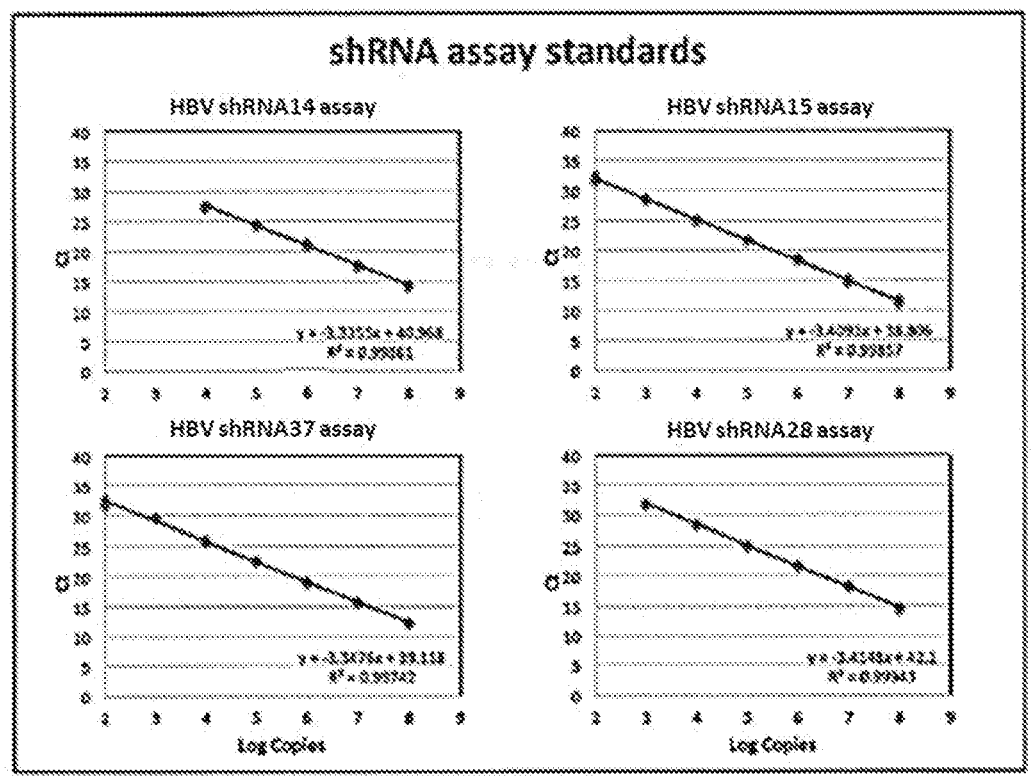
FIG. 10 shows standard curves obtained by qPCR determining the number of shRNAs expressed per cell following transductions thereof with HBV AdVs.
Figure 11A:
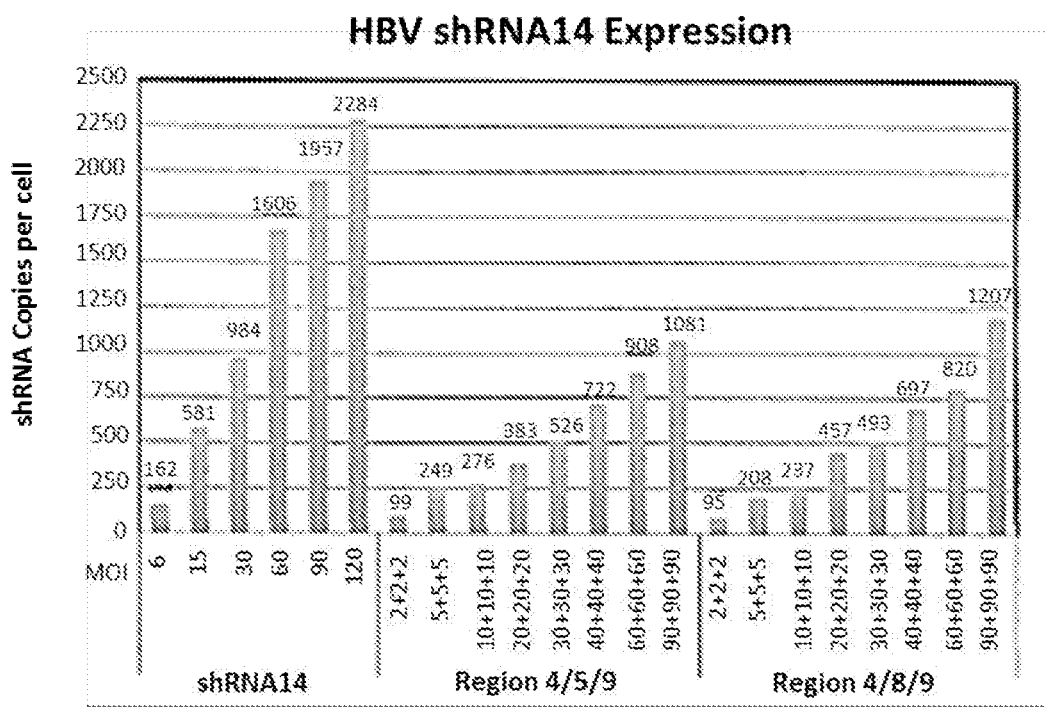
FIGS. 11(a)-(d) show the level of expression for shRNAs designated shRNA14, shRNA15, shRNA37 and shRNA28 respectively in: (i) HepG2.2.15 cells transduced with an HBV shRNA AdV vector expressing the respective shRNA individually at the various MOIs; (ii) HepG2.2.15 cells simultaneously transduced with three HBV shRNA AdV vectors expressing the shRNAs designated shRNA14, shRNA37 and shRNA28 respectively at various MOIs; and (iii) HepG2.2.15 cells simultaneously transduced with three HBV shRNA AdV vectors expressing the shRNAs designated shRNA14, shRNA15 and shRNA28 respectively at various MOIs.
Figure 11B:
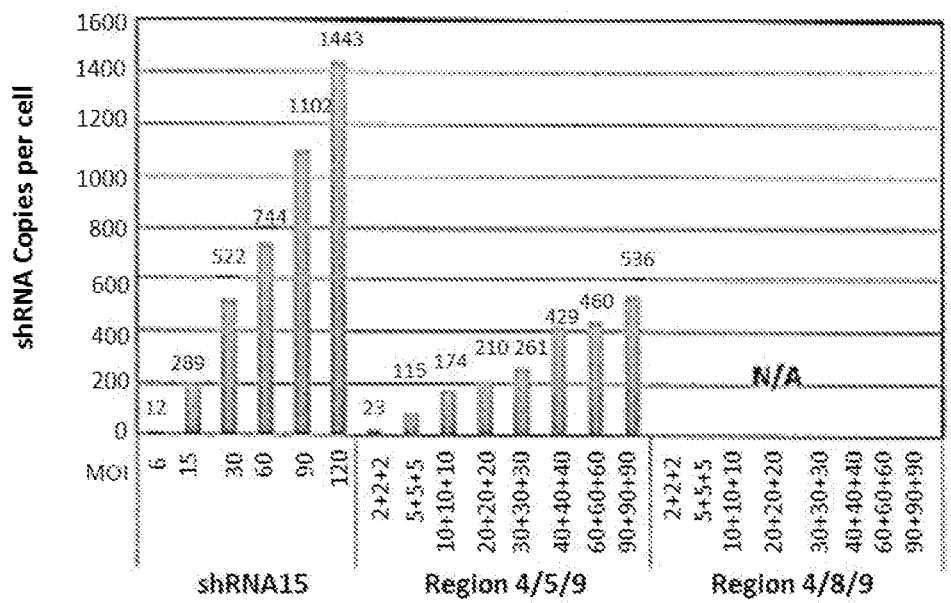
Figure 11C:
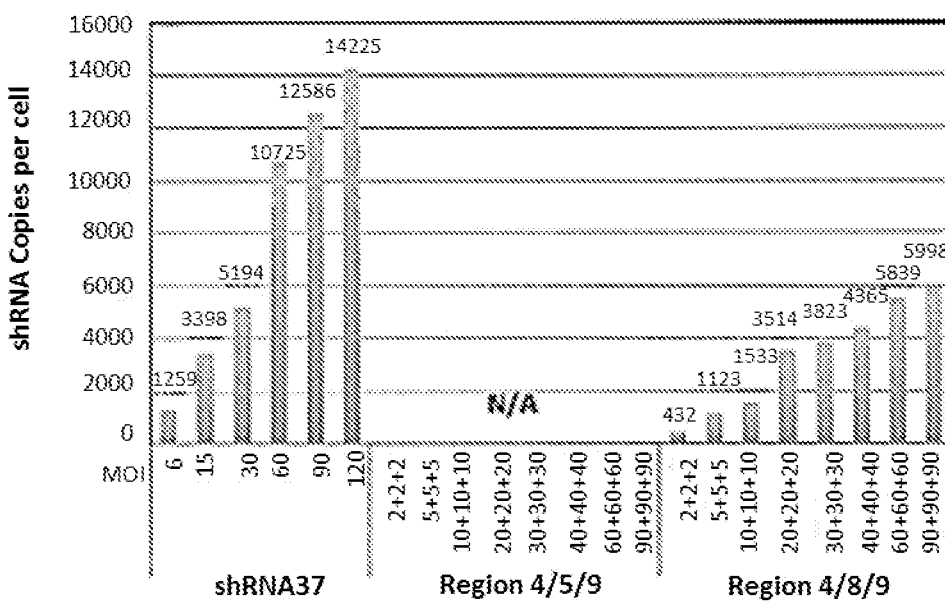
Figure 11D:
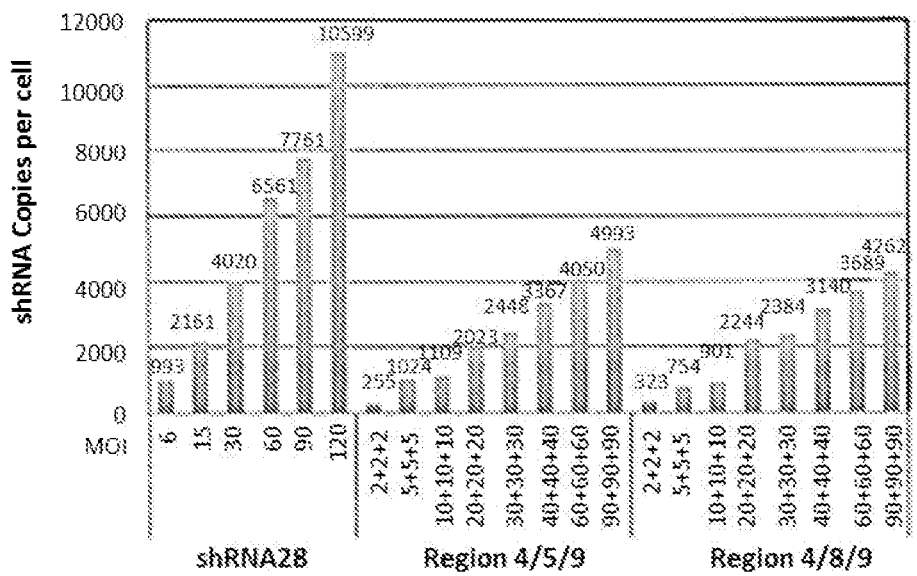
Figure 12A:
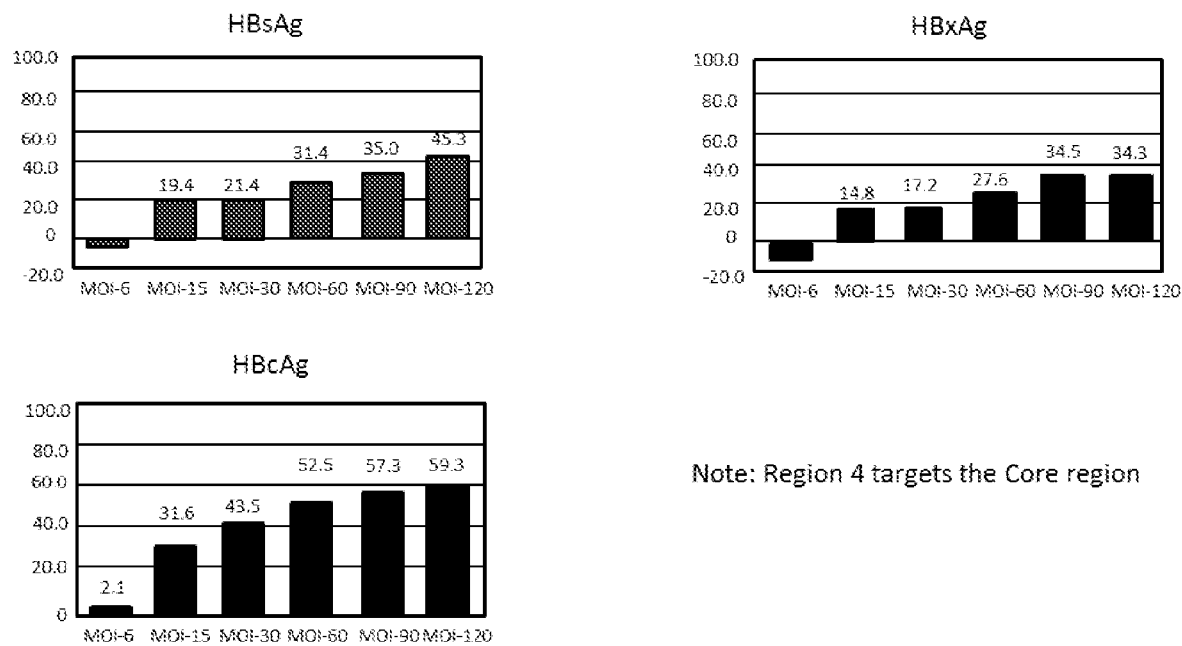
FIGS. 12(a)-(f) illustrate the level of inhibition of HBV transcripts at regions corresponding to HBV antigens HBsAg, HBcAg and HbxAg relative to expression of GAPDH in HepG2.2.15 cells transduced with: (a) a HBV shRNA AdV vector expressing shRNA14; (b) a HBV shRNA AdV vector expressing shRNA15; (c) a HBV shRNA AdV vector expressing shRNA37; (d) a HBV shRNA AdV vector expressing shRNA28; (e) three HBV shRNA AdV vectors expressing the shRNAs designated shRNA14, shRNA37 and shRNA28 respectively at various MOIs; and (f) three HBV shRNA AdV vectors expressing the shRNAs designated shRNA14, shRNA15 and shRNA28 respectively at various MOIs.
Figure 12B:
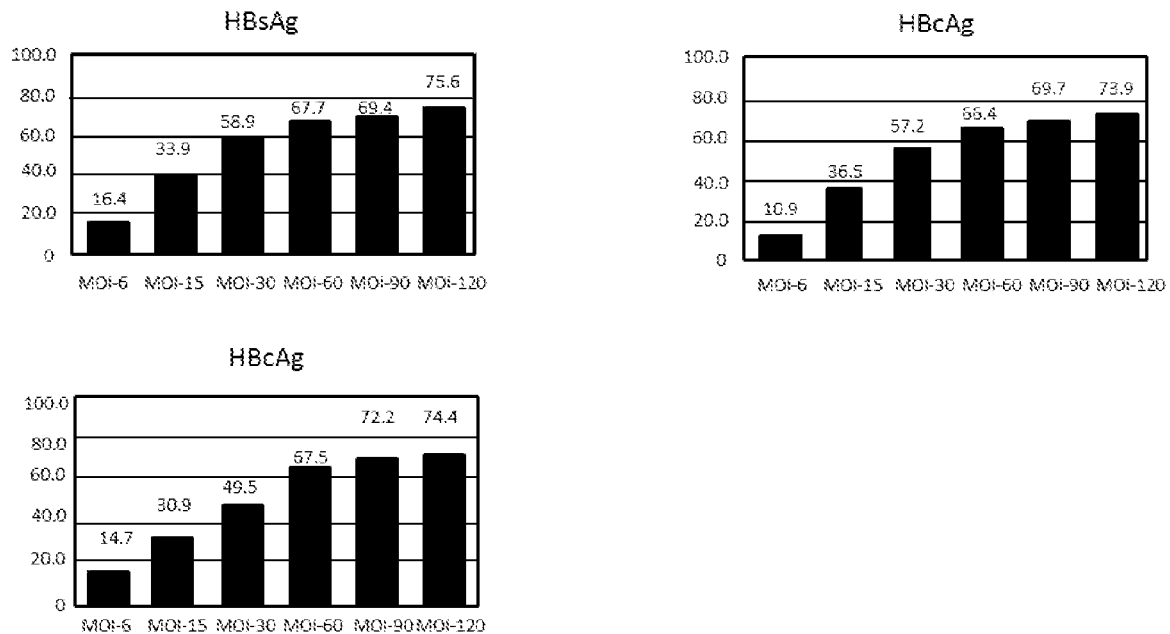
Figure 12C:
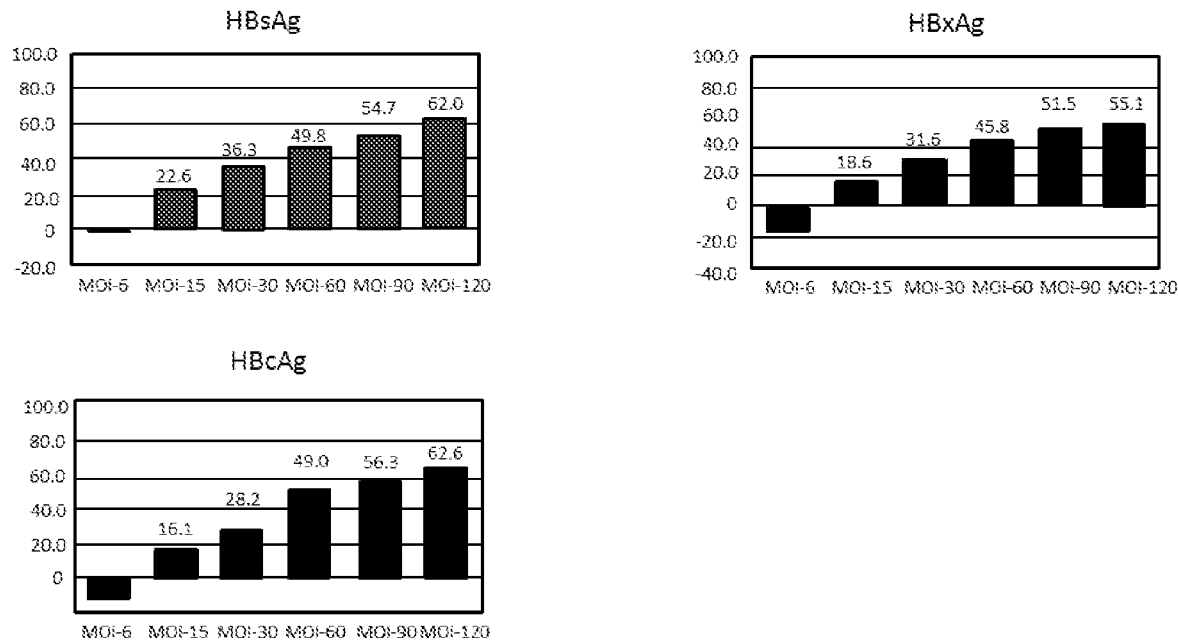
Figure 12D:
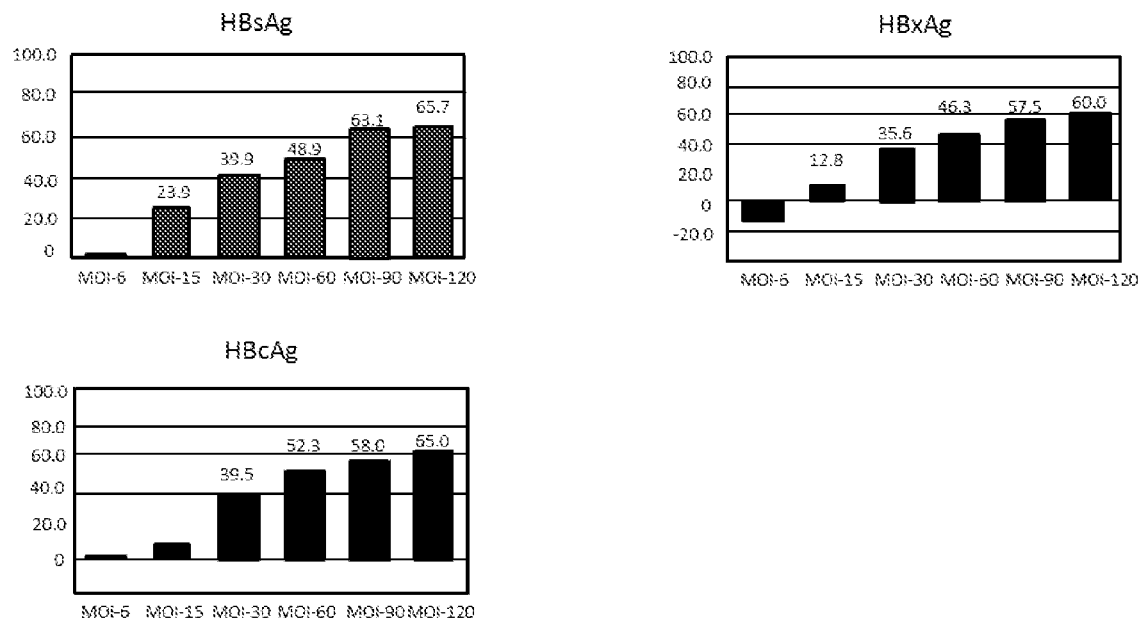
Figure 12E:
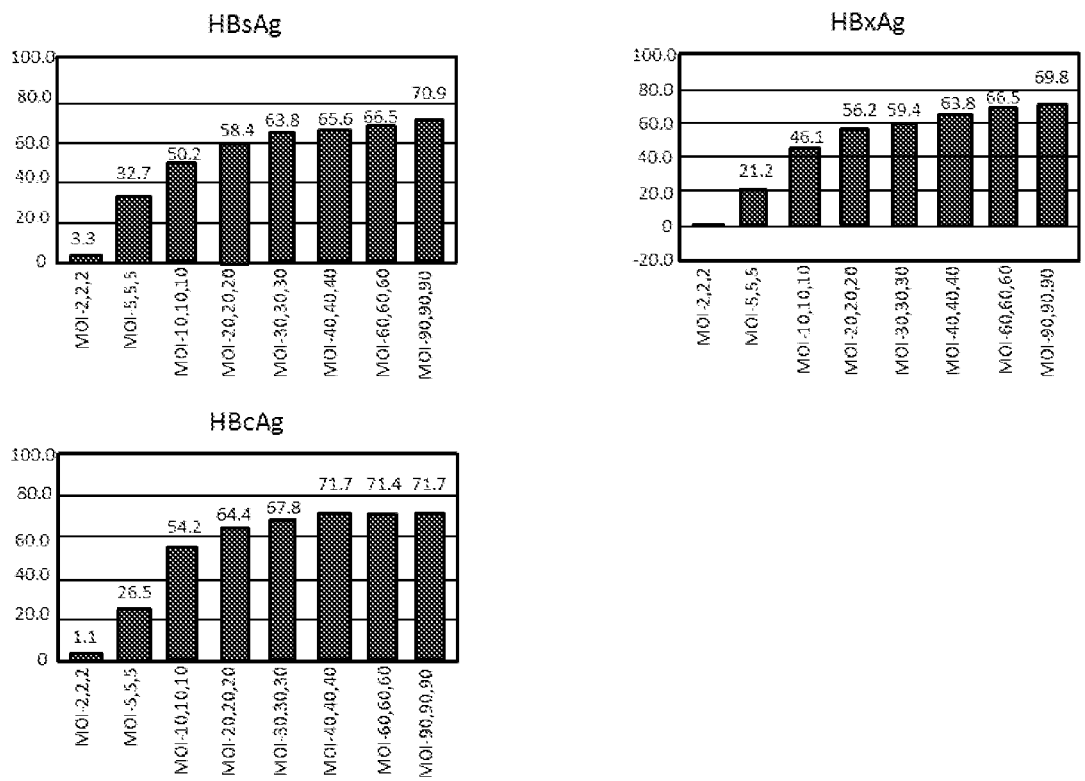
Figure 12F:
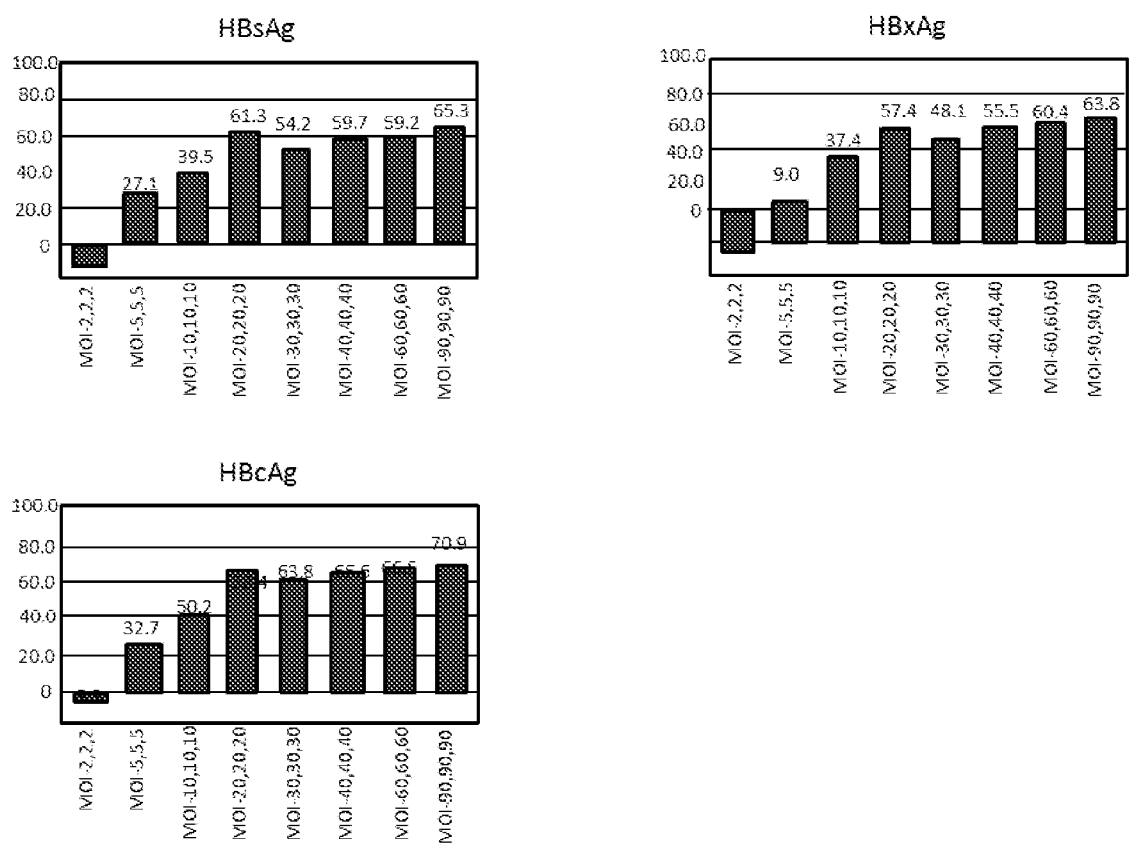
Figure 13A:
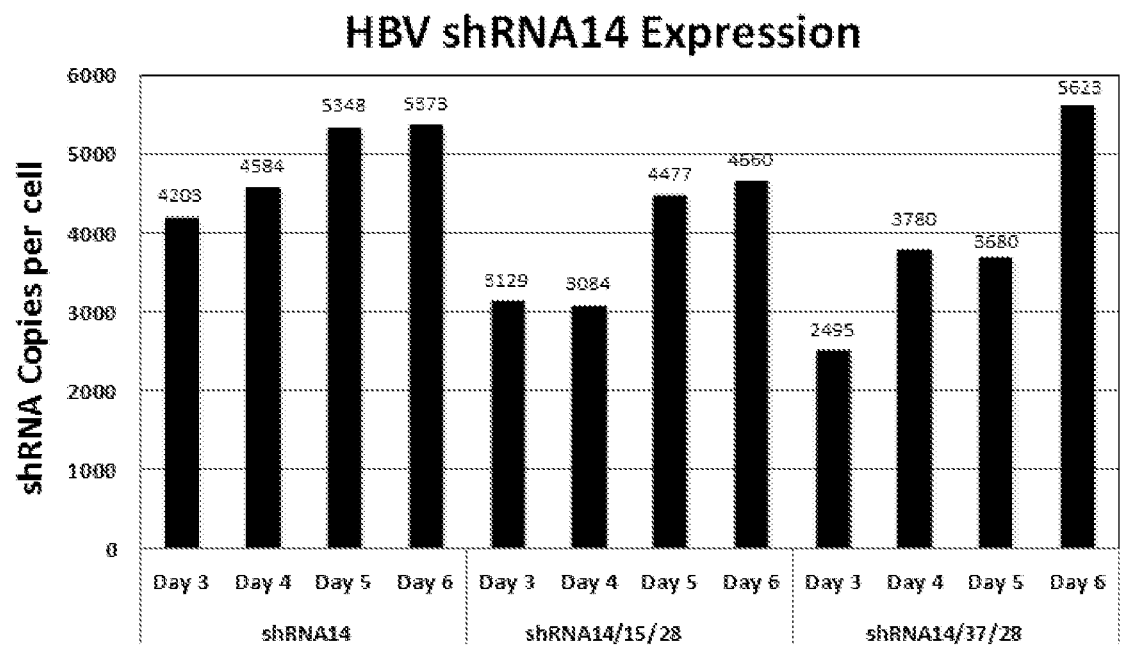
FIGS. 13(a)-(d) show the level of expression for shRNAs designated shRNA14, shRNA15, shRNA37 and shRNA28 respectively in: (i) HepG2.2.15 cells transduced with a HBV shRNA AdV vector expressing the respective shRNA14, shRNA15, shRNA37 or shRNA28 individually at MOI 100; (ii) HepG2.2.15 cells transduced with a triple HBV shRNA AdV vector expressing three shRNAs designated shRNA14, shRNA37 and shRNA28 respectively at MOI 100; and (iii) HepG2.2.15 cells transduced with a triple HBV shRNA AdV vector expressing three shRNAs designated shRNA14, shRNA15 and shRNA28 respectively at MOI 100.
Figure 13B:
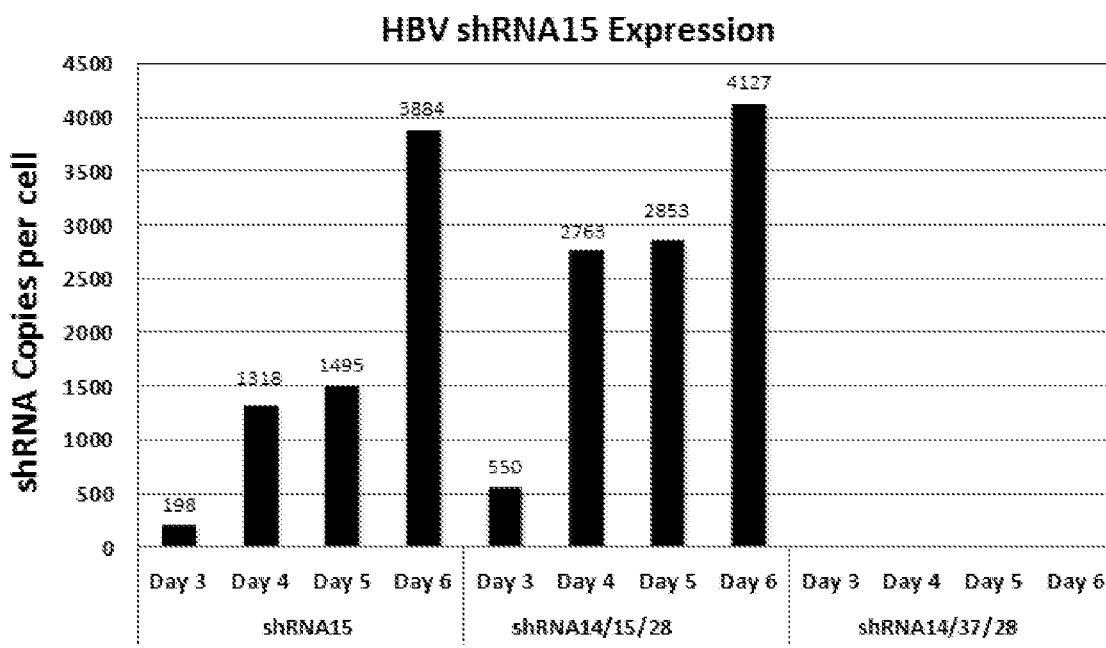
Figure 13C:
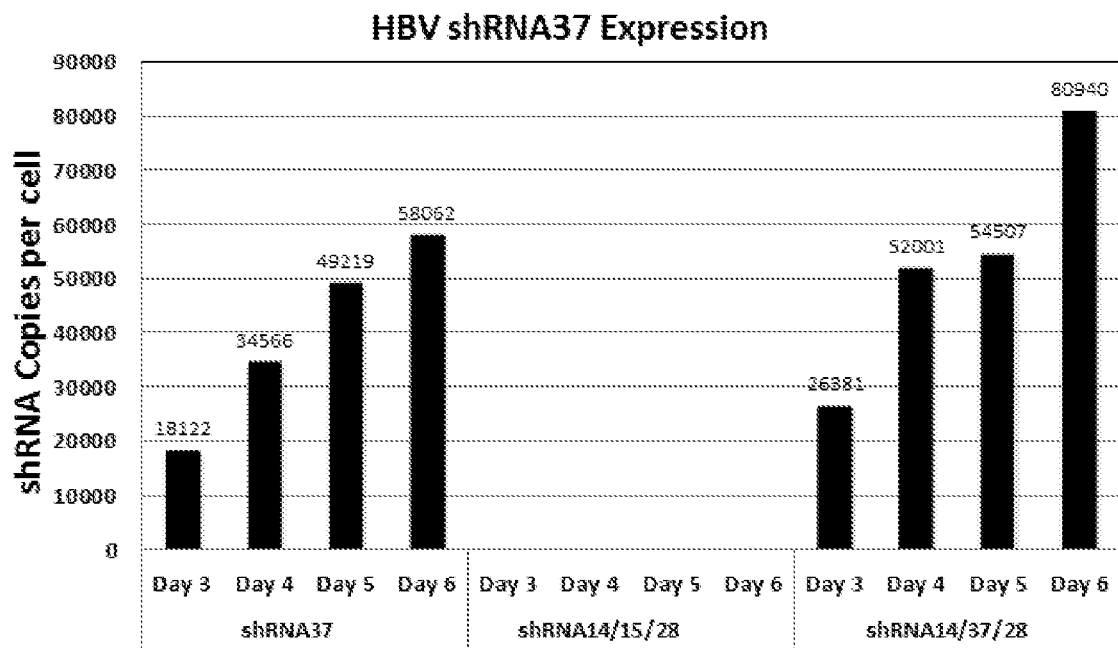
Figure 13D:
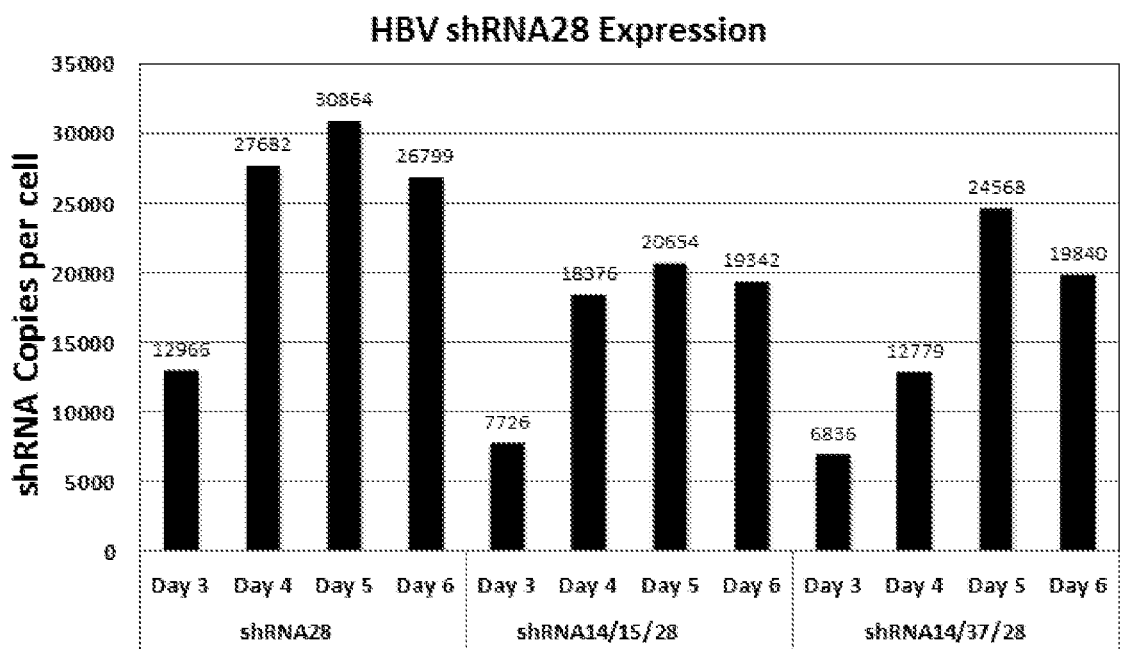
Figure 14A:
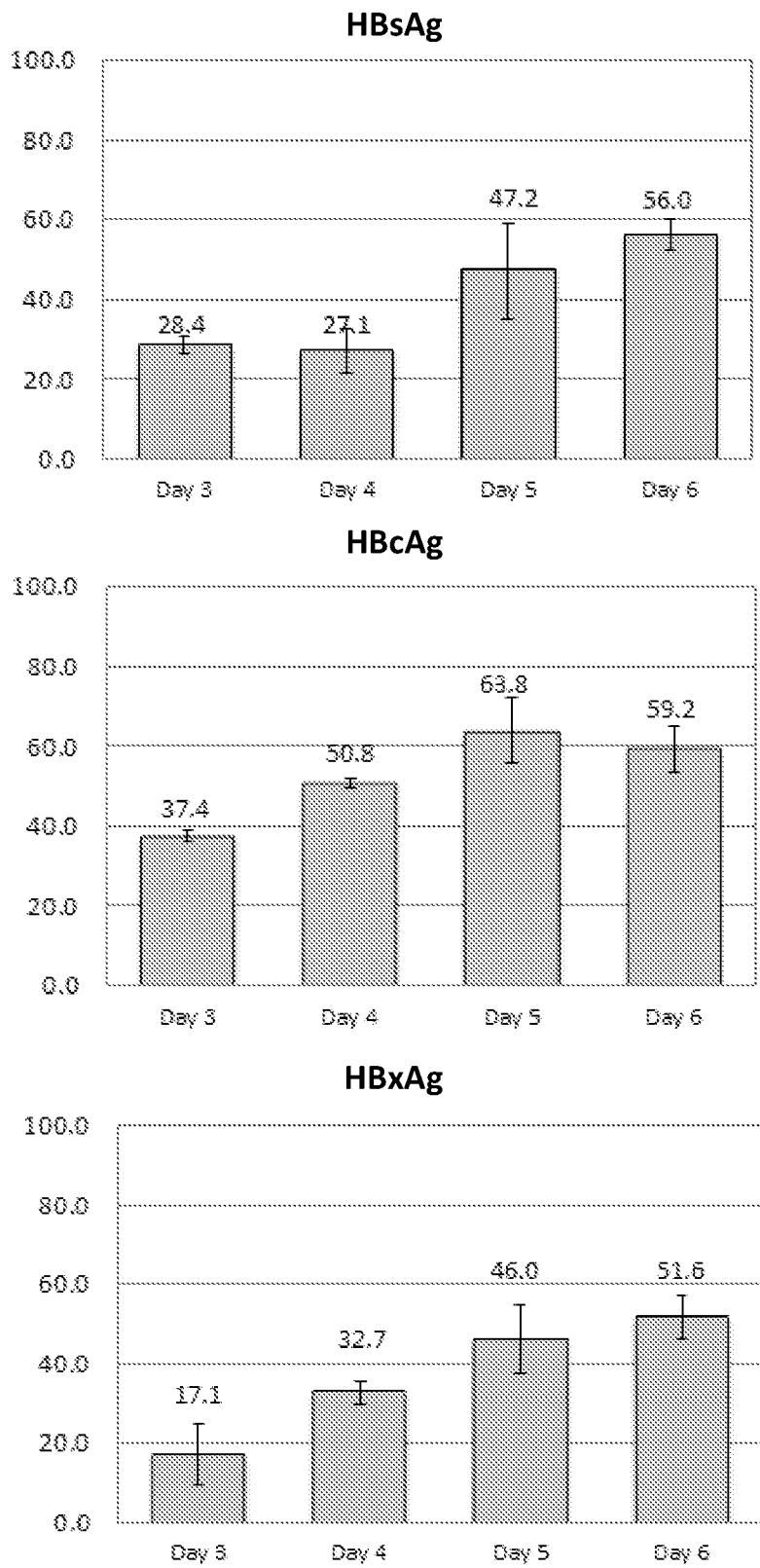
FIGS. 14(a)-(f) illustrate the level of inhibition of HBV transcripts at regions corresponding to HBV antigens HBsAg, HBcAg and HbxAg relative to expression of GAPDH in HepG2.2.15 cells transduced with: (a) a HBV shRNA AdV vector expressing shRNA14; (b) a HBV shRNA AdV vector expressing shRNA15; (c) a HBV shRNA AdV vector expressing shRNA37; (d) a HBV shRNA AdV vector expressing shRNA28; (e) a triple HBV shRNA AdV vector expressing three shRNAs designated shRNA14, shRNA37 and shRNA28; and (f) a triple HBV shRNA AdV vector expressing three shRNAs designated shRNA14, shRNA15 and shRNA28.
Figure 14B:
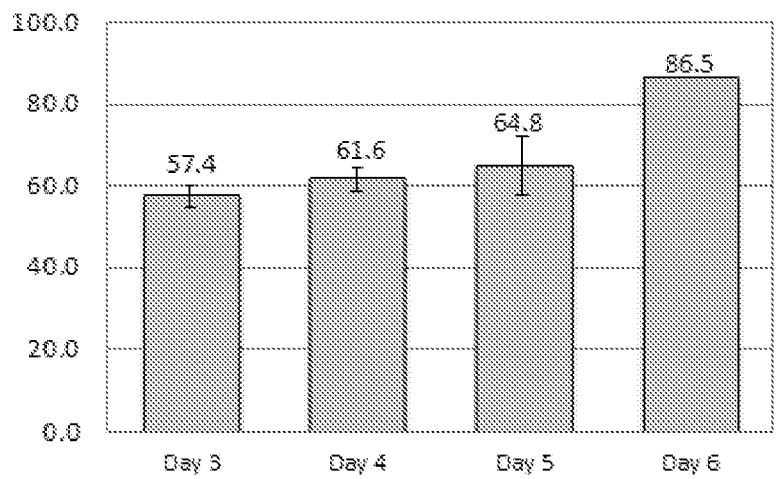
Figure 14B:
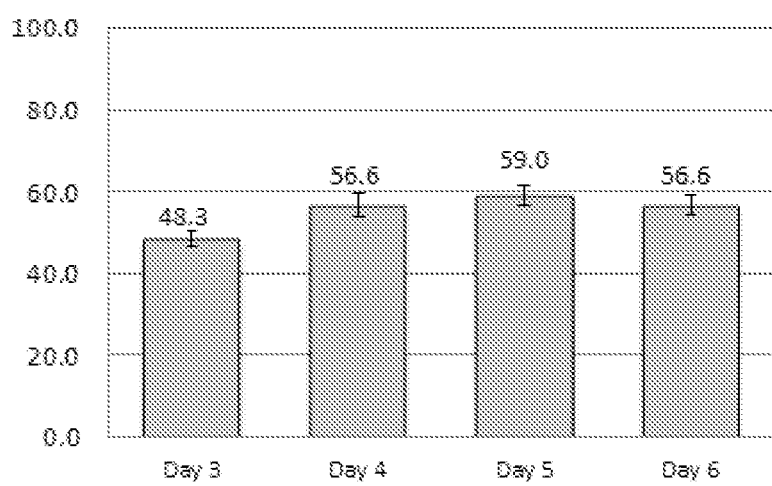
Figure 14B:
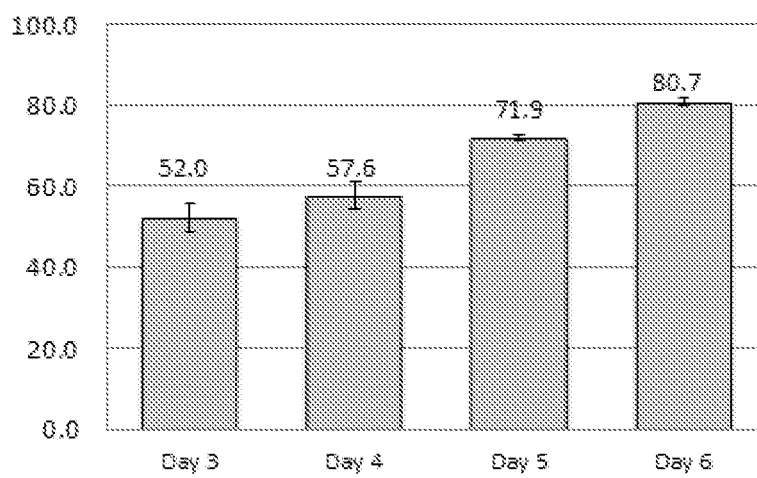
Figure 14C:
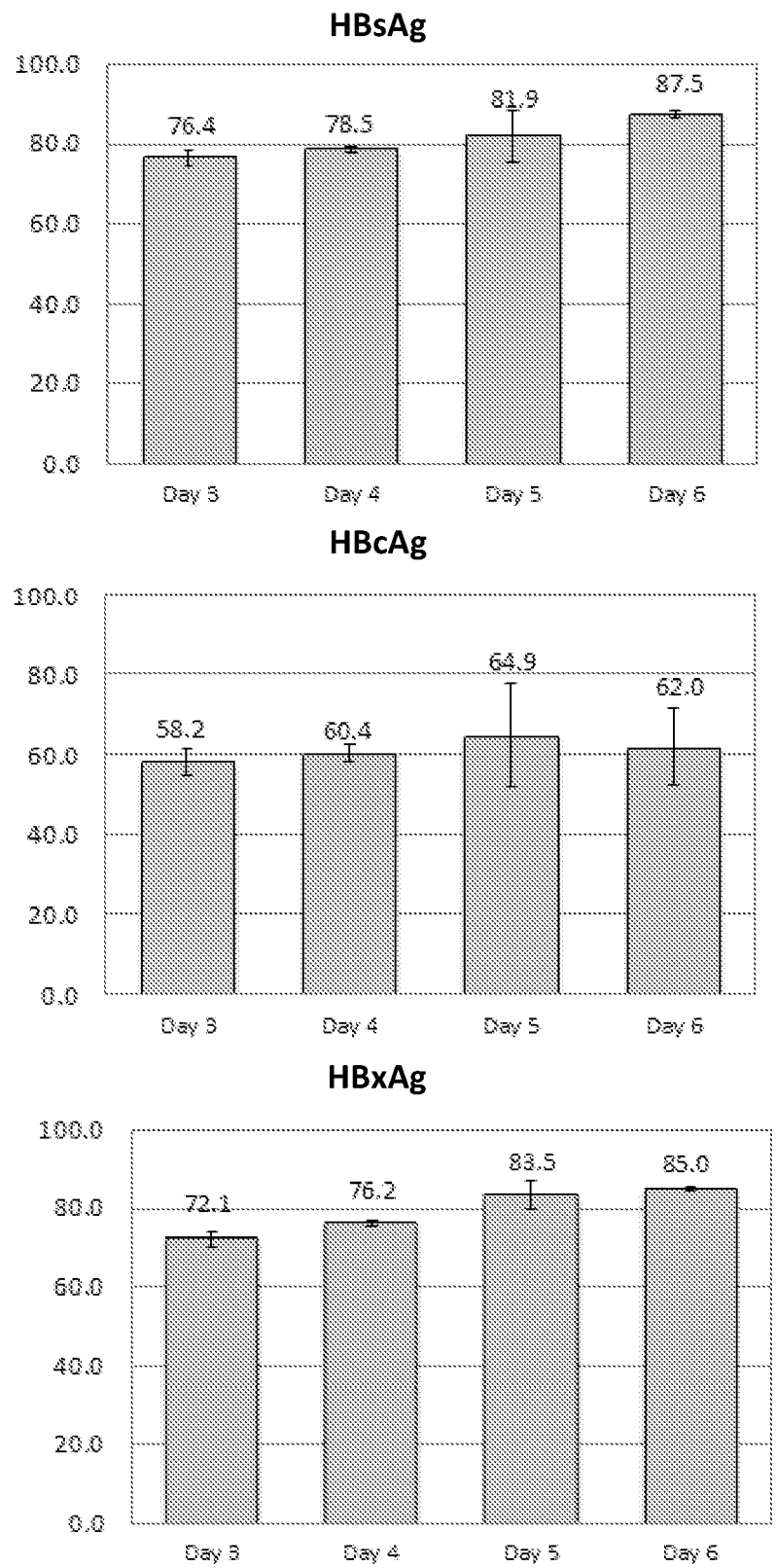
Figure 14D:
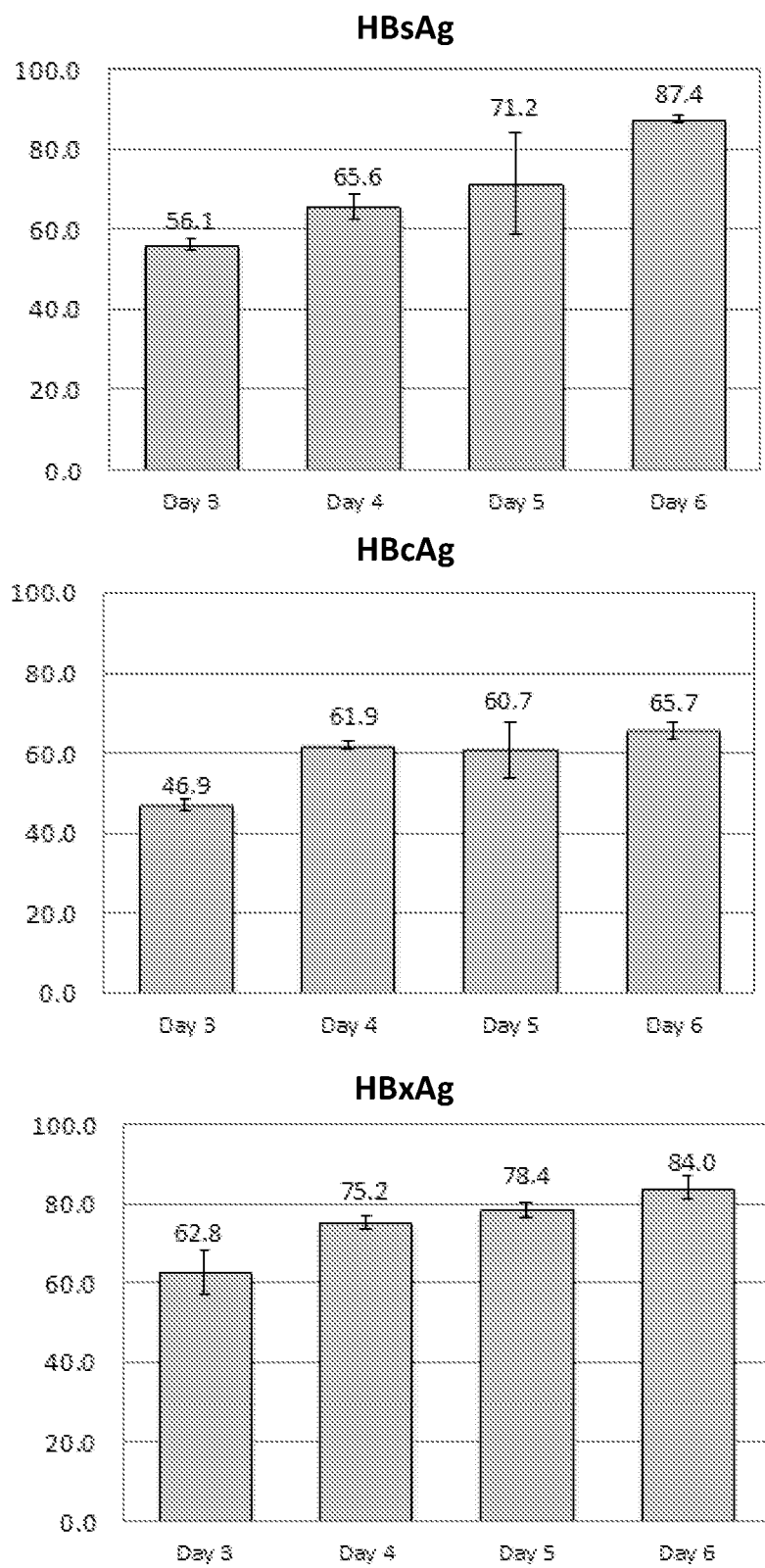
Figure 14E:
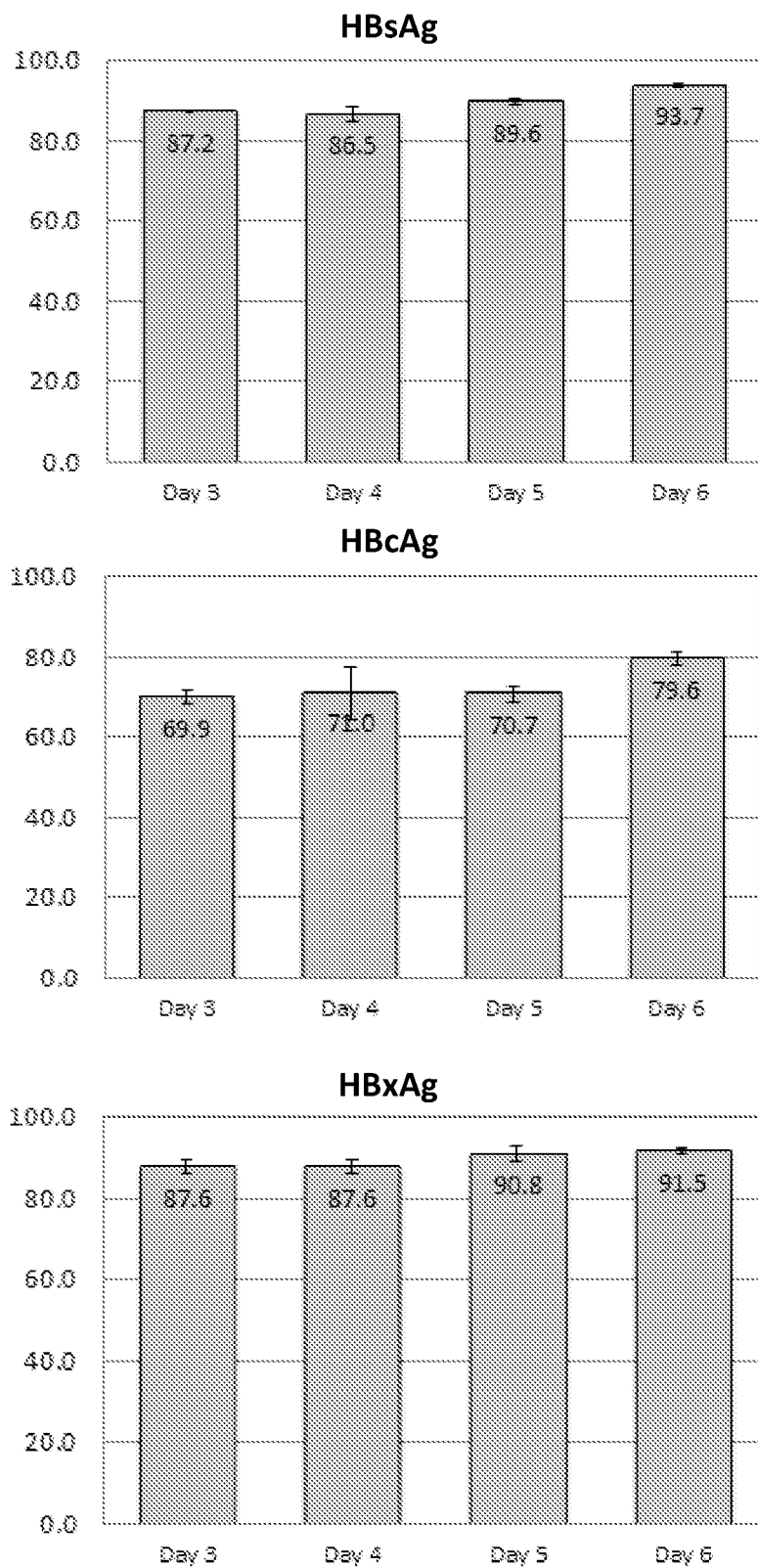
Figure 14F:
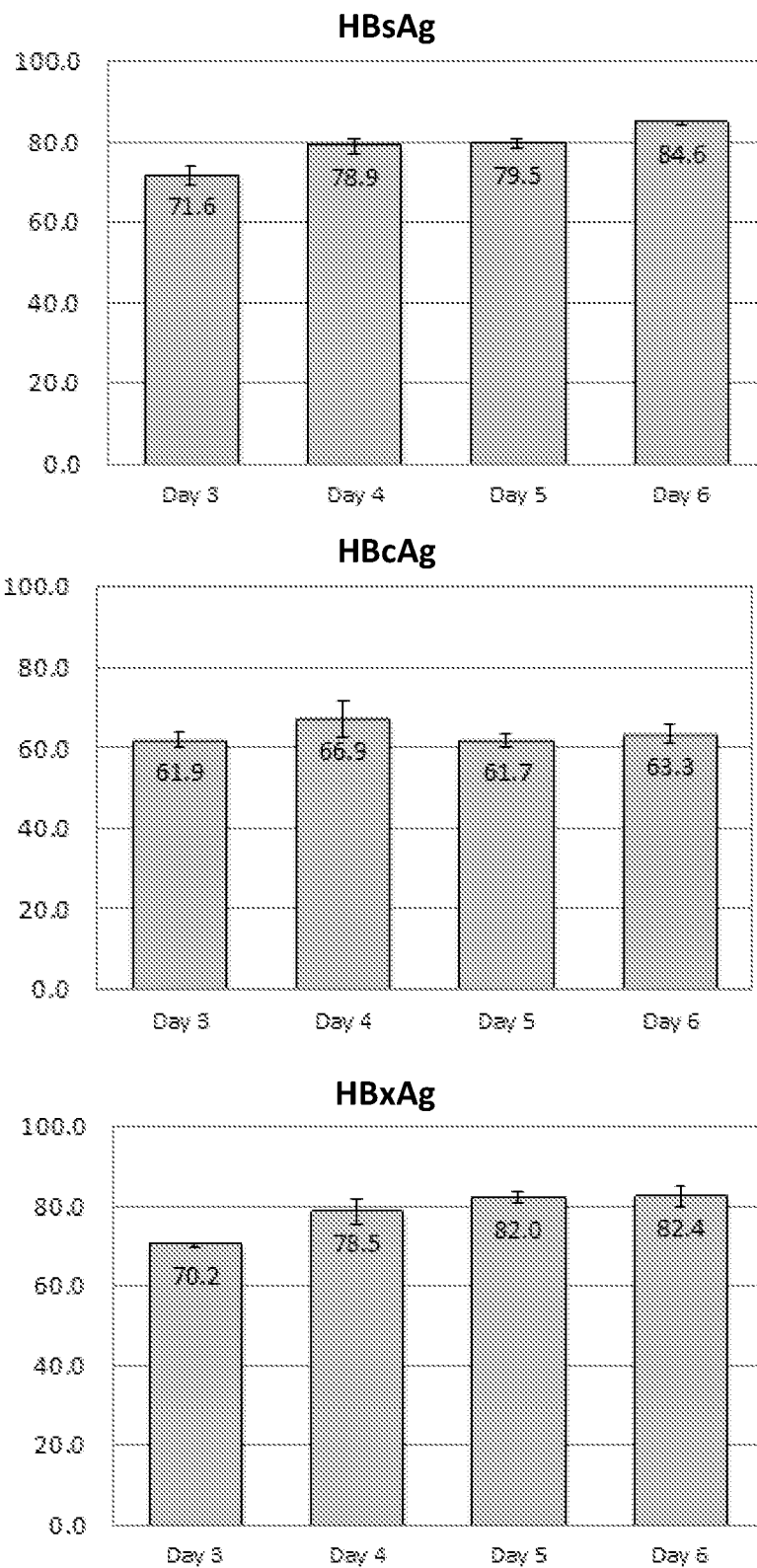

Standard curves for these assays were generated by amplifying known amounts of these guide RNAs and are presented in FIG. 10. RNA copy numbers per cell were calculated based on the estimate of 20 ng total RNA in each cell. shRNA copies per cell were determined for each of shRNA14, shRNA15, shRNA37 and shRNA28 when expressed individually at the various MOIs and when expressed simultaneously in the triplet combinations at the various MOIs (FIGS. 11a-11d). Overall, individual shRNA expression in cells transduced with the triplet HBV shRNA AdV combinations was 1.5-2.0 fold lower than those cells transduced with the single HBV shRNA AdV vector at equivalent doses e.g., MOI of 30 vs MOI 30+30+30.

Levels of inhibition of HBV transcripts at regions corresponding to HBV antigens HBsAg, HBcAg and HbxAg, relative to levels of GAPDH mRNA, were then determined by normalizing the HBV mRNA transcript levels to GAPDH mRNA for each sample. Briefly, 100 ng of total RNA was used to synthesize cDNA using High Capacity cDNA Reverse Transcription Kit (Life Technologies, Carlsbad, Calif.) according to manufacturer instructions. Quantitative PCR amplifications of regions within HBV antigens HBsAg, HBcAg, HbxAg, and GAPDH were performed using Power SYBR Green PCR Master Mix (Life Technologies) and the primer sets listed in Table 9. Standard real-time PCR conditions were used: initial denaturation at 95° C. for 10 min followed by 40 cycles of 95° C. for 15 sec and 60° C. for 1 min.

The levels of inhibition of HBV transcripts at regions corresponding to HBV antigens HBsAg, HBcAg and HbxAg, relative to levels of GAPDH mRNA, for each of shRNA14, shRNA15, shRNA37 and shRNA28 when expressed individually, and when expressed simultaneously in the triplet combinations, at various MOIs are illustrated in FIGS. 12a-12f. As will be apparent from FIGS. 12a-12f, the triplet combinations showed significantly better knockdown of HBV RNA relative to the single shRNA constructs, particularly when transduced as lower equivalent doses.

Example 10—shRNA Knockdown of HBV Transcripts in HepG2.2.15 Cells

Single HBV shRNA AdV vectors were prepared for shRNAs designated shRNA14, shRNA15, shRNA37 and shRNA28 respectively in accordance with Example 8.

Two triple HBV shRNA AdV vectors were also prepared, each comprising a triple HBV shRNA expression cassette. The triple HBV shRNA expression cassettes comprised sequence coding for (i) shRNA14/shRNA15/shRNA28 and (ii) shRNA14/shRNA37/shRNA28, respectively, and three modified U6 promoters (i.e., U6-1, U6-8, or U6-9 promoters), one positioned immediately upstream of each shRNA coding sequence in the cassette. The triple HBV shRNA expression cassettes were each synthesized and subcloned into adenovirus (AdV) construct for virus production from Vector Biolabs (Malvern, Pa.).

HepG2.2.15 cells were prepared in accordance with methods described in Example 4. The HepG2.2.15 cells were then infected with a single or triple HBV shRNA AdV vector in cell suspension and cultured on 24-well plates. Briefly, each well contained a suspension of $1.2 \times 10^5$ HepG2.2.15 cells and one of the single or triple HBV shRNA AdV vectors at MOI 100. After transduction, the cells were cultured at 37° C. at 5% $CO_2$ for 72 h, 96 h, 120 h and 144 h before being harvested for RNA and DNA extraction using Qiagen miRNeasy mini kit and QiAmp DNA mini kit, respectively (Valencia, Calif.).

Total RNA was isolated and prepared in accordance with methods described in Example 9. Production of shRNA by the AdV vectors was also measured in accordance with methods described in Example 9.

shRNA copies per cell were determined for each of shRNA14, shRNA15, shRNA37 and shRNA28 when expressed from the single or triple HBV shRNA AdV vector(s) at MOI 100 (FIGS. 13a-d). Overall, individual shRNA expression in cells transduced with the triplet HBV shRNA AdV vector at 72 h was comparable to cells transduced with the single HBV shRNA AdV vector. shRNA15 and shRNA37 continued to accumulate even after 6 days of transduction whereas shRNA14 and shRNA28 expression levels appeared to plateau at day 5.

Levels of inhibition of HBV transcripts at regions corresponding to HBV antigens HBsAg, HBcAg and HbxAg, relative to levels of GAPDH mRNA, were then determined by normalizing the HBV mRNA transcript levels to GAPDH mRNA for each sample in accordance with methods described in Example 9.

The levels of inhibition of HBV transcripts at regions corresponding to HBV antigens HBsAg, HBcAg and HbxAg, relative to levels of GAPDH mRNA, for each of shRNA14, shRNA15, shRNA37 and shRNA28 when expressed from the single or triple HBV shRNA AdV vector(s) at MOI 100 at 72 h, 96 h, 120 h and 144 h are illustrated in FIGS. 14a-f. As will be apparent from FIGS. 14a-14f, the triple HBV shRNA AdV vectors showed significantly better knockdown of HBV RNA relative to the corresponding single shRNA vectors at 72 h (day 3). All single HBV shRNA AdV vectors showed increased knockdown levels with prolonged time course and were comparable to the triple HBV shRNA AdV vectors at 144 h (day 6). At 144 h, the triple HBV shRNA AdV vector expressing shRNA14/shRNA37/shRNA28 achieved over 90% knockdown in the HBsAg and HBxAg region and close to 80% knockdown in the HBcAg region.

Example 11—Inhibition of HBV Transcripts In Vitro

The inventors determined the effect of the triple HBV shRNA AdV vector expressing shRNA14/shRNA37/shRNA28 on formation of covalently-closed circular DNA (cccDNA) in a cell model infected de novo with HBV inoculum.

The triple HBV shRNA AdV vector expressing shRNA14/shRNA37/shRNA28 was prepared in accordance with Example 10.

Human hepatocytes were isolated from the PhoenixBio mouse model (PXB-Mice®), which is a chimeric mouse with a liver highly replaced with human hepatocytes (i.e., a humanized liver). The isolated human hepatocytes (PXB-cells) were seeded at a density of $4.0 \times 10^5$ cells per well into 24-well culture plates one day prior to inoculation. The PXB-cells were then inoculated with HBV on day 0. After inoculation, the cells were treated with (i) the triple HBV shRNA AdV vector at MOIs: 10, 30, 60 and 100 or (ii) the AdV vector backbone at MOIs: 10, 30, 60 and 100, or (iii) received no treatment, and were then cultured at 37° C. at 5% $CO_2$ for 6, 11 and 16 days before being harvested for RNA and DNA extraction using Qiagen miRNeasy mini kit and QiAmp DNA mini kit, respectively (Valencia, Calif.).

Figure 15A:
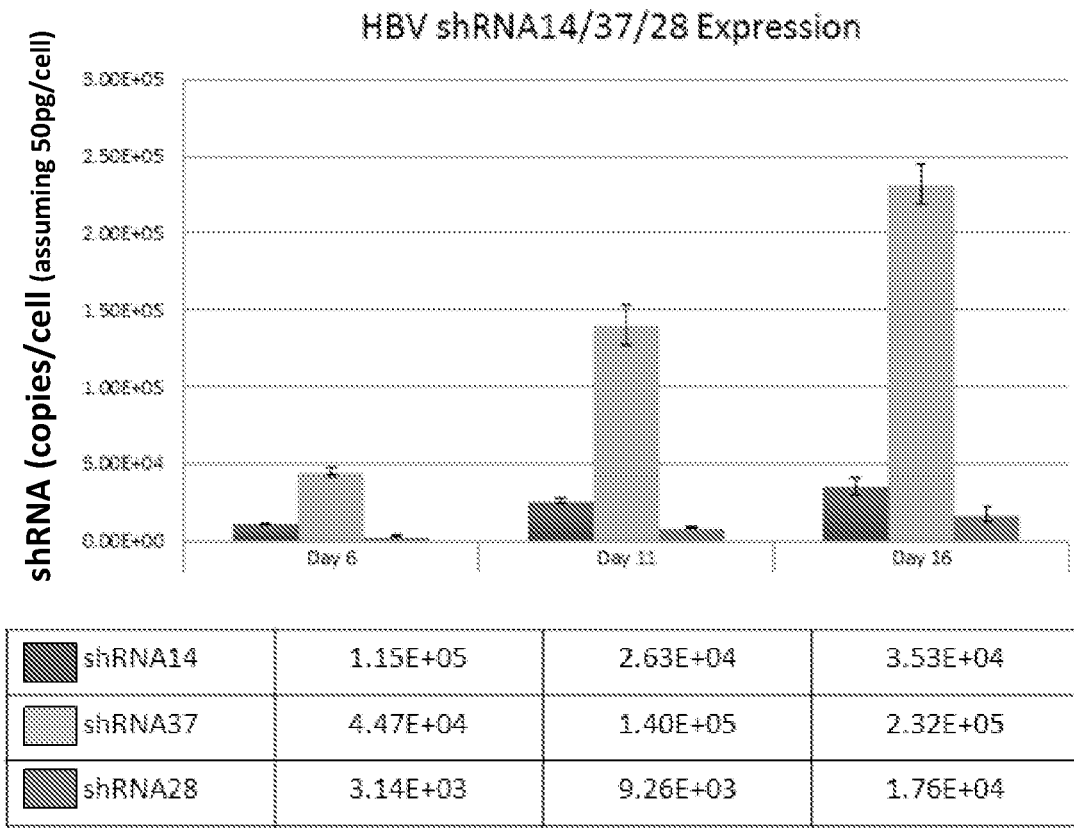
FIG. 15 shows the following for human hepatocytes inoculated with HBV and treated with a triple HBV shRNA AdV vector expressing three shRNAs designated shRNA14, shRNA37 and shRNA28 at MOI 10: (a) the level of expression for shRNAs designated shRNA14, shRNA37 and shRNA28; (b) the level of inhibition of HBV transcripts at regions corresponding to HBV antigens HBsAg, HBcAg and HbxAg; (c) the level of intracellular and extracellular HBV DNA; (d) the level of extracellular HBV transcripts at regions corresponding to HBV antigens HBcAg and HBsAg; and (e) the level of cccDNA.

For PXB-cells inoculated with the triple HBV shRNA AdV vector at MOI 10, shRNA copies per cell were determined for each of shRNA14, shRNA37 and shRNA28 at day 6, 11 and 16 post treatment in accordance with methods described in Example 9 (FIG. 15a). Effective knockdown of HBV transcripts (78-85%) was observed at day 6 post treatment with the triple HBV shRNA AdV vector, and this knockdown was observed to increase up to 97-99% at day 16 post treatment. This increase in knockdown of HBV transcripts between day 6 and day 16 was found to coincide with a concomitant increase in the production of shRNAs by the AdV vector.

Figure 15B:
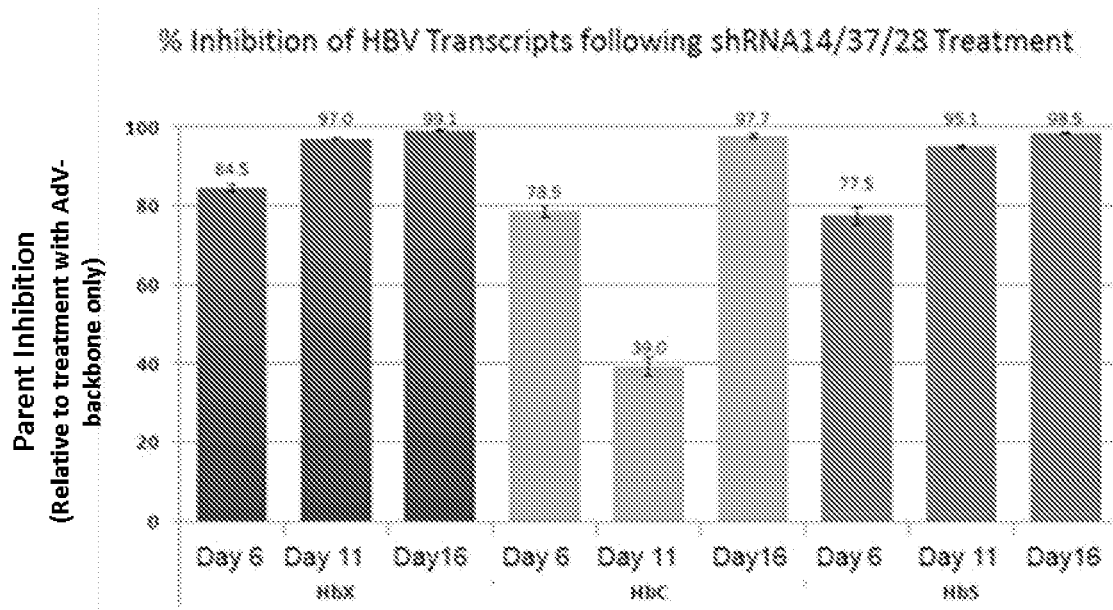

The level of inhibition of HBV transcripts at regions corresponding to HBV antigens HBsAg, HBcAg and HbxAg was measured in accordance with methods described in Example 9 for cells treated with the triple HBV shRNA AdV vector relative to those cells treated with the AdV backbone only (FIG. 15b).

Figure 15C:
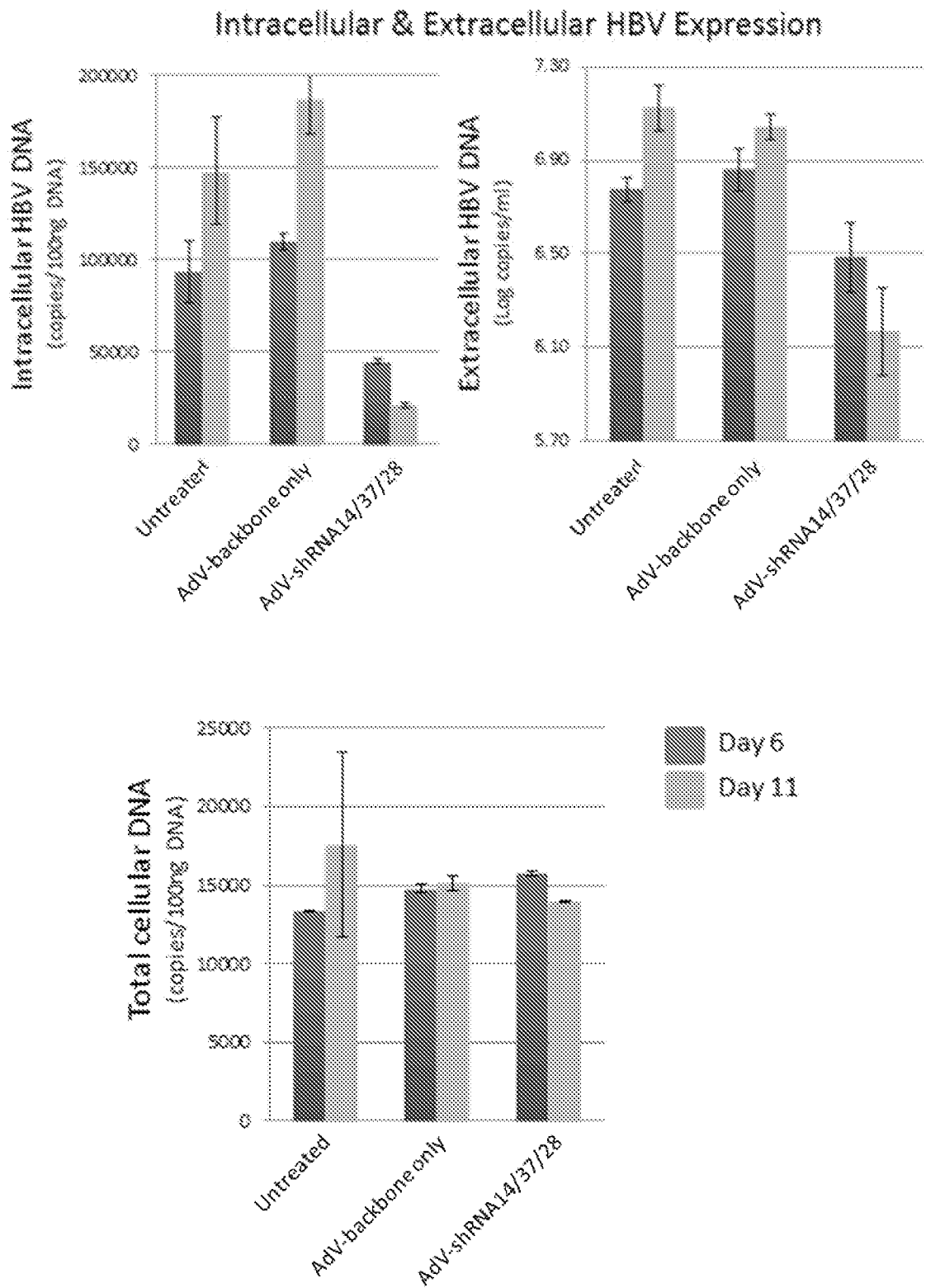

The levels of intracellular and extracellular HBV DNA following treatment with the triple HBV shRNA AdV vector were also measured by real time PCR assay and are illustrated in FIG. 15c. An 85% and 1 log drop in intracellular and extracellular HBV DNA, respectively, was observed at day 11 following treatment.

Figure 15D:
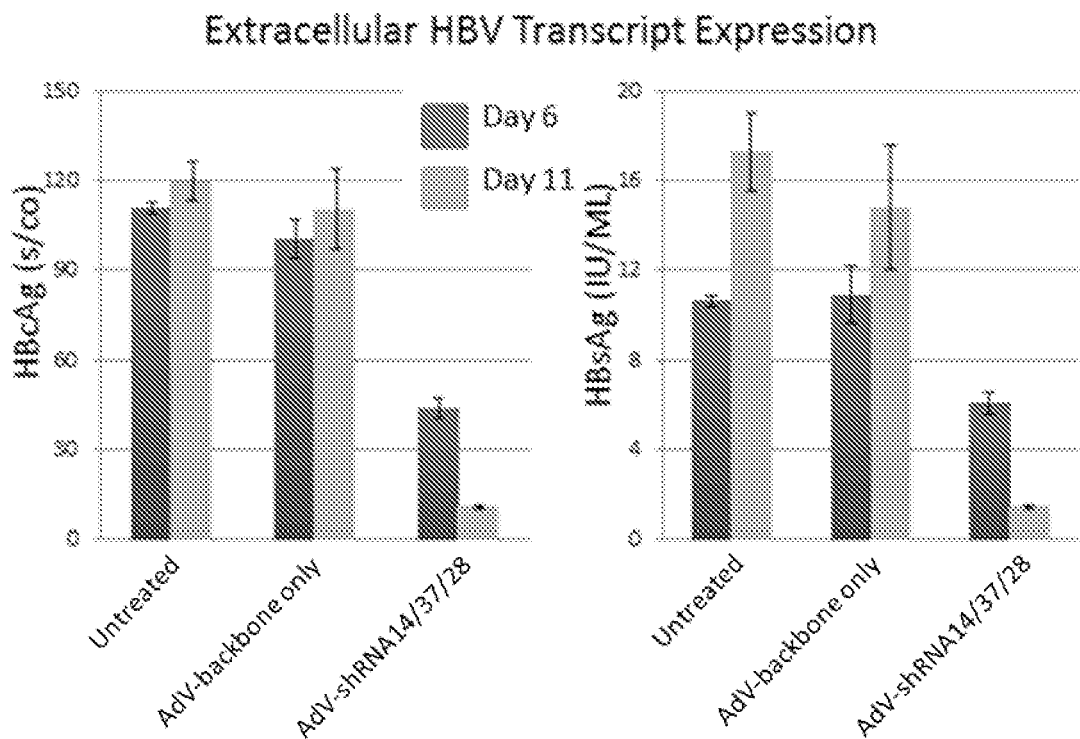

The levels of HBV transcripts at regions corresponding to HBV antigens HBsAg and HBcAg were measured in accordance with methods described in Example 9, the results of which are illustrated in FIG. 15d. The level of extracellular HBcAg and HBsAg was observed to drop by approximately 90% at day 11 in cells treated with the triple HBV shRNA AdV vector as compared to the AdV backbone control.

Figure 15E:
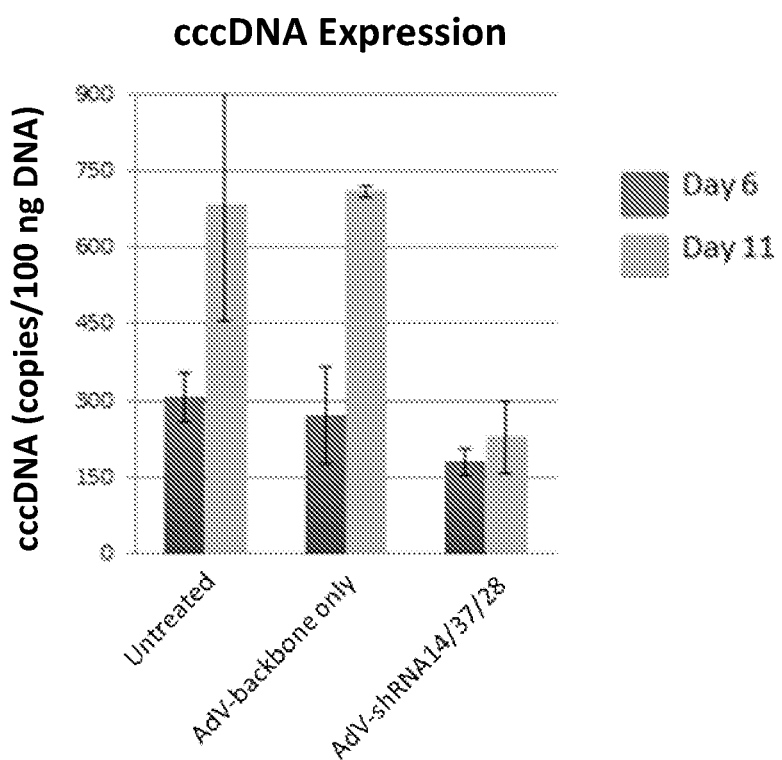

The levels cccDNA were also measured in PXB-cells following treatment with the triple HBV shRNA AdV vector, the results of which are illustrated in FIG. 15e. At day 11 post treatment, a 66% decrease in cccDNA was observed in the HBV infected PXB-cells treated with the triple HBV shRNA AdV vector compared to HBV infected PXB-cells treated with the AdV backbone control and untreated PXB-cells.

Example 12—Inhibition of HBV Transcripts In Vivo

The in vivo effect of the triple HBV shRNA AdV vector expressing shRNA14/shRNA37/shRNA28 on (i) expression of HBV viral transcripts, (ii) extracellular HBsAg and HBeAg, (iii) extracellular and intracellular HBV DNA, and (iv) formation of cccDNA, was determined in a PXB mouse model infected de novo with HBV inoculum.

Methods

The triple HBV shRNA AdV vector expressing shRNA14/shRNA37/shRNA28 was prepared in accordance with Example 10.

Chimeric PXB mice (PXB-Mice®) were obtained from PhoenixBio. All mice were housed individually at 23±5° C. and a humidity of 55±25% humidity, exposed to 12 hours-light/dark cycles and fed and watered ad libitum throughout the experiment.

Briefly, 19-23 week-old male PXB mice were inoculated with HBV genotype C and incubated for 4 weeks to allow baseline HBV infection to establish. To determine baseline HBV infection, blood was taken from mice at days −28, −21, −14 and −7 (i.e., 0, 7, 14 and 21 days post inoculation, respectively), from which the human albumin (h-Alb) concentration and serum concentrations of HBV DNA, HBsAg and HBeAg determined.

Blood was collected from animals under isoflurane (Escain®, Mylan, Osaka, Japan) anesthesia via the retro-orbital plexus/sinus using Intramedic™ Polyethylene Tubing (Becton, Dickinson and Company, NJ, USA) at each time point.

To measure blood h-Alb concentration, 2 µL of the whole blood was diluted in saline and a clinical chemistry analyzer (BioMajesty™ Series JCA-BM6050, JEOL Ltd., Tokyo, Japan) was used to measure the blood h-Alb concentration using latex agglutination immunonephelometry (LZ Test "Eiken" U-ALB, Eiken Chemical Co., Ltd., Tokyo, Japan).

Whole blood was centrifuged to separate serum for HBV DNA quantification, HBsAg and HBeAg analysis.

To measure serum HBV DNA, HBV DNA was extracted from 5 µL of serum using the SMITESTEX-R&D Nucleic Acid Extraction Kit (MEDICAL & BIOLOGICAL LABORATORIES CO., LTD., Nagoya, Japan). The purified DNA was then dissolved in 20 µL nuclease-free water (Ambion). Serum from an HBV-infected PXB-mouse was used as the HBV DNA standard. Synthetic HBV DNA was used to determine the concentration of the HBV DNA standard which was then used in quantification of the serum HBV DNA level. The HBV DNA was extracted from the HBV DNA standard and used for real-time PCR after appropriate dilution. For this study, the range of the standard used was between $4.0E^{+04}$ and $2.0E^{+09}$ copies/mL.

Real-time PCR to measure the serum HBV DNA concentration was performed using the TaqMan Fast Advanced Master Mix (Applied Biosystems, Thermo Fisher Scientific Inc.) and ABI Prism 7500 sequence detector system (Applied Biosystems). The PCR reaction mixture was added into 5 µL of the extracted DNA. The initial activation of uracil-N-glycosylase at 50° C. for 2 minutes was followed by the polymerase activation at 95° C. for 20 seconds. Subsequent PCR amplification consisted of 53 cycles of denaturation at 95° C. for 3 seconds and annealing and extension at 60° C. for 32 seconds per cycle in an ABI 7500 sequence detector. The average serum HBV DNA level was calculated from the values of two separate wells.

The primers and probes used for real time PCR are as follows:

| Identification | Target Location | Dye | Sequence Information 5' Nucleotides 3' | SEQ ID NO | Dye |
|---|---|---|---|---|---|
| Forward primer | 166-186 | n/a | CACATCAGGATTCCTAGGACC | 124 | n/a |
| Reverse primer | 344-325 | n/a | AGGTTGGTGAGTGATTGGAG | 125 | n/a |
| TaqMan probe | 242-267 | 6-FAM | CAGAGTCTAGACTCGTGGTGGACTTC | 126 | TAMRA |

The lowest quantification limit of this assay was $4.0E^{+04}$ copies/mL serum.

Serum HBsAg concentration was determined by SRL, Inc. (Tokyo, Japan) using ChemiLuminescence ImmunoAssay (CLIA) developed by Abbott (ARCHITECT® SYSTEM). The dilution factor was 30, and the measurement range of this assay was between 0.05 and 250 IU/mL. For the 30-fold diluted samples, the measurement range was adjusted to be between 1.5 and 7500 IU/mL.

Serum HBeAg concentration was determined by SRL, Inc. (Tokyo, Japan) using ChemiLuminescence ImmunoAssay (CLIA) developed by Abbott (ARCHITECT® SYSTEM). The dilution factor was 30 and the lowest quantification limit of this assay was 0.5 S/CO. For the 30-fold diluted samples, the lowest quantification limit was adjusted to be 15 S/CO.

Animals were included in subsequent treatment experiment if they met the following criteria:
  (i) weighed 15 g or more at day −1 (i.e., day 27 post HBV inoculation);
  (ii) had a serum HBV DNA concentration of at least $1.0E^{+6}$ copies/mL at day −7 (i.e., day 21 post HBV inoculation); and
  (iii) had a h-Alb measurement of 10 mg/mL or more at day −7 (i.e., day 21 post HBV inoculation).

Those mice in which baseline HBV infection was established and met the criteria above were placed into three treatment groups i.e., treatment groups 1-3 (n=4 per group). To minimise variance between groups, the group composition was randomised based on the arithmetic mean values for body weight and geometric mean values for blood h-Alb concentration and serum HBV DNA concentration.

The treatment groups were as follows:
  Group 1: no treatment;
  Group 2: a single bolus, having a dose volume of 10 µL/gram body weight, containing $2.00E^{+11}$ vg/mL of the triple HBV shRNA AdV vector, delivered to the tail vein by IV injection; and
  Group 3: a single bolus, having a dose volume of 10 µL/gram body weight, containing $2.00E^{+12}$ vg/mL triple HBV shRNA AdV vector, delivered to the tail vein by IV injection.

Following administration of the treatment (day 0), animals were then incubated for a further 56 days. During this time blood was taken on a weekly basis for 8 weeks (at days 7, 14, 21, 28, 35, 42, 49 and 56 post treatment), and serum concentrations of extracellular HBsAg, extracellular HBeAg and extracellular HBV DNA determined by real time PCR, using the methodologies described.

After the completion of blood sampling on Day 56, all the surviving animals were kept under isoflurane anesthesia and sacrificed by cardiac puncture and exsanguination.

Once sacrificed, whole livers were harvested from mice and weighed. A slice of 3 to 5 mm in thickness was obtained from left lateral lobe and cut into cubes approximately 1 to 2 mm on a side. These liver cubes were transferred into a labelled tube and immersed in RNAlater® solution (Ambion, Thermo Fisher Scientific Inc., Waltham, Mass., USA) as quickly as possible. The liver samples were incubated in >5 volumes of RNAlater® overnight at 4° C. to allow the solution to penetrate the tissue. After the incubation, the RNAlater® solution was removed and the liver pieces were stored at −80° C. for later quantification of hepatic HBV DNA levels.

To determine the level of hepatic HBV DNA following treatment, HBV DNA was extracted from frozen RNAlater®-preserved liver tissue using the DNeasy® Blood & Tissue Kits (Qiagen K.K., Tokyo, Japan). The DNA was dissolved in 200 µL nuclease-free water, after which the concentration of the DNA solution was determined using BioPhotometer 6131 (Eppendorf Co., Ltd., Tokyo, Japan). The concentration of DNA solution was adjusted to 20 ng/µL using Nuclease-free water.

Real-time PCR to measure liver HBV cccDNA concentration was then performed using the TaqMan Fast Advanced Master Mix and ABI Prism 7500 sequence detector system. Briefly, the PCR reaction mixture was added into 5 µL of the extracted DNA.

The PCR reaction was conducted based on the Takkenberg's condition. The initial activation of uracil-N-glycosylase at 50° C. for 2 minutes was followed by the polymerase activation at 95° C. for 20 seconds. Subsequent 55 cycles of PCR amplification was conducted at 95° C. for 3 seconds and 60° C. for 32 seconds per cycle in an ABI 7500 sequence detector. The average HBV cccDNA level was calculated from the values of the two separate wells. A plasmid containing the HBV full-genome sequence was used as a standard sample for HBV cccDNA quantification. The range of the standard used was between $1.0E^{+02}$ and $1.0E^{+05}$ copies/100 ng DNA.

The primers and probes used for real time PCR are as follows:

| Target | | | Sequence Information | | |
|---|---|---|---|---|---|
| Identification | Location | Dye | 5' Nucleotides 3' | SEQ ID NO | Dye |
| Forward primer | 1545-1563 | n/a | CTCCCCGTCTGTGCCTTCT | 127 | n/a |
| Reverse primer | 1900-1883 | n/a | GCCCCAAAGCCACCCAAG | 128 | n/a |
| TaqMan probe | 1602-1628 | 6-FAM | CGTCGCATGGARACCACCGTGAACGCC | 129 | TAMRA |

The lowest quantification limit of this assay was $1.0E^{+02}$ copies/100 ng DNA in extracted DNA solution.

Results

All animals maintained body weight of more than 80% of the initial level throughout the treatment. In addition, the lowest average values of the body weights in Groups 2 and 3 were slightly lower than that in the control group receiving no treatment.

Figure 16:
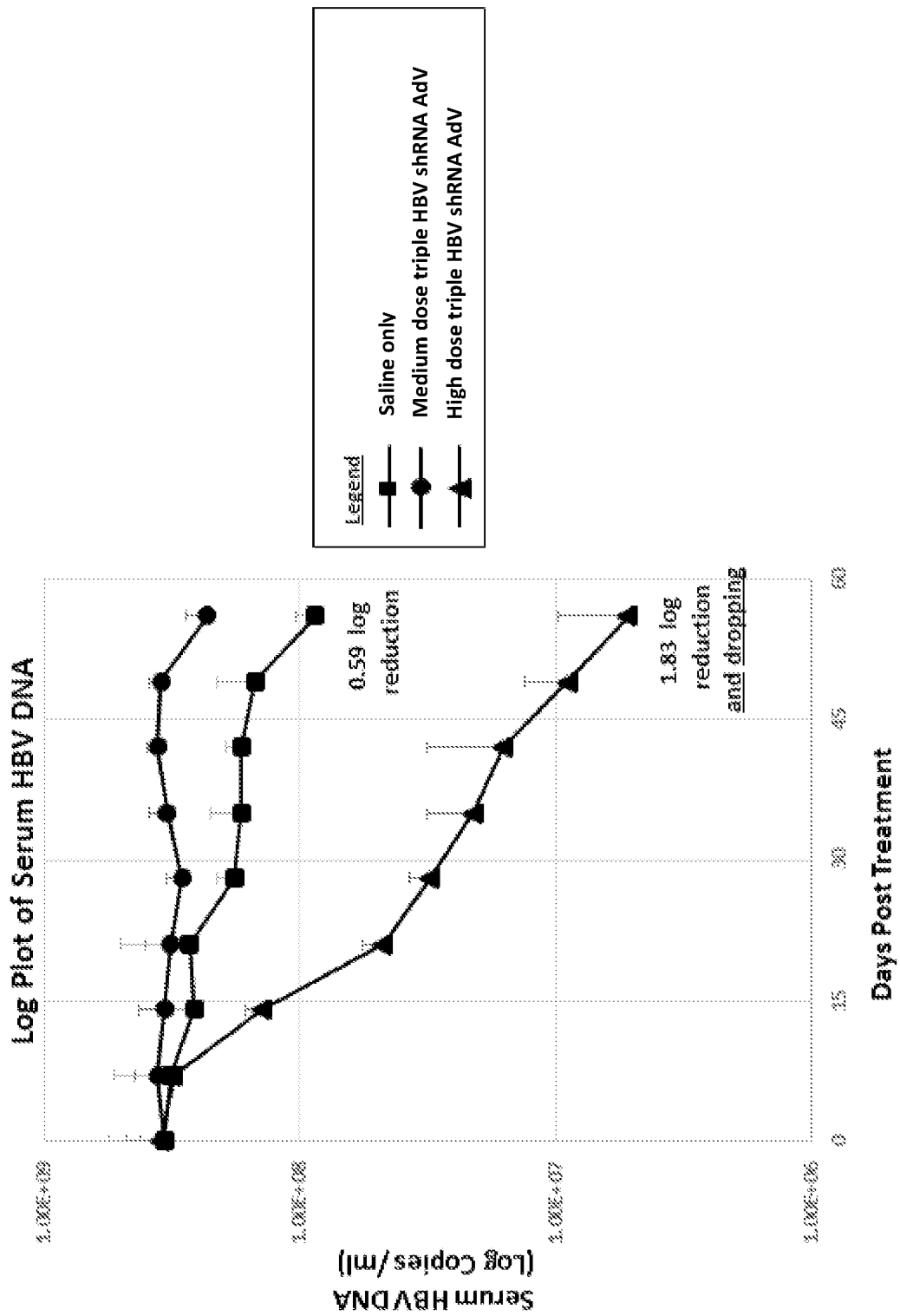
FIG. 16 is a plot showing serum levels of extracellular HBV DNA (expressed in Log copies/mL) in animals from (i) Group 1 treated with saline only (control), (ii) Group 2 treated with medium dose of the triple HBV shRNA AdV vector, and (iii) Group 3 treated with high dose of the triple HBV shRNA AdV vector, over the course of 56 days.
Figure 17:
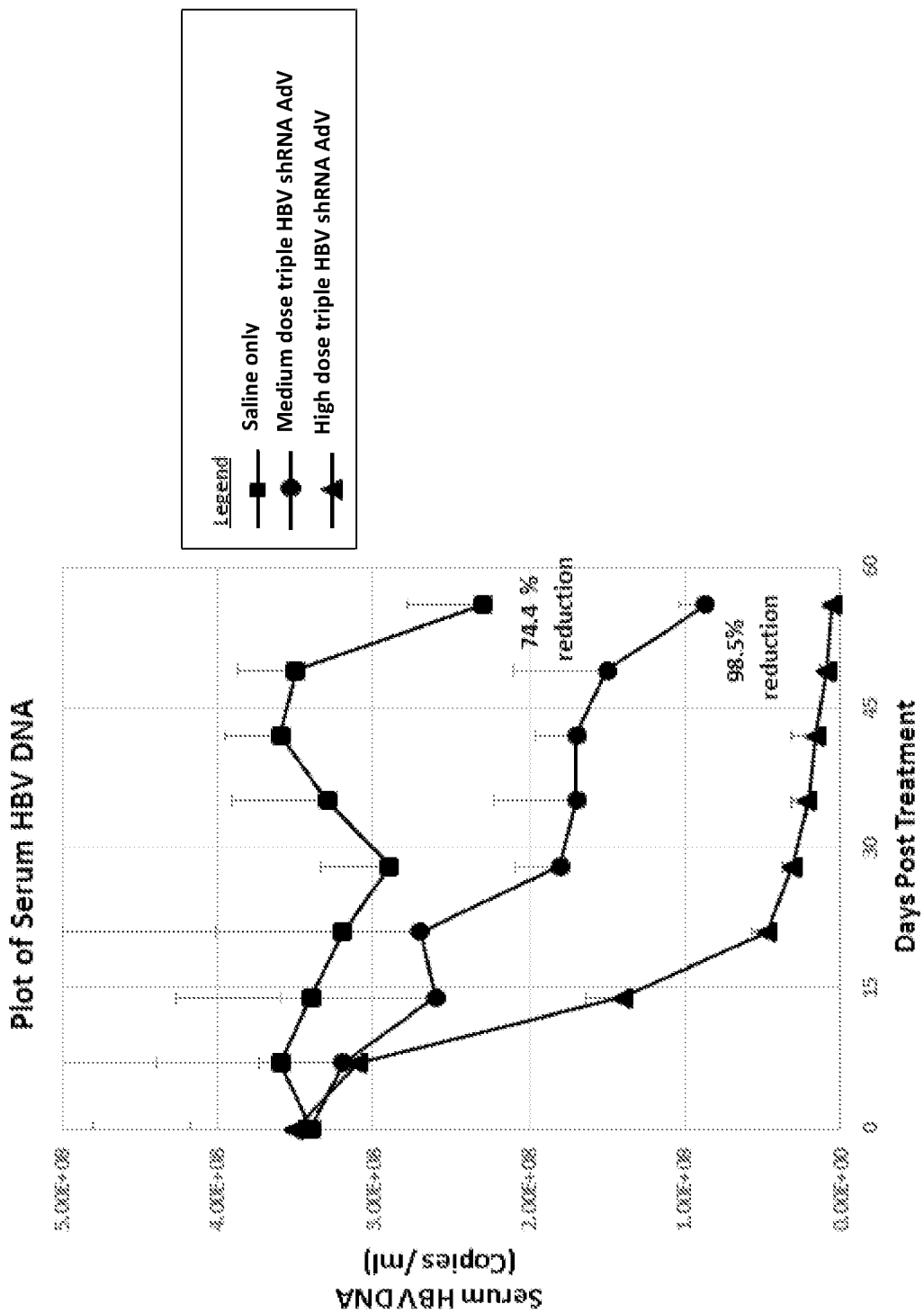
FIG. 17 is a plot showing serum levels of extracellular HBV DNA (expressed in copies/mL) in animals from (i) Group 1 treated with saline only (control), (ii) Group 2 treated with medium dose of the triple HBV shRNA AdV vector, and (iii) Group 3 treated with high dose of the triple HBV shRNA AdV vector, over the course of 56 days.

As will be apparent from FIGS. 16 and 17, animals in treatment groups receiving the triple HBV shRNA AdV vector showed a steady reduction in serum HBV DNA throughout the course of the experiment relative to animals in group 1 which received the control treatment. At day 56, animals receiving the medium dose treatment (Group 2) showed an average of 0.59 log and 74.4% reduction in serum HBV DNA, and animals receiving the high dose treatment (Group 3) showed an average of 1.83 log and 98.5% reduction in serum HBV DNA.

Figure 18:
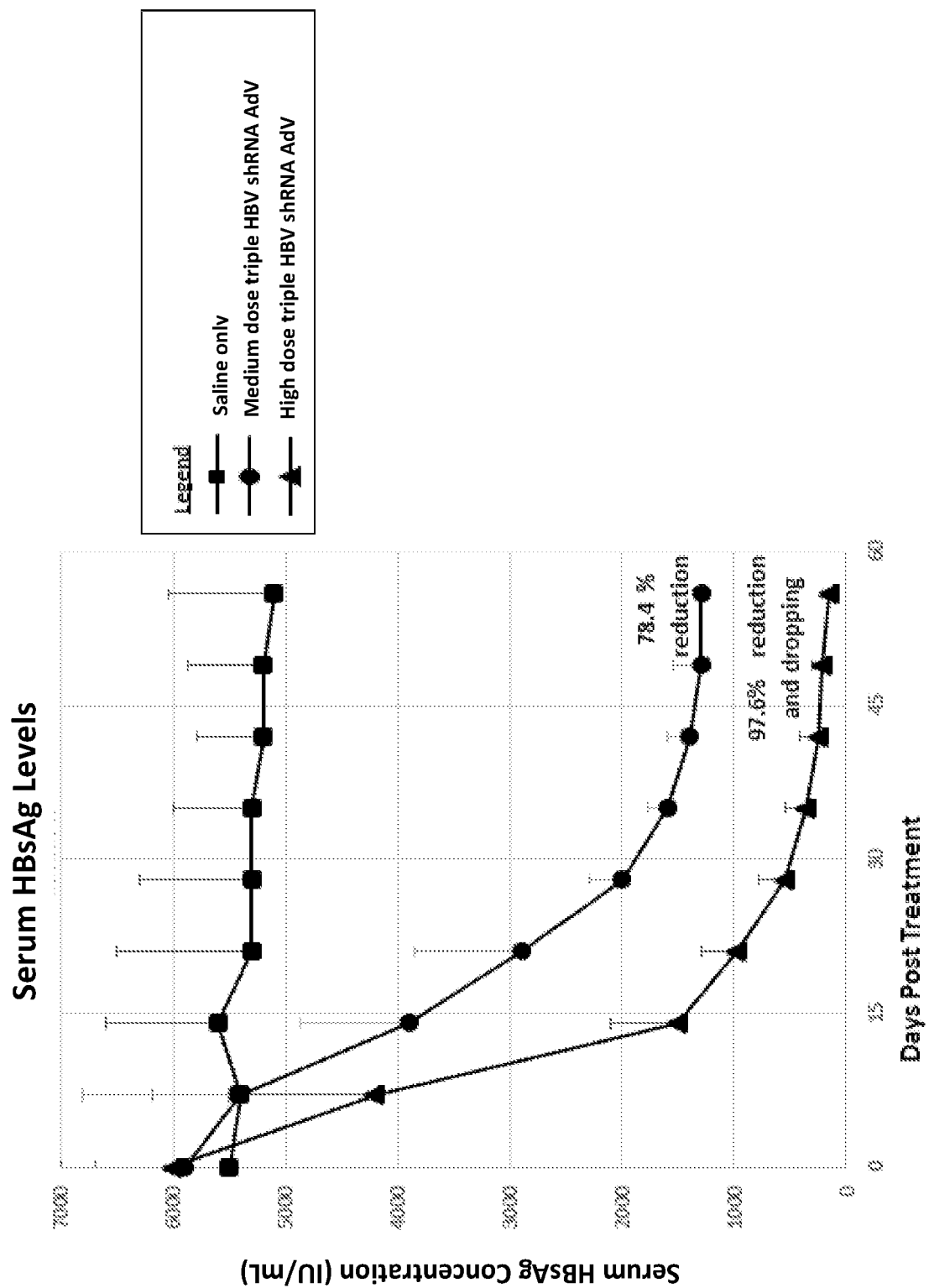
FIG. 18 is a plot showing serum levels of HBsAg (IU/mL) in animals from (i) Group 1 treated with saline only (control), (ii) Group 2 treated with medium dose of the triple HBV shRNA AdV vector, and (iii) Group 3 treated with high dose of the triple HBV shRNA AdV vector, over the course of 56 days.
Figure 19:
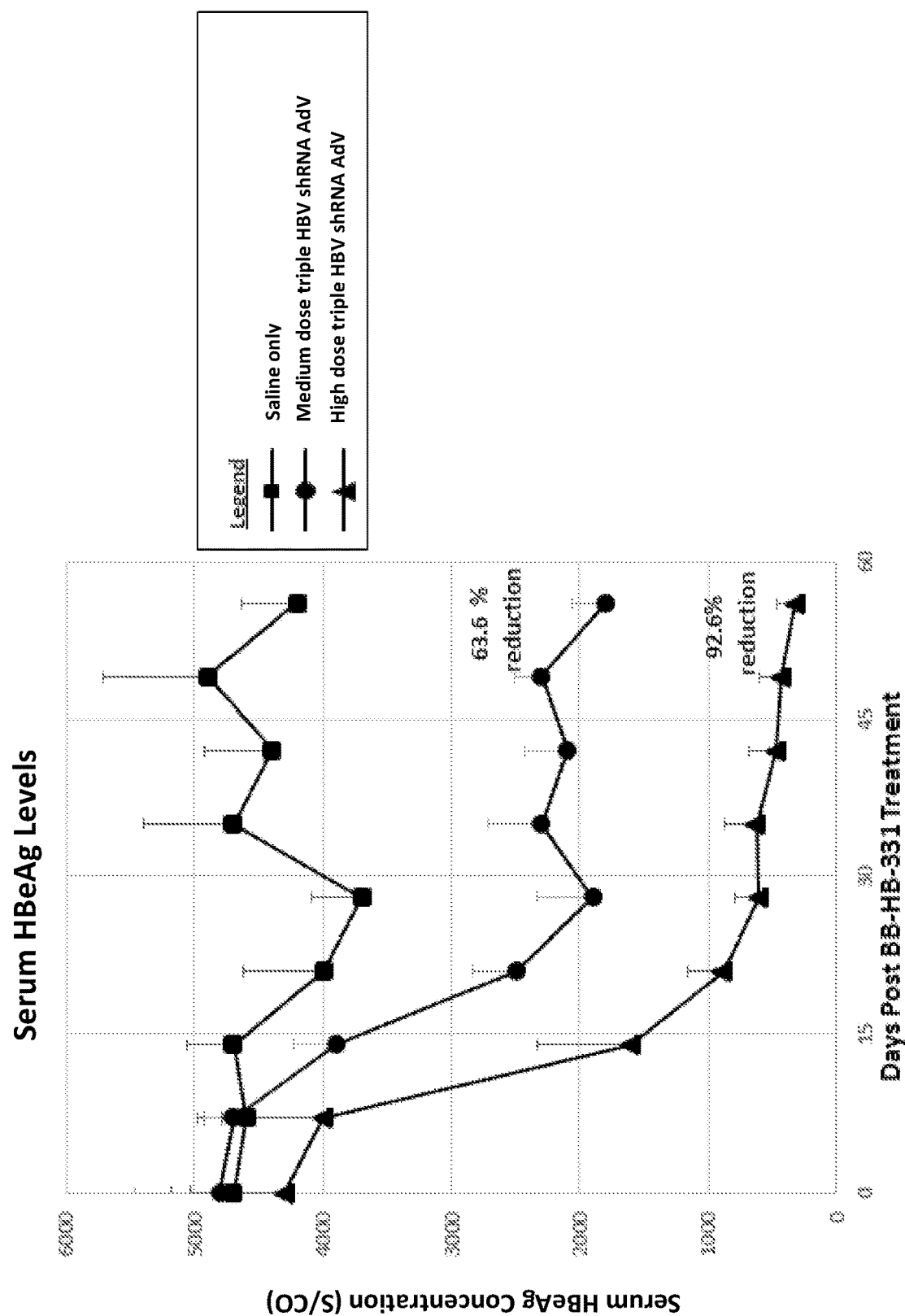
FIG. 19 is a plot showing serum levels of HBeAg (IU/mL) in animals from (i) Group 1 treated with saline only (control), (ii) Group 2 treated with medium dose of the triple HBV shRNA AdV vector, and (iii) Group 3 treated with high dose of the triple HBV shRNA AdV vector, over the course of 56 days.

Similarly, serum concentrations of HBsAg and HBeAg steadily reduced following treatment with the triple HBV shRNA AdV vector (FIGS. 18 and 19) relative to those animals in Group 1 which received the control treatment. At day 56, animals receiving the medium dose treatment (Group 2) showed an average reduction of 78.4% and 63.6% in serum levels of HBsAg and HBeAg respectively, and animals receiving the high dose treatment (Group 3) showed an average reduction of 97.6% and 92.6% in serum levels of HBsAg and HBeAg respectively.

Figures 20, 21:
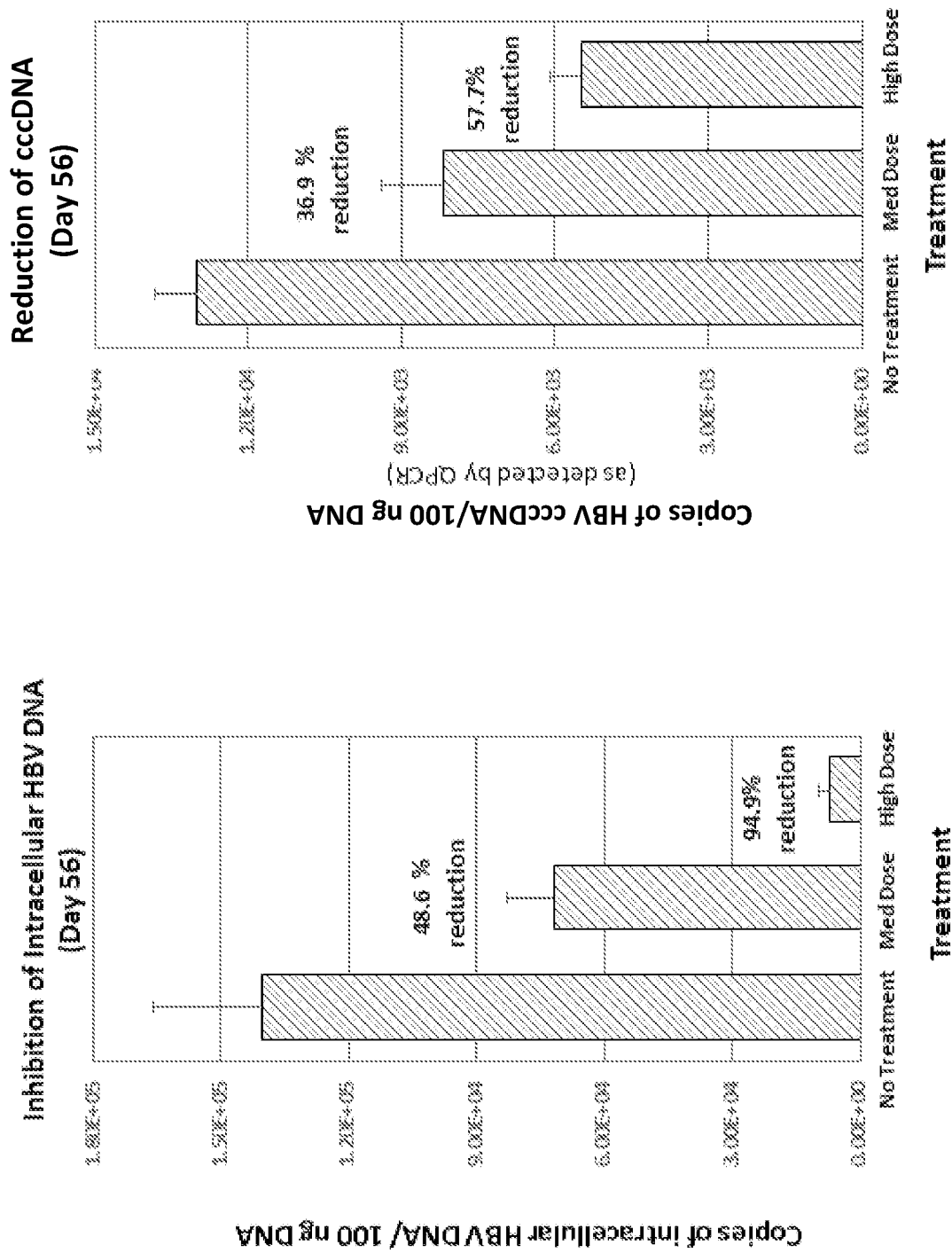
FIG. 20 shows the level of intracellular HBV DNA (copies of intracellular HBV DNA/100 ng DNA) in animals from (i) Group 1 treated with saline only (control), (ii) Group 2 treated with medium dose of the triple HBV shRNA AdV vector, and (iii) Group 3 treated with high dose of the triple HBV shRNA AdV vector, 56 days post treatment. This figures illustrates the level of inhibition of intracellular HBV DNA by medium and high doses of the triple HBV shRNA AdV vector relative to the control saline treatment.
FIG. 21 shows the level of intracellular cccDNA (copies of HBV cccDNA/100 ng DNA) in animals from (i) Group 1 treated with saline only (control), (ii) Group 2 treated with medium dose of the triple HBV shRNA AdV vector, and (iii) Group 3 treated with high dose of the triple HBV shRNA AdV vector, 56 days post treatment. This figures illustrates the level of inhibition of HBV cccDNA by medium and high doses of the triple HBV shRNA AdV vector relative to the control saline treatment.

The levels of intracellular HBV DNA and cccDNA at day 56 were also shown to be reduced for animals in the medium and high dose treatments (Groups 2 and 3 respectively) relative to animals receiving the control treatment (Group 1). For example, as illustrated in FIG. 20, treatment with medium and high doses of the triple HBV shRNA AdV vector resulted in a 48.6% and 94.9% reduction, respectively, in copy number of intracellular HBV DNA at day 56. Similarly, FIG. 21 shows that treatment with medium and high doses of the triple HBV shRNA AdV vector resulted in a 36.9% and 57.7% reduction, respectively, in copy number of cccDNA at day 56.

Figure 22:
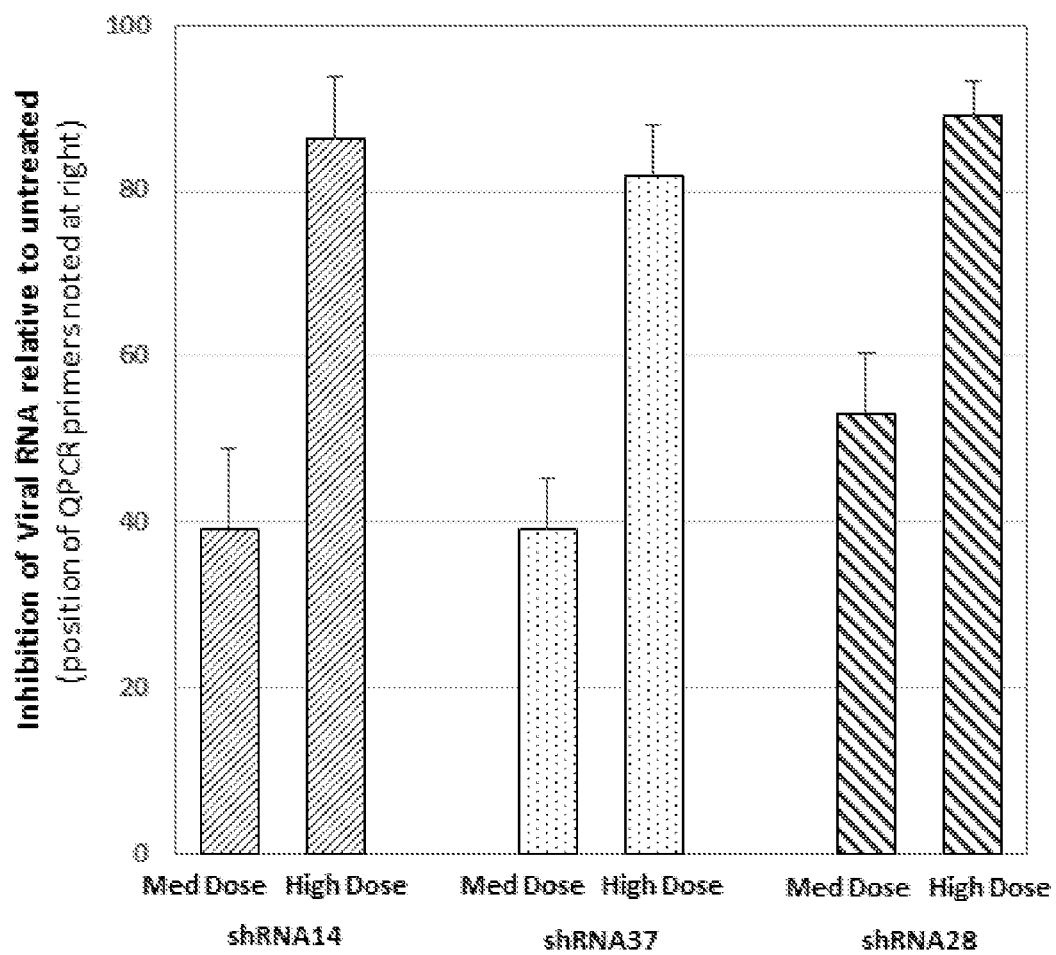
FIG. 22 illustrates the level of inhibition of HBV viral transcripts corresponding to shRNAs expressed by the triple HBV shRNA AdV vector (shRNA14, shRNA 37 and shRNA28, respectively) at 56 days post treatment with the triple HBV shRNA AdV vector at medium and high doses.

The level of inhibition of HBV viral transcripts corresponding to the shRNAs expressed by the triple HBV shRNA AdV vector (i.e., shRNA14, shRNA 37 and shRNA28) was also measured at day 56 by real time PCR. As shown in FIG. 22, viral RNA corresponding to shRNA14, shRNA 37 and shRNA28 was reduced by 39.4%, 39.2% and 53.3% in animals in Group 2 treated with the medium dose relative to levels of expression of those HBV viral transcripts in animals from group 1 administered the control treatment. Likewise, Figure Y shows that viral RNA corresponding to shRNA14, shRNA 37 and shRNA28 was reduced by 86.2%, 82.0% and 89.1% in animals in Group 3 treated with the high dose relative to levels of expression of those HBV viral transcripts in animals from group 1 administered the control treatment.

Based on the results from the present study, the triple HBV shRNA AdV vector was shown to have clear effects on the viral parameters of serum HBV DNA, serum HBsAg, serum HBeAg and hepatic HBV DNA when administered to HBV infected PXB-mice with a humanized liver. These antiviral effects were observed at a dosage of $2.00E^{+12}$ vg/kg (Group 2) and $2.00E^{+13}$ vg/kg (Group 3) demonstrating the efficacy of the triple HBV shRNA AdV vector at different dosages.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

We claim:

1. A DNA-directed RNA interference (ddRNAi) construct comprising:
   (a) a first nucleic acid comprising a DNA sequence which encodes a short hairpin RNA (shRNA) comprising an effector sequence of at least 19 nucleotides in length which is substantially complementary to a RNA transcript encoded by the sequence set forth in SEQ ID NO: 4; and
   (b) a second nucleic acid comprising a DNA sequence which encodes a shRNA comprising an effector sequence of at least 19 nucleotides in length which is substantially complementary to a RNA transcript encoded by the sequence set forth in SEQ ID NO: 9 or SEQ ID NO: 58.

2. The ddRNAi construct of claim 1, comprising:
   (a) a first nucleic acid comprising a DNA sequence which encodes a shRNA comprising an effector sequence of at least 19 nucleotides in length which is substantially complementary to a RNA transcript encoded by the sequence set forth in SEQ ID NO: 4;
   (b) a second nucleic acid comprising a DNA sequence which encodes a shRNA comprising an effector sequence of at least 19 nucleotides in length which is substantially complementary to a RNA transcript encoded by the sequence set forth in SEQ ID NO: 9; and
   (c) a third nucleic acid comprising a DNA sequence which encodes a shRNA comprising an effector sequence of at least 19 nucleotides in length which is substantially complementary to a RNA transcript encoded by the sequence set forth in SEQ ID NO: 58.

3. The ddRNAi construct of claim 1, wherein:
   (a) the first nucleic acid comprises a DNA sequence which encodes a shRNA comprising an effector sequence which is substantially complementary to a RNA transcript encoded by the sequence set forth in SEQ ID NO: 28; and
   (b) the second nucleic acid comprises a DNA sequence which encodes a shRNA comprising an effector sequence which is substantially complementary to a RNA transcript encoded by the sequence set forth in SEQ ID NO: 48 or SEQ ID NO: 58.

4. The ddRNAi construct of claim 2, wherein:
   (a) the first nucleic acid comprises a DNA sequence which encodes a shRNA comprising an effector sequence which is substantially complementary to a RNA transcript encoded by the sequence set forth in SEQ ID NO: 28;
   (b) the second nucleic acid comprises a DNA sequence which encodes a shRNA comprising an effector sequence which is substantially complementary to a RNA transcript encoded by the sequence set forth in SEQ ID NO: 48; and
   (c) the third nucleic acid comprises a DNA sequence which encodes a shRNA comprising an effector sequence which is substantially complementary to a RNA transcript encoded by the sequence set forth in SEQ ID NO: 58.

5. The ddRNAi construct of claim 3, wherein:
   (a) the first nucleic acid comprises a DNA sequence encoding a shRNA comprising an effector sequence set forth in SEQ ID NO:27 and an effector complement sequence set forth in SEQ ID NO:28; and
   (b) the second nucleic acid comprises: (i) a DNA sequence encoding a shRNA comprising an effector sequence set forth in SEQ ID NO:47 and an effector complement sequence set forth in SEQ ID NO:48; or (ii) a DNA sequence encoding a shRNA comprising an effector sequence set forth in SEQ ID NO:57 and an effector complement sequence set forth in SEQ ID NO:58.

6. The ddRNAi construct of claim 4, wherein:
(a) the first nucleic acid comprises a DNA sequence encoding a shRNA comprising an effector sequence set forth in SEQ ID NO:27 and an effector complement sequence set forth in SEQ ID NO:28;
(b) the second nucleic acid comprises a DNA sequence encoding a shRNA comprising an effector sequence set forth in SEQ ID NO:47 and an effector complement sequence set forth in SEQ ID NO:48; and
(c) the third nucleic acid comprises a DNA sequence encoding a shRNA comprising an effector sequence set forth in SEQ ID NO:57 and an effector complement sequence set forth in SEQ ID NO:58.

7. The ddRNAi construct according to claim 5, wherein:
(a) the first nucleic acid comprises a DNA sequence encoding a shRNA comprising or consisting of the sequence set forth in SEQ ID NO:78; and
(b) the second nucleic acid comprises a DNA sequence encoding a shRNA comprising or consisting of the sequence set forth in SEQ ID NO:92 or SEQ ID NO:101.

8. The ddRNAi construct according to claim 6, wherein:
(a) the first nucleic acid comprises a DNA sequence encoding a shRNA comprising or consisting of the sequence set forth in SEQ ID NO:78;
(b) the second nucleic acid comprises a DNA sequence encoding a shRNA comprising or consisting of the sequence set forth in SEQ ID NO:92; and
(c) the third nucleic acid comprises a DNA sequence encoding a shRNA comprising or consisting of the sequence set forth in SEQ ID NO:101.

9. The ddRNAi construct according to claim 1, comprising a RNA pol III promoter upstream of each nucleic acid encoding a shRNA, wherein each RNA pol III promoter is selected from a U6 and a H1 promoter.

10. An expression vector comprising the ddRNAi construct of claim 1.

11. The expression vector of claim 10, wherein:
(i) the expression vector is a plasmid or minicircle;
(ii) the expression vector is a plasmid or minicircle complexed with a cationic DNA binding polymer; or
(iii) the expression vector is a viral vector selected from the group consisting of: an adeno-associated viral (AAV) vector, a retroviral vector, an adenoviral (AdV) vector and a lentiviral (LV) vector.

12. A composition comprising:
(i) the ddRNAi construct according to claim 1 and one or more pharmaceutically acceptable carriers; or
(ii) the ddRNAi construct according to claim 1, and one or more pharmaceutically acceptable carriers, wherein the ddRNAi construct is comprised within an expression vector.

13. A composition comprising:
(i) the ddRNAi construct according to claim 2 and one or more pharmaceutically acceptable carriers; or
(ii) the ddRNAi construct according to claim 2 and one or more pharmaceutically acceptable carriers, wherein the ddRNAi construct is comprised within an expression vector.

14. A method of treating Hepatitis B virus (HBV) infection in a subject, said method comprising administering to the subject a composition of claim 12.

15. A method of treating Hepatitis B virus (HBV) infection in a subject, said method comprising administering to the subject a composition of claim 13.

16. The method according to claim 14, wherein the subject is suffering from chronic HBV infection.

17. The method according to claim 15, wherein the subject is suffering from chronic HBV infection.

18. The method of claim 14, wherein administering the nucleic acid to the subject reduces HBV viral load in the subject and/or reduces severity of symptoms associated with HBV infection in the subject and/or reduces infectivity of HBV in the subject.

19. The method of claim 15, wherein administering the nucleic acid to the subject reduces HBV viral load in the subject and/or reduces severity of symptoms associated with HBV infection in the subject and/or reduces infectivity of HBV in the subject.

20. A pharmaceutical composition comprising a ddRNAi construct comprising:
(a) a first nucleic acid comprising a DNA sequence encoding a shRNA comprising an effector sequence set forth in SEQ ID NO:27 and an effector complement sequence set forth in SEQ ID NO:28;
(b) a second nucleic acid comprising a DNA sequence encoding a shRNA comprising an effector sequence set forth in SEQ ID NO:47 and an effector complement sequence set forth in SEQ ID NO:48; and
(c) a third nucleic acid comprising a DNA sequence encoding a shRNA comprising an effector sequence set forth in SEQ ID NO:57 and an effector complement sequence set forth in SEQ ID NO:58;
wherein each DNA sequence encoding a shRNA comprises a U6 and a H1 promoter,
wherein the ddRNAi construct is comprised with an adeno-associated viral (AAV) vector, and
wherein the composition comprises one or more pharmaceutically acceptable carriers.

* * * * *

SEQUENCE LISTING

```
<160> NUMBER OF SEQ ID NOS: 129

<210> SEQ ID NO 1
<211> LENGTH: 20
<212> TYPE: DNA
<213> ORGANISM: Hepatitis B virus
<220> FEATURE:
<223> OTHER INFORMATION: DNA sequence for target region within HBV
      genome designated Region 1

<400> SEQUENCE: 1
catcctgctg ctatgcctca                                              20

<210> SEQ ID NO 2
<211> LENGTH: 23
<212> TYPE: DNA
<213> ORGANISM: Hepatitis B virus
```

```
<220> FEATURE:
<223> OTHER INFORMATION: DNA sequence for target region within HBV
      genome designated Region 2

<400> SEQUENCE: 2
tttgctgacg caaccccac tgg                                              23

<210> SEQ ID NO 3
<211> LENGTH: 20
<212> TYPE: DNA
<213> ORGANISM: Hepatitis B virus
<220> FEATURE:
<223> OTHER INFORMATION: DNA sequence for target region within HBV
      genome designated Region 3

<400> SEQUENCE: 3
aagcctccaa gctgtgcctt                                                 20

<210> SEQ ID NO 4
<211> LENGTH: 34
<212> TYPE: DNA
<213> ORGANISM: Hepatitis B virus
<220> FEATURE:
<223> OTHER INFORMATION: DNA sequence for target region within HBV
      genome designated Region 4

<400> SEQUENCE: 4
gcaggtcccc tagaagaaga actccctcgc ctca                                 34

<210> SEQ ID NO 5
<211> LENGTH: 23
<212> TYPE: DNA
<213> ORGANISM: Hepatitis B virus
<220> FEATURE:
<223> OTHER INFORMATION: DNA sequence for target region within HBV
      genome designated Region 5

<400> SEQUENCE: 5
caaggtatgt tgcccgtttg tcc                                             23

<210> SEQ ID NO 6
<211> LENGTH: 20
<212> TYPE: DNA
<213> ORGANISM: Hepatitis B virus
<220> FEATURE:
<223> OTHER INFORMATION: DNA sequence for target region within HBV
      genome designated Region 6

<400> SEQUENCE: 6
ctcgtggtgg acttctctca                                                 20

<210> SEQ ID NO 7
<211> LENGTH: 23
<212> TYPE: DNA
<213> ORGANISM: Hepatitis B virus
<220> FEATURE:
<223> OTHER INFORMATION: DNA sequence for target region within HBV
      genome designated Region 7

<400> SEQUENCE: 7
ctcgtgttac aggcggggtt ttt                                             23

<210> SEQ ID NO 8
<211> LENGTH: 30
<212> TYPE: DNA
<213> ORGANISM: Hepatitis B virus
```

```
<220> FEATURE:
<223> OTHER INFORMATION: DNA sequence for target region within HBV
      genome designated Region 8

<400> SEQUENCE: 8
ccgtgtgcac ttcgcttcac ctctgcacgt                                    30

<210> SEQ ID NO 9
<211> LENGTH: 22
<212> TYPE: DNA
<213> ORGANISM: Hepatitis B virus
<220> FEATURE:
<223> OTHER INFORMATION: DNA sequence for target region within HBV
      genome designated Region 9

<400> SEQUENCE: 9
tacgtcccgt cggcgctgaa tc                                            22

<210> SEQ ID NO 10
<211> LENGTH: 19
<212> TYPE: DNA
<213> ORGANISM: Hepatitis B virus
<220> FEATURE:
<223> OTHER INFORMATION: DNA sequence for target region within HBV
      genome designated Region 10

<400> SEQUENCE: 10
aaatgcccct atcttatca                                                19

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA1 and shRNA4

<400> SEQUENCE: 11
ugaggcauag cagcaggaug                                               20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA1 and
      shRNA4

<400> SEQUENCE: 12
cauccugcug cuaugccuca                                               20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA2

<400> SEQUENCE: 13
gaugaggcau agcagcagga                                               20
```

```
<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA2

<400> SEQUENCE: 14
uccugcugcu augccucauc                                                   20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA3

<400> SEQUENCE: 15
gaggcauagc agcaggaugc                                                   20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA3

<400> SEQUENCE: 16
gcauccugcu gcuaugccuc                                                   20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA5 and shRNA6

<400> SEQUENCE: 17
ccaguggggg uugcgucagc                                                   20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA5 and
      shRNA6

<400> SEQUENCE: 18
gcugacgcaa cccccacugg                                                   20

<210> SEQ ID NO 19
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA7 and shRNA8

<400> SEQUENCE: 19
aaggcacagc uuggaggcuu                                                   20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA7 and
      shRNA8

<400> SEQUENCE: 20
aagccuccaa gcugugccuu                                                   20

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA9 and shRNA10

<400> SEQUENCE: 21
gaguucuucu ucuaggggac c                                                 21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA9 and
      shRNA10

<400> SEQUENCE: 22
gguccccuag aagaagaacu c                                                 21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA11 and shRNA12

<400> SEQUENCE: 23
gagggaguuc uucuucuagg g                                                 21

<210> SEQ ID NO 24
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA11 and
      shRNA12

<400> SEQUENCE: 24
cccuagaaga agaacucccu c                                              21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effect sequence for shRNA13

<400> SEQUENCE: 25
gcgaguucuu cuucuagggg a                                              21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effect complement sequence for shRNA13

<400> SEQUENCE: 26
uccccuagaa gaagaacucg c                                              21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA14

<400> SEQUENCE: 27
uucuucuucu agggaccug c                                               21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA14

<400> SEQUENCE: 28
gcaggucccc uagaagaaga a                                              21

<210> SEQ ID NO 29
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Effector sequence for shRNA15 and shRNA18

<400> SEQUENCE: 29
acaaacgggc aacauaccuu g                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA15 and
      shRNA18

<400> SEQUENCE: 30
caagguaugu ugcccguuug u                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA16

<400> SEQUENCE: 31
ggacaaacgg gcaacauacc u                                              21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA16

<400> SEQUENCE: 32
agguauguug cccguuuguc c                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA17

<400> SEQUENCE: 33
gacaaacggg caacauaccu u                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Effector complement sequence for shRNA17

<400> SEQUENCE: 34
aagguauguu gcccguuugu c                                              21

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA19 and shRNA20

<400> SEQUENCE: 35
ugagagaagu ccaccacgag                                                20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA19 and
      shRNA20

<400> SEQUENCE: 36
cucguggugg acuucucuca                                                20

<210> SEQ ID NO 37
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA21

<400> SEQUENCE: 37
auugagagaa guccaccacg                                                20

<210> SEQ ID NO 38
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA21

<400> SEQUENCE: 38
cgugguggac uucucucaau                                                20

<210> SEQ ID NO 39
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA22
```

<400> SEQUENCE: 39 agagaaguccaccacgaguc                                            20

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA22

<400> SEQUENCE: 40 gacucgugguggacuucucu                                            20

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA23 and shRNA24

<400> SEQUENCE: 41 aaaccccgccuguaacacgag                                           21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA23 and
      shRNA24

<400> SEQUENCE: 42 cucguguuacaggcgggguu u                                          21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA25 and shRNA26

<400> SEQUENCE: 43 ugcagagguga agcgaagug c                                         21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA25 and
      shRNA26

```
<400> SEQUENCE: 44
gcacuucgcu ucaccucugc a                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA27 and shRNA30

<400> SEQUENCE: 45
gauucagcgc cgacgggacg u                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA27 and
      shRNA30

<400> SEQUENCE: 46
acgucccguc ggcgcugaau c                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA28 and shRNA31

<400> SEQUENCE: 47
ggauucagcg ccgacgggac g                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA28 and
      shRNA31

<400> SEQUENCE: 48
cgucccgucg gcgcugaauc c                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA29 and shRNA32
```

```
<400> SEQUENCE: 49
auucagcgcc gacgggacgu a                                              21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA29 and
      shRNA32

<400> SEQUENCE: 50
uacgucccgu cggcgcugaa u                                              21

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA33 and shRNA34

<400> SEQUENCE: 51
ugauaagaua ggggcauuu                                                 19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA33 and
      shRNA34

<400> SEQUENCE: 52
aaaugccccu aucuuauca                                                 19

<210> SEQ ID NO 53
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA35

<400> SEQUENCE: 53
ugaggcccac ucccauaggu au                                             22

<210> SEQ ID NO 54
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA35
```

```
<400> SEQUENCE: 54
auaccuaugg gagugggccu ca                                           22

<210> SEQ ID NO 55
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA36

<400> SEQUENCE: 55
ggaaagcccu acgaaccacu ga                                           22

<210> SEQ ID NO 56
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA36

<400> SEQUENCE: 56
ucagugguuc guagggcuuu cc                                           22

<210> SEQ ID NO 57
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA37

<400> SEQUENCE: 57
gggaaagccc uacgaaccac ug                                           22

<210> SEQ ID NO 58
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA37

<400> SEQUENCE: 58
cagugguucg uagggcuuuc cc                                           22

<210> SEQ ID NO 59
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA38

<400> SEQUENCE: 59
ggggaaagcc cuacgaacca cu                                           22
```

```
<210> SEQ ID NO 60
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA38

<400> SEQUENCE: 60
agugguucgu agggcuuucc cc                                              22

<210> SEQ ID NO 61
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA39

<400> SEQUENCE: 61
gggaaagccc uacgaaccac ug                                              22

<210> SEQ ID NO 62
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA39

<400> SEQUENCE: 62
cauuguuucg ucgggcuuuc cc                                              22

<210> SEQ ID NO 63
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector sequence for shRNA40

<400> SEQUENCE: 63
ccgggcaacg ggguaaaggu uc                                              22

<210> SEQ ID NO 64
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Effector complement sequence for shRNA40

<400> SEQUENCE: 64
gaaccuuuac cccguugccc gg                                              22

<210> SEQ ID NO 65
<211> LENGTH: 47
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: shRNA1 sequence

<400> SEQUENCE: 65
cauccugcug cuaugccuca caagagauga ggcauagcag caggaug               47

<210> SEQ ID NO 66
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA2 sequence

<400> SEQUENCE: 66
uccugcugcu augccucauc caagagagau gaggcauagc agcagga               47

<210> SEQ ID NO 67
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA3 sequence

<400> SEQUENCE: 67
gcauccugcu gcuaugccuc caagagagag gcauagcagc aggaugc               47

<210> SEQ ID NO 68
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA4 sequence

<400> SEQUENCE: 68
ugaggcauag cagcaggaug caagagacau ccugcugcua ugccuca               47

<210> SEQ ID NO 69
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA5 sequence

<400> SEQUENCE: 69
gcugacgcaa cccccacugg caagagacca guggggguug cgucagc               47

<210> SEQ ID NO 70
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: shRNA6 sequence

<400> SEQUENCE: 70 ccagugggg uugcgucagc caagagagcu gacgcaaccc ccacugg                47

<210> SEQ ID NO 71
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA7 sequence

<400> SEQUENCE: 71
aagccuccaa gcugugccuu ugugcuuaag gcacagcuug gaggcuu                47

<210> SEQ ID NO 72
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA8 sequence

<400> SEQUENCE: 72
aaggcacagc uuggaggcuu ugugcuuaag ccuccaagcu gugccuu                47

<210> SEQ ID NO 73
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA9 sequence

<400> SEQUENCE: 73
gguccccuag aagaagaacu ccaagagaga guucuucuuc uaggggacc              49

<210> SEQ ID NO 74
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA10 sequence

<400> SEQUENCE: 74
gaguucuucu ucuaggggac ccaagagagg uccccuagaa gaagaacuc              49

<210> SEQ ID NO 75
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: shRNA11 sequence
<400> SEQUENCE: 75
cccuagaaga agaacucccu ccaagagaga gggaguucuu cuucuaggg              49

<210> SEQ ID NO 76
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA12 sequence

<400> SEQUENCE: 76
gagggaguuc uucuucuagg gcaagagacc cuagaagaag aacucccuc              49

<210> SEQ ID NO 77
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA13 sequence

<400> SEQUENCE: 77 ucccuagaa gaagaacucg ccaagagagc gaguucuucu ucuagggga              49

<210> SEQ ID NO 78
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA14 sequence

<400> SEQUENCE: 78 gcagguccccc uagaagaaga acaagagauu cuucuucuag gggaccugc             49

<210> SEQ ID NO 79
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA15 sequence

<400> SEQUENCE: 79
caagguaugu ugcccguuug ucaagagaac aaacgggcaa cauaccuug              49

<210> SEQ ID NO 80
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA16 sequence
```

```
<400> SEQUENCE: 80
agguauguug cccguuuguc ccaagagagg acaaacgggc aacauaccu                49

<210> SEQ ID NO 81
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA17 sequence

<400> SEQUENCE: 81
aagguauguu gcccguuugu ccaagagaga caaacgggca acauaccuu                49

<210> SEQ ID NO 82
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA18 sequence

<400> SEQUENCE: 82
acaaacgggc aacauaccuu gcaagagaca agguauguug cccguuugu                49

<210> SEQ ID NO 83
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA19 sequence

<400> SEQUENCE: 83
cucguggugg acuucucuca caagagauga gagaagucca ccacgag                  47

<210> SEQ ID NO 84
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA20 sequence

<400> SEQUENCE: 84
ugagagaagu ccaccacgag caagagacuc gugguggacu ucucuca                  47

<210> SEQ ID NO 85
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA21 sequence

<400> SEQUENCE: 85
auugagagaa guccaccacg caagagacgu gguggacuuc ucucaau                  47
```

<210> SEQ ID NO 86
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA22 sequence

<400> SEQUENCE: 86
agagaagucc accacgaguc caagagagac ucguggugga cuucucu                47

<210> SEQ ID NO 87
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA23 sequence

<400> SEQUENCE: 87
cucguguuac aggcgggguu uugugcuuaa accccgccug uaacacgag              49

<210> SEQ ID NO 88
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA24 sequence

<400> SEQUENCE: 88 aaacccgcc uguaacacga gugugcuucu cguguuacag gcggggguuu              49

<210> SEQ ID NO 89
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA25 sequence

<400> SEQUENCE: 89
gcacuucgcu ucaccucugc acaagagaug cagaggugaa gcgaagugc              49

<210> SEQ ID NO 90
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA26 sequence

<400> SEQUENCE: 90
ugcagaggug aagcgaagug ccaagagagc acuucgcuuc accucugca              49

<210> SEQ ID NO 91
<211> LENGTH: 49
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: shRNA27 sequence

<400> SEQUENCE: 91
acgucccguc ggcgcugaau cugugcuuga uucagcgccg acgggacgu        49

<210> SEQ ID NO 92
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA28 sequence

<400> SEQUENCE: 92
cgucccgucg gcgcugaauc cugugcuugg auucagcgcc gacgggacg        49

<210> SEQ ID NO 93
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA29 sequence

<400> SEQUENCE: 93
uacgucccgu cggcgcugaa uugugcuuau ucagcgccga cgggacgua        49

<210> SEQ ID NO 94
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA30 sequence

<400> SEQUENCE: 94
gauucagcgc cgacgggacg uugugcuuac gucccgucgg cgcugaauc        49

<210> SEQ ID NO 95
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA31 sequence

<400> SEQUENCE: 95
ggauucagcg ccgacgggac gugugcuucg ucccgucggc gcugaaucc        49

<210> SEQ ID NO 96
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: shRNA32 sequence

<400> SEQUENCE: 96
auucagcgcc gacgggacgu augugcuuua cgucccgucg gcgcugaau                49

<210> SEQ ID NO 97
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA33 sequence

<400> SEQUENCE: 97
aaaugccccu aucuuaucau gugcuuugau aagauagggg cauuu                   45

<210> SEQ ID NO 98
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA34 sequence

<400> SEQUENCE: 98
ugauaagaua ggggcauuuu gugcuuaaau gccccuaucu auca                    45

<210> SEQ ID NO 99
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA35 sequence

<400> SEQUENCE: 99
auaccuaugg gagugggccu cacaagagau gaggcccacu cccauaggua u            51

<210> SEQ ID NO 100
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA36 sequence

<400> SEQUENCE: 100
ucagugguuc guagggcuuu cccaagagag gaaagcccua cgaaccacug a            51

<210> SEQ ID NO 101
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA37 sequence
```

<400> SEQUENCE: 101
cagugguucg uagggcuuuc cccaagagag ggaaagcccu acgaaccacu g               51

<210> SEQ ID NO 102
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA38 sequence

<400> SEQUENCE: 102
agugguucgu agggcuuucc cccaagagag gggaaagccc uacgaaccac u               51

<210> SEQ ID NO 103
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA39 sequence

<400> SEQUENCE: 103
gggaaagccc uacgaaccac ugcaagagac auuguuucgu cgggcuuucc c               51

<210> SEQ ID NO 104
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: shRNA40 sequence

<400> SEQUENCE: 104
gaaccuuuac cccguugccc ggcaagagac cgggcaacgg gguaaagguu c               51

<210> SEQ ID NO 105
<211> LENGTH: 1856
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pBL184_HBV_Triple_V2
<220> FEATURE:
<221> NAME/KEY: modified_base
<222> LOCATION: (696)..(696)
<223> OTHER INFORMATION: a, c, t or g
<220> FEATURE:
<221> NAME/KEY: modified_base
<222> LOCATION: (699)..(699)
<223> OTHER INFORMATION: a, c, t or g

<400> SEQUENCE: 105
gcatgcaggg cggtgcggct caggctctgc cccgcctccg ggctatttg catacgacca        60 tttccagtaa ttcccagcag ccaccgtagc tatatttggt agaacaacga gcactttctc      120
aactccagtc aataactacg ttagttgcat tacacattgg gctaatataa atagaggtta     180
aatctctagg tcatttaaga gaacggtcac cgtaaggaaa acaaatgaaa agactcccgt     240 gcctttataag gcctgtgggt gacttcttct caacggatcc gcaggtcccc tagaagaaga     300

| | |
|---|---|
| acaagagatt cttcttctag ggggacctgct ttttagatc tgttcggctt tacgtcacgc | 360 |
| gagggcggca gggaggacgg aatggcgggg tttggggtgg gtccctcctc ggggggagccc | 420 |
| tgggaaaaga ggactgcgtg tgggaagaga aggtggaaat ggcgttttgg ttgacatgtg | 480 |
| ccgcctgcga gcgtgctgcg gggaggggcc gagggcagat tcgggaatga tggcgcgggg | 540 |
| tggggggcgtg ggggctttct cgggagaggc ccttccctgg aagtttgggg tgcgatggtg | 600 |
| aggttctcgg ggcacctctg gagggggcctc ggcacggaaa gcgaccacct gggagggcgt | 660 |
| gtggggacca ggttttgcct ttagttttgc acacdnadna actgtagttc atctttatgg | 720 |
| agatgctcat ggcctcattg aagccccacg gatctgggca ggaagagggc ctatttccca | 780 |
| tgattccttc atatttgcat atacgataca aggctgttag agagataatt agaattaatt | 840 |
| tgactgtaaa cacaaagata ttagtacaaa atacgtgacg tagaaagtaa taatttcttg | 900 |
| ggtagtttgc agttttaaaa ttatgtttta aaatggacta tcatatggtt accgtaagga | 960 |
| aaacaaatga tttcgatttc ttggctttat atatcttgtg gaaaggacga ggatccgcaa | 1020 |
| ggtatgttgc ccgtttgtca agagaacaaa cgggcaacat accttgtttt ttctagagaa | 1080 |
| ttgtacagct ctggtagcgg taaccatgcg tatttgacac acgaaggaac tagggaaaag | 1140 |
| gcattaggtc atttcaagcc gaaattcaca tgtgctagaa tccagattcc atgctgaccg | 1200 |
| atgccccagg atatagaaaa tgagaatctg tccttacct tcaagaacat tcttaaccgt | 1260 |
| aatcagcctc tggtatctta gctccaccct cactggtttt ttcttgtttg ttgaaccggc | 1320 |
| caagctgctg gcctccctcc tcaaccgttc tgatcatgct tgctaaaata gtcaaaaccc | 1380 |
| cggccagtta aatatgcttt agcctgcttt attatgatta ttttttgttgt tttggcaatg | 1440 |
| acctggctac ctgttgtttc tcccactaaa acttttttaag ggcagggaat tgatctagaa | 1500 |
| aaaaaaagc tagtggtacc ggtcctacgc ggggcccttt acccagggtg ccccgggcgc | 1560 |
| tcatttgcat gtcccacca acaggtaaac ctgacaggtc atcgcggcca ggtacgacct | 1620 |
| cggtcagagc accaaacata cgagccttgt gatgagttcc gttgcatgaa attctcccaa | 1680 |
| aggctccaag atgacagga aagggcgcgg ttcggtcacc gtaaggaaaa caaatgaaaa | 1740 |
| gactcccgtg cctataagg cctgtgggtg acttcttctc aacggatccg cgtcccgtcg | 1800 |
| gcgctgaatc ctgtgcttgg attcagcgcc gacgggacgt ttttctaga gaattc | 1856 |

<210> SEQ ID NO 106
<211> LENGTH: 1851
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: pBL183_HBV_Triple_V1

<400> SEQUENCE: 106

| | |
|---|---|
| gcatgcaggg cggtgcggct caggctctgc cccgcctccg ggctatttg catacgacca | 60 |
| tttccagtaa ttcccagcag ccaccgtagc tatatttggt agaacaacga gcactttctc | 120 |
| aactccagtc aataactacg ttagttgcat tacacattgg gctaatataa atagaggtta | 180 |
| aatctctagg tcatttaaga gaacggtcac cgtaaggaaa acaaatgaaa agactcccgt | 240 |
| gccttataag gcctgtgggt gacttcttct caacggatcc gcaggtcccc tagaagaaga | 300 |
| acaagagatt cttcttctag ggggacctgct ttttagatc tgttcggctt tacgtcacgc | 360 |
| gagggcggca gggaggacgg aatggcgggg tttggggtgg gtccctcctc ggggggagccc | 420 |

```
tgggaaaaga ggactgcgtg tgggaagaga aggtggaaat ggcgttttgg ttgacatgtg      480
ccgcctgcga gcgtgctgcg gggaggggcc gagggcagat tcgggaatga tggcgcgggg      540
tgggggcgtg ggggctttct cgggagaggc ccttccctgg aagtttgggg tgcgatggtg      600
aggttctcgg ggcacctctg gaggggcctc ggcacggaaa gcgaccacct gggagggcgt      660
gtggggacca ggttttgcct ttagttttgc acacactgta gttcatcttt atggagatgc      720
tcatggcctc attgaagccc acggatctg ggcaggaaga gggcctattt cccatgattc      780
cttcatattt gcatatacga tacaaggctg ttagagagat aattagaatt aatttgactg      840
taaacacaaa gatattagta caaaatacgt gacgtagaaa gtaataattt cttgggtagt      900
ttgcagtttt aaaattatgt tttaaaatgg actatcatat ggttaccgta aggaaaacaa      960
atgatttcga tttcttggct ttatatatct tgtggaaagg acgaggatcc gcagtggttc     1020
gtagggcttt ccccaagaga gggaaagccc tacgaaccac tgttttttcta gagaattgta     1080 cagctctggt agcggtaacc atgcgtattt gacacacgaa ggaactaggg aaaaggcatt     1140
aggtcatttc aagccgaaat tcacatgtgc tagaatccag attccatgct gaccgatgcc     1200
ccaggatata gaaatgaga atctggtcct taccttcaag aacattctta accgtaatca     1260
gcctctggta tcttagctcc accctcactg gttttttctt gtttgttgaa ccggccaagc     1320
tgctggcctc cctcctcaac cgttctgatc atgcttgcta aaatagtcaa aaccccggcc     1380
agttaaatat gctttagcct gctttattat gattattttt gttgttttgg caatgacctg     1440
gctacctgtt gtttctccca ctaaaacttt ttaagggcag ggaattgatc tagaaaaaaa     1500
aaagctagtg gtaccggtcc tacgcggggc cctttaccca gggtgccccg ggcgctcatt     1560
tgcatgtccc acccaacagg taaacctgac aggtcatcgc ggccaggtac gacctcggtc     1620
agagcaccaa acatacgagc cttgtgatga gttccgttgc atgaaattct cccaaaggct     1680
ccaagatgga caggaaggg cgcggttcgg tcaccgtaag gaaaacaaat gaaaagactc     1740
ccgtgcctta taaggcctgt gggtgacttc ttctcaacgg atccgcgtcc cgtcggcgct     1800
gaatcctgtg cttggattca gcgccgacgg gacgtttttt ctagagaatt c             1851
```

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
atgttgcccg tttgtcctct                                                   20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ccgtccgaag gtttggtaca                                                   20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cgtcctttgt ttacgtcccg                                              20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
agtccgcgta aagagaggtg                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ccaccaaatg cccctatcct                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
attgagacct tcgtctgcga                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acaccatggg gaaggtgaag                                              20

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gtgaccaggc gcccaata                                                18

<210> SEQ ID NO 115
<211> LENGTH: 100
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 115
cgtcggtacc acaagcaaga gtcggcagta agaagatggc gtatatatta tgaaaggtac    60
cgagattggc cattcggagt gtttagtcga ccaaactgat                         100

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
acaaacgggc aacatacctt g                                              21

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gggaaagccc tacgaaccac tg                                             22

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ggattcagcg ccgacgggac g                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ttcttcttct aggggacctg c                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
acaaacgggc aacauaccuu g                                              21

<210> SEQ ID NO 121
<211> LENGTH: 22
<212> TYPE: RNA
```

<213> ORGANISM: Artificial Sequence
<220> FEATURE:
<223> OTHER INFORMATION: Description of Artificial Sequence: Synthetic
     oligonucleotide

<400> SEQUENCE: 121
gggaaagccc uacgaaccac ug                                            22

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 122
ggauucagcg ccgacgggac g                                             21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 123
uucuucuucu agggaccug c                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 124
cacatcagga ttcctaggac c                                             21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 125
aggttggtga gtgattggag                                               20

<210> SEQ ID NO 126
<211> LENGTH: 26
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 126
cagagtctag actcgtggtg gacttc                                        26

<210> SEQ ID NO 127
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 127
ctccccgtct gtgccttct                                                    19

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gccccaaagc cacccaag                                                     18

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
cgtcgcatgg araccaccgt gaacgcc                                           27
```